(12) United States Patent
Edgar et al.

(10) Patent No.: US 7,355,042 B2
(45) Date of Patent: Apr. 8, 2008

(54) TREATMENT OF CNS DISORDERS USING CNS TARGET MODULATORS

(75) Inventors: Dale M. Edgar, Wayland, MA (US); David G. Hangauer, East Amherst, NY (US); Harry Jefferson Leighton, Boston, MA (US); Emmanuel J. M. Mignot, Palo Alto, CA (US); James F. White, Carlisle, MA (US); Michael Solomon, Concord, MA (US); Kazumi Shiosaki, Wellesley, MA (US)

(73) Assignee: Hypnion, Inc., Lexington, MA (US)

( * ) Notice: Subject to any disclaimer, the term of this patent is extended or adjusted under 35 U.S.C. 154(b) by 24 days.

(21) Appl. No.: 10/831,553

(22) Filed: Apr. 23, 2004

(65) Prior Publication Data

US 2005/0080265 A1    Apr. 14, 2005

Related U.S. Application Data

(63) Continuation-in-part of application No. 10/272,510, filed on Oct. 16, 2002.

(60) Provisional application No. 60/418,821, filed on Oct. 16, 2002, provisional application No. 60/414,243, filed on Sep. 27, 2002, provisional application No. 60/381,507, filed on May 17, 2002, provisional application No. 60/329,701, filed on Oct. 16, 2001.

(51) Int. Cl.
  *A61P 25/00*     (2006.01)
  *A61K 31/55*     (2006.01)
  *C07D 267/16*    (2006.01)

(52) U.S. Cl. .................. 540/542; 540/548; 540/551

(58) Field of Classification Search ........... 540/542, 540/548, 551
See application file for complete search history.

(56) References Cited

U.S. PATENT DOCUMENTS

| | | | |
|---|---|---|---|
| 3,534,041 A | 10/1970 | van der Burg et al. ..... 260/268 |
| 3,928,356 A | 12/1975 | Umino et al. ......... 260/268 TR |
| 4,062,848 A | 12/1977 | van der Burg ............. 260/268 |
| 4,383,999 A | 5/1983 | Bondinell et al. .......... 424/266 |
| 4,397,855 A | 8/1983 | Sircar ...................... 424/250 |
| 4,514,414 A | 4/1985 | Bondinell et al. .......... 514/422 |
| 4,610,995 A | 9/1986 | Coker et al. ............... 514/343 |
| 4,629,691 A | 12/1986 | Collins et al. ................. 435/7 |
| 4,772,697 A | 9/1988 | Collins et al. ............. 540/591 |
| 4,929,618 A | 5/1990 | Koda et al. ................ 514/253 |
| 4,931,450 A | 6/1990 | Sonnewald ................ 514/326 |
| 5,095,022 A | 3/1992 | Ito et al. .................... 514/320 |
| 5,134,147 A | 7/1992 | Peglion et al. ............. 514/300 |
| 5,153,207 A | 10/1992 | Ito et al. .................... 814/327 |
| 5,225,559 A | 7/1993 | Kita et al. .................. 546/194 |
| 5,229,400 A | 7/1993 | Hirasawa et al. ........... 514/325 |
| 5,231,105 A | 7/1993 | Shoji et al. ................. 514/325 |
| 5,250,681 A | 10/1993 | Shoji et al. ................. 540/577 |
| 5,256,409 A | 10/1993 | Blincko ....................... 424/85.8 |
| 5,344,828 A | 9/1994 | Sawanishi et al. .......... 514/211 |
| 5,362,725 A | 11/1994 | Fukumi et al. ............. 514/214 |
| 5,364,866 A | 11/1994 | Strupczewski et al. ..... 514/321 |
| 5,393,890 A | 2/1995 | Syoji et al. .................... 546/80 |
| 5,407,933 A | 4/1995 | Fukumi et al. ............. 514/219 |
| 5,432,179 A | 7/1995 | Kumagai et al. ........... 514/255 |
| 5,461,051 A | 10/1995 | Fukumi et al. ............. 514/214 |
| 5,476,848 A | 12/1995 | Fukumi et al. ............. 514/214 |
| 5,595,989 A | 1/1997 | Andersen et al. ........... 514/217 |
| 5,641,781 A | 6/1997 | Cuberes-Altisent et al. 514/253 |
| 5,658,908 A | 8/1997 | Chang et al. ............... 514/252 |
| 5,741,791 A | 4/1998 | Olsen ......................... 514/212 |
| 5,776,963 A | 7/1998 | Strupczewski et al. ..... 514/373 |
| 5,801,175 A | 9/1998 | Afonso et al. .............. 514/254 |
| 5,807,858 A | 9/1998 | Chang et al. ............... 514/255 |
| 5,854,249 A | 12/1998 | Chang et al. ............... 514/255 |
| 5,874,428 A | 2/1999 | Dørwald et al. ............ 514/217 |
| 5,985,880 A | 11/1999 | Chang et al. ............... 514/255 |
| 6,004,983 A | 12/1999 | Andersen et al. ........... 514/325 |
| 6,054,458 A | 4/2000 | Jørgensen et al. .......... 514/255 |
| 6,071,901 A | 6/2000 | Dörwald et al. ............ 514/217 |
| 6,110,913 A | 8/2000 | Dörwald et al. ......... 514/225.2 |
| 6,166,009 A | 12/2000 | Dörwald et al. ......... 514/225.2 |
| 6,174,898 B1 | 1/2001 | Weis et al. .................. 514/315 |
| 6,191,165 B1 | 2/2001 | Ognyanov et al. .......... 514/523 |
| 6,214,816 B1 | 4/2001 | Hohlweg et al. ........... 514/183 |
| 6,214,827 B1 | 4/2001 | Afonso et al. .......... 514/252.13 |
| 6,218,404 B1 | 4/2001 | Bigge et al. ................ 514/317 |
| 6,288,083 B1 | 9/2001 | Luly et al. .................. 514/318 |
| 6,288,084 B1 | 9/2001 | Luly et al. .................. 514/318 |
| 6,307,052 B1 | 10/2001 | Kita et al. .................. 546/194 |
| 6,331,541 B1 | 12/2001 | Ko et al. ................... 514/237.2 |
| 6,391,890 B1 | 5/2002 | Jørgensen et al. .......... 514/316 |
| 6,420,560 B1 | 7/2002 | Numerof et al. ............ 544/362 |
| 6,503,926 B2 | 1/2003 | Luly et al. .................. 514/318 |
| 6,569,849 B1 | 5/2003 | Jorgensen et al. .......... 514/217 |
| 6,605,623 B1 | 8/2003 | Ko et al. .................... 514/331 |

(Continued)

FOREIGN PATENT DOCUMENTS

DE    1 801 523    6/1969

(Continued)

OTHER PUBLICATIONS

Andersen et al. *J. Med. Chem.*, 36(12):1716-1725 (1993).

(Continued)

*Primary Examiner*—Brenda Coleman
(74) *Attorney, Agent, or Firm*—Ivor R. Elrifi; Heidi A. Erlacher; Mintz, Levin, Cohn, Ferris, Glovsky and Popeo, P.C.

(57) ABSTRACT

The invention is directed to compositions and methods useful for treating Central Nervous System (CNS) disorders. Furthermore, the invention provides compositions and methods of treating sleep disorders. More specifically, the invention is directed to the compositions and use of derivatized, histamine antagonists for the treatment of sleep disorders.

1 Claim, 11 Drawing Sheets

U.S. PATENT DOCUMENTS

| | | |
|---|---|---|
| RE38,257 E | 9/2003 | Shoji et al. ............... 546/80 |
| 6,686,353 B1 | 2/2004 | Shiota et al. ............... 514/218 |
| 6,706,753 B2 | 3/2004 | Artis et al. ............... 514/422 |
| 2006/0063755 A1* | 3/2006 | Edgar et al. ............ 514/211.13 |
| 2006/0063928 A1* | 3/2006 | Edgar et al. ............... 540/551 |

FOREIGN PATENT DOCUMENTS

| | | |
|---|---|---|
| EP | 0 335 586 A1 | 10/1989 |
| EP | 0 399 414 A1 | 11/1990 |
| EP | 0 447 857 A1 | 9/1991 |
| EP | 0 451 772 A1 | 10/1991 |
| EP | 0 479 601 B1 | 4/1992 |
| EP | 0 542 136 B1 | 5/1993 |
| EP | 0 598 123 A1 | 5/1994 |
| EP | 0 649 414 B1 | 4/1995 |
| EP | 0 738 262 B1 | 10/1996 |
| EP | 0 820 451 B1 | 1/1998 |
| EP | 0 869 954 B1 | 10/1998 |
| EP | 0 938 317 B1 | 9/1999 |
| EP | 0 949 260 A1 | 10/1999 |
| EP | 1 003 373 B1 | 5/2000 |
| GB | 1 280 290 | 7/1972 |
| JP | 03-184963 A | 8/1991 |
| JP | 03-246287 | 11/1991 |
| JP | 05-17442 A | 1/1993 |
| JP | 05-17443 A2 | 1/1993 |
| JP | 05-148234 A | 6/1993 |
| JP | 05-294929 A | 11/1993 |
| JP | 3352184 B2 | 5/1995 |
| JP | 09-20755 A2 | 1/1997 |
| JP | 2000-256354 A | 9/2000 |
| JP | 2001-261553 A | 9/2001 |
| JP | 2004-051600 A2 | 2/2004 |
| WO | WO 95/01350 | 1/1995 |
| WO | WO 96/31469 | 10/1996 |
| WO | WO 96/31478 | 10/1996 |
| WO | WO 97/45115 | 12/1997 |
| WO | WO 97/45422 | 12/1997 |
| WO | WO 97/49698 | 12/1997 |
| WO | WO 99/00376 | 1/1999 |
| WO | 0 934 313 B1 | 8/1999 |
| WO | WO 00/14064 | 3/2000 |
| WO | WO 02/066446 A1 | 8/2002 |
| WO | WO 02/073208 A2 | 9/2002 |
| WO | WO 03/033489 A1 | 4/2003 |
| WO | WO 03/039255 A1 | 5/2003 |
| WO | WO 03/079970 A2 | 10/2003 |
| WO | WO 2004/056182 A1 | 7/2004 |

OTHER PUBLICATIONS

Andersen et al. *J. Med. Chem.*, 42:4281-4291 (1999).
Dhar et al. *Bioorg. Med. Chem. Lett.*, 6(13):1535-1540 (1996).
Falch et al. *Eur. J. Med. Chem.*, 26:69-78 (1991).
Iwasaki et al. *Chem. Pharm. Bull.*, 42(11):2276-2284 (1994).
Iwasaki et al. *Chem. Pharm. Bull.*, 42(11):2285-2290 (1994).
Muramatsu et al. *Yakugaku Zasshi*, in Chinese, Abstract in English only, 112(7):479-488 (1992).
Muramatsu et al. *Chem. Pharm. Bull.*, 41(11)1987-1993 (1993).
Nakano et al. *Chem. Pharm. Bull.*, 47(11):1573-1578 (1999).
N'Goka et al. *J. Med. Chem.*, 34(8):2547-2557 (1991).
Ohshima et al. *J. Med. Chem.*, 35(11):2074-2084 (1992).
Patani et al. *Chem. Rev.*, 96(8):3147-3176 (1996).
Yunger et al. *J. Pharmacol. Exp. Ther.*, 228(1):109-115 (1984).
International Search Report for PCT/US05/34015, mailed Jun. 29, 2006.
Patent Abstracts of Japan for JP 03184963 A2, published Aug. 12, 1991.
Chemical Abstracts Service HCAplus and MARPAT file records for JP 09020755, published Jan. 21, 1997.

* cited by examiner

TREATMENT OF CNS DISORDERS USING CNS TARGET MODULATORS

REFERENCE TO RELATED APPLICATIONS

This patent application is a continuation-in-part of U.S. Ser. No. 10/272,510, filed Oct. 16, 2002, which claims the benefit of U.S. Provisional Patent Application Ser. No. 60/329,701, filed on Oct. 16, 2001, entitled "Treatment of CNS Disorders Using CNS Target Modulators"; pending U.S. Provisional Patent Application Ser. No. 60/381,507, filed on May 17, 2002, entitled "Treatment of CNS Disorders Using CNS Target Modulators"; U.S. Provisional Patent Application Ser. No. 60/414,243, filed on Sep. 27, 2002, entitled "Treatment of CNS Disorders Using CNS Target Modulators"; and U.S. Provisional Patent Application Ser. No. 60/418,821, filed on Oct. 16, 2002, entitled "Treatment of CNS Disorders Using CNS Target Modulators". The entire content of each of the above-identified applications is hereby incorporated herein by reference.

FIELD OF THE INVENTION

The invention relates to methods for treating CNS disorders and compositions useful for such methods.

BACKGROUND OF THE INVENTION

Difficulties in falling asleep, remaining asleep, sleeping for adequate lengths of time, or abnormal sleep behavior are common symptoms for those suffering with a sleep disorder. A number of sleep disorders, e.g., insomnia or sleep apnea, are described in the online Merck Manual of Medicinal Information.

Current treatment of many sleep disorders include the use of prescription hypnotics, e.g., benzodiazapines, that may be habit-forming, lose their effectiveness after extended use, and metabolize more slowly for certain designated groups, e.g., elderly persons, resulting in persisting medicative effects.

Other, more mild manners of treatment include over-the-counter antihistamines, e.g., diphenhydramine or dimenhydrinate, which are not designed to be strictly sedative in their activity. This method of treatment is also associated with a number of adverse side effects, e.g., persistence of the sedating medication after the prescribed time of treatment, or the so-called "hangover effect". Many of these side effects result from nonspecific activity in both the periphery as well as the Central Nervous System (CNS) during this period of extended medication.

SUMMARY OF THE INVENTION

A need exists for the development of new compositions used for the improved treatment of sleep disorders that remain active for a discrete period of time to reduce side effects, such as the "hangover effect." The strategy of treatment is applicable to a broader array of CNS targets.

Therefore, the invention is directed to compositions used for treating Central Nervous System (CNS) disorders. In addition, the invention provides convenient methods of treatment of a CNS disorder. Furthermore, the invention provides methods of treating sleep disorders using compositions that remain active for a discrete period of time to reduce side effects. More specifically, the invention is directed to the compositions and use of derivatized, e.g., ester or carboxylic acid derivatized, histamine antagonists for the treatment of sleep disorders.

Thus, in one aspect of the invention, the invention is a method of treating a sleep disorder. The method comprises administering an effective amount of an antihistamine compound, such that the sleep disorder is treated, wherein the antihistamine compound has a favorable biological property (FBP).

An additional aspect of the invention is a method of treating a Central Nervous System (CNS) disorder. The method comprises administering an effective amount of a therapeutic compound to a subject, such that the therapeutic compound penetrates into the CNS and modulates the CNS target to treat the CNS disorder. Accordingly, the therapeutic compound can have the formula:

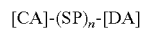

[CA]-(SP)$_n$-[DA]

wherein CA is a moiety that modulates an active CNS target receptor or a collection of active CNS target receptors, DA is a drug activity modulating moiety that provides the ability to modulate the activity of the therapeutic compound, e.g., ester or carboxylic acid, SP is a spacer molecule, and n is 0 or 1.

Another aspect of the invention is a method of treating a Central Nervous System (CNS) disorder. The method comprises administering an effective amount of a therapeutic compound to a subject, such that the therapeutic compound penetrates into the CNS and modulates the CNS target to treat the CNS disorder. Accordingly, the therapeutic compound can have the formula:

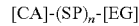

[CA]-(SP)$_n$-[EG]

wherein CA is a moiety that modulates an active CNS target receptor or a collection of active CNS target receptors, EG is an ester group that modifies the half-life of the therapeutic compound, SP is a spacer molecule, and n is 0 or 1.

In a more specific aspect of the invention, the invention is directed to a method of treating a sleep disorder. The method comprises administering an effective amount of a therapeutic compound to a subject, such that the sleep disorder is treated. Accordingly, the therapeutic compound can have the formula:

[CA]-(SP)$_n$-[EG]

wherein CA is a moiety that modulates an active CNS target receptor or a collection of active CNS target receptors, EG is an ester group that modifies the half-life of the therapeutic compound, SP is a spacer molecule, and n is 0 or 1.

In an additional aspect, the invention is directed to a method of treating a sleep disorder target. The method comprises administering an effective amount of a therapeutic compound to a subject, such that the sleep disorder is treated. Accordingly, the therapeutic compound can have the formula:

[AD]-(SP)$_n$-[EG]

wherein AD is a moiety that agonizes an adenosine receptor or a collection of adenosine receptors, EG is an ester group that modifies the half-life of the therapeutic compound, SP is a spacer molecule, and n is 0 or 1.

Another aspect of the invention is directed to a method of treating a sleep disorder target. The method comprises administering an effective amount of a therapeutic compound to a subject, such that the sleep disorder is treated. Accordingly, the therapeutic compound can have the formula:

[AH]-(SP)$_n$-[DA]

wherein AH is a moiety that antagonizes a histamine receptor or a collection of histamine receptors, DA is a drug activity modulating moiety that provides the ability to modulate the activity of the therapeutic compound, SP is a spacer molecule, and n is 0 or 1.

In another aspect, the invention is directed to a method of treating a sleep disorder. The method comprises administering an effective amount of a therapeutic compound to a subject, such that the sleep disorder is treated. Accordingly, the therapeutic compound can have the formula:

[AH]-(SP)$_n$-[EG]

wherein AH is a moiety that antagonizes a histamine receptor or a collection of histamine receptors, EG is an ester group that modifies the half-life of the therapeutic compound, SP is a spacer molecule, and n is 0 or 1.

Another aspect of the invention is a method of modulating a sleep disorder target. The method comprises administering an effective amount of a therapeutic compound to a subject, such that the sleep disorder target is modulated, wherein the therapeutic compound comprises the formula:

[CA]-(SP)n-[DA]

wherein CA is a moiety that modulates an active CNS target receptor or a collection of active CNS target receptors, DA is a drug activity modulating moiety that provides the ability to modulate the activity of the therapeutic compound, e.g., ester or carboxylic acid, SP is a spacer molecule, and n is 0 or 1.

Another aspect of the invention is a method of modulating a sleep disorder target. The method comprises administering an effective amount of a therapeutic compound to a subject, such that the sleep disorder target is modulated, wherein the therapeutic compound comprises the formula:

[CA]-(SP)n-[EG]

wherein CA is a moiety that modulates an active CNS target receptor or a collection of active CNS target receptors, EG is an ester group that modifies the half-life of the therapeutic compound, SP is a spacer molecule, and n is 0 or 1.

Another aspect of the invention is a method of modulating a sleep disorder target. The method comprises administering an effective amount of a therapeutic compound to a subject, such that the sleep disorder target is modulated, wherein the therapeutic compound comprises the formula:

[AD]-(SP)n-[EG]

wherein AD is a moiety that agonizes an adenosine receptor or a collection of adenosine receptors, EG is an ester group that modifies the half-life of the therapeutic compound, SP is a spacer molecule, and n is 0 or 1.

Another aspect of the invention is a method of modulating a sleep disorder target. The method comprises administering an effective amount of a therapeutic compound to a subject, such that the sleep disorder target is modulated, wherein the therapeutic compound comprises the formula:

[AH]-(SP)n-[DA]

wherein AH is a moiety that antagonizes a histamine receptor or a collection of histamine receptors, DA is a drug activity modulating moiety that provides the ability to modulate the activity of the therapeutic compound, e.g., ester or carboxylic acid, SP is a spacer molecule, and n is 0 or 1.

Another aspect of the invention is a method of modulating a sleep disorder target. The method comprises administering an effective amount of a therapeutic compound to a subject, such that the sleep disorder target is modulated, wherein the therapeutic compound comprises the formula:

[AH]-(SP)n-[EG]

wherein AH is a moiety that antagonizes a histamine receptor or a collection of histamine receptors, EG is an ester group that modifies the half-life of the therapeutic compound, SP is a spacer molecule, and n is 0 or 1.

One aspect of the invention is a Central Nervous System (CNS) disorder target modulator comprising the formula:

[CA]-(SP)n-[DA]

wherein CA is a moiety that modulates an active CNS target receptor or a collection of active CNS target receptors, DA is a drug activity modulating moiety that provides the ability to modulate the activity of the therapeutic compound, e.g., ester or carboxylic acid, SP is a spacer molecule, and n is 0 or 1.

Another aspect of the invention is a CNS disorder target modulator comprising the formula:

[CA]-(SP)n-[EG]

wherein CA is a moiety that modulates an active CNS target receptor or a collection of active CNS target receptors, EG is an ester group that modifies the half-life of the therapeutic compound, SP is a spacer molecule, and n is 0 or 1.

Another aspect of the invention is a sleep disorder target modulator comprising the formula:

[CA]-(SP)n-[EG]

wherein CA is a moiety that modulates an active CNS target receptor or a collection of active CNS target receptors, EG is an ester group that modifies the half-life of the therapeutic compound, SP is a spacer molecule, and n is 0 or 1.

In a another aspect of the invention a sleep disorder target modulator comprises the formula:

[AH]-(SP)n-[DA]

wherein AH is a moiety that antagonizes a histamine receptor, DA is a drug activity modulating moiety that provides the ability to modulate the activity of the therapeutic compound, e.g., ester or carboxylic acid, SP is a spacer molecule, and n is 0 or 1.

In a particular aspect of the invention a sleep disorder target modulator comprises the formula:

[AH]-(SP)n-[EG]

wherein AH is a moiety that antagonizes a histamine receptor, EG is an ester group that modifies the half-life of the therapeutic compound, SP is a spacer molecule, and n is 0 or 1.

Another aspect of the invention is a pharmaceutical composition comprising a therapeutic compound as prepared according to the methodology of this invention, and a pharmaceutically acceptable carrier.

In one aspect, the invention provides modified antihistamine compounds for modulating sleep, wherein the compound has the formula

[AH]-A wherein AH is an antihistamine moiety and A is a linker molecule comprising SP and Z, wherein SP comprises a spacer molecule and Z comprises a drug modulating moiety; wherein the spacer molecule has the structure

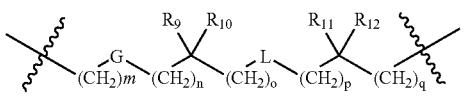

wherein m, n, o, p, q are, individually, an integer from zero to six; the $CH_2$ groups are optionally branched, and any member of the alkylene linker is substituted with one or more substituents; G and L are, individually, absent or O, S, C(O), SO or $SO_2$; $R_9$-$R_{12}$ are H, $C_1$-$C_5$ straight chain or branched alkyl (optionally containing a heteroatom); and substituents on nearby atoms are optionally connected to form a ring of size 3-7 or substituents on the same atom (i.e., geminal substituents) are connected to form a ring of size 3-7; wherein Z is $CO_2H$, $CONHS(O)_2$-Aryl, $CONHS(O)_2$-Alkyl, $CONHS(O)_2$-Heteroaryl, $SO_3H$, $SO_2H$, $S(O)_2$NHCO-alkyl, $S(O)_2$NHCO-aryl, $S(O)$NHCO-alkyl, $S(O)$NHCO-aryl, $P(O)(OH)_2$, $P(O)OH$,

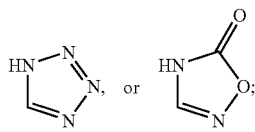

and the compound has one or more of the following characteristics: ((i) an inhibition constant ($K_i$) with regard to H1 receptor binding of less than 500 nM; (ii) a $K_i$ with regard to off target binding to an off target selected from the group consisting of M1, M2, M3, D1, D2, D3, α1 and α2 that is more than 10 times greater than the $K_i$ with regard to the H1 receptor; (iii) a nonREM peak time value that is greater than 55% nonREM sleep per hour by the third hour after said compound is administered to a subject; (iv) a cumulative total increase in nonREM sleep not less than 20 minutes for compound doses that produce maximum sleep consolidation; (v) a longest sleep bout that is greater than 13 minutes in duration; (vi) net longest sleep bout post treatment is greater than or equal to 3 minutes when adjusted using a baseline value obtained at least 24 hours prior to administration of said compound to a subject; (vii) an average sleep bout that is greater than 5 minutes at absolute peak; (viii) administration of said compound to a subject does not produce appreciable amounts of rebound insomnia; (ix) administration of said compound to a subject does not appreciably inhibit REM sleep; and (x) and administration of said compound to a subject does not disproportionately inhibit locomotor activity relative to the normal effects of sleep.

In one embodiment, the compound has one or more of the following characteristics: (i) an inhibition constant ($K_i$) with regard to H1 receptor binding of less than 150 nM; (ii) a $K_i$ with regard to off target binding to an off target selected from the group consisting of M1, M2, and M3, that is greater than 10 μM; (iii) a nonREM peak time value that is greater than 55% nonREM sleep per hour by the third hour after said compound is administered to a subject; (iv) a cumulative total increase in nonREM sleep not less than 20 minutes for compound doses that produce maximum sleep consolidation; (v) a longest sleep bout that is greater than 17 minutes in duration; (vi) net longest sleep bout post treatment is greater than or equal to 5 minutes when adjusted using a baseline value obtained at least 24 hours prior to administration of said compound to a subject; (vii) an average sleep bout that is greater than 6 minutes at absolute peak; (viii) administration of said compound to a subject does not produce appreciable amounts of rebound insomnia; (ix) administration of said compound to a subject does not appreciably inhibit REM sleep; and (x) administration of said compound to a subject does not disproportionately inhibit locomotor activity or motor tone relative to the normal effects of sleep.

In another embodiment, the spacer molecule has the structure

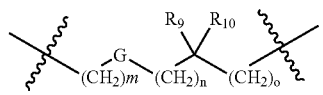

wherein m, n, and o, are, individually, an integer from zero to six, and the $CH_2$ groups in the linker are optionally branched; G is absent or O, S, C(O), SO or $SO_2$; $R_9$-$R_{10}$ are H, $C_1$-$C_5$ straight chain or branched alkyl (optionally containing a heteroatom), and/or are connected to form a ring of size 3-7; and Z is $CO_2H$, $CONHS(O)_2$-Aryl, $CONHS(O)_2$-Alkyl, or

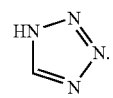

In one embodiment, the spacer molecule has the structure

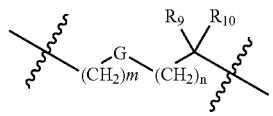

wherein m and n are, individually, an integer from zero to four, and the $CH_2$ moieties are optionally branched; G is absent or O, S, C(O), SO or $SO_2$; $R_9$-$R_{10}$ are H, $C_1$-$C_3$ alky, optionally with heteroatom substitution, branching and/or connected to form a ring of size 3-5 and Z is $CO_2H$, $CONHS(O)_2$-Aryl, $CONHS(O)_2$-Alkyl, or

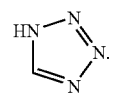

In one embodiment, the spacer molecule has the structure

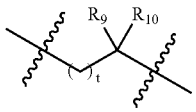

wherein t is an integer from 0 to 6; $R_9$-$R_{10}$ are H, $CH_3$ or $CH_2CH_3$, and are optionally connected to form a spiro ring of size 3 to 6; and wherein further Z is $CO_2H$ or

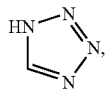

provided that t is not zero when Z is $CO_2H$.

In another aspect, the invention relates to modified antihistamine compounds for modulating sleep wherein the compound is

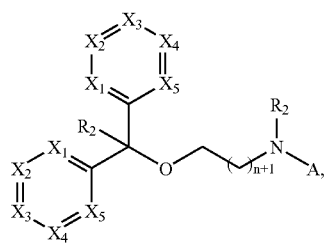

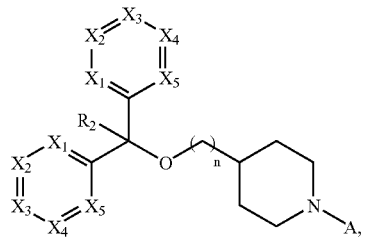

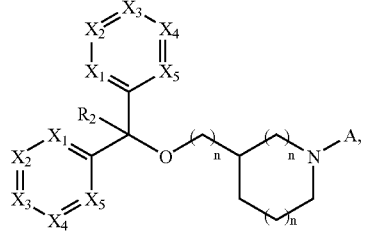

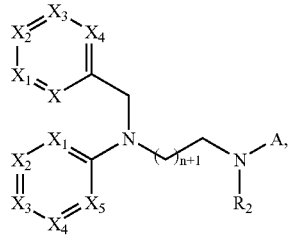

-continued

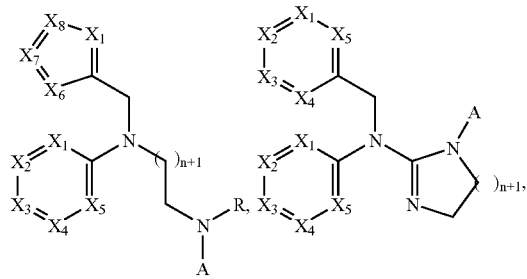

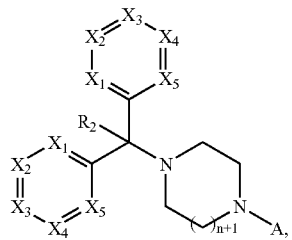

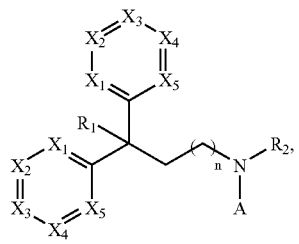

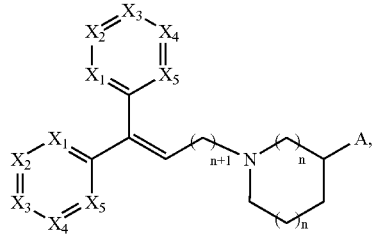

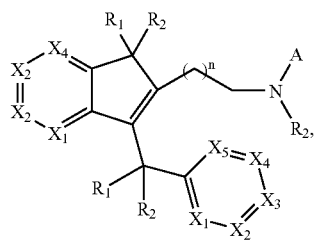

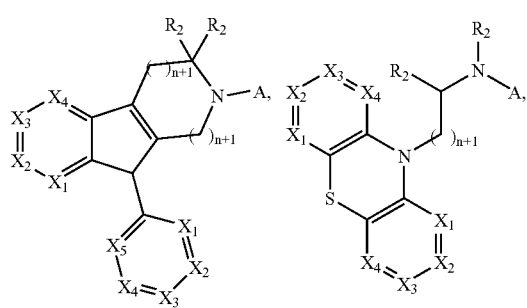

-continued
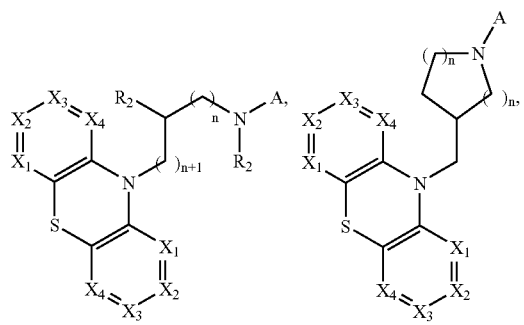
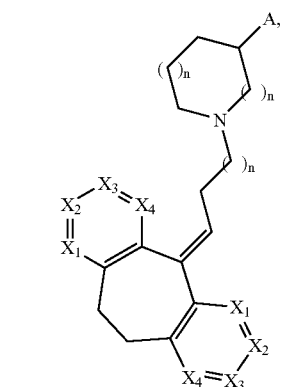
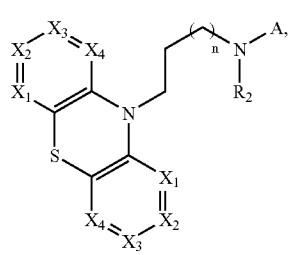
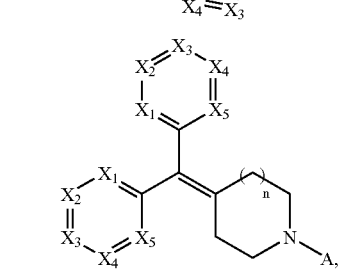
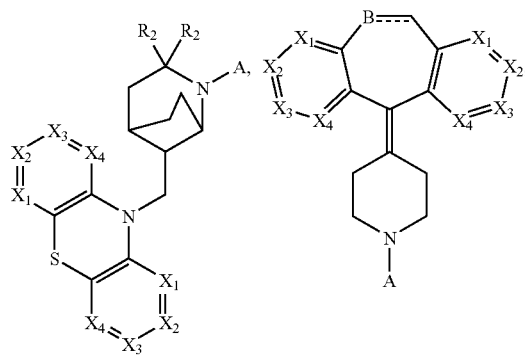
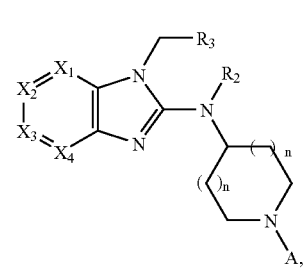
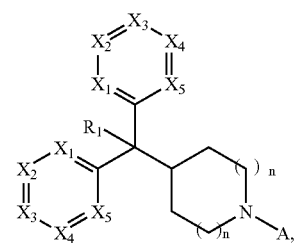
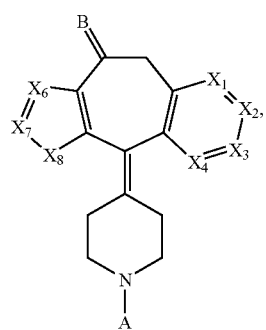
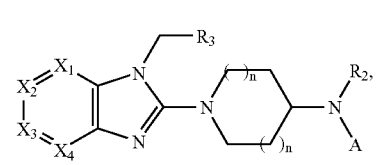
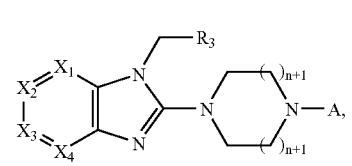
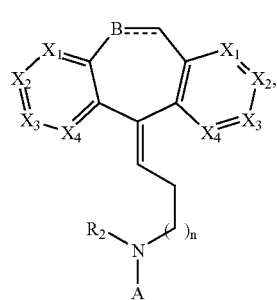
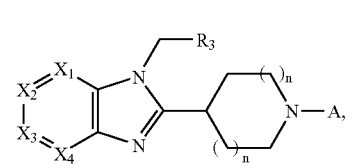

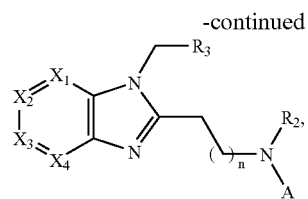
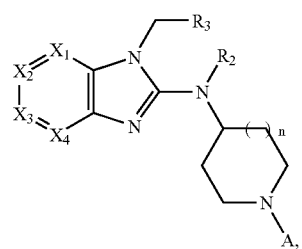
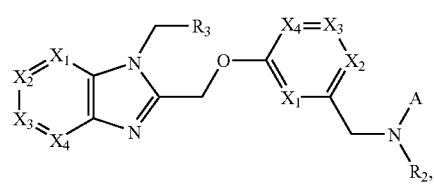
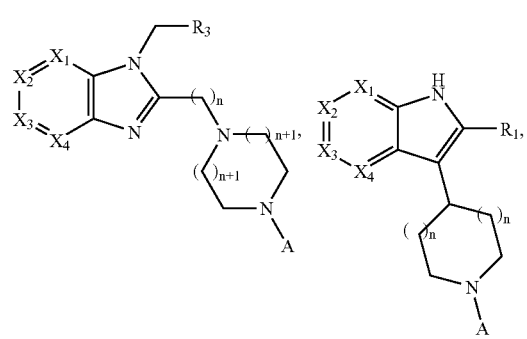
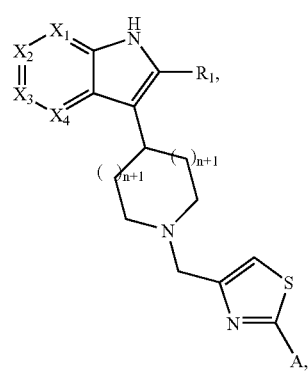
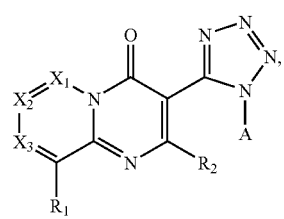
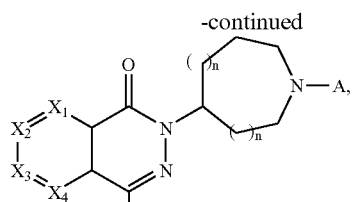
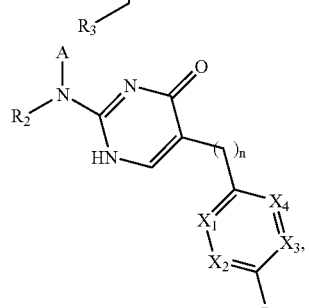
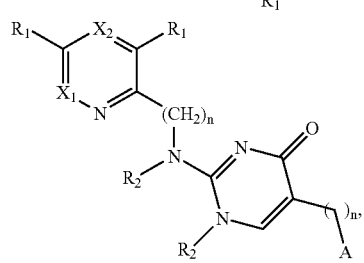
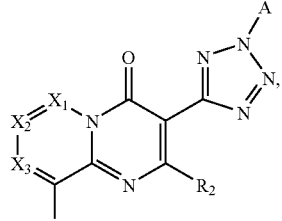
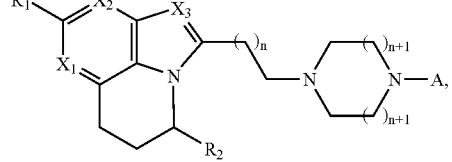
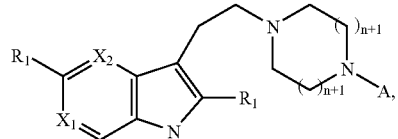
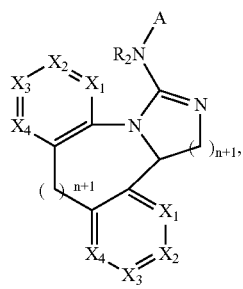

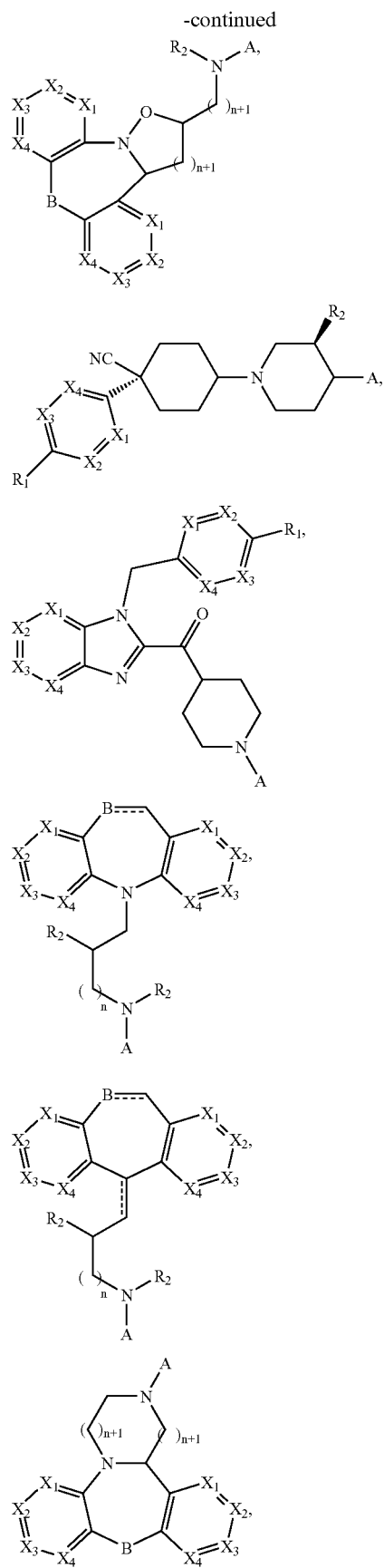
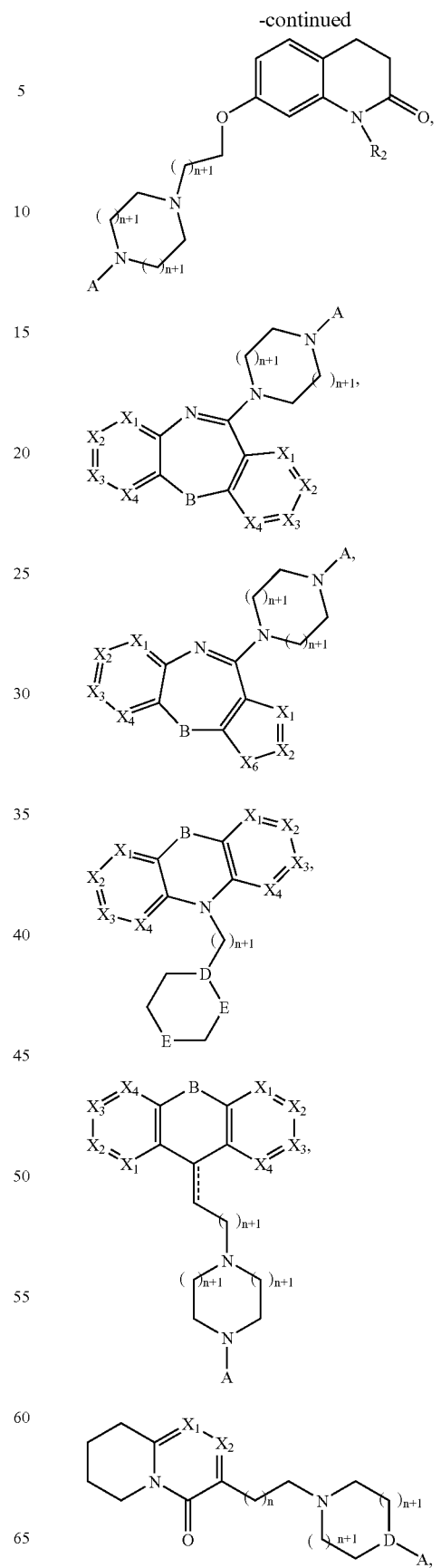

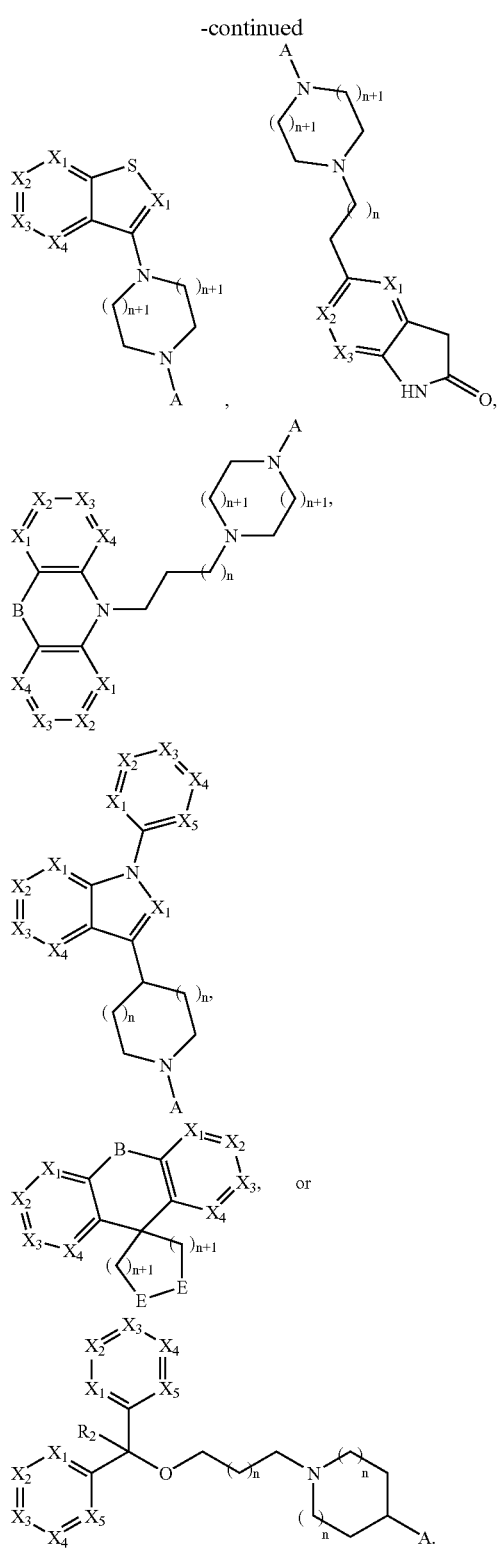

wherein $X_1$-$X_5$ are, independently, CR or N, wherein R is H, lower alkyl, fluoroalkyl (e.g., $CF_3$), F, Cl, Br, lower alkoxy, thioalkyl, lower alkoxyalkyl, fluoroalkoxy, alkylcarboxyl, or alkylcarboxyl ester, and where the $X_n$ of one aryl ring is the same or different from the corresponding $X_n$ of another aryl ring; $X_6$-$X_8$ is N, S, Se, O or CR, wherein R is H, lower alkyl, fluoroalkyl, F, Cl, Br, lower alkyloxy, thioalkyl, lower alkoxyalkyl, fluoroalkoxy, alkylcarboxyl, alkylcarboxyl ester; $R_1$ is H, OH, lower alkyl, or lower alkyloxy; $R_2$ is H or lower alkyl; $R_3$ is H, alkyl, alkyloxy, or alkylaryl; wherein each $R_1$, $R_2$, $R_3$ are the same or different when multiply attached to a structure; B is NR, S, O, $CH_2$ when double bond is absent, or CR when a double bond is present; n is an integer from 0 to 4 and is the same or different when present more than once in a structure; D is CH or N; E is $CH_2$ or N-A, provided that one E in each formula is N-A; and A is a linker molecule comprising SP and Z, wherein SP comprises a spacer molecule and Z comprises a drug modulating moiety; wherein the spacer has the structure

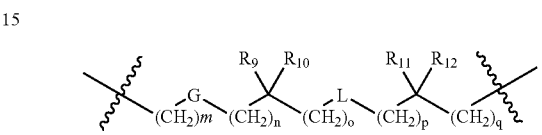

wherein m, n, o, p, q are, individually, an integer from zero to six; the $CH_2$ groups are optionally branched, and any member of the alkylene linker is substituted with one or more substituents; G and L are, individually, absent or O, S, C(O), SO or $SO_2$; $R_9$-$R_{12}$ are H, $C_1$-$C_5$ straight chain or branched alkyl (optionally containing a heteroatom); and substituents on nearby atoms are optionally connected to form a ring of size 3-7 or substituents on the same atom (i.e., geminal substituents) are connected to form a ring of size 3-7; wherein Z is $CO_2H$, $CONHS(O)_2$-Aryl, $CONHS(O)_2$-Alkyl, $CONHS(O)_2$-Heteroaryl, $SO_3H$, $SO_2H$, $S(O)_2$NHCO-alkyl, $S(O)_2$NHCO-aryl, S(O)NHCO-alkyl, S(O)NHCO-aryl, $P(O)(OH)_2$, P(O)OH,

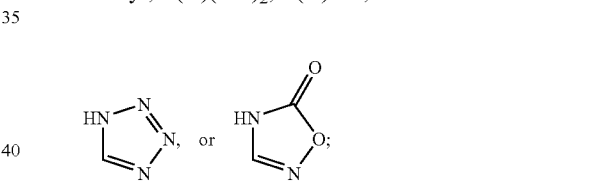

and the compound has one or more of the following characteristics: ((i) an inhibition constant ($K_i$) with regard to H1 receptor binding of less than 500 nM; (ii) a $K_i$ with regard to off target binding to an off target selected from the group consisting of M1, M2, M3, D1, D2, D3, α1 and α2 that is more than 10 times greater than the $K_i$ with regard to the H1 receptor; (iii) a nonREM peak time value that is greater than 55% nonREM sleep per hour by the third hour after said compound is administered to a subject; (iv) a cumulative total increase in nonREM sleep not less than 20 minutes for compound doses that produce maximum sleep consolidation; (v) a longest sleep bout that is greater than 13 minutes in duration; (vi) net longest sleep bout post treatment is greater than or equal to 3 minutes when adjusted using a baseline value obtained at least 24 hours prior to administration of said compound to a subject; (vii) an average sleep bout that is greater than 5 minutes at absolute peak; (viii) administration of said compound to a subject does not produce appreciable amounts of rebound insomnia; (ix) administration of said compound to a subject does not appreciably inhibit REM sleep; and (x) and administration of said compound to a subject does not disproportionately inhibit locomotor activity relative to the normal effects of sleep.

In one embodiment, the compound has one or more of the following characteristics: (i) an inhibition constant ($K_i$) with regard to H1 receptor binding of less than 150 nM; (ii) a $K_i$ with regard to off target binding to an off target selected from the group consisting of M1, M2, and M3, that is greater than 10 μM; (iii) a nonREM peak time value that is greater than 55% nonREM sleep per hour by the third hour after said compound is administered to a subject; (iv) a cumulative total increase in nonREM sleep not less than 20 minutes for compound doses that produce maximum sleep consolidation; (v) a longest sleep bout that is greater than 17 minutes in duration; (vi) net longest sleep bout post treatment is greater than or equal to 5 minutes when adjusted using a baseline value obtained at least 24 hours prior to administration of said compound to a subject; (vii) an average sleep bout that is greater than 6 minutes at absolute peak; (viii) administration of said compound to a subject does not produce appreciable amounts of rebound insomnia; (ix) administration of said compound to a subject does not appreciably inhibit REM sleep; and (x) administration of said compound to a subject does not disproportionately inhibit locomotor activity or motor tone relative to the normal effects of sleep.

In another embodiment, the spacer molecule has the structure

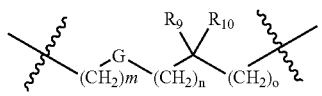

wherein m, n, and o, are, individually, an integer from zero to six, and the $CH_2$ groups in the linker are optionally branched; G is absent or O, S, C(O), SO or $SO_2$; $R_9$-$R_{10}$ are H, $C_1$-$C_5$ straight chain or branched alkyl (optionally containing a heteroatom), and/or are connected to form a ring of size 3-7; and Z is $CO_2H$, $CONHS(O)_2$-Aryl, $CONHS(O)_2$-Alkyl, or

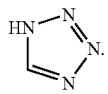

In one embodiment, the spacer molecule has the structure

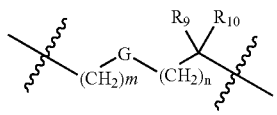

wherein m and n are, individually, an integer from zero to four, and the $CH_2$ moieties are optionally branched; G is absent or O, S, C(O), SO or $SO_2$; $R_9$-$R_{10}$ are H, $C_1$-$C_3$ alkyl, optionally with heteroatom substitution, branching and/or connected to form a ring of size 3-5 and Z is $CO_2H$, $CONHS(O)_2$-Aryl, $CONHS(O)_2$-Alkyl, or

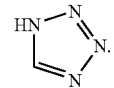

In another embodiment, the spacer molecule has the structure

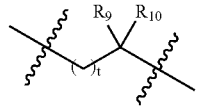

wherein t is an integer from 0 to 6; $R_9$-$R_{10}$ are H, $CH_3$ or $CH_2CH_3$, and are optionally connected to form a Spiro ring of size 3 to 6; and wherein further Z is $CO_2H$ or

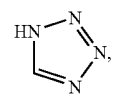

provided that t is not zero when Z is $CO_2H$.

In another aspect, the invention relates to modified antihistamine compounds for modulating sleep, wherein the compound is

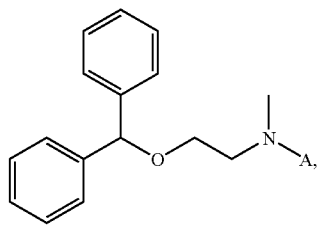

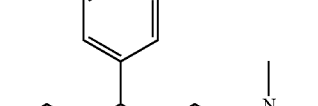

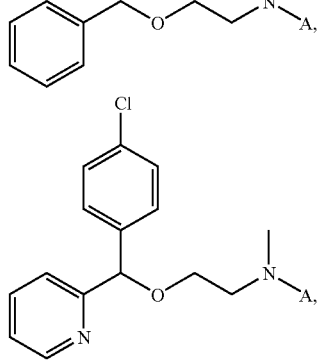

-continued
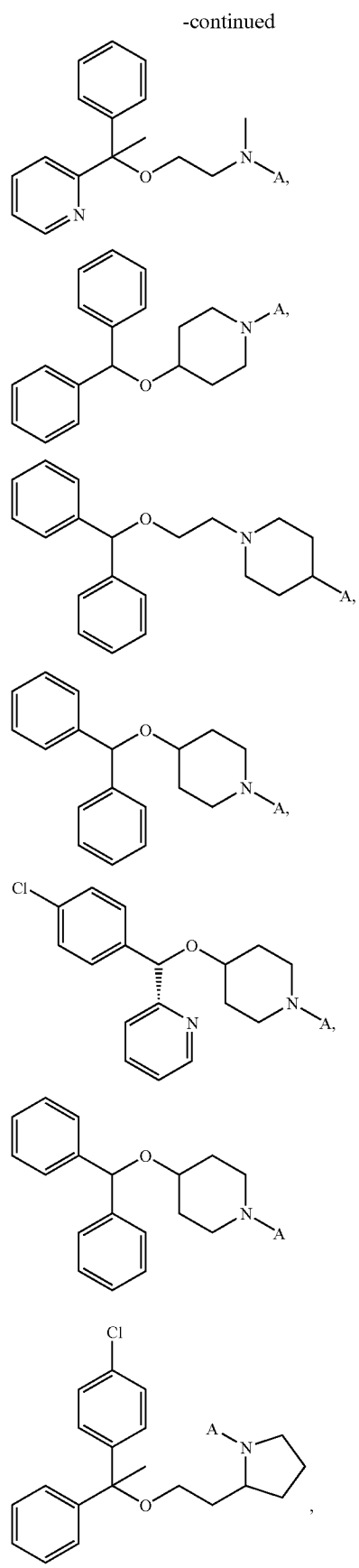
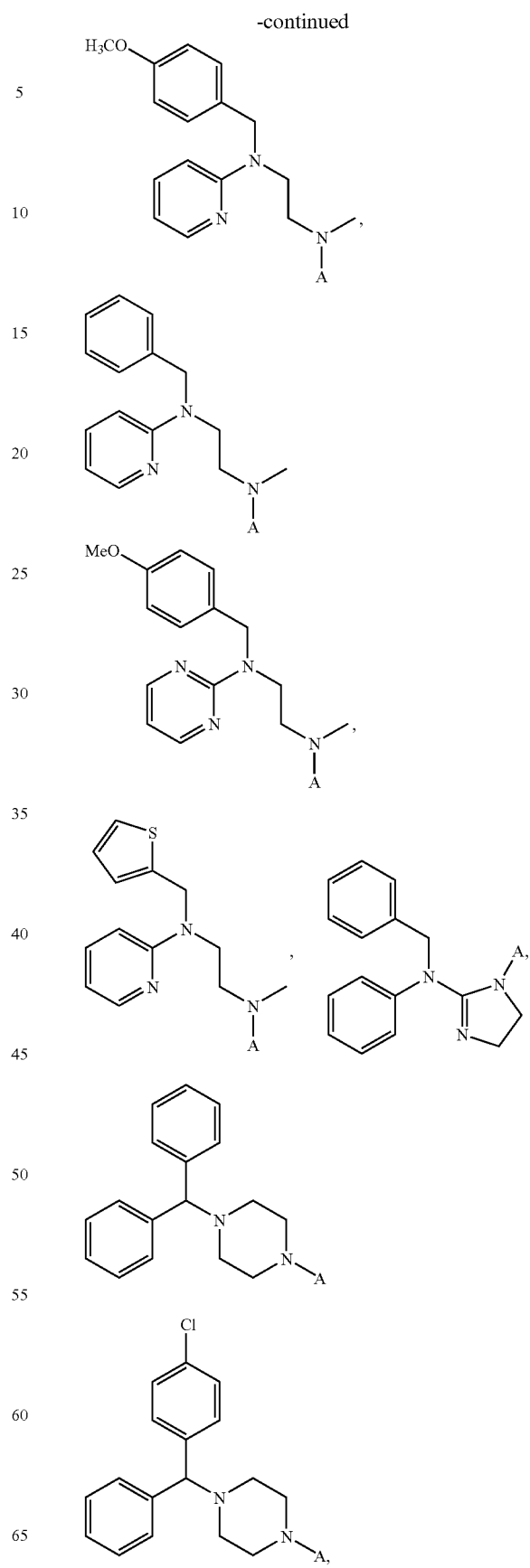

-continued
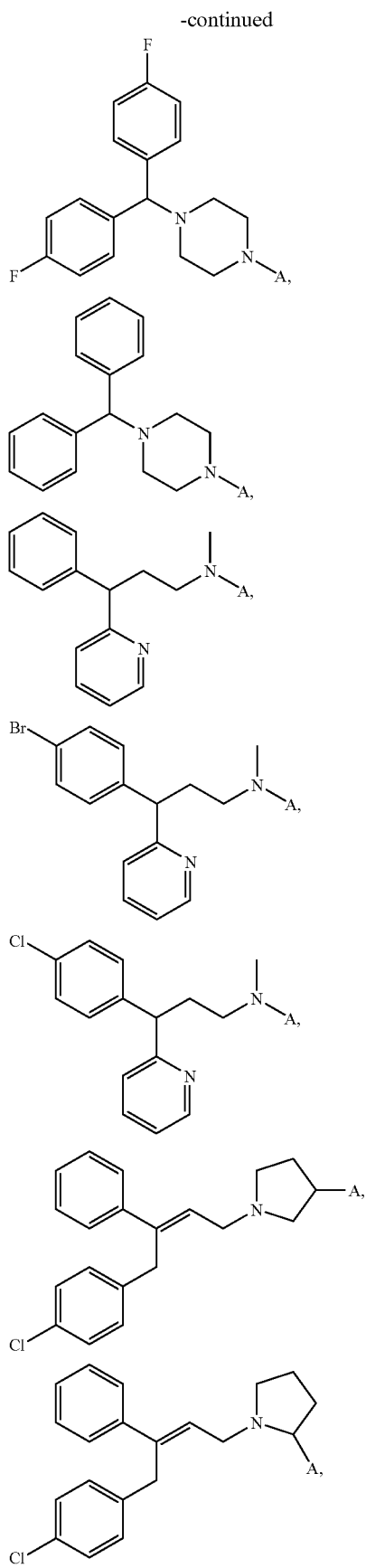
-continued
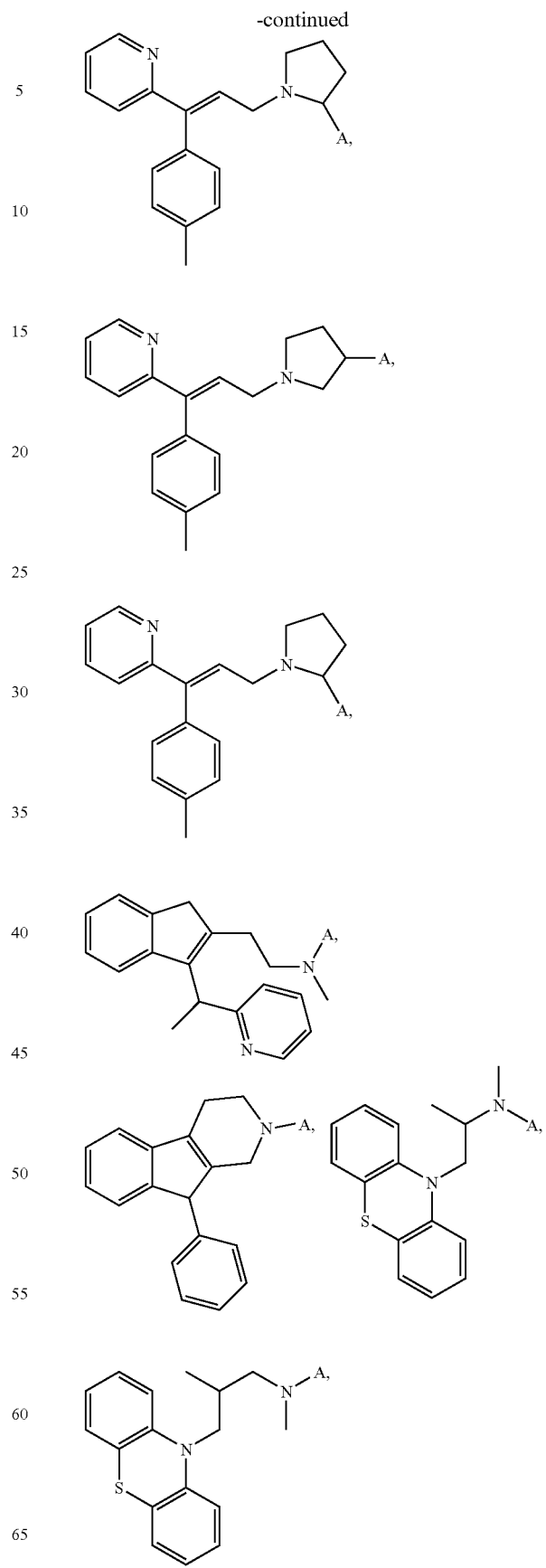

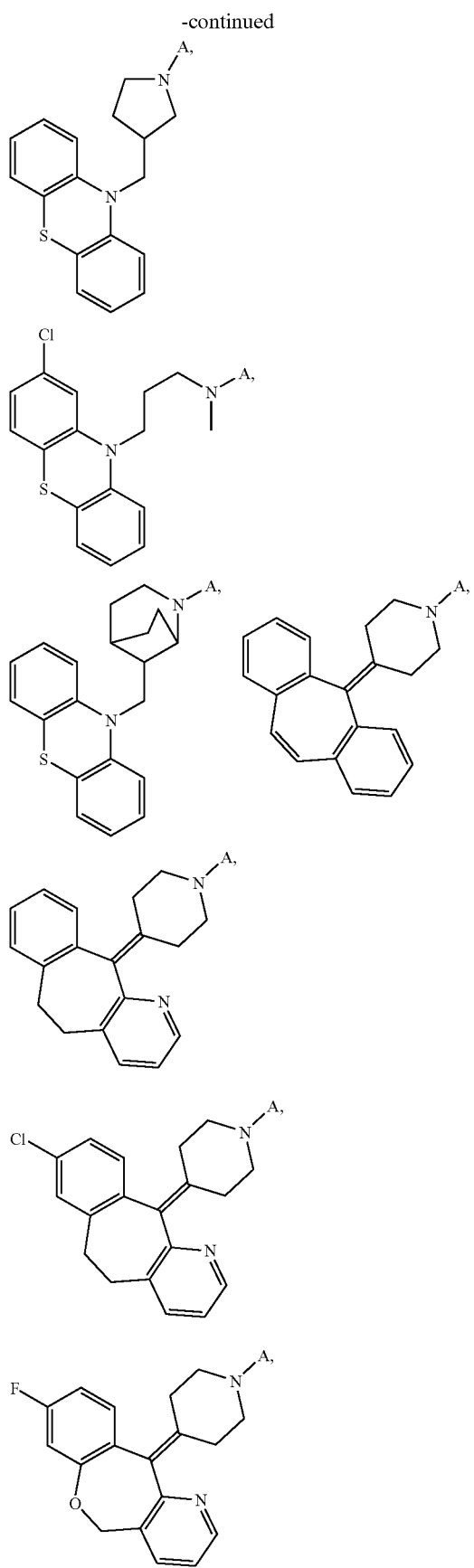
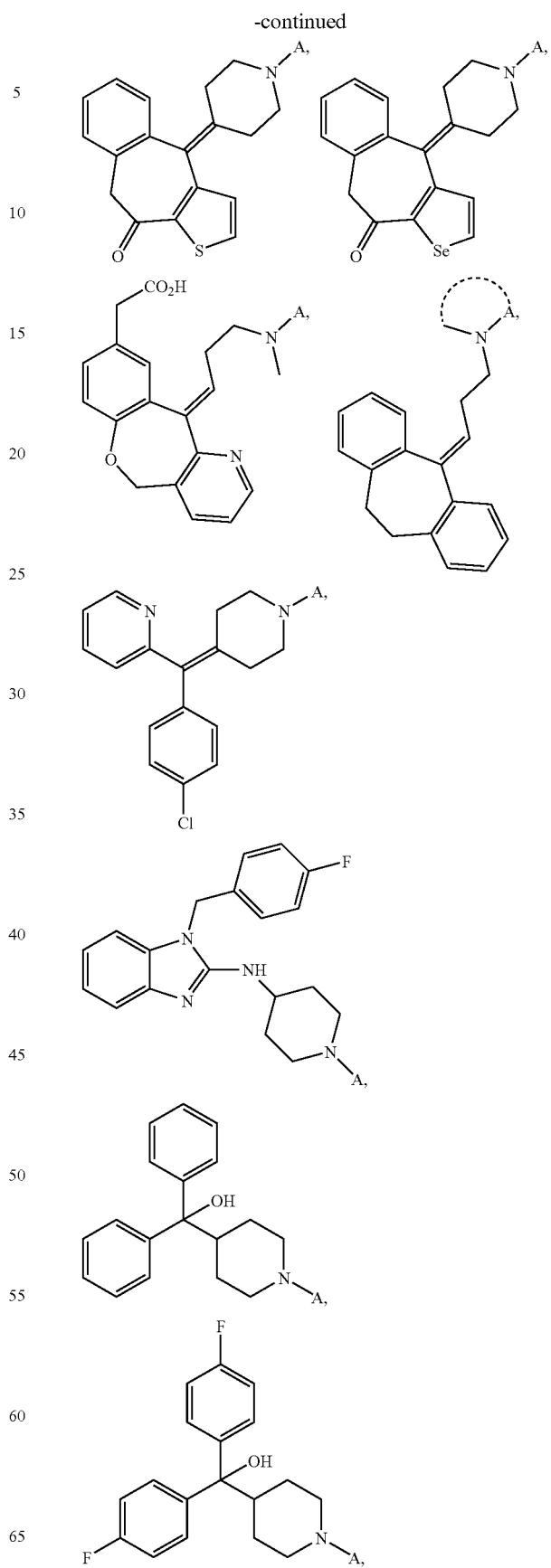

-continued
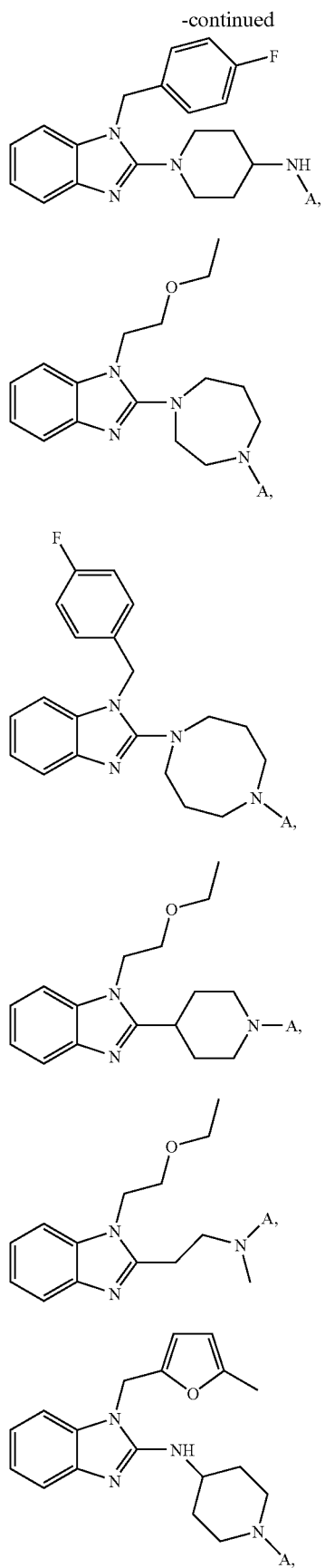
-continued
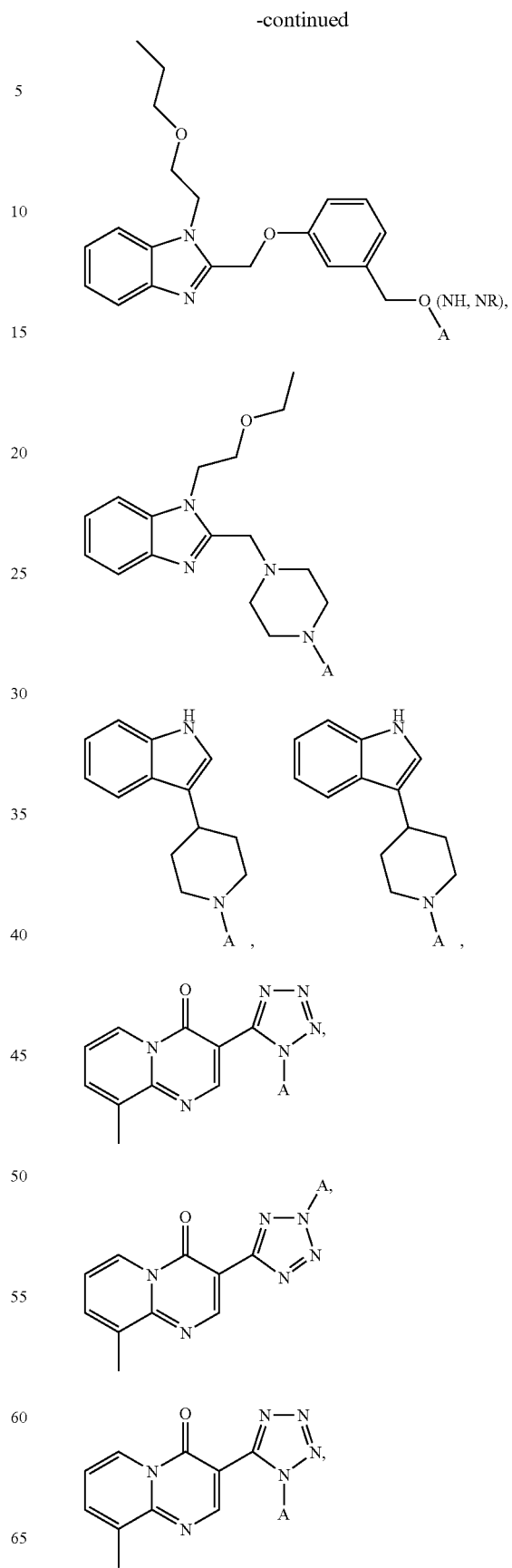

-continued
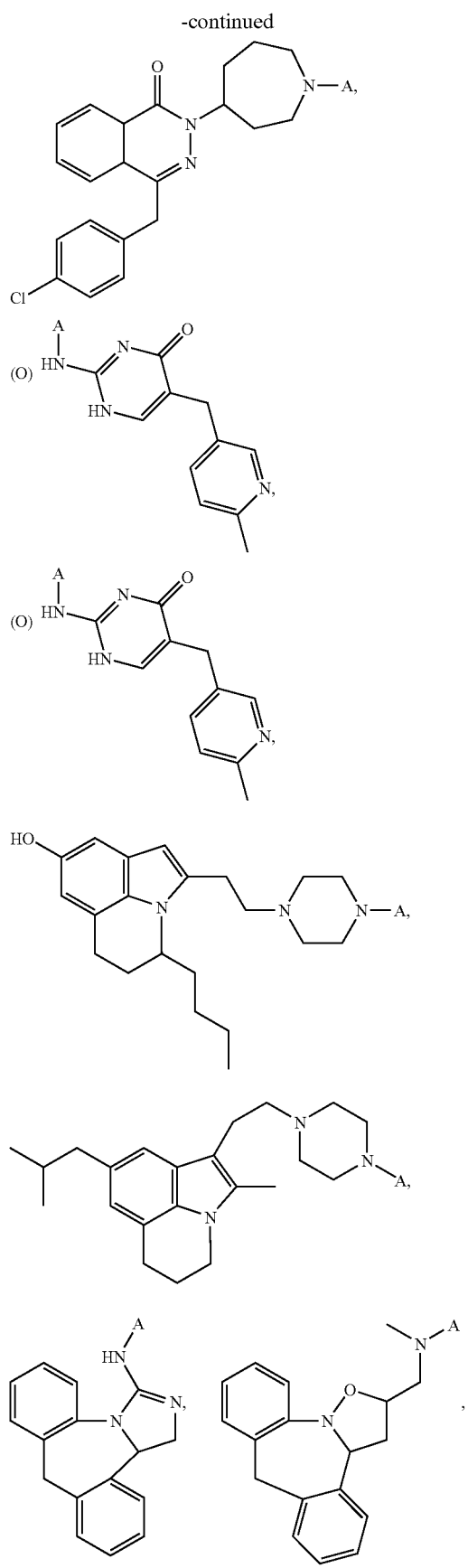
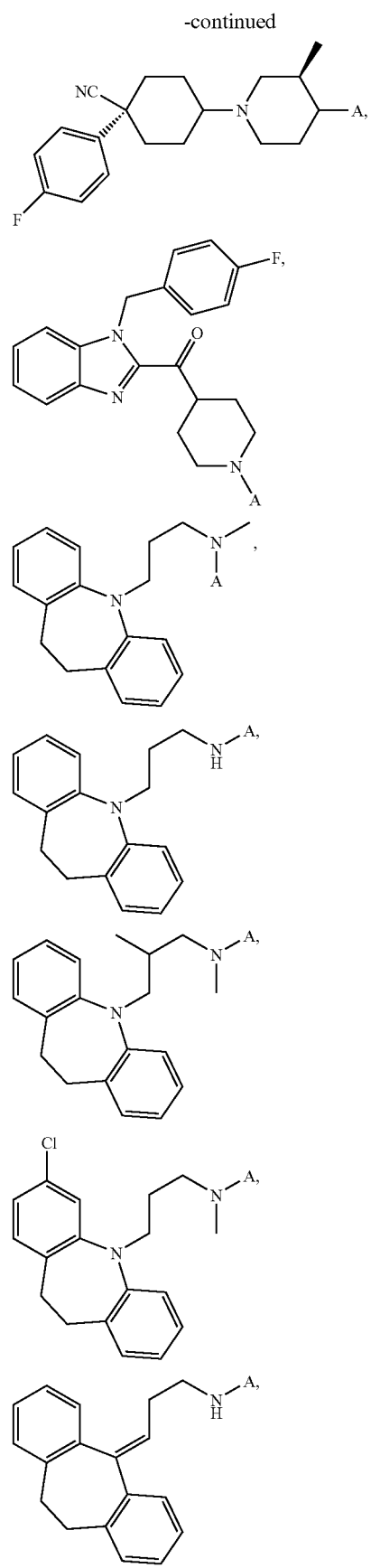

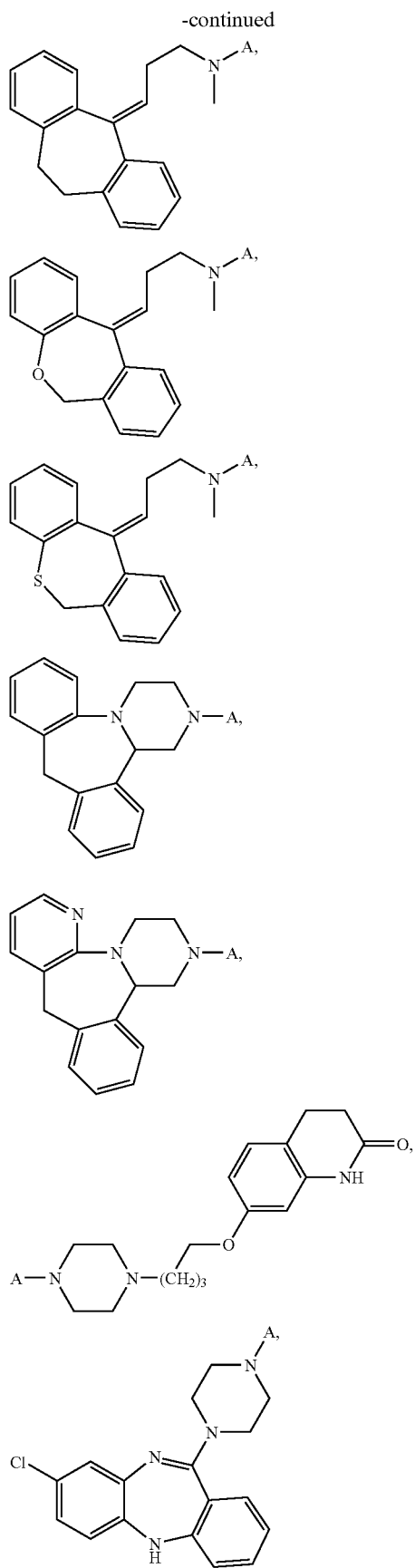
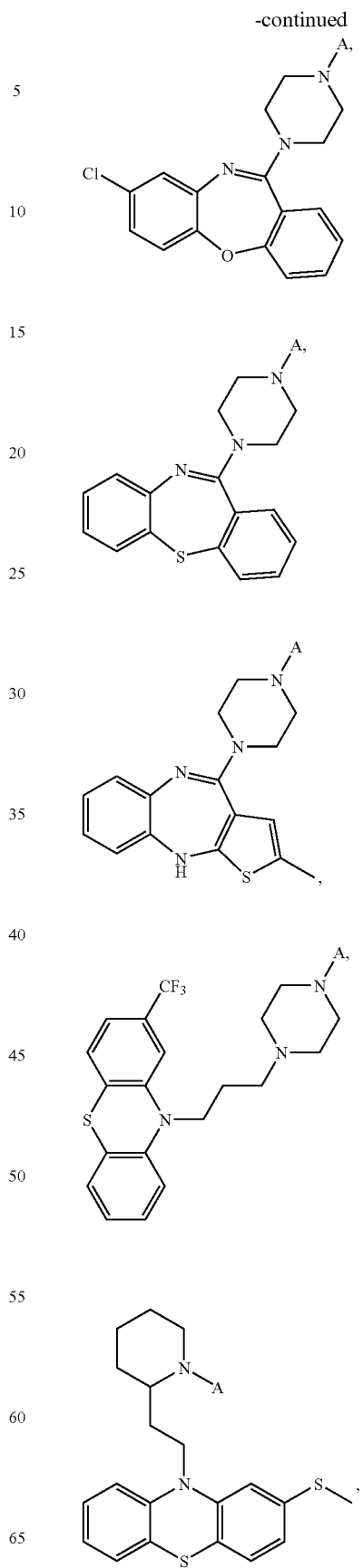

-continued

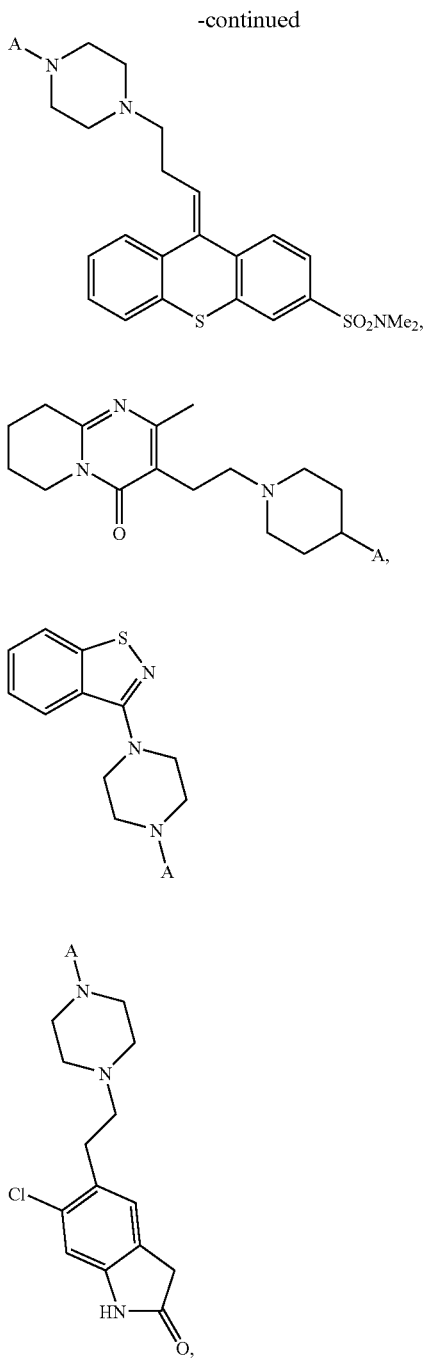

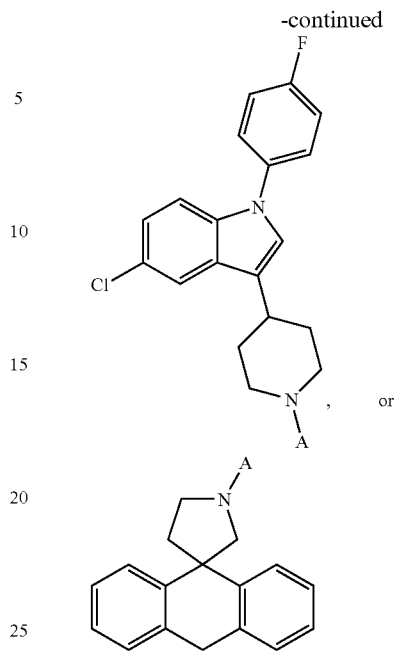

, or

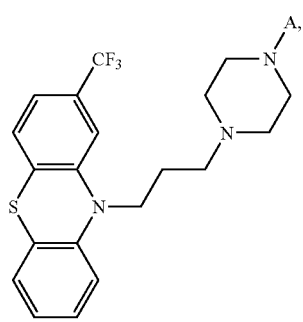

wherein A is a linker molecule comprising SP and Z, wherein SP comprises a spacer molecule and Z comprises a drug modulating moiety; wherein the spacer has the structure

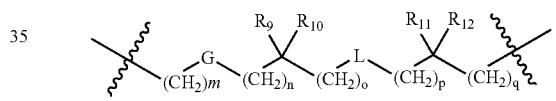

wherein m, n, o, p, q are, individually, an integer from zero to six; the $CH_2$ groups are optionally branched, and any member of the alkylene linker is substituted with one or more substituents; G and L are, individually, absent or O, S, C(O), SO or $SO_2$; $R_9$-$R_{12}$ are H, $C_1$-$C_5$ straight chain or branched alkyl (optionally containing a heteroatom); and substituents on nearby atoms are optionally connected to form a ring of size 3-7 or substituents on the same atom (i.e., geminal substituents) are connected to form a ring of size 3-7; wherein Z is $CO_2H$, $CONHS(O)_2$-Aryl, $CONHS(O)_2$-Alkyl, $CONHS(O)_2$-Heteroaryl, $SO_3H$, $SO_2H$, $S(O)_2$NHCO-alkyl, $S(O)_2$NHCO-aryl, S(O)NHCO-alkyl, S(O)NHCO-aryl, $P(O)(OH)_2$, P(O)OH,

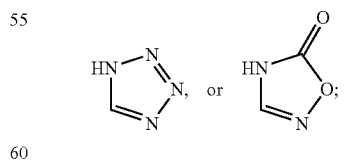

, or and the compound has one or more of the following characteristics: (i) an inhibition constant ($K_i$) with regard to H1 receptor binding of less than 500 nM; (ii) a $K_i$ with regard to off target binding to an off target selected from the group consisting of M1, M2, M3, D1, D2, D3, α1 and α2 that is more than 10 times greater than the $K_i$ with regard to the H1 receptor; (iii) a nonREM peak time value that is greater than 55% nonREM sleep per hour by the third hour after said compound is administered to a subject; (iv) a cumulative total increase in nonREM sleep not less than 20 minutes for compound doses that produce maximum sleep consolidation; (v) a longest sleep bout that is greater than 13 minutes in duration; (vi) net longest sleep bout post treatment is greater than or equal to 3 minutes when adjusted using a baseline value obtained at least 24 hours prior to administration of said compound to a subject; (vii) an average sleep bout that is greater than 5 minutes at absolute peak; (viii) administration of said compound to a subject does not produce appreciable amounts of rebound insomnia; (ix) administration of said compound to a subject does not appreciably inhibit REM sleep; and (x) and administration of said compound to a subject does not disproportionately inhibit locomotor activity relative to the normal effects of sleep.

In one embodiment, the compound has one or more of the following characteristics: (i) an inhibition constant ($K_i$) with regard to H1 receptor binding of less than 150 nM; (ii) a $K_i$ with regard to off target binding to an off target selected from the group consisting of M1, M2, and M3, that is greater than 10 μM; (iii) a nonREM peak time value that is greater than 55% nonREM sleep per hour by the third hour after said compound is administered to a subject; (iv) a cumulative total increase in nonREM sleep not less than 20 minutes for compound doses that produce maximum sleep consolidation; (v) a longest sleep bout that is greater than 17 minutes in duration; (vi) net longest sleep bout post treatment is greater than or equal to 5 minutes when adjusted using a baseline value obtained at least 24 hours prior to administration of said compound to a subject; (vii) an average sleep bout that is greater than 6 minutes at absolute peak; (viii) administration of said compound to a subject does not produce appreciable amounts of rebound insomnia; (ix) administration of said compound to a subject does not appreciably inhibit REM sleep; and (x) administration of said compound to a subject does not disproportionately inhibit locomotor activity or motor tone relative to the normal effects of sleep.

In another embodiment, the spacer molecule has the structure

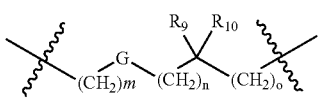

wherein m n, and o, are, individually, an integer from zero to six, and the $CH_2$ groups in the linker are optionally branched; G is absent or O, S, C(O), SO or $SO_2$; $R_9$-$R_{10}$ are H, $C_1$-$C_5$ straight chain or branched alkyl (optionally containing a heteroatom), and/or are connected to form a ring of size 3-7; and Z is $CO_2H$, $CONHS(O)_2$-Aryl, $CONHS(O)_2$-Alkyl, or

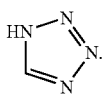

In one embodiment, the spacer molecule has the structure

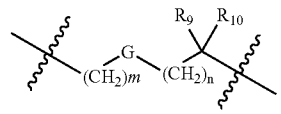

wherein m and n are, individually, an integer from zero to four, and the $CH_2$ moieties are optionally branched; G is absent or O, S, C(O), SO or $SO_2$; $R_9$-$R_{10}$ are H, $C_1$-$C_3$ alkyl, optionally with heteroatom substitution, branching and/or connected to form a ring of size 3-5 and Z is $CO_2H$, $CONHS(O)_2$-Aryl, $CONHS(O)_2$-Alkyl, or

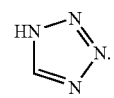

In another embodiment, the spacer molecule has the structure

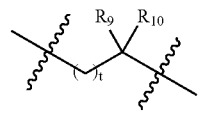

wherein t is an integer from 0 to 6; $R_9$-$R_{10}$ are H, $CH_3$ or $CH_2CH_3$, and are optionally connected to form a Spiro ring of size 3 to 6; and Z is $CO_2H$ or

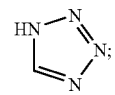

provided that t is not zero when Z is $CO_2H$.

In one aspect, the invention relates to a modified antihistamine compound for modulating sleep, wherein the compound is

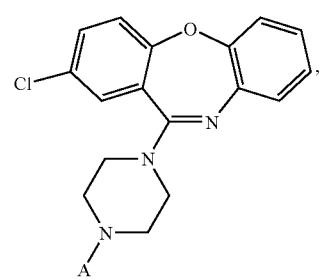

-continued

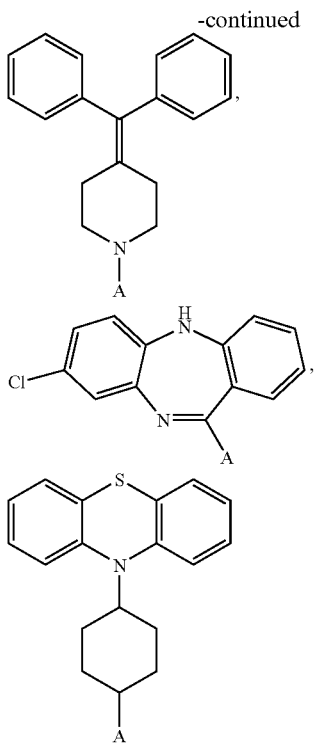

wherein A is a linker molecule comprising SP and Z, wherein SP comprises a spacer molecule and Z comprises a drug modulating moiety; wherein the spacer has the structure

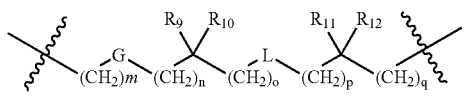

wherein m, n, o, p, q are, individually, an integer from zero to six; the $CH_2$ groups are optionally branched, and any member of the alkylene linker is substituted with one or more substituents; G and L are, individually, absent or O, S, C(O), SO or $SO_2$; $R_9$-$R_{12}$ are H, $C_1$-$C_5$ straight chain or branched alkyl (optionally containing a heteroatom); and substituents on nearby atoms are optionally connected to form a ring of size 3-7 or substituents on the same atom (i.e., geminal substituents) are connected to form a ring of size 3-7; wherein Z is $CO_2H$, $CONHS(O)_2$-Aryl, $CONHS(O)_2$-Alkyl, $CONHS(O)_2$-Heteroaryl, $SO_3H$, $SO_2H$, $S(O)_2$NHCO-alkyl, $S(O)_2$NHCO-aryl, $S(O)$NHCO-alkyl, $S(O)$NHCO-aryl, $P(O)(OH)_2$, $P(O)OH$,

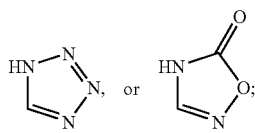

and the compound has one or more of the following characteristics: (i) an inhibition constant ($K_i$) with regard to H1 receptor binding of less than 500 nM; (ii) a $K_i$ with regard to off target binding to an off target selected from the group consisting of M1, M2, M3, D1, D2, D3, α1 and α2 that is more than 10 times greater than the $K_i$ with regard to the H1 receptor; (iii) a nonREM peak time value that is greater than 55% nonREM sleep per hour by the third hour after said compound is administered to a subject; (iv) a cumulative total increase in nonREM sleep not less than 20 minutes for compound doses that produce maximum sleep consolidation; (v) a longest sleep bout that is greater than 13 minutes in duration; (vi) net longest sleep bout post treatment is greater than or equal to 3 minutes when adjusted using a baseline value obtained at least 24 hours prior to administration of said compound to a subject; (vii) an average sleep bout that is greater than 5 minutes at absolute peak; (viii) administration of said compound to a subject does not produce appreciable amounts of rebound insomnia; (ix) administration of said compound to a subject does not appreciably inhibit REM sleep; and (x) and administration of said compound to a subject does not disproportionately inhibit locomotor activity relative to the normal effects of sleep.

In one embodiment, the compound has one or more of the following characteristics: (i) an inhibition constant ($K_i$) with regard to H1 receptor binding of less than 150 nM; (ii) a $K_i$ with regard to off target binding to an off target selected from the group consisting of M1, M2, and M3, that is greater than 10 μM; (iii) a nonREM peak time value that is greater than 55% nonREM sleep per hour by the third hour after said compound is administered to a subject; (iv) a cumulative total increase in nonREM sleep not less than 20 minutes for compound doses that produce maximum sleep consolidation; (v) a longest sleep bout that is greater than 17 minutes in duration; (vi) net longest sleep bout post treatment is greater than or equal to 5 minutes when adjusted using a baseline value obtained at least 24 hours prior to administration of said compound to a subject; (vii) an average sleep bout that is greater than 6 minutes at absolute peak; (viii) administration of said compound to a subject does not produce appreciable amounts of rebound insomnia; (ix) administration of said compound to a subject does not appreciably inhibit REM sleep; and (x) administration of said compound to a subject does not disproportionately inhibit locomotor activity or motor tone relative to the normal effects of sleep.

In another embodiment, the spacer molecule has the structure

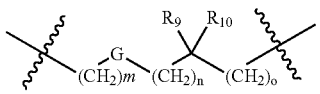

wherein m, n, and o, are, individually, an integer from zero to six, and the $CH_2$ groups in the linker are optionally branched; G is absent or O, S, C(O), SO or $SO_2$; $R_9$-$R_{10}$ are H, $C_1$-$C_5$ straight chain or branched alkyl (optionally containing a heteroatom), and/or are connected to form a ring of size 3-7; and Z is $CO_2H$, $CONHS(O)_2$-Aryl, $CONHS(O)_2$-Alkyl, or

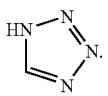

In one embodiment, the spacer molecule has the structure

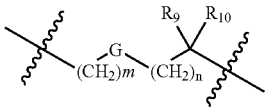

wherein m and n are, individually, an integer from zero to four, and the $CH_2$ moieties are optionally branched; G is absent or O, S, C(O), SO or $SO_2$; $R_9$-$R_{10}$ are H, $C_1$-$C_3$ alkyl, optionally with heteroatom substitution, branching and/or connected to form a ring of size 3-5 and Z is $CO_2H$, $CONHS(O)_2$-Aryl, $CONHS(O)_2$-Alkyl, or

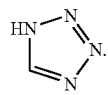

In another embodiment, the spacer molecule has the structure

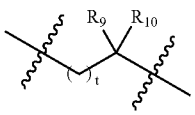

wherein t is an integer from 0 to 6; $R_9$-$R_{10}$ are H, $CH_3$ and $CH_2CH_3$, and are optionally connected to form a spiro ring of size 3 to 6; and Z is $CO_2H$ or

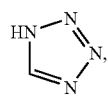

provided that t is not zero when Z is $CO_2H$.20.

In one embodiment, the modified antihistamine compound is selected from the group consisting of

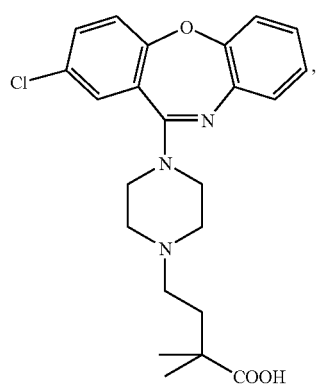

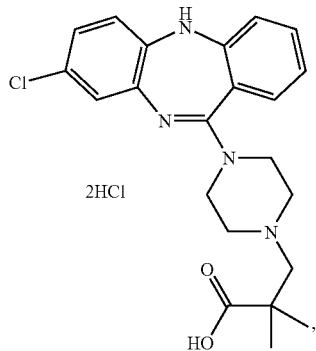

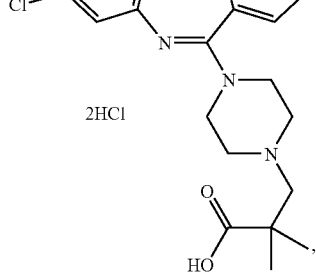

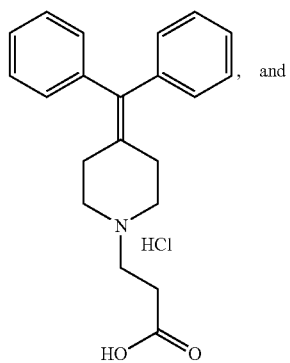

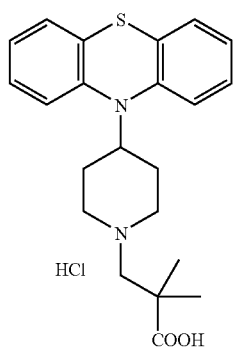

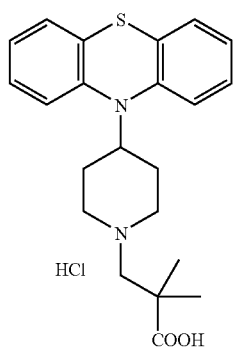

In another aspect, the invention relates to a method of modulating sleep in a subject, by administering a therapeutically effective amount of a modified antihistamine with the formula

[AH]-A wherein AH is an antihistamine moiety and A is a linker molecule comprising SP and Z, wherein SP comprises a spacer molecule and Z comprises a drug modulating moiety; wherein the spacer has the structure

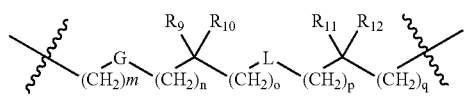

wherein m, n, o, p, q are, individually, an integer from zero to six; the $CH_2$ groups are optionally branched, and any member of the alkylene linker is substituted with one or more substituents; G and L are, individually, absent or O, S, C(O), SO or $SO_2$; $R_9$-$R_{12}$ are H, $C_1$-$C_5$ straight chain or branched alkyl (optionally containing a heteroatom); and substituents on nearby atoms are optionally connected to form a ring of size 3-7 or substituents on the same atom (i.e., geminal substituents) are connected to form a ring of size 3-7; wherein Z is $CO_2H$, $CONHS(O)_2$-Aryl, $CONHS(O)_2$-Alkyl, $CONHS(O)_2$-Heteroaryl, $SO_3H$, $SO_2H$, $S(O)_2$NHCO-alkyl, $S(O)_2$NHCO-aryl, S(O)NHCO-alkyl, S(O)NHCO-aryl, $P(O)(OH)_2$, P(O)OH,

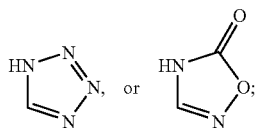

and the compound has one or more of the following characteristics: (i) an inhibition constant ($K_i$) with regard to H1 receptor binding of less than 500 nM; (ii) a $K_i$ with regard to off target binding to an off target selected from the group consisting of M1, M2, M3, D1, D2, D3, α1 and α2 that is more than 10 times greater than the $K_i$ with regard to the H1 receptor; (iii) a nonREM peak time value that is greater than 55% nonREM sleep per hour by the third hour after said compound is administered to a subject; (iv) a cumulative total increase in nonREM sleep not less than 20 minutes for compound doses that produce maximum sleep consolidation; (v) a longest sleep bout that is greater than 13 minutes in duration; (vi) net longest sleep bout post treatment is greater than or equal to 3 minutes when adjusted using a baseline value obtained at least 24 hours prior to administration of said compound to a subject; (vii) an average sleep bout that is greater than 5 minutes at absolute peak; (viii) administration of said compound to a subject does not produce appreciable amounts of rebound insomnia; (ix) administration of said compound to a subject does not appreciably inhibit REM sleep; and (x) and administration of said compound to a subject does not disproportionately inhibit locomotor activity relative to the normal effects of sleep.

In one embodiment, the compound has one or more of the following characteristics: (i) an inhibition constant ($K_i$) with regard to H1 receptor binding of less than 150 nM; (ii) a $K_i$ with regard to off target binding to an off target selected from the group consisting of M1, M2, and M3, that is greater than 10 μM; (iii) a nonREM peak time value that is greater than 55% nonREM sleep per hour by the third hour after said compound is administered to a subject; (iv) a cumulative total increase in nonREM sleep not less than 20 minutes for compound doses that produce maximum sleep consolidation; (v) a longest sleep bout that is greater than 17 minutes in duration; (vi) net longest sleep bout post treatment is greater than or equal to 5 minutes when adjusted using a baseline value obtained at least 24 hours prior to administration of said compound to a subject; (vii) an average sleep bout that is greater than 6 minutes at absolute peak; (viii) administration of said compound to a subject does not produce appreciable amounts of rebound insomnia; (ix) administration of said compound to a subject does not appreciably inhibit REM sleep; and (x) administration of said compound to a subject does not disproportionately inhibit locomotor activity or motor tone relative to the normal effects of sleep.

In another aspect, the invention relates to a method of modulating sleep in a subject, by administering a therapeutically effective amount of one of the following modified antihistamines

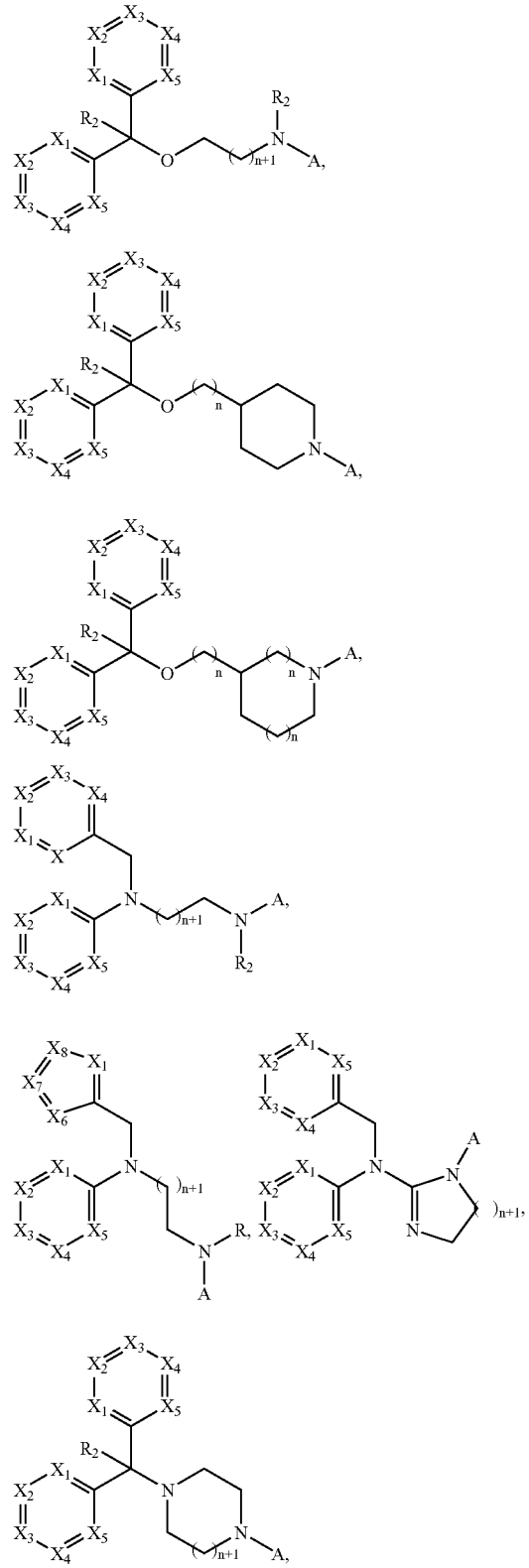

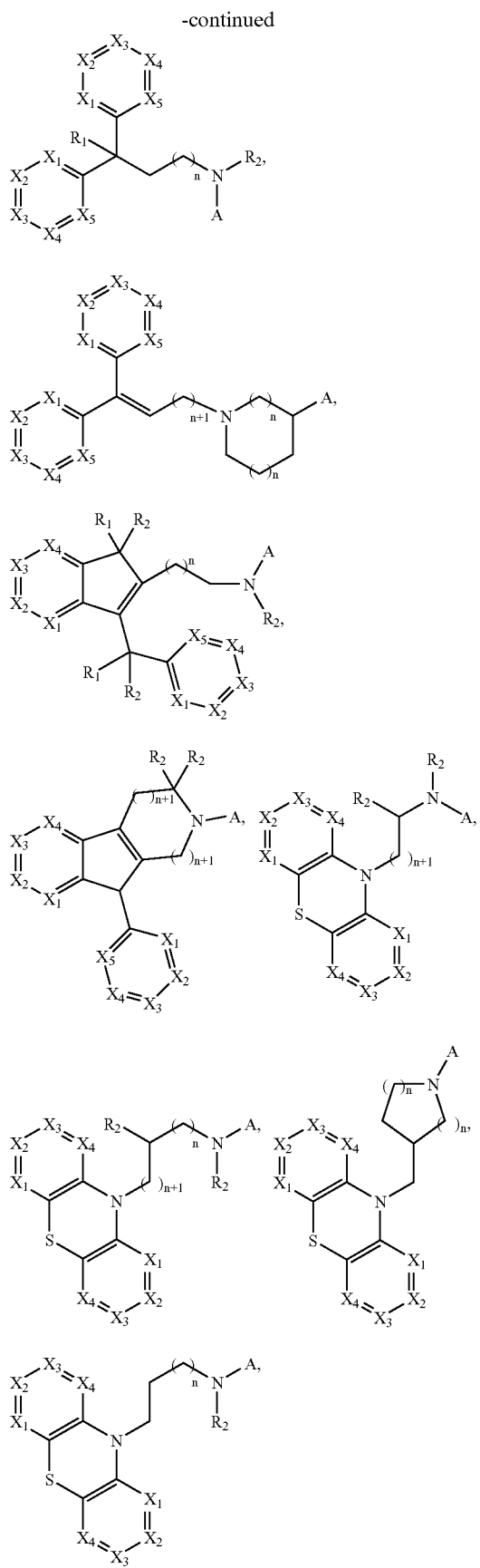
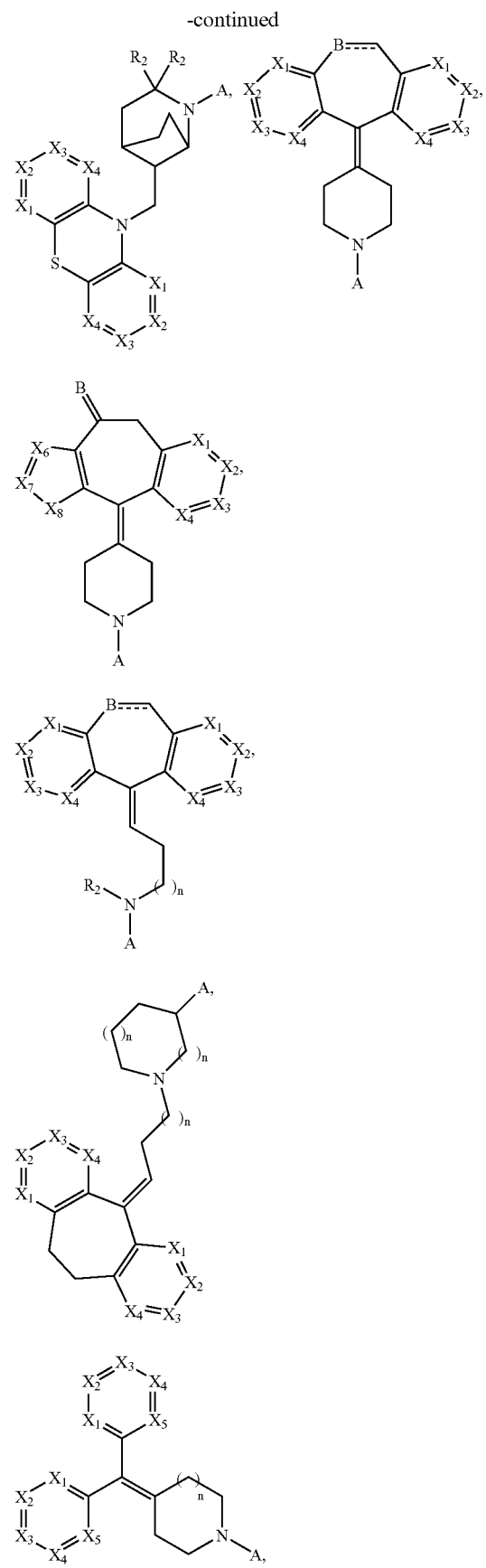

-continued
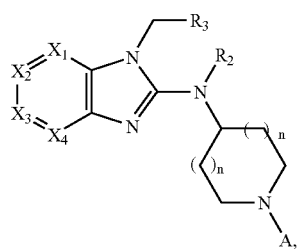
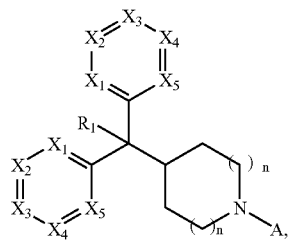
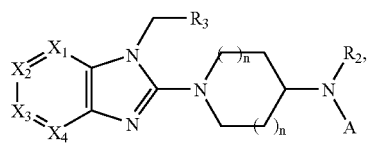
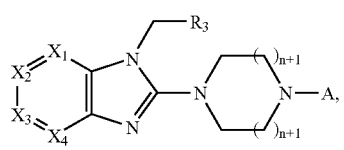
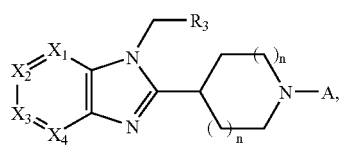
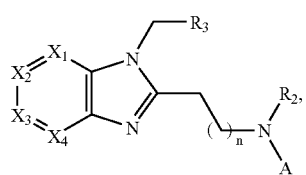
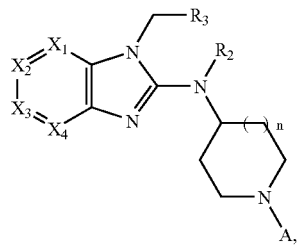
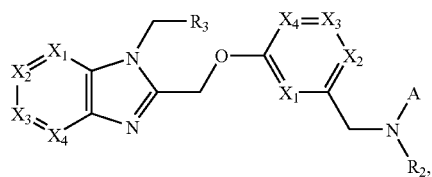
-continued
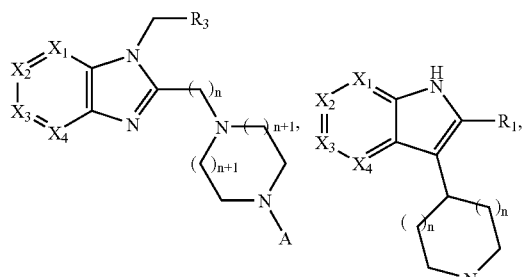
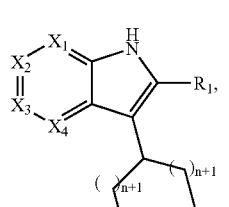
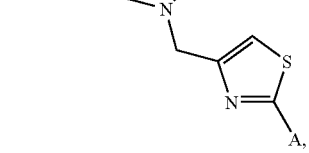
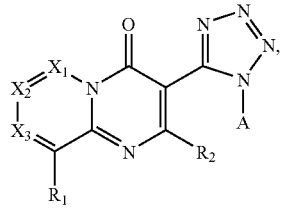
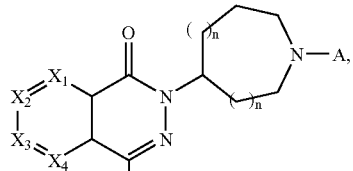
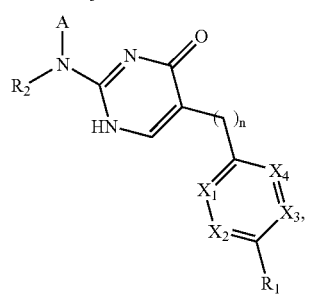
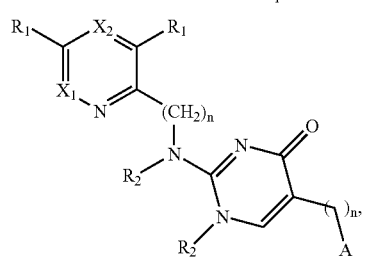

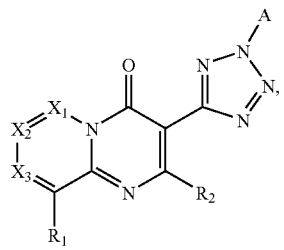
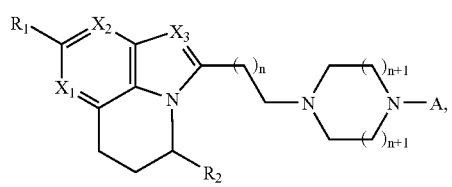
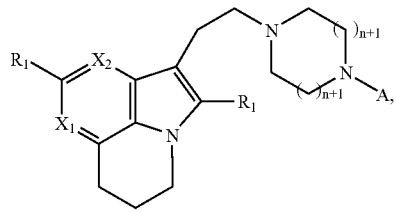
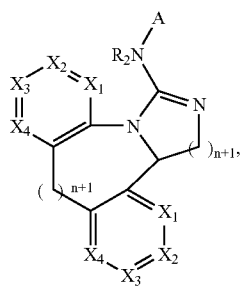
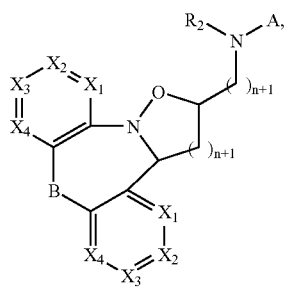
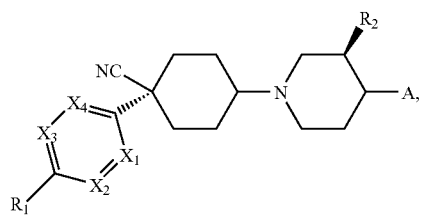
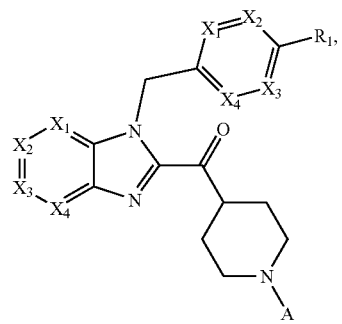
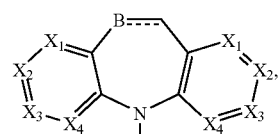
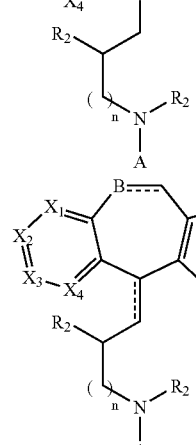
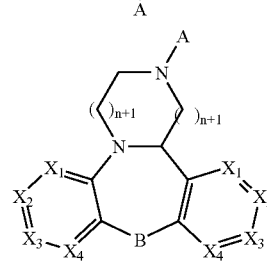
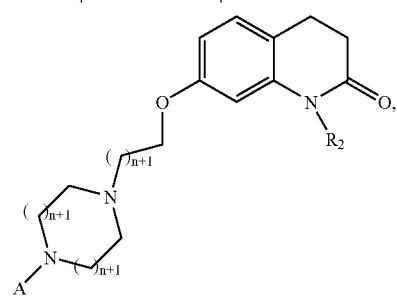
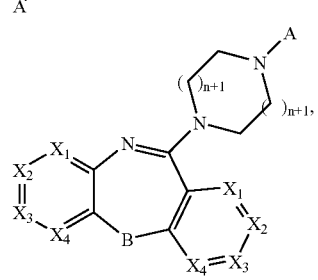

-continued

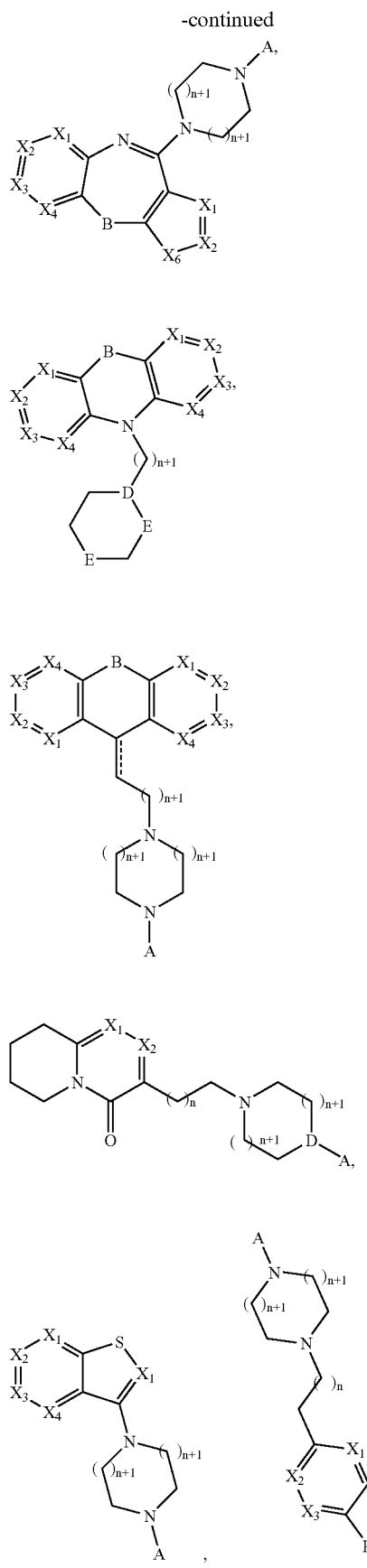
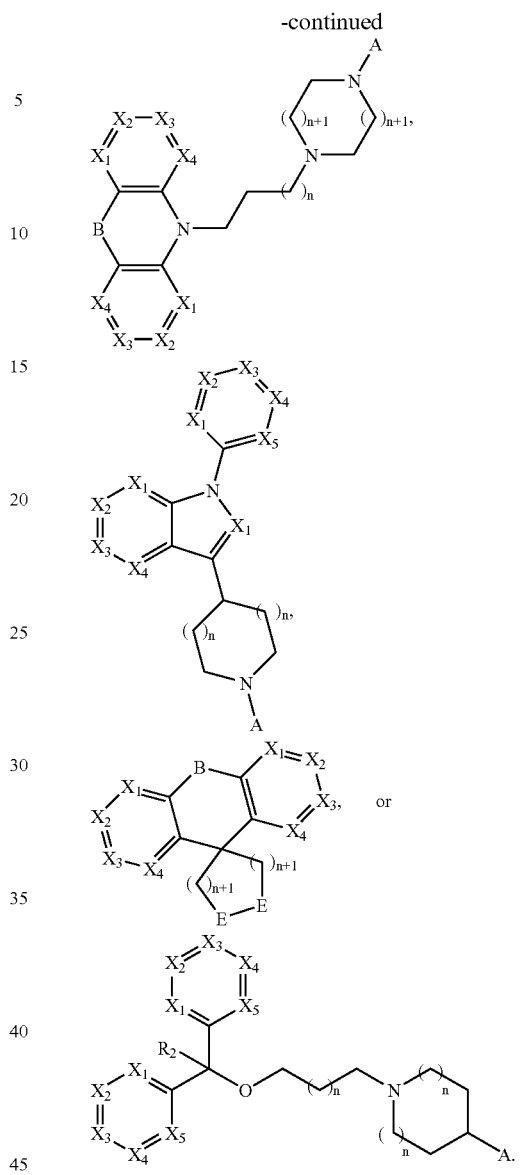

wherein $X_1$-$X_5$ are, independently, CR or N, wherein R is H, lower alkyl, fluoroalkyl (e.g., $CF_3$), F, Cl, Br, lower alkoxy thioalkyl, lower alkoxyalkyl, fluoroalkoxy, alkylcarboxyl, or alkylcarboxyl ester, and wherein the $X_n$ of one aryl ring is the same or different from the corresponding $X_n$ of another aryl ring; $X_6$-$X_8$ is N, S, Se, O or CR, wherein R is H, lower alkyl, fluoroalkyl, F, Cl, Br, lower alkyloxy, thioalkyl, lower alkoxyalkyl, fluoroalkoxy, alkylcarboxyl, alkylcarboxyl ester; $R_1$ is H, OH, lower alkyl, or lower alkyloxy; $R_2$ is H or lower alkyl; $R_3$ is H, alkyl, alkyloxy or alkylaryl; wherein each $R_1$, $R_2$, $R_3$ are the same or different when multiply attached to a structure; B is NR, S, O, $CH_2$ when double bond is absent, or CR when a double bond is present; n is an integer from 0 to 4 and is the same or different when present more than once in a structure; D is CH or N; E is $CH_2$ or N-A, provided that one E in each formula is N-A; and A is a linker molecule comprising SP and Z, wherein SP comprises a spacer molecule and Z comprises a drug modulating moiety; wherein the spacer has the structure

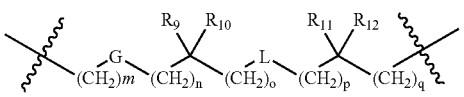

wherein m, n, o, p, q are, individually, an integer from zero to six; the CH$_2$ groups are optionally branched, and any member of the alkylene linker is substituted with one or more substituents; G and L are, individually, absent or O, S, C(O), SO or SO$_2$; R$_9$-R$_{12}$ are H, C$_1$-C$_5$ straight chain or branched alkyl (optionally containing a heteroatom); and substituents on nearby atoms are optionally connected to form a ring of size 3-7 or substituents on the same atom (i.e., geminal substituents) are connected to form a ring of size 3-7; wherein Z is CO$_2$H, CONHS(O)$_2$-Aryl, CONHS(O)$_2$-Alkyl, CONHS(O)$_2$-Heteroaryl, SO$_3$H, SO$_2$H, S(O)$_2$NHCO-alkyl, S(O)$_2$NHCO-aryl, S(O)NHCO-alkyl, S(O)NHCO-aryl, P(O)(OH)$_2$, P(O)OH,

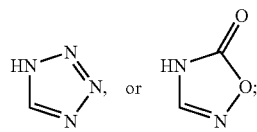

and the compound has one or more of the following characteristics: (i) an inhibition constant (K$_i$) with regard to H1 receptor binding of less than 500 nM; (ii) a K$_i$ with regard to off target binding to an off target selected from the group consisting of M1, M2, M3, D1, D2, D3, α1 and α2 that is more than 10 times greater than the K$_i$ with regard to the H1 receptor; (iii) a nonREM peak time value that is greater than 55% nonREM sleep per hour by the third hour after said compound is administered to a subject; (iv) a cumulative total increase in nonREM sleep not less than 20 minutes for compound doses that produce maximum sleep consolidation; (v) a longest sleep bout that is greater than 13 minutes in duration; (vi) net longest sleep bout post treatment is greater than or equal to 3 minutes when adjusted using a baseline value obtained at least 24 hours prior to administration of said compound to a subject; (vii) an average sleep bout that is greater than 5 minutes at absolute peak; (viii) administration of said compound to a subject does not produce appreciable amounts of rebound insomnia; (ix) administration of said compound to a subject does not appreciably inhibit REM sleep; and (x) and administration of said compound to a subject does not disproportionately inhibit locomotor activity relative to the normal effects of sleep.

In one embodiment, the compound has one or more of the following characteristics: (i) an inhibition constant (K$_i$) with regard to H1 receptor binding of less than 150 nM; (ii) a K$_i$ with regard to off target binding to an off target selected from the group consisting of M1, M2, and M3, that is greater than 10 μM; (iii) a nonREM peak time value that is greater than 55% nonREM sleep per hour by the third hour after said compound is administered to a subject; (iv) a cumulative total increase in nonREM sleep not less than 20 minutes for compound doses that produce maximum sleep consolidation; (v) a longest sleep bout that is greater than 17 minutes in duration; (vi) net longest sleep bout post treatment is greater than or equal to 5 minutes when adjusted using a baseline value obtained at least 24 hours prior to administration of said compound to a subject; (vii) an average sleep bout that is greater than 6 minutes at absolute peak; (viii) administration of said compound to a subject does not produce appreciable amounts of rebound insomnia; (ix) administration of said compound to a subject does not appreciably inhibit REM sleep; and (x) administration of said compound to a subject does not disproportionately inhibit locomotor activity or motor tone relative to the normal effects of sleep.

In one aspect, the invention relates to a method of modulating sleep in a subject, by administering a therapeutically effective amount of one of the following modified antihistamines

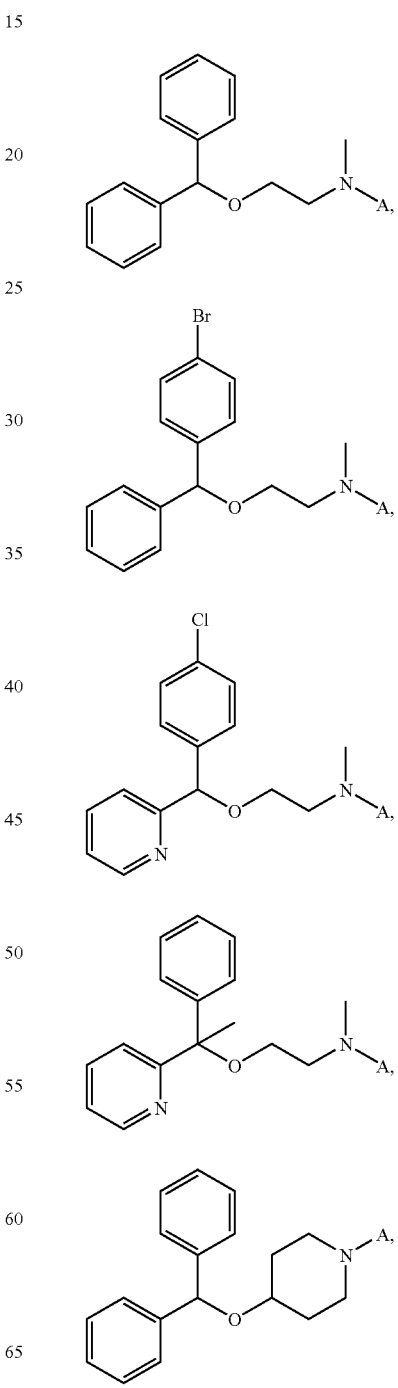

-continued
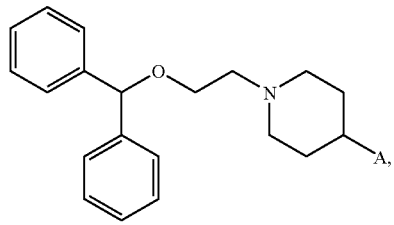
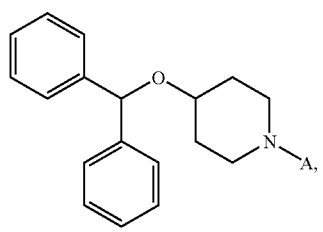
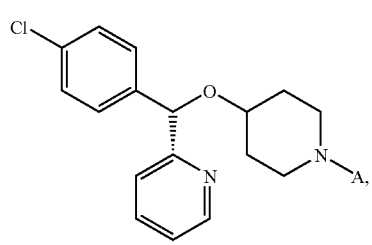
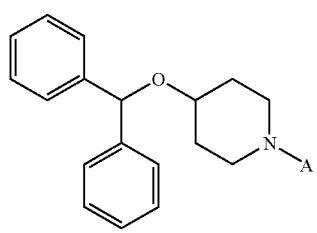
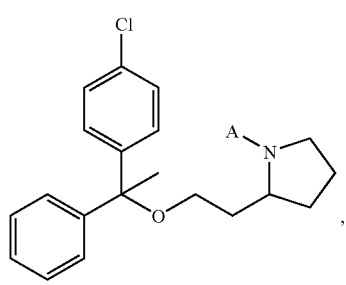
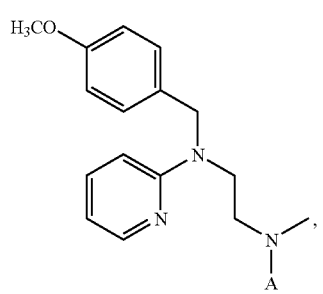
-continued
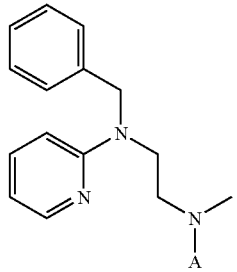
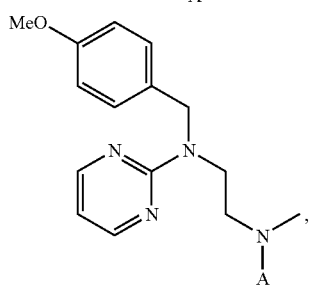
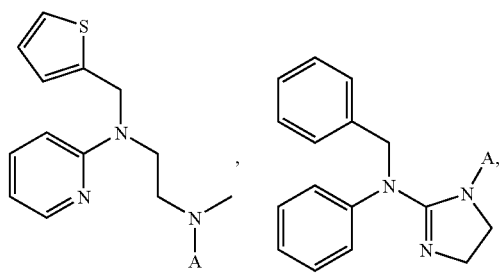
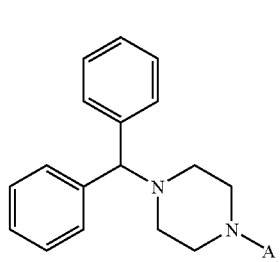
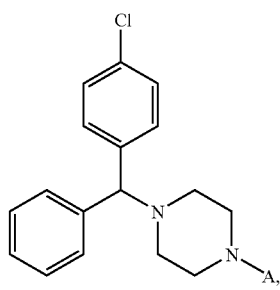
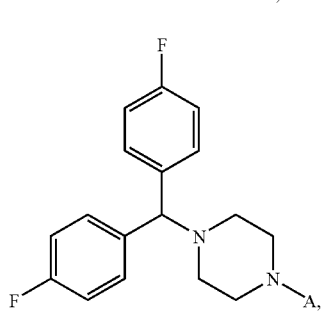

-continued
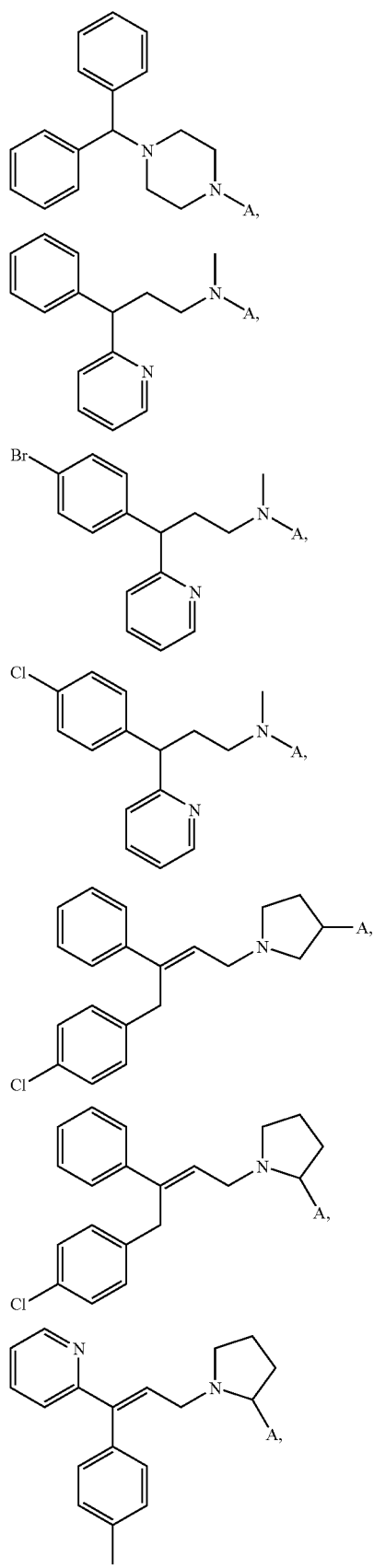
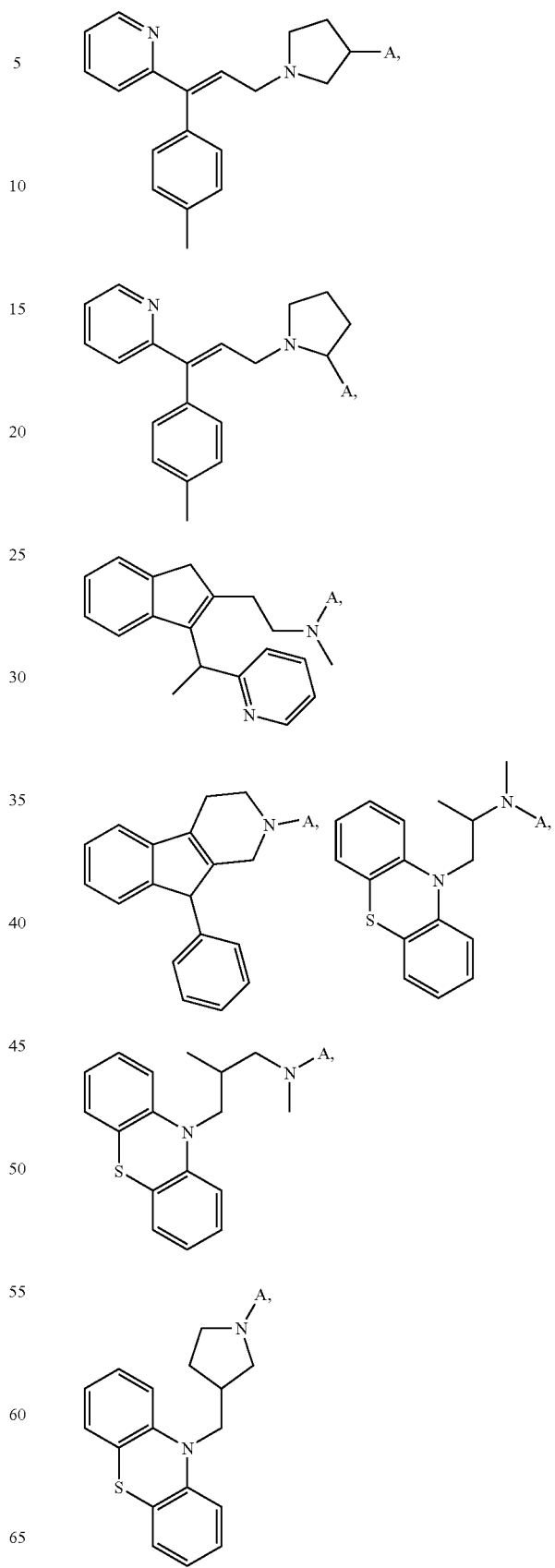

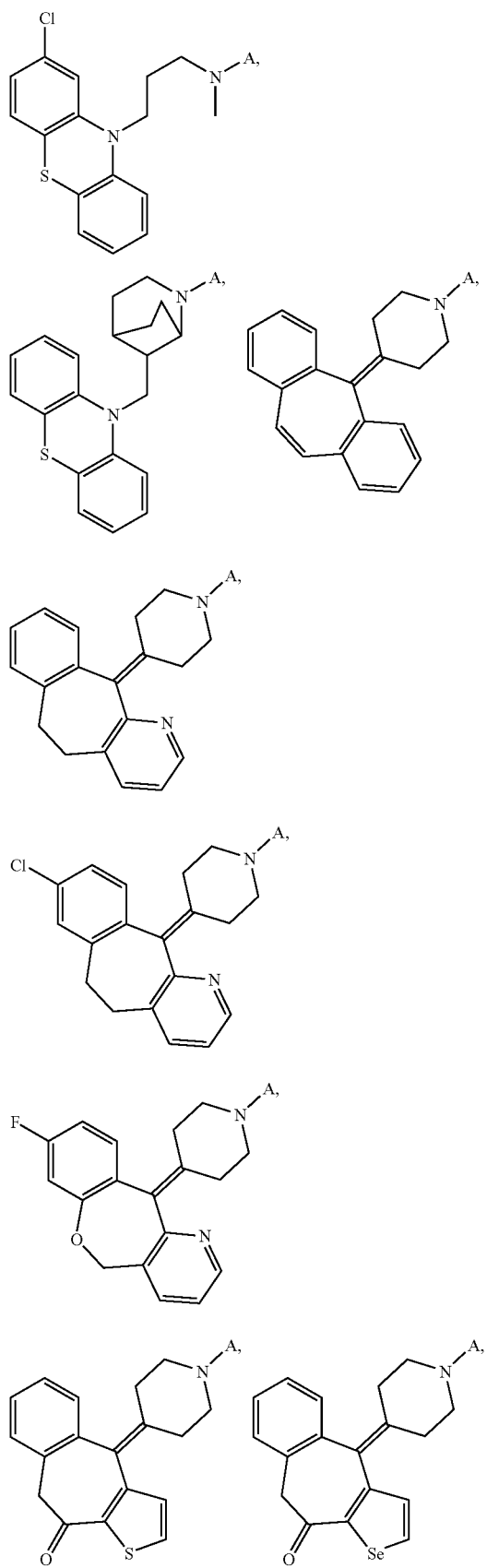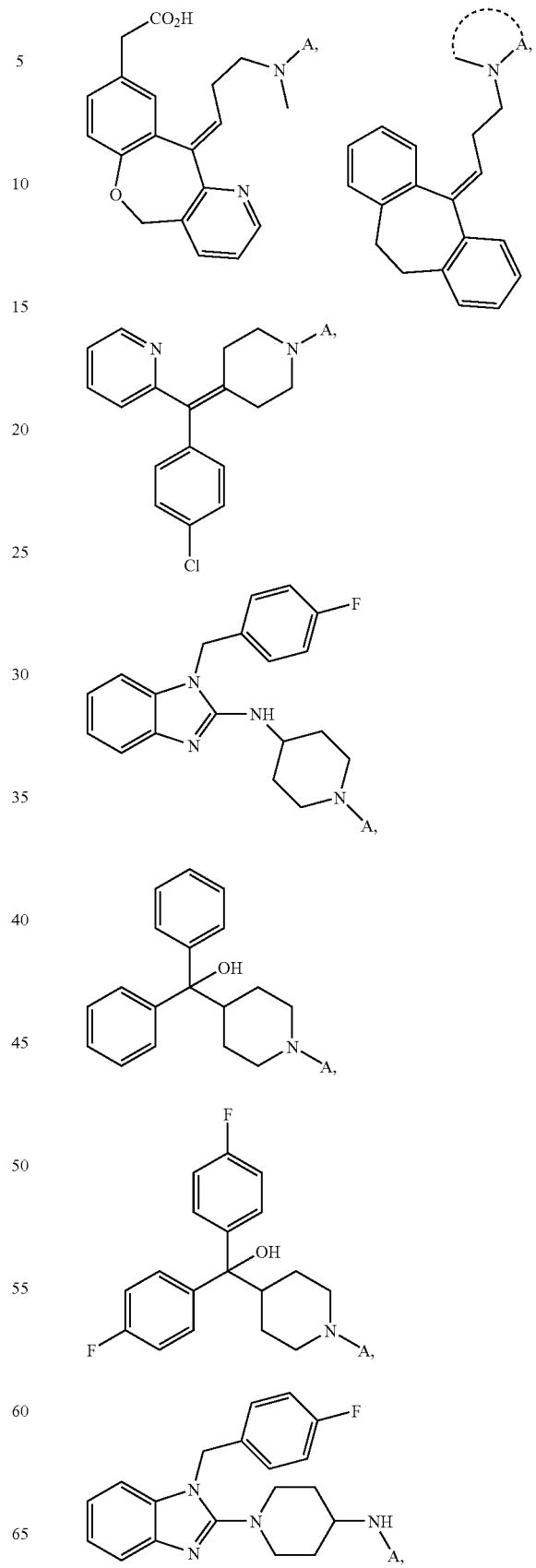

-continued
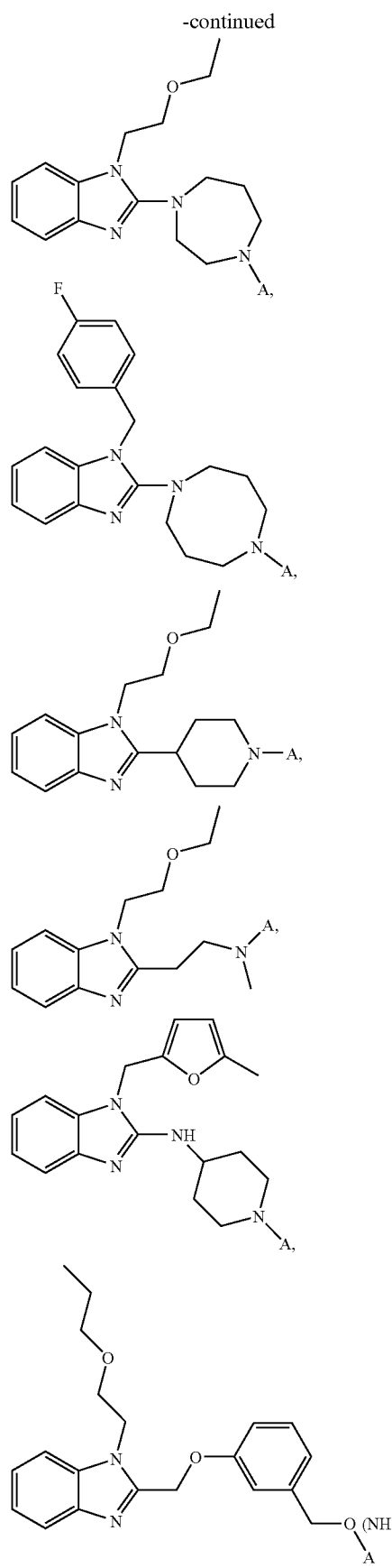
-continued
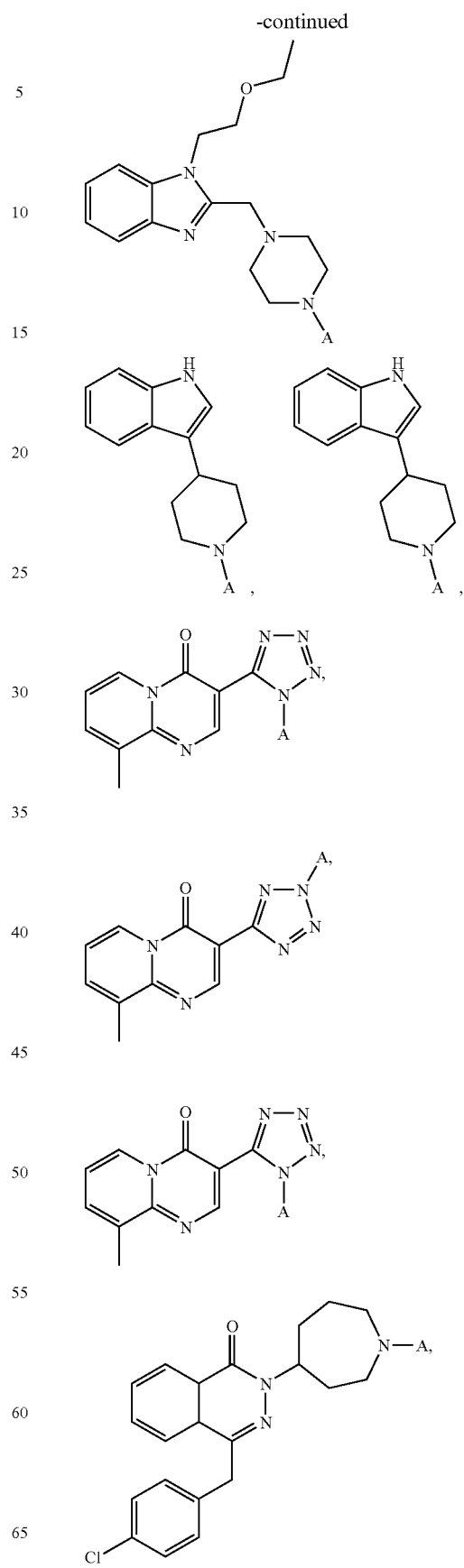

-continued
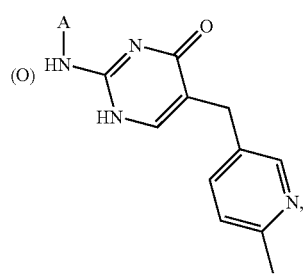
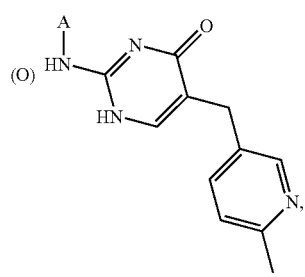
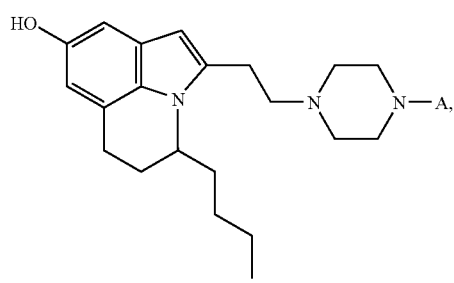
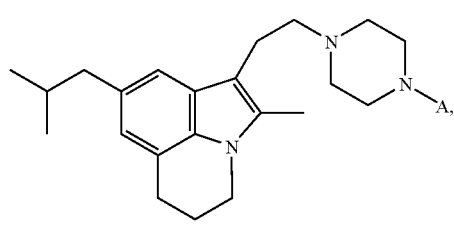
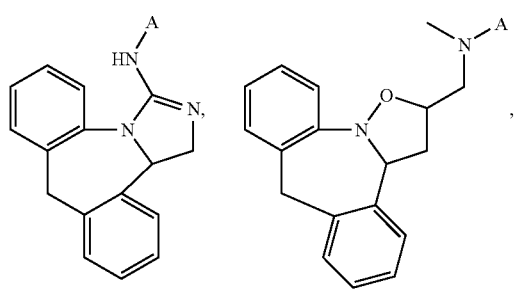
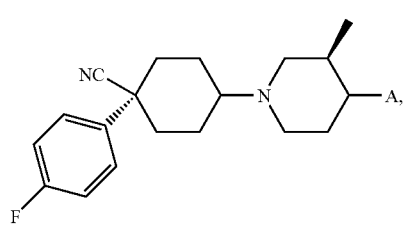
-continued
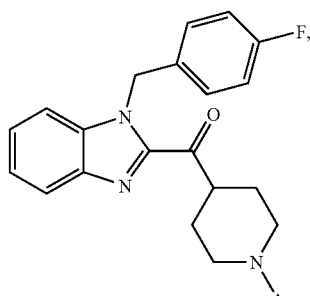
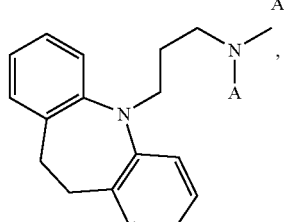
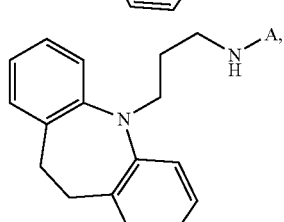
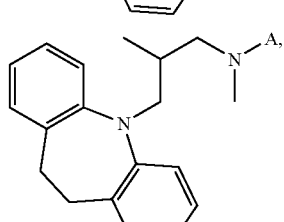
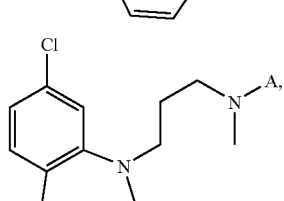
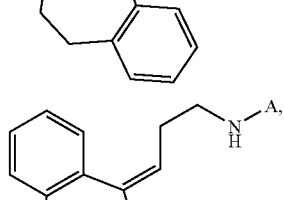
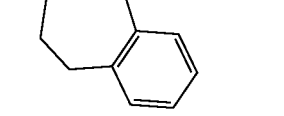
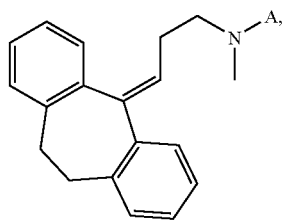

-continued
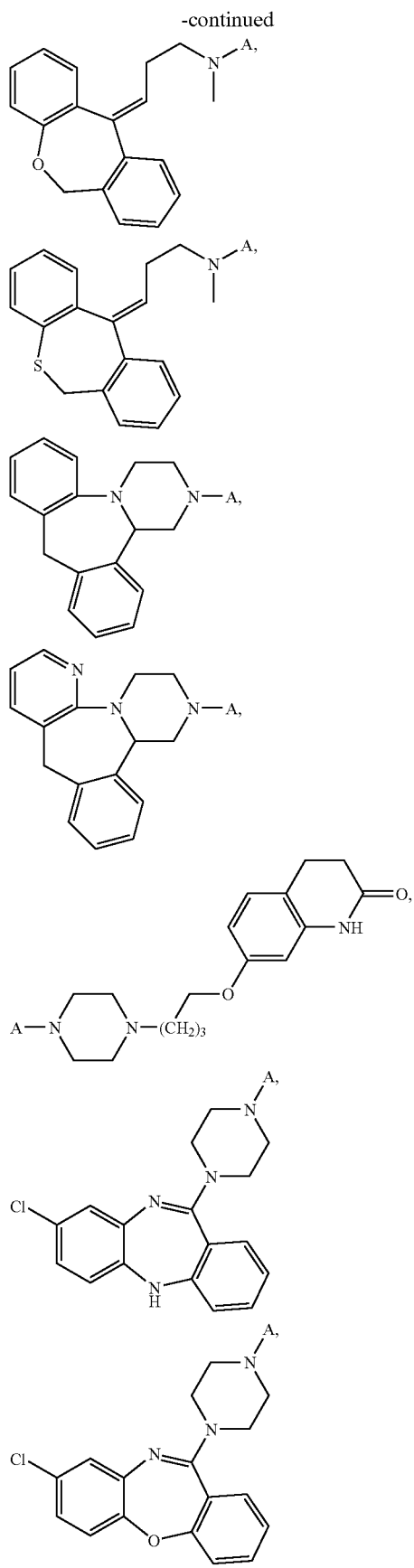
-continued
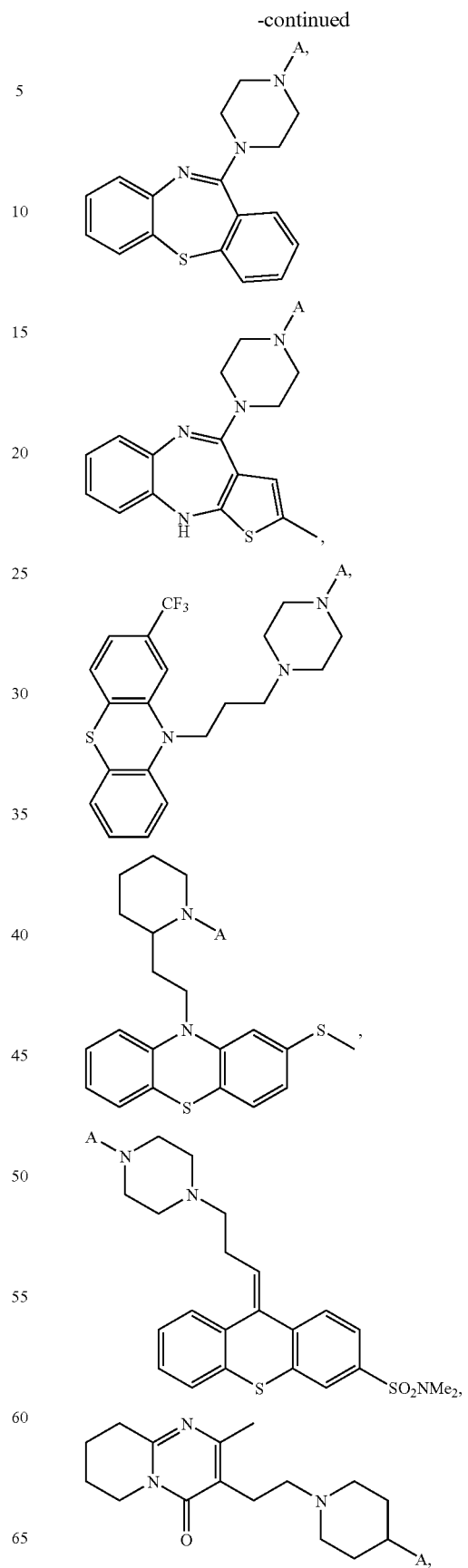

-continued

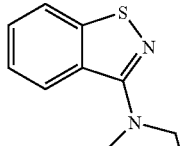

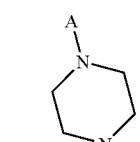

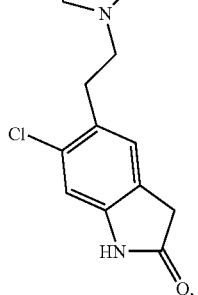

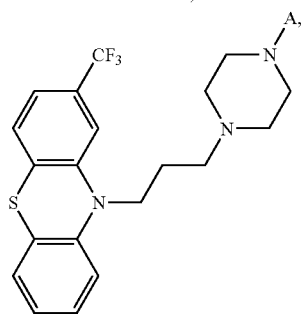

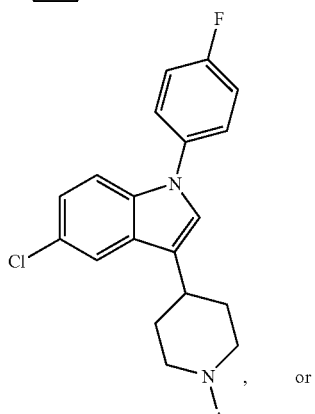

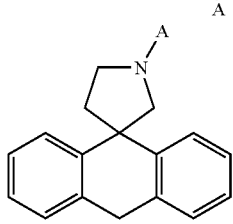, or wherein A is a linker molecule comprising SP and Z, wherein SP is a spacer molecule and Z is a drug modulating moiety;

wherein the spacer has the structure

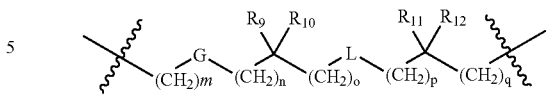

wherein m, n, o, p, q are, individually, an integer from zero to six; the $CH_2$ groups are optionally branched, and any member of the alkylene linker is substituted with one or more substituents; G and L are, individually, absent or O, S, C(O), SO or $SO_2$; $R_9$-$R_{12}$ are H, $C_1$-$C_5$ straight chain or branched alkyl (optionally containing a heteroatom); and substituents on nearby atoms are optionally connected to form a ring of size 3-7 or substituents on the same atom (i.e., geminal substituents) are connected to form a ring of size 3-7; wherein Z is $CO_2H$, $CONHS(O)_2$-Aryl, $CONHS(O)_2$-Alkyl, $CONHS(O)_2$-Heteroaryl, $SO_3H$, $SO_2H$, $S(O)_2$NHCO-alkyl, $S(O)_2$NHCO-aryl, S(O)NHCO-alkyl, S(O)NHCO-aryl, $P(O)(OH)_2$, P(O)OH,

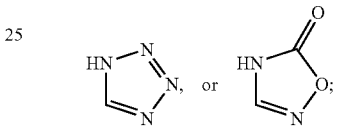

or a pharmaceutically acceptable salt thereof;

and the compound has one or more of the following characteristics: (i) an inhibition constant ($K_i$) with regard to H1 receptor binding of less than 500 nM; (ii) a $K_i$ with regard to off target binding to an off target selected from the group consisting of M1, M2, M3, D1, D2, D3, α1 and α2 that is more than 10 times greater than the $K_i$ with regard to the H1 receptor; (iii) a nonREM peak time value that is greater than 55% nonREM sleep per hour by the third hour after said compound is administered to a subject; (iv) a cumulative total increase in nonREM sleep not less than 20 minutes for compound doses that produce maximum sleep consolidation; (v) a longest sleep bout that is greater than 13 minutes in duration; (vi) net longest sleep bout post treatment is greater than or equal to 3 minutes when adjusted using a baseline value obtained at least 24 hours prior to administration of said compound to a subject; (vii) an average sleep bout that is greater than 5 minutes at absolute peak; (viii) administration of said compound to a subject does not produce appreciable amounts of rebound insomnia; (ix) administration of said compound to a subject does not appreciably inhibit REM sleep; and (x) and administration of said compound to a subject does not disproportionately inhibit locomotor activity relative to the normal effects of sleep.

In one embodiment, the compound has one or more of the following characteristics: (i) an inhibition constant ($K_i$) with regard to H1 receptor binding of less than 150 nM; (ii) a $K_i$ with regard to off target binding to an off target selected from the group consisting of M1, M2, and M3, that is greater than 10 μM; (iii) a nonREM peak time value that is greater than 55% nonREM sleep per hour by the third hour after said compound is administered to a subject; (iv) a cumulative total increase in nonREM sleep not less than 20 minutes for compound doses that produce maximum sleep consolidation; (v) a longest sleep bout that is greater than 17 minutes in duration; (vi) net longest sleep bout post treatment is greater than or equal to 5 minutes when adjusted using a baseline value obtained at least 24 hours prior to administration of said compound to a subject; (vii) an average sleep bout that is greater than 6 minutes at absolute peak; (viii) administration of said compound to a subject does not produce appreciable amounts of rebound insomnia; (ix) administration of said compound to a subject does not appreciably inhibit REM sleep; and (x) administration of said compound to a subject does not disproportionately inhibit locomotor activity or motor tone relative to the normal effects of sleep.

In one aspect, the invention relates to a method of modulating sleep in a subject, by administering a therapeutically effective amount of a modified antihistamine selected from the group consisting of

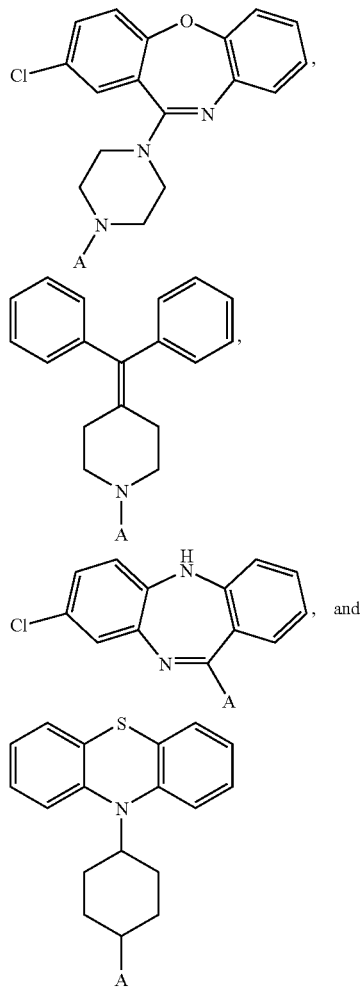

wherein A is a linker molecule comprising a spacer (SP) and a drug activity modulating moiety (Z);
wherein the spacer has the structure

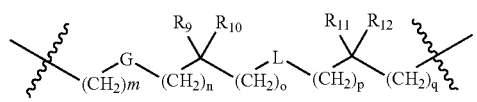

wherein m, n, o, p, q are, individually, an integer from zero to six; the $CH_2$ groups are optionally branched, and any member of the alkylene linker is substituted with one or more substituents; G and L are, individually, absent or O, S, C(O), SO or SO2; $R_9$-$R_{12}$ are H, $C_1$-$C_5$ straight chain or branched alkyl (optionally containing a heteroatom); and substituents on nearby atoms are optionally connected to form a ring of size 3-7 or substituents on the same atom (i.e., geminal substituents) are connected to form a ring of size 3-7; wherein Z is $CO_2H$, CONHS(O)$_2$-Aryl, CONHS(O)$_2$-Alkyl, CONHS(O)$_2$-Heteroaryl, $SO_3H$, $SO_2H$, $S(O)_2$NHCO-alkyl, $S(O)_2$NHCO-aryl, S(O)NHCO-alkyl, S(O)NHCO-aryl, $P(O)(OH)_2$, P(O)OH,

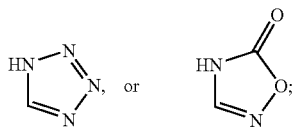

and the compound has one or more of the following characteristics: (i) an inhibition constant ($K_i$) with regard to H1 receptor binding of less than 500 nM; (ii) a $K_i$ with regard to off target binding to an off target selected from the group consisting of M1, M2, M3, D1, D2, D3, α1 and α2 that is more than 10 times greater than the $K_i$ with regard to the H1 receptor; (iii) a nonREM peak time value that is greater than 55% nonREM sleep per hour by the third hour after said compound is administered to a subject; (iv) a cumulative total increase in nonREM sleep not less than 20 minutes for compound doses that produce maximum sleep consolidation; (v) a longest sleep bout that is greater than 13 minutes in duration; (vi) net longest sleep bout post treatment is greater than or equal to 3 minutes when adjusted using a baseline value obtained at least 24 hours prior to administration of said compound to a subject; (vii) an average sleep bout that is greater than 5 minutes at absolute peak; (viii) administration of said compound to a subject does not produce appreciable amounts of rebound insomnia; (ix) administration of said compound to a subject does not appreciably inhibit REM sleep; and (x) and administration of said compound to a subject does not disproportionately inhibit locomotor activity relative to the normal effects of sleep.

In one embodiment, the compound has one or more of the following characteristics: (i) an inhibition constant ($K_i$) with regard to H1 receptor binding of less than 150 nM; (ii) a $K_i$ with regard to off target binding to an off target selected from the group consisting of M1, M2, and M3, that is greater than 10 μM; (iii) a nonREM peak time value that is greater than 55% nonREM sleep per hour by the third hour after said compound is administered to a subject; (iv) a cumulative total increase in nonREM sleep not less than 20 minutes for compound doses that produce maximum sleep consolidation; (v) a longest sleep bout that is greater than 17 minutes in duration; (vi) net longest sleep bout post treatment is greater than or equal to 5 minutes when adjusted using a baseline value obtained at least 24 hours prior to administration of said compound to a subject; (vii) an average sleep bout that is greater than 6 minutes at absolute peak; (viii) administration of said compound to a subject does not produce appreciable amounts of rebound insomnia; (ix) administration of said compound to a subject does not appreciably inhibit REM sleep; and (x) administration of said compound to a subject does not disproportionately inhibit locomotor activity or motor tone relative to the normal effects of sleep.

In another embodiment, the spacer is

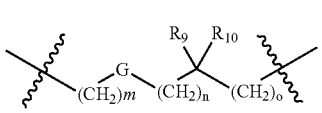

wherein m, n, and o individually are integers from zero to six, and the CH$_2$ groups in the linker are optionally branched; G is absent or is either O, S, C(O), SO or SO2; R$_9$-R$_{10}$ are H, C$_1$-C$_5$ straight chain or branched alkyl, wherein the straight chain or branched alkyl optionally contains one or more heteroatoms and are optionally connected to form a ring of size three to seven; and Z is CO$_2$H, CONHS(O)$_2$-Aryl, CONHS(O)$_2$-Alkyl, or

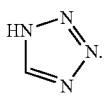

In one embodiment, the spacer is

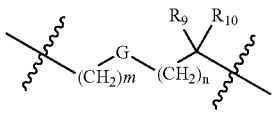

wherein m and n are, individually, integers from zero to four, and the CH$_2$ groups in the linker are optionally branched; G is absent or O, S, C(O), SO or SO$_2$; R$_9$-R$_{10}$ are H or C$_1$-C$_3$ alkyl, wherein the alkyl is optionally substituted with one or more heteroatoms, and optionally branched, wherein further atoms in R$_9$ and R$_{10}$ are optionally connected to form a ring of size three to five; and Z is CO$_2$H, CONHS(O)$_2$-Aryl, CONHS(O)$_2$-Alkyl, or

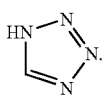

In another embodiment, the spacer is

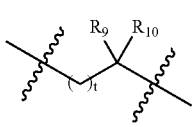

wherein t is an integer from zero to six; R$_9$-R$_{10}$ are H, CH$_3$ or CH$_2$CH$_3$, and are optionally connected to form a spiro ring of size three to six; and Z is either CO$_2$H and

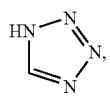

provided that t is not zero when Z is CO$_2$H.

In another embodiment the sleep modulation is decreasing the time to sleep onset, increasing the average sleep bout length, or increasing the maximum sleep bout length. In one embodiment, the sleep modulation treats a sleep disorder. In another embodiment, the sleep disorder is circadian rhythm abnormality, insomnia, parasomnia, sleep apnea syndrome, narcolepsy and hypersomnia.

In one embodiment, the sleep disorder is circadian rhythm abnormality. In another embodiment, the sleep disorder is insomnia. In one embodiment, the sleep disorder is sleep apnea. In another embodiment, the sleep disorder is narcolepsy. In one embodiment, the sleep disorder is hypersomnia. In another embodiment, the modified antihistamine compound or a pharmaceutically acceptable salt thereof is administered as a pharmaceutical composition comprising a pharmaceutically acceptable excipient.

In one embodiment, the modified antihistamine compound or pharmaceutically acceptable salt thereof is co-administered with one or more additional therapies. In another embodiment, the subject is selected from the group consisting of humans, companion animals, farm animals, laboratory animals and wild animals. In one embodiment, the subject is a human.

In another aspect, the invention relates to a method of modulating sleep in a subject, by administering a therapeutically effective amount of one of the following modified antihistamines

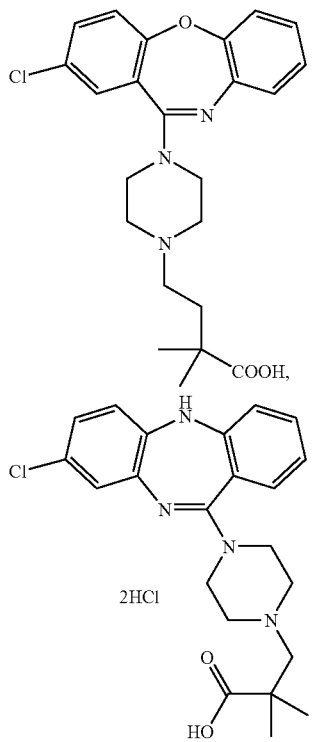

-continued

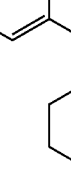

DETAILED DESCRIPTION OF THE INVENTION

Figure 1:
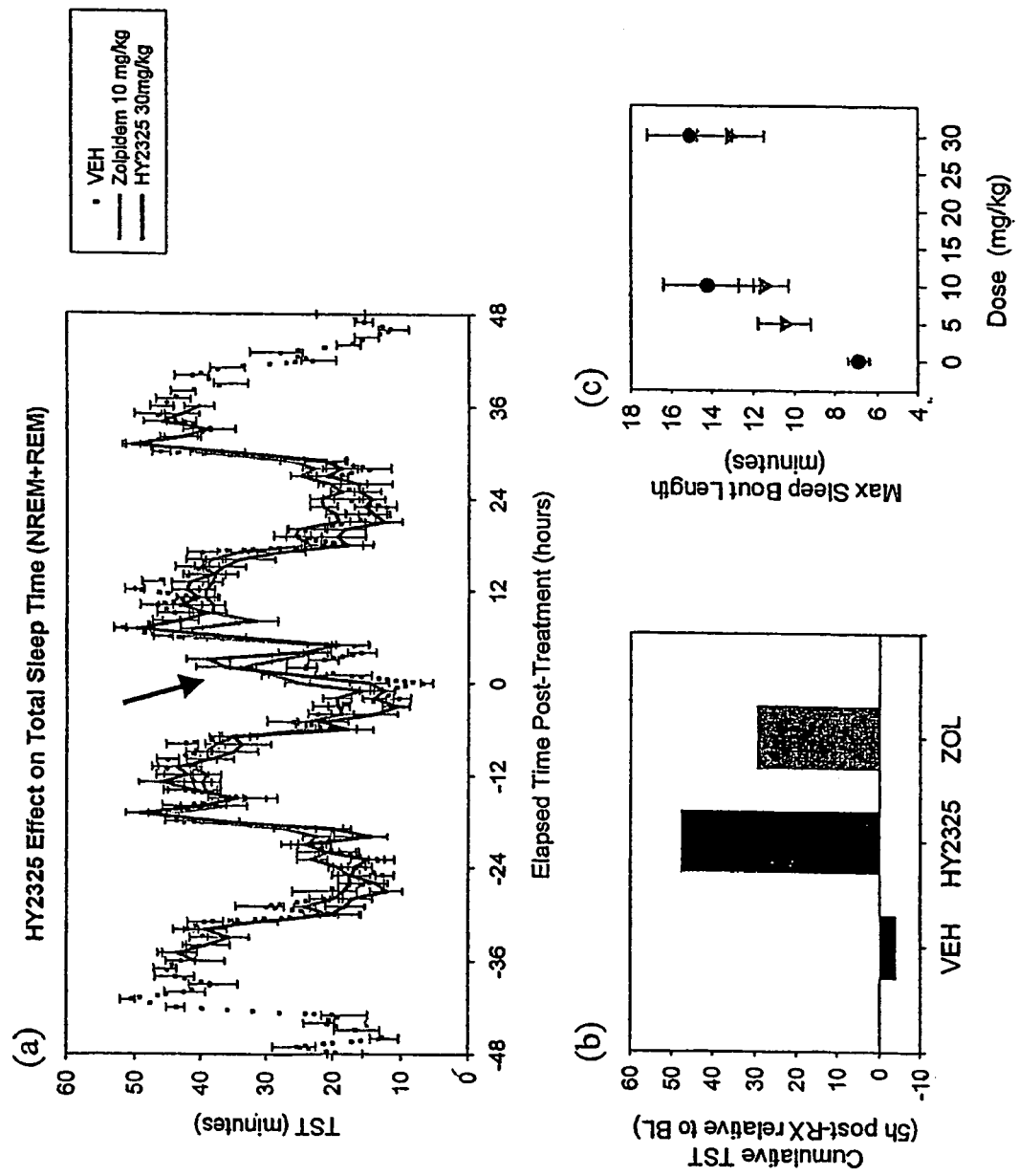
FIGS. 1A-C are graphs depicting the effect of a compound of the invention on parameters pertinent to sleep disorders.
Figure 2:
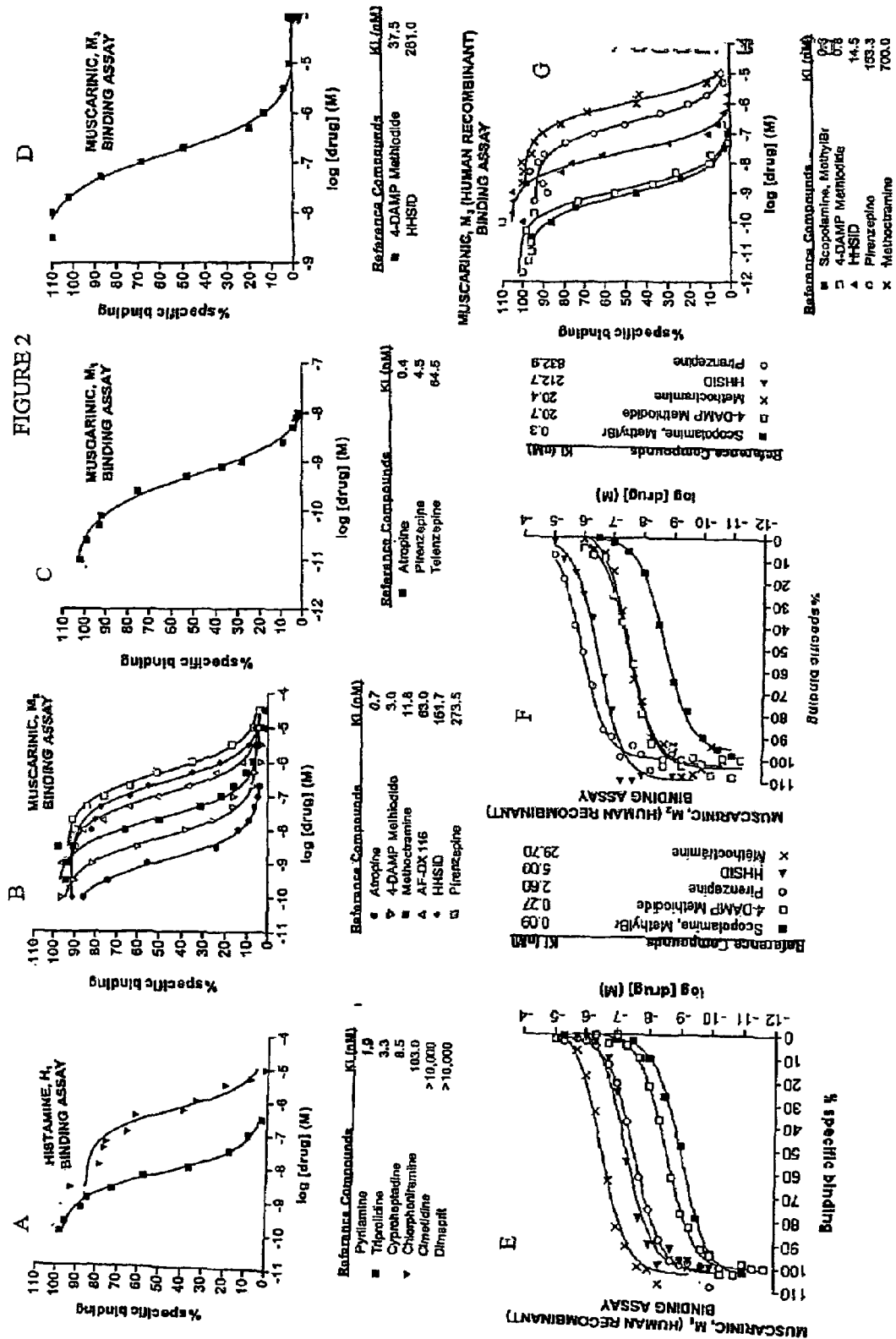
FIGS. 2A-G are graphs depicting the binding of reference compounds to the receptors as indicated.

The details of one or more embodiments of the invention are set forth in the accompanying description below. Although any methods and materials similar or equivalent to those described herein can be used in the practice or testing of the present invention, the preferred methods and materials are now described. Other features, objects, and advantages of the invention will be apparent from the description. In the specification, the singular forms also include the plural unless the context clearly dictates otherwise. Unless defined otherwise, all technical and scientific terms used herein have the same meaning as commonly understood by one of ordinary skill in the art to which this invention belongs. In the case of conflict, the present specification will control.

The invention is directed to compositions used for treating Central Nervous System (CNS) disorders. In addition, the invention provides convenient methods of treatment of a CNS disorder. Furthermore, the invention provides methods of treating sleep disorders using compositions that remain active for a discrete period of time to reduce side effects. More specifically, the invention is directed to the compositions and use of derivatized, e.g., ester or carboxylic acid derivatized, histamine antagonists for the treatment of sleep disorders.

Methods of the Invention

One embodiment of the invention is a method of treating a Central Nervous System (CNS) disorder. The method of treating comprises the treatment of a Central Nervous System (CNS) disorder, comprising administering to a subject an effective amount of a therapeutic compound, such that the therapeutic compound penetrates into the CNS and modulates the CNS target, thereby treating the CNS disorder.

The language "Central Nervous System (CNS) disorder," includes disorders or states of the central nervous system and that are treatable by the compounds described herein. Examples include, but are not limited to depression; anxiety; addictions; obsessive compulsive disorder; affective neurosis/disorder; depressive neurosis/disorder; anxiety neurosis; dysthymic disorder; behavior disorder; mood disorder; sexual dysfunction; psychosexual dysfunction; sex disorder; sexual disorder; schizophrenia; manic depression; delirium; dementia; severe mental retardation and dyskinesias such as Huntington's disease and Gilles de la Tourett's syndrome; disturbed biological and circadian rhythms; feeding disorders, such as anorexia, bulimia, cachexia, and obesity; diabetes; appetite/taste disorders; vomiting/nausea; asthma; cancer; Parkinson's disease; Cushing's syndrome/disease; basophil adenoma; prolactinoma; hyperprolactinemia; hypopituitarism; hypophysis tumor/adenoma; hypothalamic diseases; Froehlich's syndrome; adrenohypophysis disease; hypophysis tumor/adenoma; pituitary growth hormone; adrenohypophysis hypofunction; adrenohypophysis hyperfunction; hypothalamic hypogonadism; Kallman's syndrome (anosmia, hyposmia); functional or psychogenic amenorrhea; hypopituitarism; hypothalamic hypothyroidism; hypothalamic-adrenal dysfunction; idiopathic hyperprolactinemia; hypothalamic disorders of growth hormone deficiency; idiopathic growth hormone deficiency; dwarfism; gigantism; acromegaly; disturbed biological and circadian rhythms; and sleep disturbances associated with such diseases as neurological disorders, neuropathic pain and restless leg syndrome, heart and lung diseases; acute and congestive heart failure; hypotension; hypertension; urinary retention; osteoporosis; angina pectoris; myocardial infarction; ischaemic or haemorrhagic stroke; subarachnoid haemorrhage; head injury such as subarachnoid haemorrhage associated with traumatic head injury; ulcers; allergies; benign prostatic hypertrophy; chronic renal failure; renal disease; impaired glucose tolerance; migraine; hyperalgesia; pain; enhanced or exaggerated sensitivity to pain, such as hyperalgesia, causalgia and allodynia; acute pain; burn pain; atypical facial pain; neuropathic pain; back pain; fibromyalgia; complex regional pain syndromes I and II; arthritic pain; sports injury pain; pain related to infection, e.g., HIV, post-polio syndrome, and post-herpetic neuralgia; phantom limb pain; labor pain; cancer pain; post-chemotherapy pain; post-stroke pain; post-operative pain; neuralgia; conditions associated with visceral pain including irritable bowel syndrome, migraine and angina; urinary bladder incontinence e.g. urge incontinence; tolerance to narcotics or withdrawal from narcotics; sleep disorders, sleep apnea; narcolepsy, insomnia; parasomnia; jet-lag syndrome; and neurodegenerative disorders, which include nosological entities such as disinhibition-dementia-parkinsonism-amyotrophy complex; pallido-ponto-nigral degeneration, epilepsy and seizure disorders, attention-deficit hyperactivity disorder (ADHD)/ cognition, Alzheimer's, drug abuse, stroke, multiple sclerosis (MS), and Amyotrophic Lateral Sclerosis (ALS).

The terms "treating" or "treatment" include administering a therapeutically effective amount of a compound sufficient to reduce or eliminate at least one symptom of the state, disease or disorder, e.g., a sleep disorder.

The language "administering" includes delivery to a subject by any means that does not affect the ability of the therapeutic compound to perform its intended function. The therapeutic compound may be administered by any means that sufficiently treats the disorder target. Administration includes, but is not limited to parenteral, enteral, and topical administration. While it is possible for a compound of the present invention to be administered alone, it is preferable to administer the compound as a pharmaceutical composition, which includes compositions that comprise the compounds of the present invention and a pharmaceutically acceptable carrier. In a specific embodiment, the therapeutic compound is administered orally.

Administration also includes the use of an additional modulating factor (AMF) in "combination therapy." The language "additional modulating factor (AMF)" includes additional factors, such as additional therapeutics or subject abnormalities, e.g., a chemical imbalance. It should be understood that the additional modulating factor may be directed to the same or a different disorder target as that being modulated by the compounds of the present invention.

The language "combination therapy" includes the co-administration of the modulating compound of the present invention in the presence of an additional modulating factor, e.g., an additional therapeutic agent. Administration of the modulating compound may be first, followed by the other therapeutic agent; or administration of the other therapeutic agent may be first, followed by the modulating, e.g., inhibiting, compound. The other therapeutic agent may be any agent which is known in the art to treat, prevent, or reduce the symptoms of the targeted disorder, e.g., a sleep disorder.

"Combination therapy" (or "co-therapy") includes the administration of a compound of the invention and at least a second agent as part of a specific treatment regimen intended to provide the beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination typically is carried out over a defined time period (usually minutes, hours, days or weeks depending upon the combination selected). "Combination therapy" may, but generally is not, intended to encompass the administration of two or more of these therapeutic agents as part of separate monotherapy regimens that incidentally and arbitrarily result in the combinations of the present invention. "Combination therapy" is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. The sequence in which the therapeutic agents are administered is not narrowly critical. "Combination therapy" also embraces the administration of the therapeutic agents as described above in further combination with other biologically active ingredients and non-drug therapies (e.g., surgery or radiation treatment). Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

In addition, the compounds of the present invention can also be administered in combination with other known therapies for the target disorder. Furthermore, the other therapeutic agent may be any agent of benefit to the patient when administered in combination with the administration of a modulating, e.g., inhibiting, compound. The other therapeutic agent may also be a modulating compound.

For example, a therapeutic compound of the invention may be administered in conjunction with a variety of commercially-available drugs, including, but not limited to, antimicrobial agents, such as pentamidine, lomefloxacin, metronidazole, fungistatic agents, germicidal agents, hormones, antipyretic agents, antidiabetic agents, bronchodilators, such as aminophylline, antidiarrheal agents, such as diphenoxylate hydrochloride with atropine sulfate, antiarrhythmic agents, such as disopyramide phosphate and bidisomide, coronary dilation agents, glycosides, spasmolytics, antihypertensive agents, such as verapamil and verapamil hydrochloride and their enantiomers, and betaxolol, antidepressants, antianxiety agents, other psychotherapeutic agents, such as zolpidem, cycloserine and milacemide, corticosteroids, analgesics, such as misoprostol with diclofenac, contraceptives, such as ethynodiol diacetate with ethinyl estradiol, and norethynodrel with mestranol, nonsteroidal anti-inflammatory drugs, such as oxaprozen, blood glucose lowering agents, cholesterol lowering agents, anticonvulsant agents, other antiepileptic agents, immunomodulators, antioholinergics, sympatholytics, sympathomimetics, vasodilatory agents, anticoagulants, antiarrhythmics, such as disopyramide or disobutamide, prostaglandins having various pharmacologic activities, such as misoprostol and enisoprost, diuretics, such as spironolactone and spironolactone with hydrochlorothiazide, sleep aids, such as zolpidem tartrate, antihistaminic agents, antineoplastic agents, oncolytic agents, antiandrogens, antimalarial agents, antileprosy agents, and various other types of drugs. See Goodman and Gilman's The Basis of Therapeutics (Eighth Edition, Pergamon Press, Inc., USA, 1990) and The Merck Index (Eleventh Edition, Merck & Co., Inc., USA, 1989), each of which is incorporated herein by reference In addition, a compound of the invention also may be administered in conjunction with any one or combination of the commercially-available, over-the-counter or prescription medications, including, but not limited to Avobenzene/padimate-O, ACCUPRIL® tablets (quinapril hydrochloride), Accutane capsules (isotretinoin), Achromycin V capsules (the monohydrochloride of (4S-(4.alpha.,4a.alpha., 5a.alpha.,6.beta.,12a.alpha.,))-4-(dimethylamino)-1,4,4a,5, 5a,6,11,12a-octBPydro-3,6,10,12,12a-pentBPydroxy-6-methyl-1,11-dioxo-2-naphthacenecarboxamide), Actifed cough syrup (codeine phosphate, triprolidine hydrochloride and pseudoephedrine hydrochloride), Aldactazide tablets (spironolactone and hydrochlorothiazide), ALDOCLOR® tablets (methyldopa and chlorothiazide), Aldoril tablets (methyldopa-hydrochlorothiazide), Alferon® N injection (interferon .alpha.-n3 (human leukocyte derived)), ALTACE™ capsules (ramipril), AMBIEN® tablets (zolpidem tartrate), Anafranil capsules (clomipramine hydrochloride), ANAPROX® tablets (naproxen sodium), Ancobon capsules (flucytosine), Ansaid tablets (flurbiprofen), Apresazide capsules (hydralazine hydrochloride and hydrochlorothiazide), Asendin tablets (2-chloro-11-(1-piperazinyl)dibenz(b,f)(1, 4)-oxazepine), Atretol™ tablets (carbamazepine), Aureomycin ophthalmic ointment (chlortetracycline hydrochloride), Azo Gantanol® tablets (sulfamethoxazole and phenazopyridine hydrochloride), Azo Gantrisin tablets (sulfisoxazole and phenazopyridine hydrochloride), Azulfidine® tablets and EN-tabs (5-((p-(2-pyridylsulfamoyl)phenyl)-azo)salicylic acid), Bactrim tablets (trimethoprim and sulfamethoxazole), Bactrim I.V. infusion (trimethoprim and sulfamethoxazole), Bactrim pediatric suspension (trimethoprim and sulfamethoxazole), Bactrim suspension (trimethoprim and sulfamethoxazole), Bactrim tablets (trimethoprim and sulfamethoxazole), Benadryl® capsules (diphenhydramine hydrochloride USP), Benadryl® kapseals (diphenhydramine hydrochloride USP), Benadryl® tablets (diphenhydramine hydrochloride USP), Benadryl® parenteral (diphenhydramine hydrochloride USP), Benadryl® steri-vials, ampoules, and steri-dose syringe (diphenhydramine hydrochloride USP), Capoten tablets (captopril), Capozide tablets (captopril-hydrochlorothiazide), Cardizem® CD capsules (diltiazem hydrochloride), Cardizem® SR capsules (diltiazem hydrochloride), Cardizem® tablets (diltiazem hydrochloride), Chibroxin sterile ophthalmic solution (with oral form) (norfloxacin), Children's Advil® suspension (ibuprofen), Cipro® I.V. (ciprofloxacin), Cipro® tablets (ciprofloxacin), Claritin tablets (loratadine), Clinoril tablets (sulindac), Combipres® tablets (clonidine hydrochloride and chlorthalidone), Compazine® injection (prochlorperazine maleate), Compazine® multi-dose vials (prochlorperazine maleate), Compazine® syringes (prochlorperazine maleate), Compazine® spansule capsules (prochlorperazine maleate), Compazine® suppositories (prochlorperazine maleate), Compazine® syrup (prochlorperazine maleate), Compazine® tablets (prochlorperazine maleate), Cordarone tablets (amiodarone hydrochloride), Corzide tablets (nadolol and bendroflumethiazide), Dantrium capsules (dantrolene sodium), Dapsone tablets (4-4' diaminodiphenylsulfone), DAYPRO® caplets (oxaproxin), Declomycin tablets (demeclacycline or (4S-(4.alpha.,4a.alpha.,5a.alpha.,6.beta., 12a.alpha.))-7-Chloro-4-dimethyl amino)-1,4,4a,5,5a,6,11, 12a-octBPydro-3,6,10,12,12a-pentBPydroxy-1,11-dioxo-2-naphthacenecarboxamide monohydrochloride), DECONAMINE® capsules (chlorpheniramine maleate and d-psuedoephedrine hydrochloride), DECONAMINE® syrup (chlorpheniramine maleate and d-psudoephedrine hydrochloride), DECONAMINE® tablets (chlorpheniramine maleate and d-psudoephedrine hydrochloride), Depakene capsules (valproic acid), Depakene syrup (valproic acid), Depakote sprinkle capsules (divalproex sodium), Depakote tablets (divalproex sodium), DiaBeta® tablets (glyburide), Diabinese tablets (chlorpropamide), Diamox parenteral (acetazolamide), Diamox sequels (acetazolamide), Diamox tablets (acetazolamide), Dimetane-DC cough syrup (brompheniramine maleate, phenylpropanolamine hydrochloride and codeine phosphate), Dimetane-DX cough syrup (brompheniramine maleate, phenylpropanolamine hydrochloride and codeine phosphate), Dipentum® capsules (olsalazine sodium), Diucardin tablets (hydroflumethiazide), Diupres tablets (reserpine and chlorothiazide), Diuril oral suspension (chlorothiazide), Diuril sodium intravenous (chlorothiazide), Diuril tablets (chlorothiazide), Dolobid tablets (diflunisal), DORYX® capsules (doxycycline hyclate), Dyazide capsules (hydrochlorothiazide and triamterene), Dyrenium capsules (triamterene), Efudex cream (5-fluorouracil), Efudex solutions (5-fluorouracil), Elavil injection (amitriptyline HCl), Elavil tablets (amitriptyline HCl), Eldepryl tablets (selegiline hydrochloride), Endep tablets (amitriptyline HCl), Enduron tablets (methyclothiazide), Enduronyl Forte tablets (methyclothiazide and deserpidine), Enduronyl tablets (methyclothiazide and deserpidine), Ergamisol tablets (levamisole hydrochloride), Esidrix tablets (hydrochlorothiazide USP), Esimil tablets (guanethidine monosulfate USP and hydrochlorothiazide USP), Etrafon Forte tablets (perphenazine, USP and amitriptyline hydrochloride, USP), Etrafon 2-10 tablets (perphenazine, USP and amitriptyline hydrochloride, USP), Etrafon tablets (perphenazine, USP and amitriptyline hydrochloride, USP), Etrafon-A tablets (perphenazine, USP and amitriptyline hydrochloride, USP), Eulexin capsules (flutamide), Exna tablets (benzthiazide), FUDR injection (floxuridine), Fansidar tablets (N1-(5,6-dimethoxy-4-pyrimidinyl) sulfanilamide (sulfadoxine) and 2,4-diamino-5-(p-chlorophenyl)-6-ethylpyrimidine (pyrimethamine), Feldene capsules (piroxicam), Flexeril tablets (cyclobenzaprine hydrochloride), FLOXIN® I.V. (ofloxacin injection), FLOXINS® tablets (ofloxacin), Fluorouracil injection (5-fluoro-2,4(1H, 3H)-pyrimidinedione), Fulvicin tablets (griseofulvin), Gantanol® suspension (sulfamethoxazole), Gantanol® tablets (sulfamethoxazole), Gantrisin ophthalmic ointment/solution (sulfisoxazole), Gantrisin pediatric suspension (sulfisoxazole), Gantrisin syrup (sulfisoxazole), Gantrisin tablets (sulfisoxazole), Glucotrol tablets (glipizide), Glynase PresTab tablets (glyburide), Grifulvin V tablets (griseofulvin), Grifulvin oral suspension (griseofulvin), Gristactin capsules (griseofulvin), Grisactin tablets (griseofulvin), Gris-PEG tablets (griseofulvin), Grivate tablets (griseofulvin), Grivate suspension (griseofulvin), Haldol Decanoate 50 injection (haloperidol decanoate), Haldol Decanoate 100 injection (haloperidol decanoate), Haldol tablets (haloperidol decanoate), Hibistat germicidal hand rinse (chlorhexidine gluconate), HISMANAL® tablets (astemizole), HydroDIURIL tablets (hydrochlorothiazide), Hydromox tablets (quinethazone), Hydropres tablets (reserpine and hydrochlorothiazide), Inderide® tablets (propranolol hydrochloride and hydrochlorothiazide), Inderides capsule® (propranolol hydrochloride and hydrochlorothiazide), Intal inhaler (cromolyn sodium), Intron A injection (recombinant interferon .alpha.-2b), Lamprene capsules (clofazimine), Lasix oral solution (furosemide), Lasix tablets (furosemide), Lasix injection (furosemide), Limbitrol tablets (chlordiazepoxide and amitriptyline hydrochloride), Lodine capsules (etodolac), Lopressor HCT tablets (metoprolol tartrate USP and hydrochlorothiazide USP), Lotensin tablets (benazepril hydrochloride), LOZOL® tablets (indapamide), Ludiomil tablets (maprotiline hydrochloride USP), Marplan tablets (isocarboxazid), MAXAQUIN® tablets (lomefloxacin HCl), Maxzide tablets (triamterene USP and hydrochlorothiazide USP), Mellaril® concentrate (thioridazine), Mellaril® tablets (thioridazine), Mellaril-S suspension (thioridazine), Mepergan injection (meperidine hydrochloride and promethazine hydrochloride), Methotrexate tablets (methotrexate), Mevacor tablets (lovastatin), Micronase tablets (glyburide), Minizide capsules (prazosin hydrochloride and polythiazide), Minocin intravenous ((4S-(4.alpha.,4a.alpha.,5a.alpha.,12a.alpha.))-4,7-bis(dimethylamino)-1,4,4a,5,5a,6,11,12a-octBPydro-3,10,12,12a-tetrBPydroxy-1,11-dioxo-2-naphthacenecarboxamide monohydrochloride), Minocin oral suspension ((4S-(4.alpha.,4a.alpha.,5a.alpha.,12a.alpha.))-4,7-bis(dimethylamino)-1,4,4a,5,5a,6,11,12a-octB-Pydro-3,10,12,12a-tetrBPydroxy-1,11-dioxo-2-naphthacenecarboxamide monohydrochloride), Minocin capsules ((4S-(4.alpha.,4a.alpha.,5a.alpha.,12a.alpha.))-4,7-bis(dimethylamino)-1,4,4a,5,5a,6,11,12a-octBPydro-3,10,12,12a-tetrBPydroxy-1,11-dioxo-2-naphthacenecarboxamide monohydrochloride), Moduretic tablets (amiloride HCl-hydrochlorothiazide), Monodox® capsules (doxycycline monohydrate), Monopril tablets (fosinopril sodium), Children's Motrin liquid suspension (ibuprofen), Motrin tablets (ibuprofen), Mykrox tablets (metolazone), NAPROSYN® suspension (naproxen), NAPROSYN® tablets (naproxen), Navane capsules (thiothixene), Navane intramuscular (thiothixene), NegGram caplets (nalidixic acid), NegGram suspension (nalidixic acid), Neptazane tablets (methazolamide), Nipent injection (pentostatin), Normodyne tablets (labetalol HCl), NOROXIN tablets (norfloxacin), Norpramin tablets (desipramine hydrochloride USP), oretic tablets (hydrochlorothiazide), Oreticyl Forte tablets (hydrochlorothiazide and deserpidine), Orinase tablets (tolbutamide), Ornade capsules (phenylpropanolamine hydrochloride and chlorpheniramine maleate), Orudis capsules (ketoprofen), Oxsoralen lotion (methoxypsoralen), PBZ tablets (tripelennamine hydrochloride USP), PBZ-SR tablets (tripelennamine hydrochloride USP), pHisoHex topical emulsion (hexachlorophene), P & S PLUS® topical tar gel (crude coal tar), Pamelor® capsules (nortriptyline HCl), Pamelor® solution (nortriptyline HCl), Paxil tablets (paroxetine hydrochloride), Pediazole oral suspension (erythromycin ethylsuccinate, USP and sulfisoxazole acetyl, USP), Penetrex™ tablets (enoxacin), Pentasa capsules (mesalamine), Periactin syrup (cyproheptadine HCl), Periactin tablets (cyproheptadine HCl), Phenergan tablets (promethazine hydrochloride), Phenergan injection (promethazine hydrochloride), Phenergan suppositories (promethazine hydrochloride), Phenergan syrup (promethazine hydrochloride), Polytrim® ophthalmic solution (trimethoprim sulfate and polymyxin B sulfate), Pravachol (pravastatin sodium), Prinivil® tablets (lisinopril, MSD), Prinzide tablets (lisinopril-hydrochlorothiazide), Prolixin elixir (fluphenazine hydrochloride), Prolixin enanthate (fluphenazine hydrochloride), Prolixin injection (fluphenazine hydrochloride), Prolixin oral concentrate (fluphenazine hydrochloride), Prolixin tablets (fluphenazine hydrochloride), ProSom tablets (estazolam), Prozac® oral solution (fluoxetine hydrochloride), Prozac® oral Pulvules® (fluoxetine hydrochloride), Pyrazinamide tablets (pyrazinamide), QUINAGLUTE® tablets (quinidine gluconate), Quinidex tablets (quinidine sulfate), Relafen tablets (nabumetone), Ru-Tuss II capsules (chlorpheniramine maleate and phenylpropanolamine hydrochloride), Seldane tablets (terfenadine), Septra tablets (trimethoprim and sulfamethoxazole), Septra suspension (trimethoprim and sulfamethoxazole), Septra I.V. infusion (trimethoprim and sulfamethoxazole), Septra tablets (trimethoprim and sulfamethoxazole), Ser-Ap-Es tablets (reserpine USP, hydralazine hydrochloride USP and hydrochlorothiazide USP), Sinequan capsules (doxepin HCl), Solganal injection (aurothioglucose, USP), Stelazine concentrate (trifluoperazine hydrochloride), Stelazine injection (trifluoperazine hydrochloride), Stelazine tablets (trifluoperazine hydrochloride), Surmontil capsules (trimipramine maleate), SYMMETREL capsules and syrup (amantadine hydrochloride), Taractan concentrate (chlorprothixene), Taractan injectable (chlorprothixene), Taractan tablets (chlorprothixene), TAVIST® syrup (clemastine fumarate, USP), TAVIST® tablets (clemastine fumarate, USP), TAVIST®-112 hour relief medicine (clemastine fumarate, USP), TAVIST®-D 12 hour relief medicine (clemastine fumarate, USP), Tegretol Tablets (carbamazepine USP), Tegretol suspension (carbamazepine USP), Temaril tablets (trimeprazine tartrate), Temaril syrup (trimeprazine tartrate), Temaril capsules (trimeprazine tartrate), TENORETIC® tablets (atenolol and chlorthalidone), Terramycin intramuscular solution (oxytetracycline), Thiosulfil Forte tablets (sulfamethizole), Thorazine ampuls (chlorpromazine hydrochloride), Thorazine concentrate (chlorpromazine hydrochloride), Thorazine multi-dose vials (chlorpromazine hydrochloride), Thorazine capsules (chlorpromazine hydrochloride), Thorazine suppositories (chlorpromazine hydrochloride), Thorazine syrup (chlorpromazine hydrochloride), Thorazine tablets (chlorpromazine hydrochloride), Timolide tablets (timolol maleate-hydrochlorothiazide), Tofranil ampuls (imipramine hydrochloride USP), Tofranil tablets (imipramine hydrochloride USP), Tofranil capsules (imipramine hydrochloride USP), Tolinase tablets (tolazamide), Triaminic Expectorant DH (phenylpropanolamine hydrochloride and guaifenesin), Triaminic oral infant drops (phenylpropanolamine hydrochloride, pheniramine maleate and pyrilamine maleate), Triavil tablets (perphenazine-amitriptyline HCl), Trilafon concentrate (perphenazine USP), Trilafon injection (perphenazine USP), Trilafon tablets (perphenazine, USP), Trinalin tablets (azatadine maleate, USP, and pseudoephedrine sulfate, USP), Vaseretic tablets (enalapril maleate-hydrochlorothiazide), Vasosulf opthalmic solution (sulfacetamide sodium-phenylephrine hydrochloride), Vasotec I.V. (enalapril maleate), Vasotec tablets (enalapril maleate), Velban® vials (vinblastine sulfate, USP), Vibramycin capsules (doxycycline monohydrate), Vibramycin intravenous (doxycycline monohydrate), Vibramycin oral suspension (doxycycline monohydrate), Vibra-Tabs tablets (oxytetracycline), Vivactil tablets (protriptyline HCl), Voltaren tablets (diclofenac sodium), X-SEB T® shampoo (crude coal tar), Zaroxolyn tablets (metolazone), ZESTORETIC® oral (lisinopril and hydrochlorothiazide), ZESTRIL® tablets (lisinopril), ZITHROMAX™ capsules (azithromycin), Zocor tablets (simvastatin), ZOLOFT® tablets (sertraline hydrochloride) and others.

A compound of the invention may also be administered in conjunction with the use of physical methods such as with light therapy or electrical stimulation.

The term "pharmaceutically acceptable carrier" include a pharmaceutically acceptable material, composition or vehicle, such as a liquid or solid filler, diluent, excipient, solvent or encapsulating material, involved in carrying or transporting a compound(s) of the present invention within or to the subject such that it can perform its intended function. Typically, such compounds are carried or transported from one organ, or portion of the body, to another organ, or portion of the body. Each carrier must be "acceptable" in the sense of being compatible with the other ingredients of the formulation and not injurious to the patient.

Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like.

Formulations of the present invention include those suitable for oral, nasal, topical, transdermal, buccal, sublingual, rectal, vaginal and/or parenteral administration. The formulations may conveniently be presented in unit dosage form and may be prepared by any methods well known in the art of pharmacy. The amount of active ingredient which can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol and glycerol monostearate; absorbents, such as kaolin and bentonite clay; lubricants, such a talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the active compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

The preparations of the present invention may be given orally, parenterally, topically, or rectally. They are of course given by forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administration is preferred.

The terms "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The terms "systemic administration," "administered systematically," "peripheral administration" and "administered peripherally" as used herein mean the administration of a compound, drug or other material other than directly into the central nervous system, for example, subcutaneous administration, such that it enters the patient's system and thus, is possibly subject to metabolism and other like processes.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

The regimen of administration can affect what constitutes an effective amount. The disorder target modulators, e.g., CNS disorder target modulators, can be administered to the subject either prior to or after the onset of a CNS disorder associated state. Further, several divided dosages, as well as staggered dosages, can be administered daily or sequentially, or the dose can be continuously infused, or can be a bolus injection. Further, the dosages of the disorder target modulators, e.g., CNS disorder target modulators, compound(s) can be proportionally increased or decreased as indicated by the exigencies of the therapeutic or prophylactic situation.

The language "subject" includes animals (e.g., mammals, e.g., cats, dogs, horses, pigs, cows, sheep, rodents, rabbits, squirrels, bears, primates (e.g., chimpanzees, gorillas, and humans) which are capable of suffering from a CNS associated disorder, e.g., a sleep disorder.

The language "therapeutically effective amount" of the compound is that amount necessary or sufficient to treat or prevent a state associated with a disorder, e.g., CNS disorder. The effective amount can vary depending on such factors as the size and weight of the subject, the type of illness, or the particular compound. For example, the choice of the therapeutic compound can affect what constitutes an "effective amount". One of ordinary skill in the art would be able to study the aforementioned factors and make the determination regarding the effective amount of the therapeutic compound without undue experimentation.

The language "penetrates into the CNS" includes the favorable biological property of a compound of the current invention to pass though, or penetrate, the blood brain barrier (BBB) and enter into the CNS.

The language "therapeutic compound" includes compounds of the invention capable of performing their intended function, e.g., treating CNS disorders and/or modulating CNS targets. The therapeutic compounds of the invention are described in detail herein.

Accordingly, the therapeutic compound can have the formula:

wherein CA includes moieties that modulate an active CNS target receptor or a collection of active CNS target receptors.

The language "drug activity modulating moiety", or "DA" is a moiety that provides the ability to modulate the activity of the therapeutic compound. Examples include functional moieties, e.g., ester, carboxylic acid or alcohol groups, selected and positioned within the therapeutic drug to provide the ability to modulate the activity of the drug, e.g., modulate, e.g., increase, the half-life of the drug, the ability of the drug to cross the blood brain barrier, or the ability of the drug to bind selectively to the desired receptor. In certain embodiments of the invention, the drug activity modulating moiety is an ester group, EG. In particular embodiments, the activity of the drug, e.g., half-life, of the therapeutic drug is modulated by controlling the rate of hydrolysis of the ester group by selection and positioning of steric bulk near the ester carbonyl of the ester group. In certain embodiments, the steric bulk is provided by the selection of a bulky ester group. In alternative embodiments the steric bulk is provided by substitution selected and positioned on the CA moiety, e.g., an AH moiety, near the carbonyl of the ester group.

In some aspects, the drug activity modulating moiety [DA] is represented by Z. In one embodiment, Z is $CO_2H$, $CONHS(O)_2$-Aryl (optionally substituted), $CONHS(O)_2$-Alkyl (optionally substituted), $CONHS(O)_2$-Heteroaryl (optionally substituted), $SO_3H$, $SO_2H$, $S(O)_2NHCO$-alkyl, $S(O)_2NHCO$-aryl, $S(O)NHCO$-alkyl, $S(O)NHCO$-aryl, $P(O)(OH)_2$, $P(O)OH$,

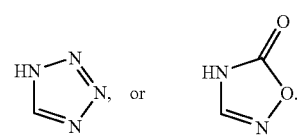

In another embodiment, Z is CO$_2$H, CONHS(O)$_2$-Aryl, CONHS(O)$_2$-Alkyl, or

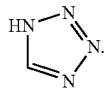

In still another embodiment, Z is CO$_2$H or

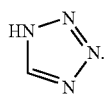

In a specific embodiment, the drug activity modulating moiety is a carboxylic acid, or a carboxylic acid bioisostere (hereinafter referred to as "bioisostere"), e.g., listed as "Z" above. In certain embodiments of the invention, the presence of the carboxylic acid or bioisostere results in the ability to form an intramolecular salt bridge that includes the carboxylate (or bioisostere) anion of the corresponding carboxylic acid (or bioisostere) with the protonated amine cation, both of which are present in the compound in the pH range that exists in the blood and in the small intestine. In one embodiment, penetration through the blood brain barrier into the CNS is allowed by conformational lipophilicity, i.e., lipophilicity as a result of a particular conformation, such as internal salt bridge formation between a carboxylate anion (or bioisostere anion) and a protonated amine. In another embodiment, due to conformational lipophilicity. the presence of the same intramolecular salt bridge also allows the oral absorption of the compound. In another embodiment, the presence of the carboxylic acid improves the ability of the compound to bind selectively to the desired receptor.

The language "ester group" includes an organic ester functionality that is selected and positioned within the compound providing the ability to modulate the activity or modify the properties of the corresponding therapeutic compound. The organic ester group may be terminal, e.g., a substituent, or internal. The carboxylate of the ester may be oriented from left to right or from right to left, e.g., a reverse ester. Examples of esters of the current invention include, but are not limited to hydrocarbons and perfluorocarbons. In a preferred embodiment, the hydrocarbons posses 1 to 20 carbons. In certain embodiments, the hydrocarbons can be linear, branched, cyclic, aromatic, and a combination of aliphatic and aromatic, which are optionally substituted with O, N, S, and/or halogens and may additionally include a center of chirality. In particular embodiments, the ester can be an n-propyl, an isopropyl, a t-butyl, a cyclopentyl, a cyclohexyl, a cycloheptyl, and a benzyl group.

The language "bulky ester" is intended to include an ester that has sufficient steric properties such that the rate of hydrolysis of the therapeutic compound is modulated, e.g., reduced, such that the activity of the therapeutic compound is modified, e.g., the length of activity is increased (i.e., the half-life of the therapeutic compound is increased). Examples of bulky ester groups are depicted in Table 1.

TABLE 1

Bulky Groups For H1 Antagonist Esters

R' = Parent Drug Core Structure
R = Ester from Alcohols below

TYPE A:

HO⏤     HO⏤     HO⏤

TYPE B:

HO⏤ H
Aldrich as R, S mixture
and pure R or S enantiomers.
Prepare esters with R, S mixture first.

HO⏤
Aldrich

HO⏤

HO⏤
Aldrich

HO⏤
1,3-dimethoxy-2-propanol
Tyger Scientific Inc.
Ewing, NJ

HO⏤
Aldrich

HO⏤
Aldrich

TABLE 1-continued

Bulky Groups For H1 Antagonist Esters

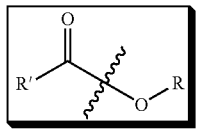

R' = Parent Drug Core Structure
R = Ester from Alcohols below

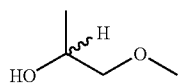

Aldrich as R, S mixture
Acros as pure R or S enantiomers.
Prepare esters with R, S mixture first.

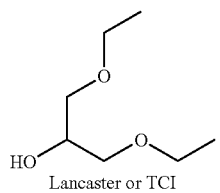

Lancaster or TCI

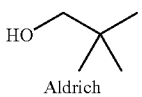

Aldrich

In certain embodiments, the ester is not methyl, ethyl, or n-propyl. In certain embodiments of the invention, the bulky ester is not an n-propyl, isopropyl, n-butyl, isobutyl, or tert-butyl ester. In certain embodiments of the invention, the ester is not a C-1 to C-4 ester. In certain embodiments of the invention wherein the therapeutic compound is a diphenhydramine-like, triprolidine-like, and doxepin-like compound, the ester is not a C-1 to C-4 ester and/or a C-3 to C-4 bulky ester.

The language "hydrocarbon" as used herein, includes substituted or unsubstituted alkyl, alkenyl, alkynyl, and aromatic or aryl moieties. The term "alkyl" includes saturated aliphatic groups, including straight-chain alkyl groups (e.g., methyl, ethyl, propyl, butyl, pentyl, hexyl, heptyl, octyl, nonyl, decyl, etc.), branched-chain alkyl groups (isopropyl, tert-butyl, isobutyl, etc.), cycloalkyl (alicyclic) groups (cyclopropyl, cyclopentyl, cyclohexyl, cycloheptyl, cyclooctyl), alkyl substituted cycloalkyl groups, and cycloalkyl substituted alkyl groups. The term alkyl further includes alkyl groups, which can further include oxygen, nitrogen, sulfur or phosphorous atoms replacing one or more carbons of the hydrocarbon backbone. In certain embodiments, a straight chain or branched chain alkyl has 6 or fewer carbon atoms in its backbone (e.g., $C_1$-$C_6$ for straight chain, $C_3$-$C_6$ for branched chain), and more preferably 4 or fewer. Likewise, preferred cycloalkyls have from 3-8 carbon atoms in their ring structure, and more preferably have 5 or 6 carbons in the ring structure. The term $C_1$-$C_6$ includes alkyl groups containing 1 to 6 carbon atoms.

Moreover, the term alkyl includes both "unsubstituted alkyls" and "substituted alkyls", the latter of which refers to alkyl moieties having substituents replacing a hydrogen on one or more carbons of the hydrocarbon backbone. Such substituents can include, for example, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Cycloalkyls can be further substituted, e.g., with the substituents described above. An "alkylaryl" or an "aralkyl" moiety is an alkyl substituted with an aryl (e.g., phenylmethyl (benzyl)). The term "alkyl" also includes the side chains of natural and unnatural amino acids.

The term "aryl" includes groups, including 5- and 6-membered single-ring aromatic groups that may include from zero to four heteroatoms, for example, benzene, phenyl, pyrrole, furan, thiophene, thiazole, isothiaozole, imidazole, triazole, tetrazole, pyrazole, oxazole, isooxazole, pyridine, pyrazine, pyridazine, and pyrimidine, and the like. Furthermore, the term "aryl" includes multicyclic aryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, napthridine, indole, benzofuran, purine, benzofuran, deazapurine, or indolizine. Those aryl groups having heteroatoms in the ring structure may also be referred to as "aryl heterocycles", "heterocycles," "heteroaryls" or "heteroaromatics". The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkylaminoacarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings which are not aromatic so as to form a polycycle (e.g., tetralin).

The term "alkenyl" includes unsaturated aliphatic groups analogous in length and possible substitution to the alkyls described above, but that contain at least one double bond.

For example, the term "alkenyl" includes straight-chain alkenyl groups (e.g., ethenyl, propenyl, butenyl, pentenyl, hexenyl, heptenyl, octenyl, nonenyl, decenyl, etc.), branched-chain alkenyl groups, cycloalkenyl (alicyclic) groups (cyclopropenyl, cyclopentenyl, cyclohexenyl, cycloheptenyl, cyclooctenyl), alkyl or alkenyl substituted cycloalkenyl groups, and cycloalkyl or cycloalkenyl substituted alkenyl groups. The term alkenyl further includes alkenyl groups which include oxygen, nitrogen, sulfur or phosphorous atoms replacing one or more carbons of the hydrocarbon backbone. In certain embodiments, a straight chain or branched chain alkenyl group has 6 or fewer carbon atoms in its backbone (e.g., $C_2$-$C_6$ for straight chain, $C_3$-$C_6$ for branched chain). Likewise, cycloalkenyl groups may have from 3-8 carbon atoms in their ring structure, and more preferably have 5 or 6 carbons in the ring structure. The term $C_2$-$C_6$ includes alkenyl groups containing 2 to 6 carbon atoms.

Moreover, the term alkenyl includes both "unsubstituted alkenyls" and "substituted alkenyls", the latter of which refers to alkenyl moieties having substituents replacing a hydrogen on one or more carbons of the hydrocarbon backbone. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "alkynyl" includes unsaturated aliphatic groups analogous in length and possible substitution to the alkyls described above, but which contain at least one triple bond.

For example, the term "alkynyl" includes straight-chain alkynyl groups (e.g., ethynyl, propynyl, butynyl, pentynyl, hexynyl, heptynyl, octynyl, nonynyl, decynyl, etc.), branched-chain alkynyl groups, and cycloalkyl or cycloalkenyl substituted alkynyl groups. The term alkynyl further includes alkynyl groups which include oxygen, nitrogen, sulfur or phosphorous atoms replacing one or more carbons of the hydrocarbon backbone. In certain embodiments, a straight chain or branched chain alkynyl group has 6 or fewer carbon atoms in its backbone (e.g., $C_2$-$C_6$ for straight chain, $C_3$-$C_6$ for branched chain). The term $C_2$-$C_6$ includes alkynyl groups containing 2 to 6 carbon atoms.

Moreover, the term alkynyl includes both "unsubstituted alkynyls" and "substituted alkynyls", the latter of which refers to alkynyl moieties having substituents replacing a hydrogen on one or more carbons of the hydrocarbon backbone. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

Unless the number of carbons is otherwise specified, "lower alkyl" as used herein means an alkyl group, as defined above, but having from one to five carbon atoms in its backbone structure. "Lower alkenyl" and "lower alkynyl" have chain lengths of, for example, 2-5 carbon atoms.

The term "acyl" includes compounds and moieties that contain the acyl radical ($CH_3CO$—) or a carbonyl group. The term "substituted acyl" includes acyl groups where one or more of the hydrogen atoms are replaced by for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "acylamino" includes moieties wherein an acyl moiety is bonded to an amino group. For example, the term includes alkylcarbonylamino, arylcarbonylamino, carbamoyl and ureido groups.

The term "aroyl" includes compounds and moieties with an aryl or heteroaromatic moiety bound to a carbonyl group. Examples of aroyl groups include phenylcarboxy, naphthyl carboxy, etc.

The terms "alkoxyalkyl", "alkylaminoalkyl" and "thioalkoxyalkyl" include alkyl groups, as described above, which further include oxygen, nitrogen or sulfur atoms replacing one or more carbons of the hydrocarbon backbone, e.g., oxygen, nitrogen or sulfur atoms.

The term "alkoxy" includes substituted and unsubstituted alkyl, alkenyl, and alkynyl groups covalently linked to an oxygen atom. Examples of alkoxy groups include methoxy, ethoxy, isopropyloxy, propoxy, butoxy, and pentoxy groups. Examples of substituted alkoxy groups include halogenated alkoxy groups. The alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy, trichloromethoxy, etc.

The term "amine" or "amino" includes compounds where a nitrogen atom is covalently bonded to at least one carbon or heteroatom. The term "alkyl amino" includes groups and compounds wherein the nitrogen is bound to at least one additional alkyl group. The term "dialkyl amino" includes groups wherein the nitrogen atom is bound to at least two additional alkyl groups. The term "arylamino" and "diarylamino" include groups wherein the nitrogen is bound to at least one or two aryl groups, respectively. The term "alkylarylamino," "alkylaminoaryl" or "arylaminoalkyl" refers to an amino group that is bound to at least one alkyl group and at least one aryl group. The term "alkaminoalkyl" refers to an alkyl, alkenyl, or alkynyl group bound to a nitrogen atom that is also bound to an alkyl group.

The term "amide" or "aminocarboxy" includes compounds or moieties that contain a nitrogen atom that is bound to the carbon of a carbonyl or a thiocarbonyl group. The term includes "alkaminocarboxy" groups that include alkyl, alkenyl, or alkynyl groups bound to an amino group bound to a carboxy group. It includes arylaminocarboxy groups that include aryl or heteroaryl moieties bound to an amino group that is bound to the carbon of a carbonyl or thiocarbonyl group. The terms "alkylaminocarboxy," "alkenylaminocarboxy," "alkynylaminocarboxy," and "arylaminocarboxy" include moieties wherein alkyl, alkenyl, alkynyl and aryl moieties, respectively, are bound to a nitrogen atom which is in turn bound to the carbon of a carbonyl group.

The term "carbonyl" or "carboxy" includes compounds and moieties that contain a carbon connected with a double bond to an oxygen atom. Examples of moieties that contain a carbonyl include aldehydes, ketones, carboxylic acids, amides, esters, anhydrides, etc.

The term "thiocarbonyl" or "thiocarboxy" includes compounds and moieties that contain a carbon connected with a double bond to a sulfur atom.

The term "ether" includes compounds or moieties that contain an oxygen bonded to two different carbon atoms or heteroatoms. For example, the term includes "alkoxyalkyl" which refers to an alkyl, alkenyl, or alkynyl group covalently bonded to an oxygen atom which is covalently bonded to another alkyl group.

The term "thioether" includes compounds and moieties that contain a sulfur atom bonded to two different carbon or hetero atoms. Examples of thioethers include, but are not limited to alkthioalkyls, alkthioalkenyls, and alkthioalkynyls. The term "alkthioalkyls" include compounds with an alkyl, alkenyl, or alkynyl group bonded to a sulfur atom that is bonded to an alkyl group. Similarly, the term "alkthioalkenyls" and "alkthioalkynyls" refer to compounds or moieties wherein an alkyl, alkenyl, or alkynyl group is bonded to a sulfur atom that is covalently bonded to an alkynyl group.

The term "hydroxy" or "hydroxyl" includes groups with an —OH or —O$^-$.

The term "halogen" includes fluorine, bromine, chlorine, iodine, etc. The term "perhalogenated," e.g., perfluorinated, generally refers to a moiety, e.g., perfluorocarbons, wherein all hydrogens are replaced by halogen atoms, e.g., fluorine.

The terms "polycyclyl" or "polycyclic radical" refer to two or more cyclic rings (e.g., cycloalkyls, cycloalkenyls, cycloalkynyls, aryls and/or heterocyclyls) in which two or more carbons are common to two adjoining rings, e.g., the rings are "fused rings". Rings that are joined through nonadjacent atoms are termed "bridged" rings. Each of the rings of the polycycle can be substituted with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, alkylaminoacarbonyl, aralkylaminocarbonyl, alkenylaminocarbonyl, alkylcarbonyl, arylcarbonyl, aralkylcarbonyl, alkenylcarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkyl, alkylaryl, or an aromatic or heteroaromatic moiety.

The term "heteroatom" includes atoms of any element other than carbon or hydrogen. Preferred heteroatoms are nitrogen, oxygen, sulfur and phosphorus.

In certain embodiments, the ester group does not substantially effect the biological activity of the therapeutic compound. Alternatively, in certain other embodiments the ester group significantly effects the biological activity of the therapeutic compound. In one embodiment of the invention, the ester group improves the biological activity of the therapeutic compound.

When the ester is a methyl or an ethyl ester, the formulation of the therapeutic compound is formulated to sufficiently treat the target disorder. In addition, formulations of the therapeutic compound can be used to provide controlled in vivo adsorption of the therapeutic compound over a discrete period of time.

In certain embodiments of the invention, the compound containing the drug activity modulating group, e.g., an ester, carboxylic acid, or alcohol group, possesses an improved selectivity of the drug for a desired receptor versus an undesired receptors over the corresponding compound without this group. In certain embodiments of the invention, the compound containing the drug activity modulating group, e.g., an ester, carboxylic acid, or alcohol group, is more active as a therapeutic agent for treating disorders than the corresponding compound without this group. In specific embodiments, the ester is more active as a therapeutic agent for treating disorders than the corresponding acid of the ester. In particular embodiments, the corresponding acid of the ester is not a therapeutically active agent for treating disorders. In alternative embodiments, the corresponding acid of an ester is more active as a therapeutic agent for treating disorders than the corresponding ester of the acid. In a particular embodiment, the carboxylic acid drug activity modulating group provides an internal salt with an amine and allows crossing of the blood brain barrier.

One skilled in the art would recognize that the ester groups, as described above, could be extended to thioesters. Labile amides may also be used in replacement of the ester group, wherein the in vivo hydrolysis would be performed by peptidases in the CNS.

The language "biological activity" includes activity associated with the intended biological function of the compounds of the present invention, e.g., treating a CNS disorder.

The language "modulate a target" or "modulation of a target" includes the act of agonizing or antagonizing a receptor or group of receptors of a target disorder. Thus, a compound that agonizes or antagonizes a receptor or group of receptors is referred to herein as a target modulator, e.g., CNS disorder target modulator. The language "target modulator" includes compounds or compositions, e.g., pharmaceutical compositions, which are used to modulate a target, e.g., a CNS disorder target, e.g., a sleep disorder target The terms "modification" or "modifies" include controlling or adjusting physical or chemical parameters, e.g., the half-life, of the therapeutic compound in vivo by changing one or more factors, e.g., the lipophilicity, electronic properties and/or steric size of the drug activity modulating moiety, e.g., ester group.

The language "spacer molecule" or "SP" includes molecules or moieties that are positioned within the compound to allow the compound to perform its intended function. In certain embodiments, the spacer molecule may be present. Alternatively, in certain other embodiments, the spacer molecule may not be present. In certain embodiments, the spacer molecule may be $(CH_2)_m$, where m is an integer number selected from 1 to 20. In addition, the spacer molecule, e.g., the $(CH_2)_m$ linker to an ester or a carboxylic acid group, can be substituted with one or more substituents. In one embodiment, the spacer molecule is mono-substituted. In another embodiment of the invention, the spacer molecule is disubstituted. In particular embodiments, the linkers of the invention may be geminally-dialkylated, e.g., gem-dimethylated, singly substituted with a substituent other than a noncyclic alkyl group, e.g., a heteroatom, or a cyclic substituent wherein one or more of the carbons of the spacer molecule is contained in the ring, e.g., heterocycle (e.g., tetrahydropyran or tetrahydrofuran), or cyclic alkyl, e.g., cyclopropyl. However, the substitution of the spacer molecule is independent of the substitution elsewhere in the molecule.

In one aspect, the spacer molecule ("SP") links an antihistamine moiety ("AH") with a drug activity modulating moiety, Z. The resulting compound has the following formula:

[AH]-SP-[Z]

In one embodiment, SP has the following chemical structure:

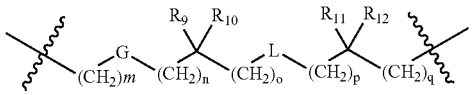

where m n, o, p, q are, individually, 0-6, the $CH_2$ groups are optionally branched, and any member of the alkylene linker (e.g., the portion of the molecule connecting the antihistamine with the Z group) is substituted with one or more substituents; G and L are, individually, absent or O, S, C(O), SO or $SO_2$; and $R_9$-$R_{12}$ are H, $C_1$-$C_5$ straight chain or branched alkyl (optionally containing a heteroatom). Optionally, substituents on nearby atoms are connected to form a ring of size 3-7 or substituents on the same atom (i.e., geminal substituents) are connected to form a ring of size 3-7. Optionally, $R_{11}$ and $R_{12}$, and the carbon to which they are attached are absent.

In another embodiment, SP has the following chemical structure

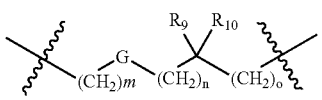

where m n, and o, are, individually, 0-6, and the $CH_2$ groups in the linker are optionally branched; G is absent or O, S, C(O), SO or $SO_2$; $R_9$-$R_{10}$ are H, $C_1$-$C_5$ straight chain or branched alkyl (optionally containing a heteroatom), and/or are connected to form a ring of size 3-7.

In yet another embodiment, SP has the following chemical structure

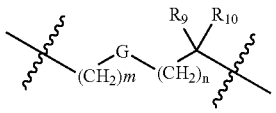

where m and n are, individually, 0-4, and the $CH_2$ moieties are optionally branched; G is absent or O, S, C(O), SO or $SO_2$; $R_9$-$R_{10}$ are H, $C_1$-$C_3$ alkyl, optionally with heteroatom substitution, branching and/or connected to form a ring of size 3-5.

In still another embodiment, SP has the following chemical structure

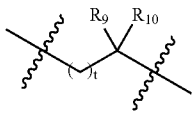

where t is between 0 and 6; $R_9$-$R_{10}$ are H, $CH_3$ or $CH_2CH_3$, or are lower alkyl or lower heteroalkyl and are connected to form a spiro ring of size 3 to 7.

The term "target" includes a receptor or group of receptors that have been identified as useful point of action for a therapeutic compound, e.g., CNS target, e.g., sleep disorder target, e.g., histamine receptor.

The language "receptor" includes specific sites of binding or action within a subject, associated or responsible for the activity of the target disorder, e.g., a histamine or adenosine receptor.

The language "group of receptors" includes two or more receptors that may comprise the same receptor type or may comprise two or more receptor types.

As used herein, the term "analog" refers to a chemical compound that is structurally similar to another but differs slightly in composition (as in the replacement of one atom by an atom of a different element or in the presence of a particular functional group, or the replacement of one functional group by another functional group). Thus, an analog is a compound that is similar or comparable in function and appearance, but not in structure or origin to the reference compound. For example, the reference compound can be a reference antihistamine such as doxepin, and an analog is a substance possessing a chemical structure or chemical properties similar to those of the reference antihistamine.

As defined herein, the term "derivative", e.g., in the term "antihistamine derivatives", refers to compounds that have a common core structure, and are substituted with various groups as described herein. For example, all of the compounds represented by formulae A-AAA are antihistamine derivatives, and have one of formulae A-AAA as a common core.

The term "nonREM peak sleep time" is defined as an absolute peak amount of nonREM sleep per hour post treatment, with drug administration occurring at Circadian Time (CT) 18, which is 6 hours after lights off in a nocturnal laboratory rat when housed in a LD 12:12 (12-hours light and 12 hours dark) light-dark cycle. The nominal criteria of 55% nonREM sleep per hour is equivalent to 33 minutes of nonREM sleep per hour.

As used herein, the term "cumulative nonREM sleep" is defined as the net total aggregate increase in the number of minutes of nonREM sleep, measured through out the entire duration of a drug's soporific effect, which typically, but not always occurs in the first 6 hours post-treatment, adjusted for the net total aggregate number of minutes of nonREM sleep that occurred during the corresponding non-treatment baseline times of day recorded 24 hours earlier, relative to like vehicle control treatment.

As defined herein, the term "sleep bout" refers to a discrete episode of continuous or near continuous sleep, comprised of nonREM sleep, REM sleep, or both nonREM and REM sleep stages, delimited prior and after the episode by greater than two contiguous 10 second epochs of wakefulness.

As used herein, the term "longest sleep bout length" is defined as the total number of minutes an animal remains asleep (nonREM and/or REM sleep stages) during the single longest sleep episode or "bout" that occurred beginning in a given hour post-treatment. The "sleep bout length" measurement criteria assumes sleep is measured continuously in 10 second epochs, and is scored based upon the predominant state, computed or otherwise determined as a discrete sleep stage (where sleep stages are defined as nonREM sleep, REM sleep, or wakefulness) during the 10 second interval that defines the epoch.

The term "average sleep bout length" is defined as the average duration (in minutes) of every sleep bout that began in a given hour, independent of the individual duration of each episode or bout.

"Rebound insomnia" is defined as period of rebound, paradoxical, or compensatory wakefulness that occurs after the sleep promoting effects of a hypnotic or soporific agent.

"REM sleep inhibition" is defined as the reduction of REM sleep time post-treatment at CT-18 (6 hours after lights-off; LD 12:12) or at CT-5 (5 hours after lights-on; LD 12:12). Compounds that reduce REM sleep time by greater than 15 minutes (relative to baseline and adjusted for vehicle treatment) when administered at either CT-18 or CT-5 are considered unacceptable.

Compared with NREM sleep or wakefulness, REM sleep causes ventilatory depression and episodic cardiovascular changes. During rebound insomnia, the physiological effects of REM sleep are magnified and interrupt the normal sleep cycles.

As defined herein, "disproportionate locomotor activity inhibition" is a reduction of locomotor activity that exceeds the normal and expected reduction in behavioral activity attributable to sleep.

The invention provides a method of modulating sleep by administering an effective amount of an antihistamine analog or antihistamine derivative of the invention, which is a moiety that antagonizes a histamine receptor or a collection of histamine receptors.

Effective sleep modulators have certain characteristics that correspond with increased efficacy and decreased side effects. These characteristics include a desired half-life in a subject, controlled onset of desired sedative effects, and minimal to no detectable effect on psychomotor or other central nervous system (CNS) side effects (e.g., memory deficits, decreased muscle tone, drooping eyelids or drowsiness). For example, effective sleep modulators have a half life in humans of less than 7 hours, less than 6 hours, less than 5 hours, less than 4 hours, approximately 3 hours, or in the range of 3 to 7 hours.

One approach to developing an effective sleep modulator is strategically derivitizing a known compound or family of compounds with sleep modulating activity. Derivitizing may enhance one or more biological properties to allow a compound to perform in an improved manner. Examples of favorable biological properties include, but are not limited, to induction of a discrete sleep or hypnotic state, activity of the therapeutic compound for a discrete period of time, penetration through the blood brain barrier into the CNS, e.g., resulting from lipophilicity of substituents or conformational lipophilicity (i.e., lipophilicity as a result of a particular conformation, such as internal salt formation between a carboxylate anion and a protonated amine), modulation of the half-life of the therapeutic compound, an alteration of charge, an alteration of pharmacokinetics, an alteration of log P by a value of one or more, increased receptor selectivity, reduced peripheral half-life, the ability to increase dosage, increased peripheral elimination, decreased anti-muscarinic activity, decreased anti-cholinergic, and any combination thereof.

Derivitizing results in a variety of effects and alter different mechanisms of action. For example, in some circumstances, a compound containing a particular functional group, such as, e.g., an ester, carboxylic acid, or alcohol group, possesses an improved selectivity for a desired receptor versus undesired receptors when compared with a compound without this group. In other circumstances, the compound containing the particular functional group is more active as a therapeutic agent for treating sleep disorders than the corresponding compound without this group. The effect of the derivitized compound depends on the identity of the addition.

By derivitizing a compound in order to enhance favorable biological properties and decrease undesirable side effects, it is possible to implement a strategy based upon maintaining a compound's desired level of effect on the desired target while minimizing effects on undesired targets.

Compounds of the invention can also be derivitized to produce prodrugs. "Prodrug" includes a precursor form of the drug which is metabolically converted in vivo to produce the active drug. The invention further contemplates the use of prodrugs which are converted in vivo to the sleep modulating compounds used in the methods of the invention (see, e.g., R. B. Silverman, 1992, "The Organic Chemistry of Drug Design and Drug Action", Academic Press, Chp. 8). Such prodrugs can be used to alter the biodistribution (e.g., to allow compounds which would not typically cross the blood-brain barrier to cross the blood-brain barrier) or the pharmacokinetics of the sleep modulating compound. For example, an anionic group, e.g., a carboxylate, sulfate or sulfonate, can be esterified, e.g., with an alkyl group (e.g., a methyl group) or a phenyl group, to yield an ester. When the ester is administered to a subject, the ester is cleaved, enzymatically or non-enzymatically, reductively or hydrolytically, to reveal the anionic group. Such an ester can be cyclic, e.g., a cyclic sulfate or sulfone, or two or more anionic moieties may be esterified through a linking group. An anionic group can be esterified with moieties (e.g., acyloxymethyl esters) which are cleaved to reveal an intermediate sleep modulating compound which subsequently decomposes to yield the active sleep modulating compound. In one embodiment, the prodrug is a reduced form of a carboxylate, sulfate or sulfonate, e.g., an alcohol or thiol, which is oxidized in vivo to the sleep modulating compound. Furthermore, an anionic moiety can be esterified to a group which is actively transported in vivo, or which is selectively taken up by target organs.

This strategy is applied to sleep modulating compounds to improve their effectiveness and safety in clinical use.

In particular, the therapeutic compound of the invention may comprise the formula:

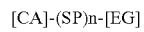
[CA]-(SP)n-[EG]

wherein CA is a compound that modulates an active CNS target receptor or a collection of active CNS target receptors, EG is an ester group that modifies the half-life of the therapeutic compound, SP is a spacer molecule, and n is 0 or 1.

In certain embodiments, the CNS disorder is a sleep disorder. In particular embodiments of the current invention wherein the CNS disorder is a sleep disorder, the therapeutic compound of the invention may comprise one of the formulae:

[AD]-(SP)n-[EG]

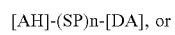
[AH]-(SP)n-[DA], or

[AH]-(SP)n-[EG]

wherein AH is a compound that antagonizes a histamine receptor or a collection of histamine receptors, AD is a compound that agonizes an adenosine receptor or a collection of adenosine receptors, DA is a drug activity modulating moiety that provides the ability to modulate the activity of the therapeutic compound, EG is an ester group that modifies the half-life of the therapeutic compound, SP is a spacer molecule, and n is 0 or 1.

The language "compounds that agonize" a receptor, e.g., agonizes an adenosine receptor, are intended to include compounds that induce the activity of the receptor and agents that up-regulate (i.e., induce) the synthesis or production of the receptor.

The language "compounds that antagonize" a receptor, e.g., a histamine receptor, are intended to include compounds that inhibit the activity of the receptor and agents that down-regulate (i.e., inhibit) the synthesis or production of the receptor.

The language "adenosine receptor agonist" is intended to include art recognized allosteric and nonallosteric adenosine receptor agonists, including, but not limited to cyclohexyladenosine, pentostatin, conformycin, and purine and adenyl derivatives that useful as adenosine precursors for the enhancement of adenosine synthesis. Adenosine has been reported to have cardioprotective and neuroprotective properties. It is reportedly released from cells in response to alterations in the supply of or demand for oxygen, is said to be a potent vasodilator, and is believed to be involved in the metabolic regulation of blood flow. However, adenosine has a short half-life (<1 sec) in human blood, and therefore high doses of adenosine would need to be administered continuously to achieve effective levels. However, high doses of adenosine have been reported to be toxic, and thus limit its therapeutic potential. It is also believed that by increasing adenosine concentration locally, i.e., at the target site within the target tissue, the beneficial effects of adenosine can be provided and the toxic systemic effects minimized. In certain embodiments, the therapeutic compounds of formula [AD]-(SP)n-[EG], described above, may be used in the methods of the current invention to increase the local adenosine concentration.

The language "histamine antagonist," "antihistamine" and "[AH]" are used interchangeably and are intended to include any compound that antagonizes a histamine or group of histamine receptors. An antihistamine is a compound that binds to a H1 receptor and blocks the action of histamine. In certain embodiments, the compound of the invention will bind to a histamine receptor with an affinity of less than about 100 μM, e.g., less than about 10 μM. In one embodiment, antihistamines of the present invention contain at least two aryl rings that are separated by about 2-5 atoms from a basic nitrogen atom. In specific embodiments, the two aryl rings are connected to the same atom. The language "histamine antagonist" is intended to include art-recognized antihistamines, including both first and second generation antihistamines. For example, the antihistamines of the invention include, but are not limited to, antihistamines such as ethylenediamines, ethanolamines, alkylamines, phenothiazines, piperazines, piperdines, ketotifen, ebastine, terfenadine, acrivastine, triprolidine, doxepin, amitriptyline, trimipramine, protriptyline, nortriptyline, desipramine, pheniramine, diphenhydramine, mequitazine, cyproheptadine, clemastine, diphenylpyraline, promethazine, homochlorocyclizine, alimemazine, mepyramine, methapyraline, peroxatine, trazodone, nefazodone, hydroxyzine, meclizine loratidine, azelastine, levocabastine, cetirizine, fexofenadine, mizolastine, mirtazapine, and astemizole.

Classes of antihistamines of the instant invention also include pheniramine-like compounds, doxepin-like compounds, diphenhydramine-like compounds, triprolidine-like compounds, pheniramine analogs, and acrivastine analogs (see for example, Tables 2 and 3). It should be understood that the classes of antihistamines can be substituted or unsubstituted. In addition, the substituent(s) is selected and positioned within the molecule such that the compound is able to perform its intended function. Specific examples and locations of the substituents are discussed below.

In one aspect, the invention relates to the development of sleep modulating compounds by modifying an antihistamine core (AH), which contains a basic nitrogen, with a linker molecule A comprising a spacer, SP, and a drug modulating moiety, Z.

In one embodiment, the modified antihistamine has the following structure

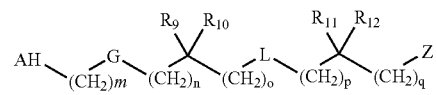

where m n, o, p, q are, individually, 0-6, the $CH_2$ groups are optionally branched, and any member of the alkylene linker (e.g., the portion of the molecule connecting the antihistamine with the Z group) is substituted with one or more substituents; G and L are, individually, absent or O, S, C(O), SO or $SO_2$; $R_9$-$R_{12}$ are H, $C_1$-$C_5$ straight chain or branched alkyl (optionally containing a heteroatom). Optionally, substituents on adjacent atoms are connected to form a ring of size 3-7 or substituents on the same atom (i.e., geminal substituents) are connected to form a ring of size 3-7; and Z is $CO_2H$, $CONHS(O)_2$-Aryl (optionally substituted), $CONHS(O)_2$-Alkyl (optionally substituted), $CONHS(O)_2$-Heteroaryl (optionally substituted), $SO_3H$, $SO_2H$, $S(O)_2NHCO$-alkyl, $S(O)_2NHCO$-aryl, $S(O)NHCO$-alkyl, $S(O)NHCO$-aryl, $P(O)(OH)_2$, $P(O)OH$, N,

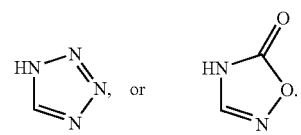

In another embodiment, the modified antihistamine has the following structure

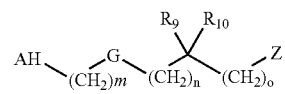

where m n, and o, are, individually, 0-6, and the $CH_2$ groups in the linker are optionally branched; G is absent or O, S, C(O), SO or $SO_2$; $R_9$-$R_{10}$ are H, $C_1$-$C_5$ straight chain or branched alkyl (optionally containing a heteroatom), and/or are connected to form a ring of size 3-7; Z is $CO_2H$, $CONHS(O)_2$-Aryl, $CONHS(O)_2$-Alkyl, or

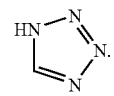

In yet another embodiment, the modified antihistamine has the following structure

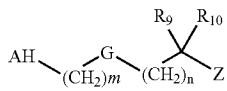

where m and n are, individually, 0-4, and the $CH_2$ moieties are optionally branched; G is absent or O, S, C(O), SO or $SO_2$; $R_9$-$R_{10}$ are H, $C_1$-$C_3$ alkyl, optionally with heteroatom substitution, branching and/or connected to form a ring of size 3-5; Z is $CO_2H$, $CONHS(O)_2$-Aryl, $CONHS(O)_2$-Alkyl, or

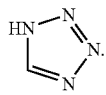

In still another embodiment, the modified antihistamine has the following structure

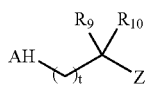

where t is between 0 and 6; $R_9$-$R_{10}$ are H, $CH_3$ or $CH_2CH_3$, and are optionally connected to form a spiro ring of size 3 to 6; and Z is $CO_2H$ or

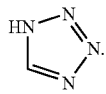

Antihistamine cores are modified by adding a linker molecule A, which comprises a spacer, SP, and a drug modulating moiety, Z. All possible isomers are contemplated, unless otherwise noted. Examples of antihistamine cores include the following generic formulae:

Formula A

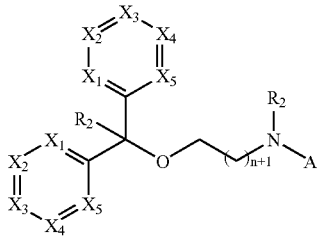

Formula B

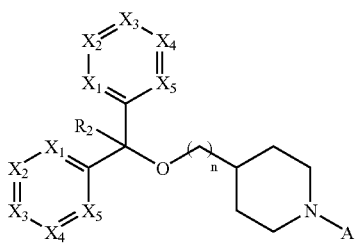

-continued

Formula C

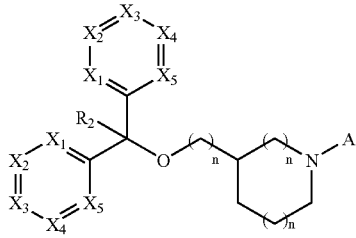

Formula D

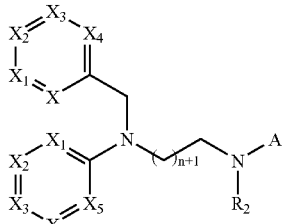

Formula E

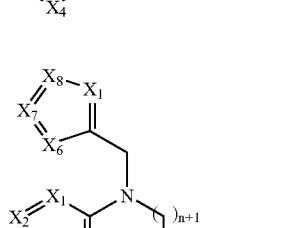

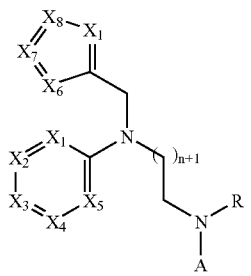

Formula F

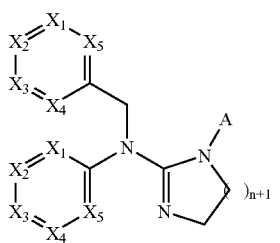

Formula G

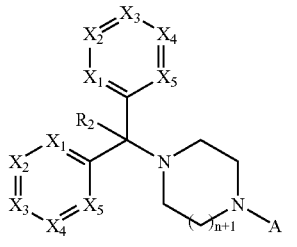

Formula H

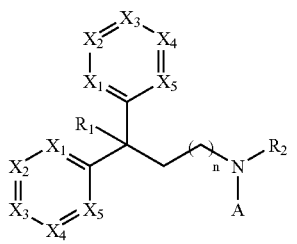

-continued
Formula I
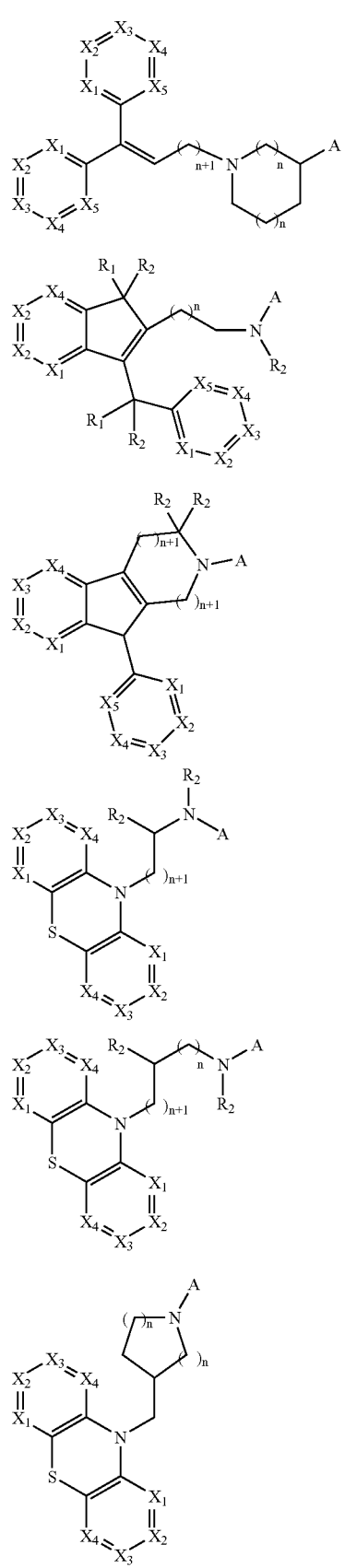
Formula J
Formula K
Formula L
Formula M
Formula N
-continued
Formula O
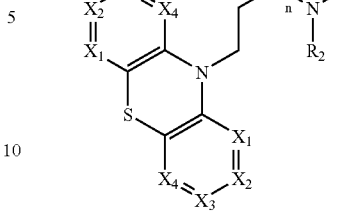
Formula P
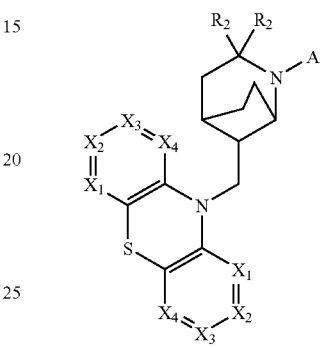
Formula Q
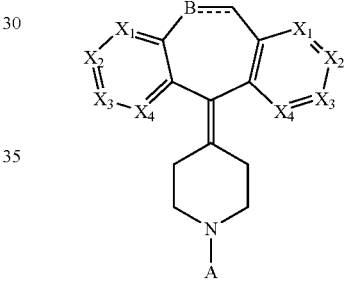
Formula R
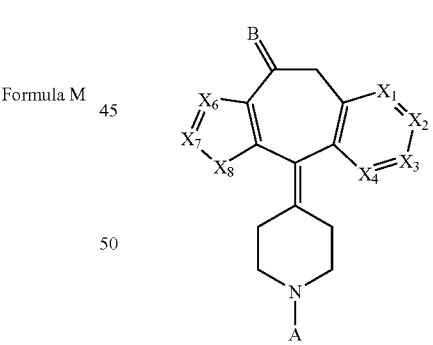
Formula S
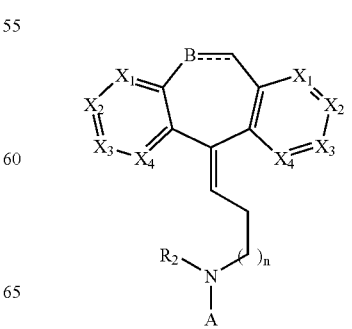

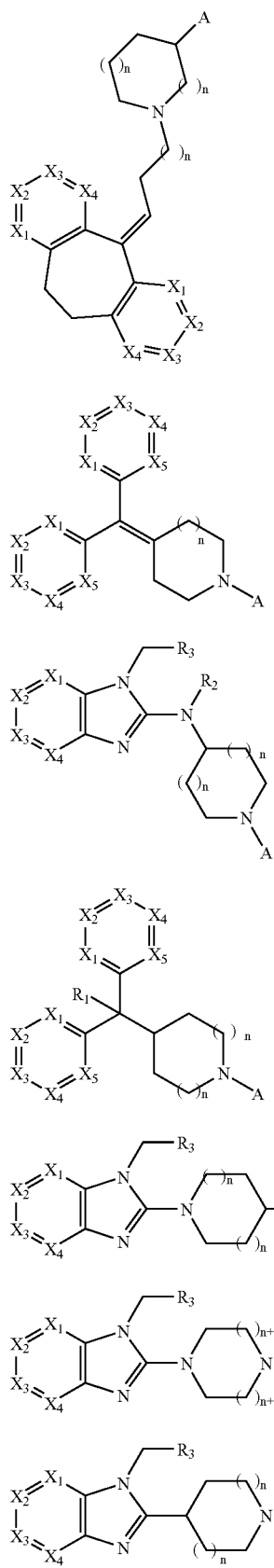
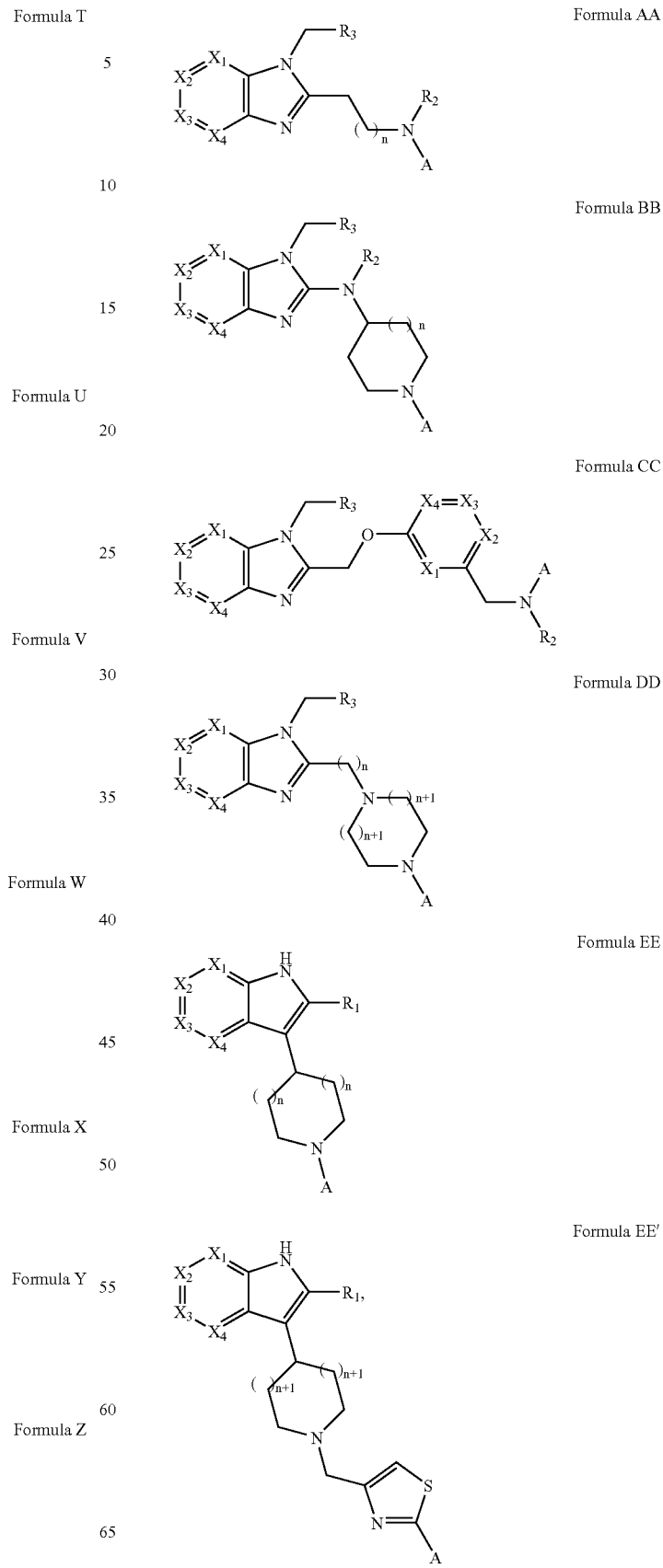

-continued
Formula FF
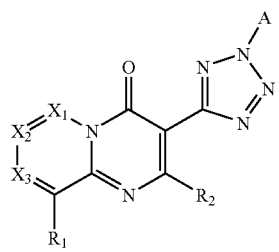
Formula FF'
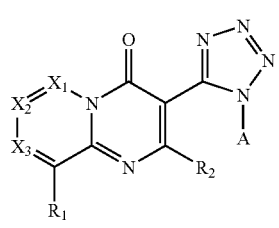
Formula GG
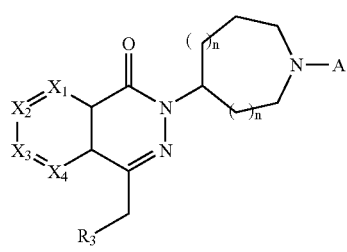
Formula HH
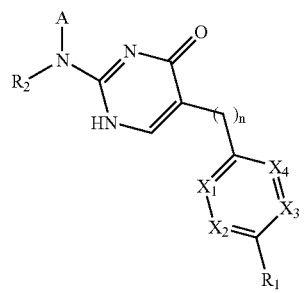
Formula HH'
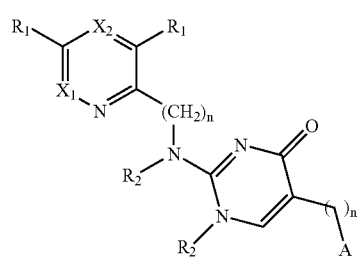
Formula II
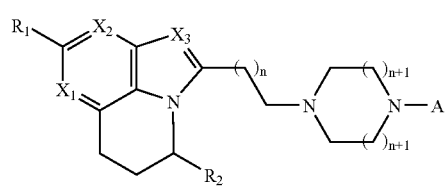
-continued
Formula JJ
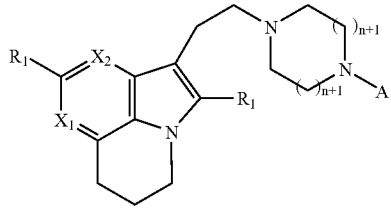
Formula KK
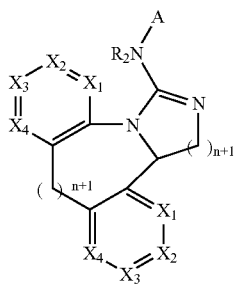
Formula LL
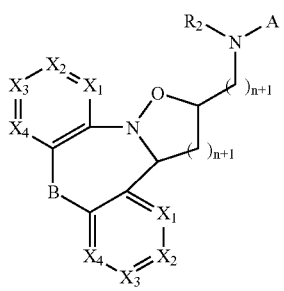
Formula MM
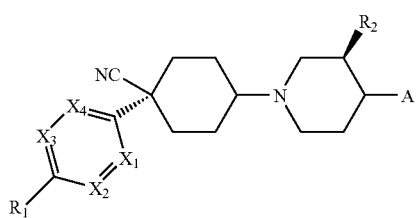
Formula NN
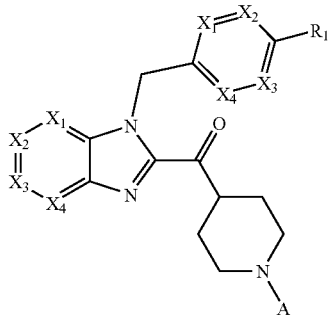
Formula OO
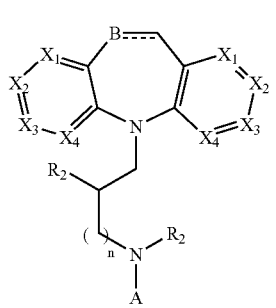

-continued
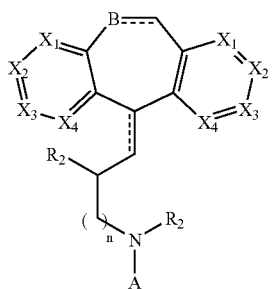
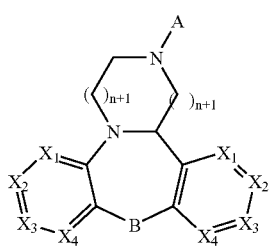
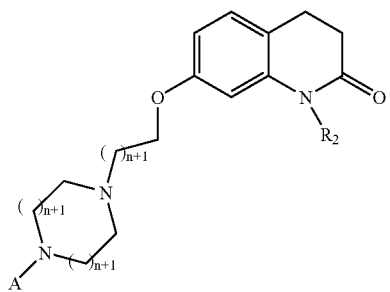
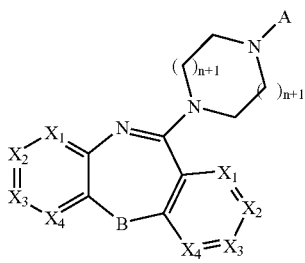
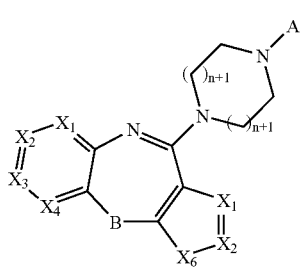
-continued
Formula PP
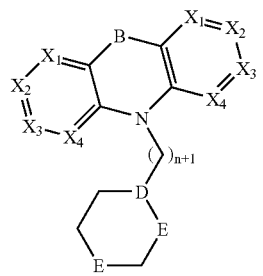
Formula QQ
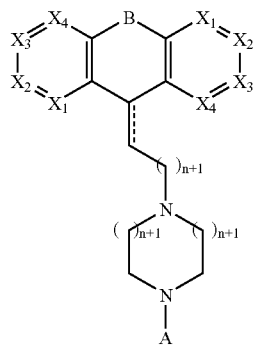
Formula RR
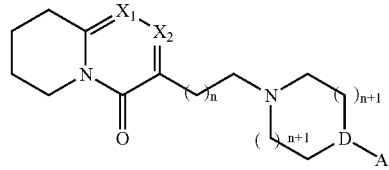
Formula SS
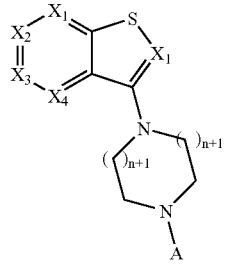
Formula TT
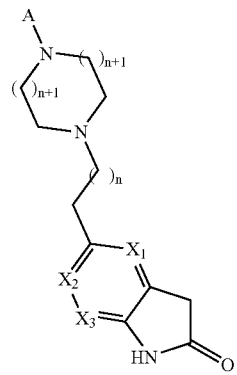
Formula UU
Formula VV
Formula WW
Formula XX
Formula XX'

-continued

Formula YY

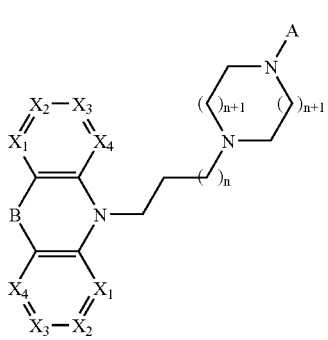

Formula ZZ

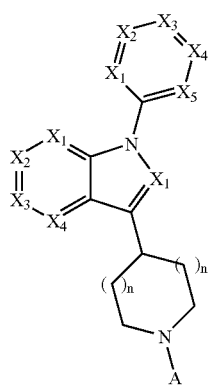

Formula AAA

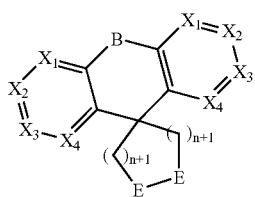

Formula BBB

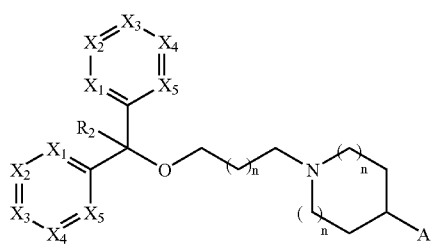

For each of formulae A-AAA $X_1$-$X_5$ are, independently, selected from CR or N, wherein R is H, lower alkyl, fluoroalkyl (e.g., $CF_3$), F, Cl, Br, lower alkoxy, thioalkyl, lower alkoxyalkyl, fluoroalkoxy (e.g. $CF_3O$), alkylcarboxyl, alkylcarboxyl ester, and wherein the $X_n$ of one aryl ring is the same or different from the corresponding $X_n$ of another aryl ring; $X_6$-$X_8$ is selected from N, S, Se, O or CR, wherein R is H, lower alkyl, fluoroalkyl (e.g., $CF_3$), F, Cl, Br, lower alkyloxy, thioalkyl, lower alkoxyalkyl, fluoroalkoxy (e.g., $CF_3O$), alkylcarboxyl, alkylcarboxyl ester; $R_1$ is H, OH, lower alkyl, lower alkyloxy; $R_2$ is H, lower alkyl; $R_3$ is H, alkyl, alkyloxy, alkylaryl; each $R_1$, $R_2$, $R_3$ is the same or different when multiply attached to a structure, e.g., if there are two $R_1$'s then each $R_1$ is defined independently and may be the same identity or different; B is NR, S, O, $CH_2$ when double bond is absent, or CR when a double bond is present; n is an integer from 0 to 4 and is the same or different when present more than once in a structure; D is CH or N; and E is $CH_2$ or N-A, provided that at least one E in each formula is N-A. All possible isomers are contemplated, unless otherwise noted.

Specific examples of modified antihistamines according to formula A include the following:

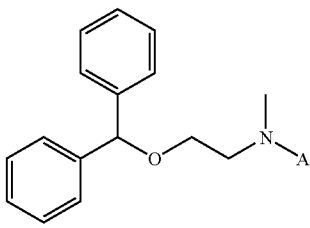

Diphenhydramine
Analogs

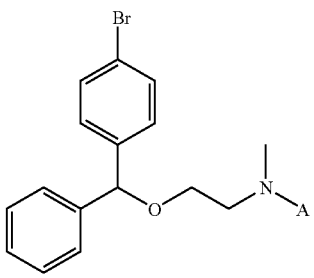

Bromodiphenhydramine
Analogs

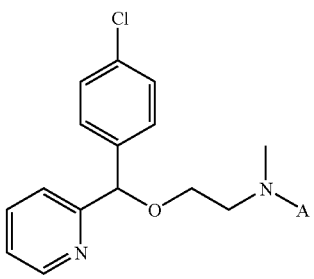

Carbinoxamine
Analogs

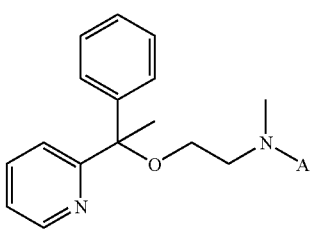

Doxylamine
Analogs

Specific examples of modified antihistamines according to Formula B include the following:

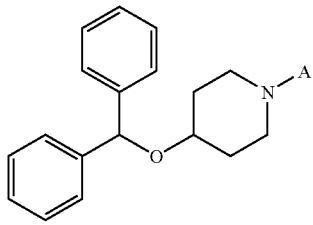

Diphenylpyraline
Analogs

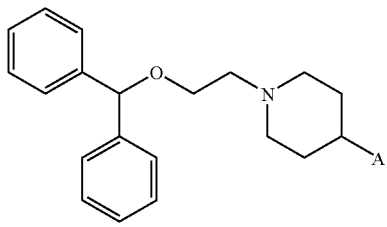

BM-113 (Les Laboratoires
Meram) Analogs

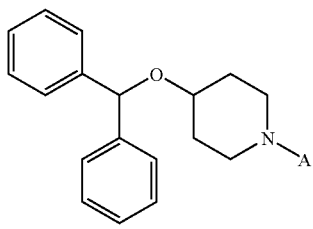

Ebastine and
Carbastine Analogs

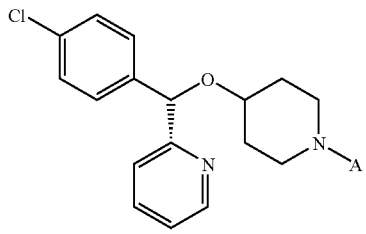

Betotastine
Analogs

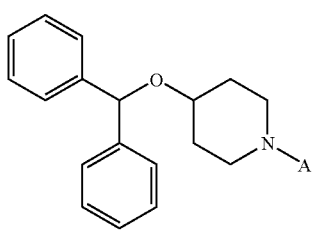

WY-49051
Analogs

Specific examples of modified antihistamines according to Formula C include the following:

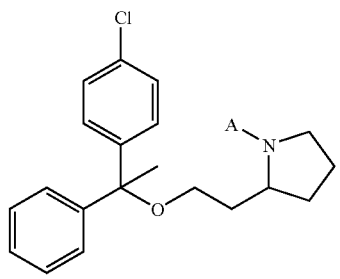

Clemastine
Analogs

Specific examples of modified antihistamines according to Formula D include the following:

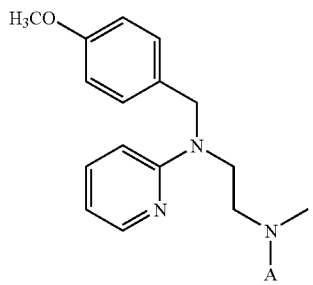

Pyrilamine
Analogs

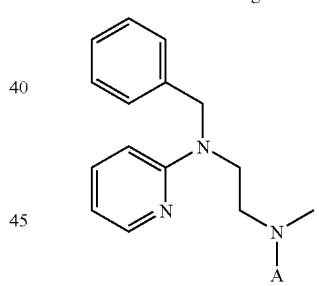

Tripelennamine
Analogs

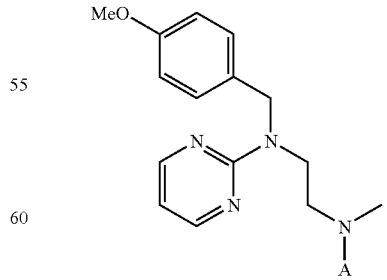

Thonzylamine
Analogs

Specific examples of modified antihistamines according to Formula E include the following:

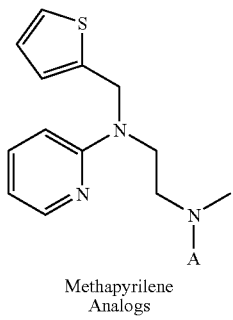

Methapyrilene
Analogs

Specific examples of modified antihistamines according to Formula F include the following:

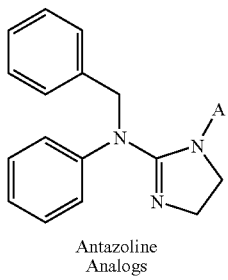

Antazoline
Analogs

Specific examples of modified antihistamines according to Formula G include the following:

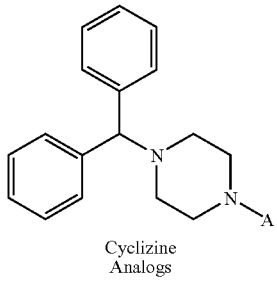

Cyclizine
Analogs

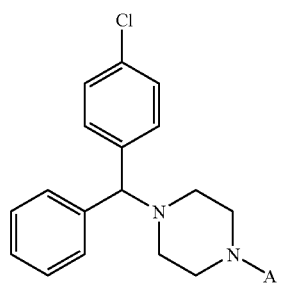

Chlorcyclizine, Meclizine,
Hydroxyzine, Buclizine, Cetirizine,
UCB-35440 (H1, Leukotriene
synthesis, 5-Lipo inhibitor) Analogs -continued

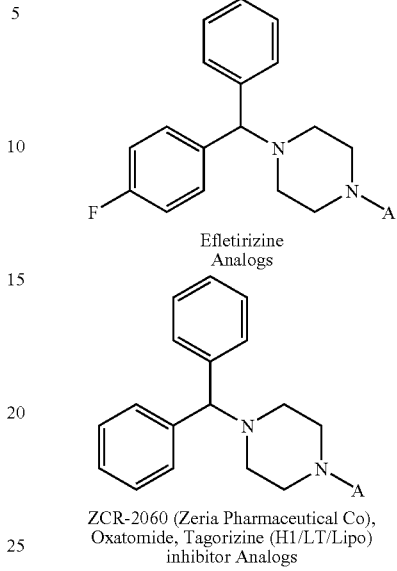

Efletirizine
Analogs

ZCR-2060 (Zeria Pharmaceutical Co),
Oxatomide, Tagorizine (H1/LT/Lipo)
inhibitor Analogs Specific examples of modified antihistamines according to Formula H include the following:

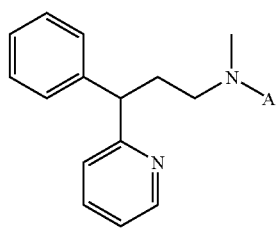

Pheniramine
Analogs

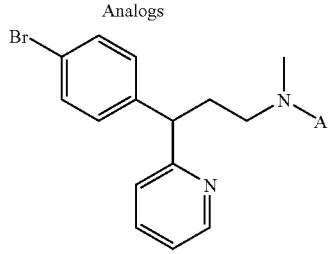

Brompheniramine
Analogs

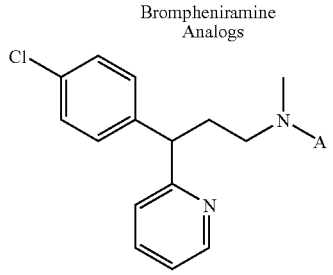

Chlorpheniramine
Analogs

Specific examples of modified antihistamines according to Formula I include the following:

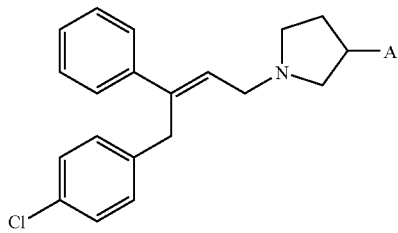

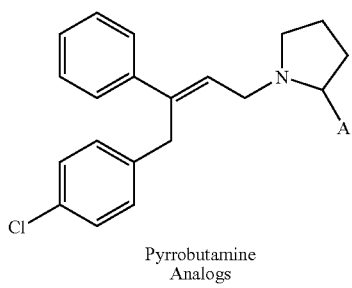

Pyrrobutamine
Analogs

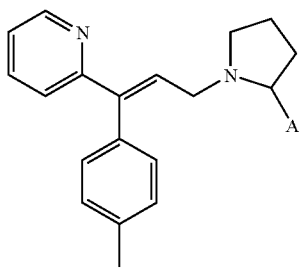

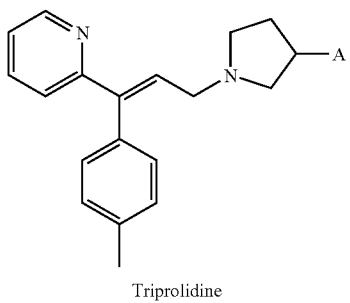

Triprolidine
Analogs

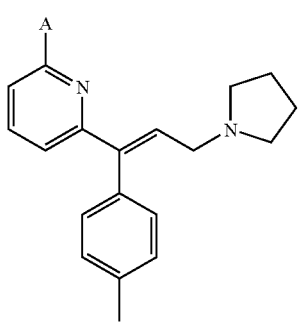

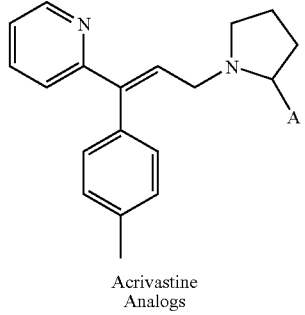

Acrivastine
Analogs

Specific examples of modified antihistimines according to Formula J include the following:

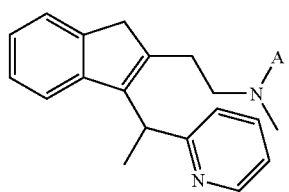

Dimethindene
Analogs

Specific examples of modified antihistamines according to Formula K include the following:

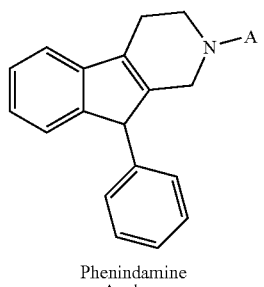

Phenindamine
Analogs

Specific examples of modified antihistamines according to Formula L include the following:

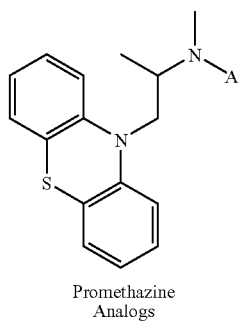

Promethazine
Analogs

Specific examples of modified antihistamines according to Formula M include the following:

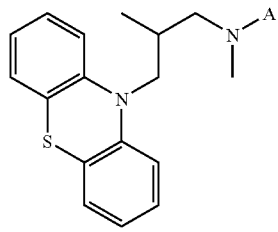

Trimeprazine
Analogs

Specific examples of modified antihistamines according to Formula N include the following:

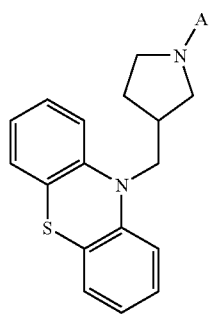

Methdilazine
Analogs

Specific examples of modified antihistamines according to Formula O include the following:

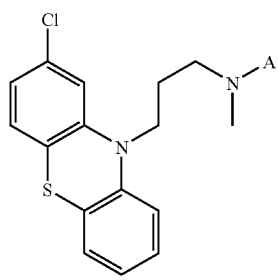

Chloropromazine
Analogs

Specific examples of modified antihistamines according to Formula P include the following:

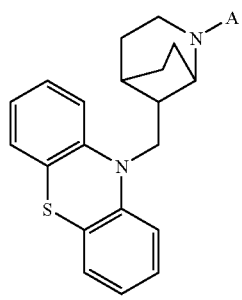

Mequitazine
Analogs

Specific examples of modified antihistamines according to Formula Q include the following:

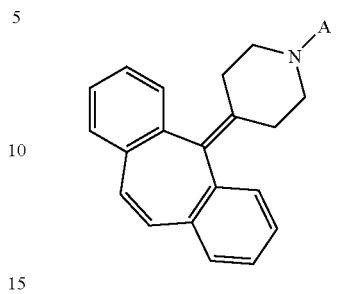

Cyclobenzaprine
Analogs

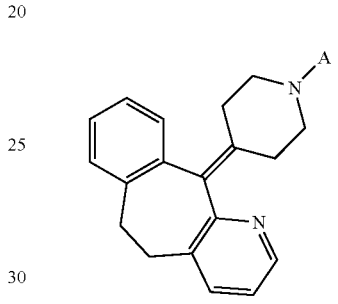

Azatadine
Analogs

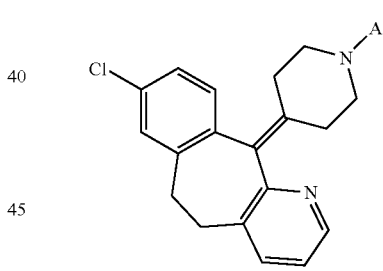

Loratadine, Desloratadine,
and Rupatadine analogs

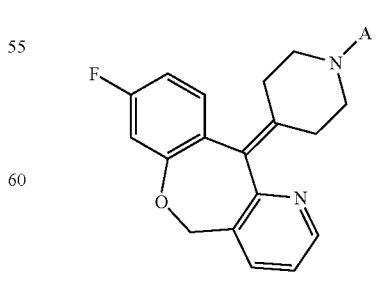

HSR-609 (Hokuriku)
Analogs

Specific examples of modified antihistamines according to Formula R include the following:

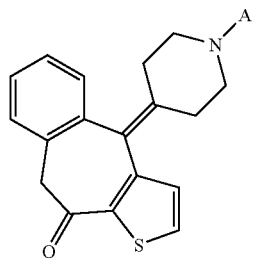

Ketotifen
Analogs

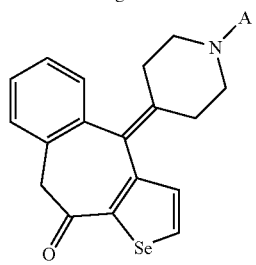

Selenotifen
Analogs

Specific examples of modified antihistamines according to Formula S include the following:

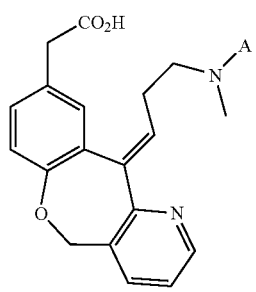

Olopatadine
Analogs

Specific examples of modified antihistamines according to Formula T include the following:

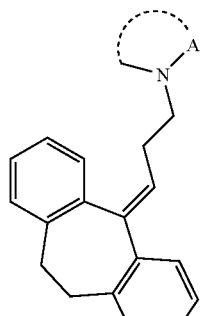

REN 1869
Analogs

Specific examples of modified antihistamines according to Formula U include the following:

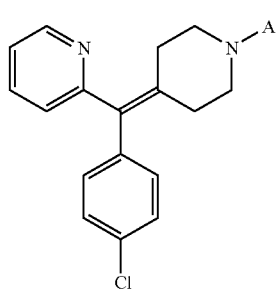

Schering Plough (Dual H1 and H3 Antagonist) Analogs

Specific examples of modified antihistamines according to Formula V include the following:

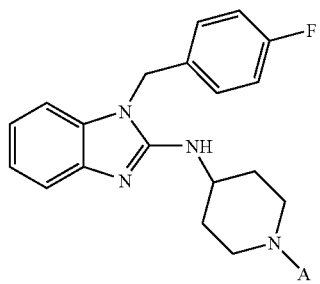

Astemizole and Tecastemizole
Analogs

Specific examples of modified antihistamines according to Formula W include the following:

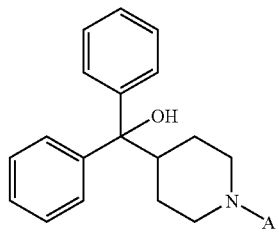

Fexofenadine, Terfenadine and Schering-Plough Analogs

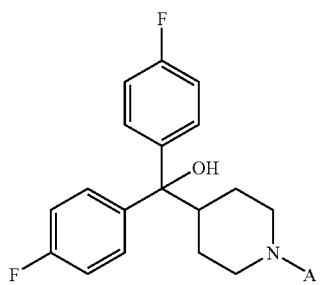

KA-398 (Dr. Willmar Schwabe GmbH & Co) Analogs

Specific examples of modified antihistamines according to Formula X include the following:

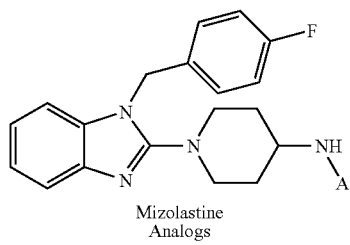

Mizolastine
Analogs

Specific examples of modified antihistamines according to Formula Y include the following:

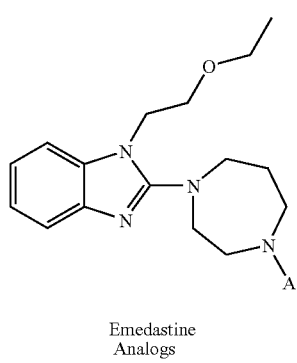

Emedastine
Analogs

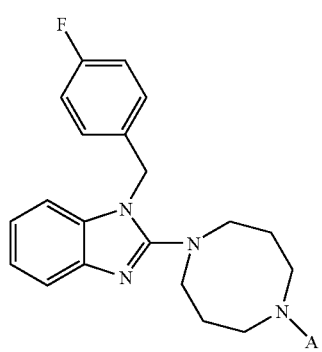

KAA-276 (Kissei)
Analogs

Specific examples of modified antihistamines according to Formula Z include the following:

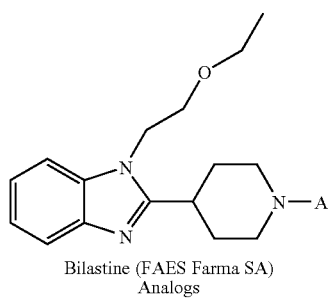

Bilastine (FAES Farma SA)
Analogs

Specific examples of modified antihistamines according to Formula AA include the following:

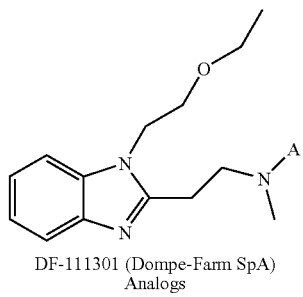

DF-111301 (Dompe-Farm SpA)
Analogs

Specific examples of modified antihistamines according to Formula BB include the following:

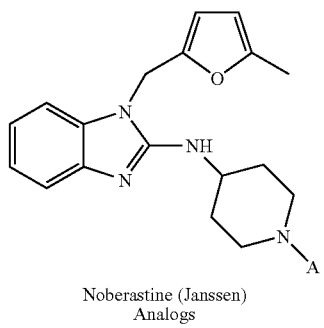

Noberastine (Janssen)
Analogs

Specific examples of modified antihistamines according to Formula CC include the following:

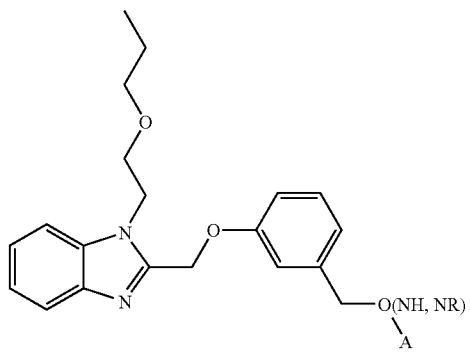

YUF-K-9015 (Dual LTD4 and H1 Antagonist)
Analogs

Specific examples of modified antihistamines according to Formula DD include the following:

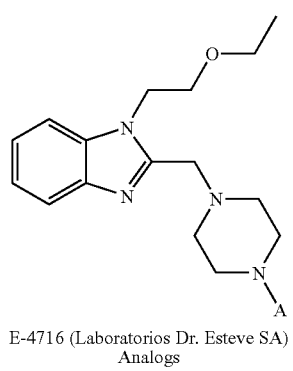

E-4716 (Laboratorios Dr. Esteve SA)
Analogs

Specific examples of modified antihistamines according to Formula EE include the following:

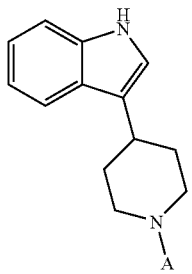

FK-613 (Fujisawa)
Analogs

Specific examples of modified antihistamines according to Formula EE' include the following:

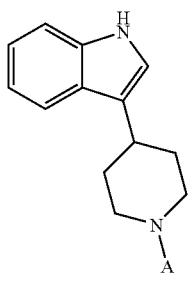

FK-613 (Fujisawa)
Analogs

Specific examples of modified antihistamines according to Formula FF include the following:

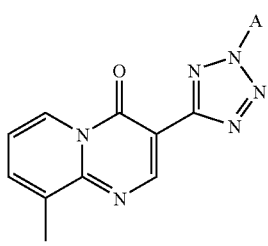

Pemirolast
Analogs

Specific examples of modified antihistamines according to Formula FF' include the following:

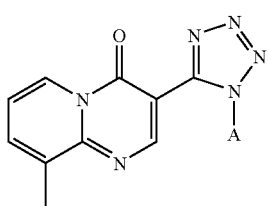

Pemirolast
Analogs

Specific examples of modified antihistamines according to Formula GG include the following:

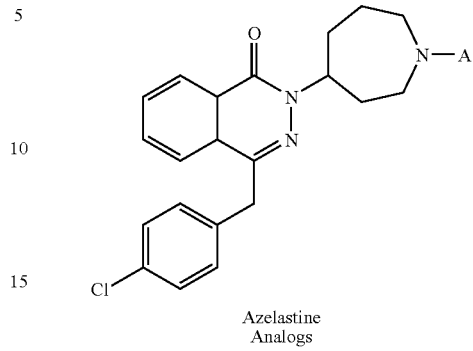

Azelastine
Analogs

Specific examples of modified antihistamines according to Formula HH include the following:

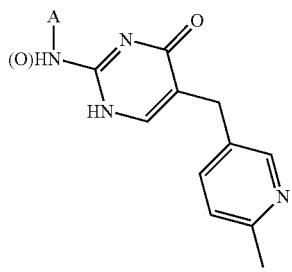

Temelastine
Analogs

Specific examples of modified antihistamines according to Formula HH' include the following:

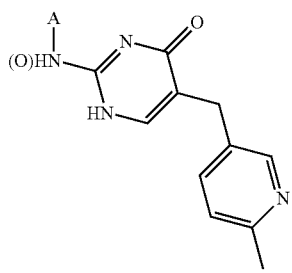

Temelastine
Analogs

Specific examples of modified antihistamines according to Formula II include the following:

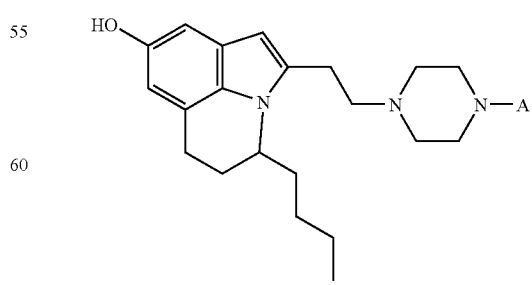

KC-11404 (Solvay Deutschland GmbH,
H1, 5-Lipo, PAF antagonist) Analogs

Specific examples of modified antihistamines according to Formula JJ include the following:

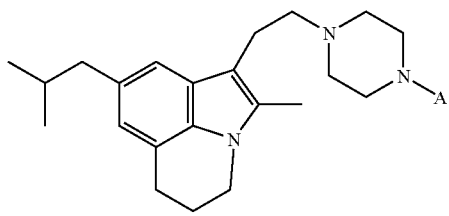

KC-11425 (Solvay Pharmaceuticals H1, 5-Lipo, PAF Antagonist Analogs)

Specific examples of modified antihistamines according to Formula KK include the following:

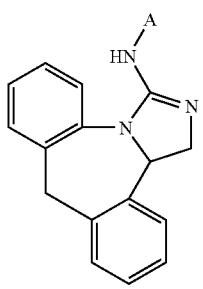

Epinastine Analogs

Specific examples of modified antihistamines according to Formula LL include the following:

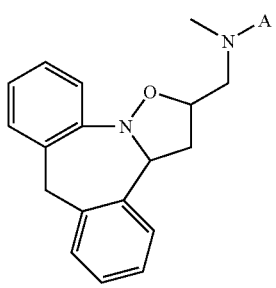

R-107500 (Janssen) Analogs

Specific examples of modified antihistamines according to Formula MM include the following:

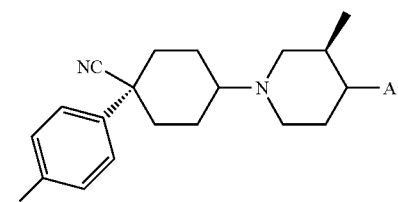

Levocabastine Analogs

Specific examples of modified antihistamines according to Formula NN include the following:

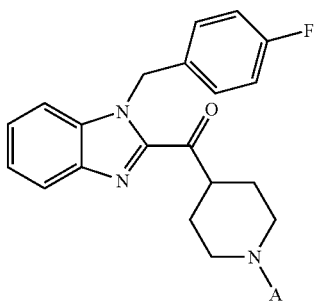

Aventis/Inflazyme Dual H1/NK1 Antagonist Analogs

Specific examples of modified antihistamines according to Formula OO include the following:

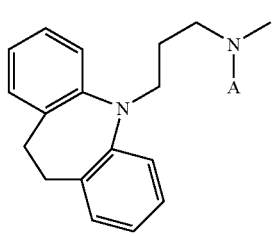

Imipramine Analogs

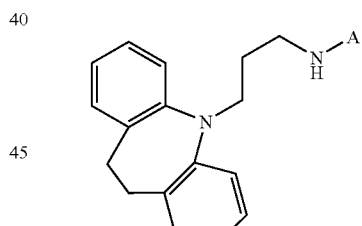

Desimipramine and Protriptyline Analogs

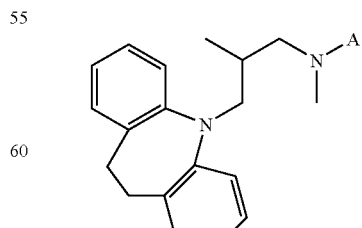

Trimipramine Analogs

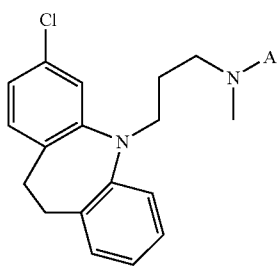

Clomipramine
Analogs

Specific examples of modified antihistamines according to Formula PP include the following:

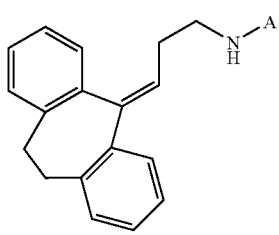

Nortriptyline
Analogs

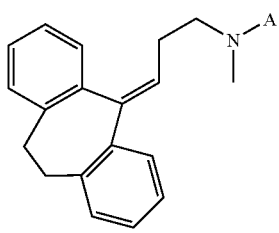

Amitriptyline
Analogs

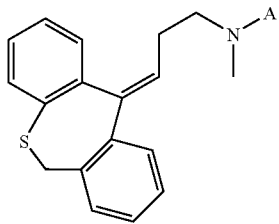

Dothiepin
Analogs

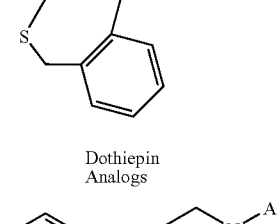

Doxepin
Analogs

Specific examples of modified antihistamines according to Formula QQ include the following:

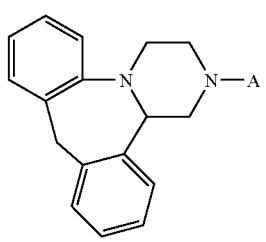

Mianserin
Analogs

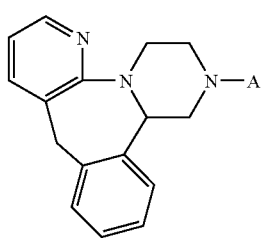

Mirtazapine
Analogs

Specific examples of modified antihistamines according to Formula RR include the following:

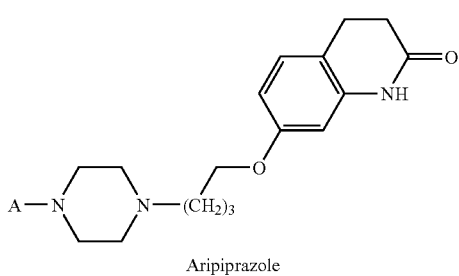

Aripiprazole
Analogs

Specific examples of modified antihistamines according to Formula SS include the following:

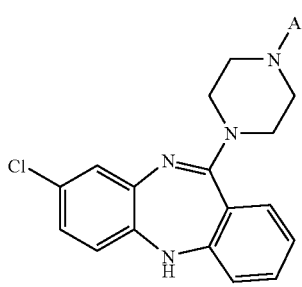

Clozapine
Analogs

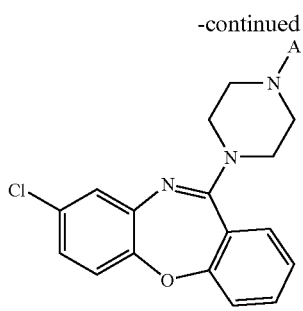

Loxapine
Analogs

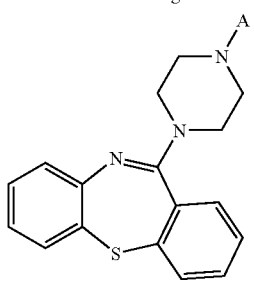

Quetiapine
Analogs

Specific examples of modified antihistamines according to Formula TT include the following:

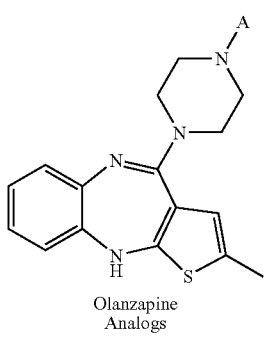

Olanzapine
Analogs

Specific examples of modified antihistamines according to Formula UU include the following:

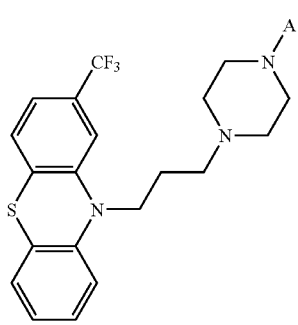

Fluphenazine and Perphenazine
Analogs

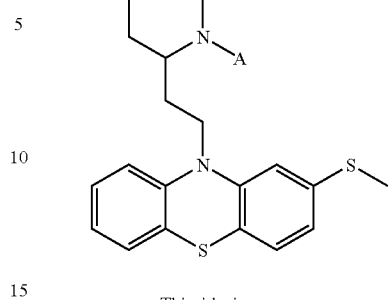

Thioridazine
Analogs

Specific examples of modified antihistamines according to Formula VV include the following:

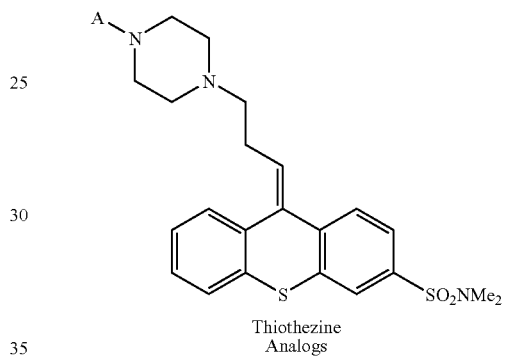

Thiothezine
Analogs

Specific examples of modified antihistamines according to Formula WW include the following:

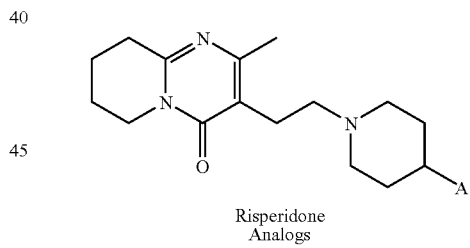

Risperidone
Analogs

Specific examples of modified antihistamines according to Formula XX include the following:

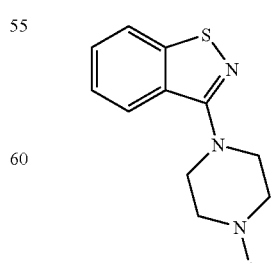

Ziprasidone
Analogs

Specific examples of modified antihistamines according to Formula XX' include the following:

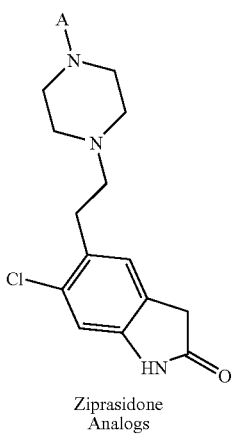

Ziprasidone
Analogs

Specific examples of modified antihistamines according to Formula YY include the following:

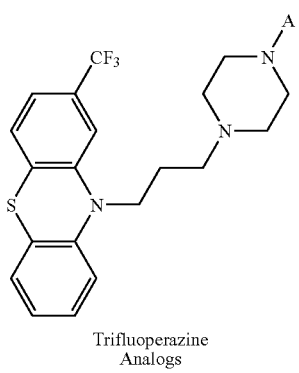

Trifluoperazine
Analogs

Specific examples of modified antihistamines according to Formula ZZ include the following:

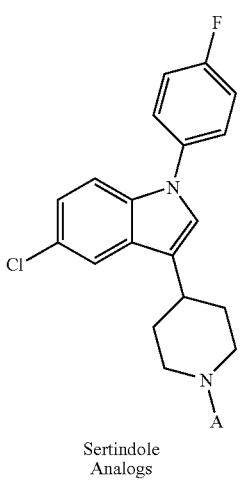

Sertindole
Analogs

Specific examples of modified antihistamines according to Formula AAA include the following:

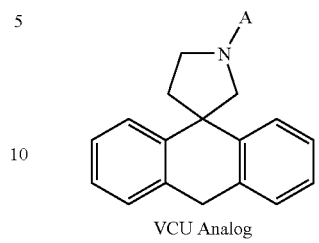

VCU Analog

In general, in another aspect, the present invention relates to the use of modified antihistamines to modulate sleep. Preferred compounds modulate sleep with decreased side effects. For example, compounds of formulae A-AAA modulate sleep with reduced side effects. First, unlike many hypnotics, these compounds do not inhibit REM sleep. Consequently, sleep induced by these compounds may more closely resemble a person's natural sleep cycles. Second, use of these does not result in rebound insomnia. Compared with NREM sleep or wakefulness, REM sleep causes ventilatory depression and episodic cardiovascular changes. During rebound insomnia, the physiological effects of REM sleep are magnified and interrupt the normal sleep cycles. Subjects treated with these compounds do not demonstrate symptoms of rebound insomnia. Finally, these compounds do not inhibit locomotor activity or adversely effect body temperature.

The preferred in vitro selection criteria for modified antihistamines of the invention are shown in Table 2.

TABLE 2

In Vitro Binding Criteria

| | |
|---|---|
| H1 Binding (Primary Target) | Ki < 500 nMolar |

| Off Target Binding | |
|---|---|
| Cholinergic M1, M2, M3 | Ki > 10 times the measured H1 receptor Ki |
| Dopamine D1, D2, D3 | Ki > 10 times the measured H1 receptor Ki |
| Adrenergic α1, α2 | Ki > 10 times the measured H1 receptor Ki |

More preferably, the off target binding Ki is 50 times the measured H1 receptor Ki. In some embodiments, the off target binding Ki is 100 times the measured H1 receptor Ki.

In vitro binding assays are used to determine H1 binding (i.e., primary target binding) and M1, M2 and M3 binding (i.e., off target binding). These binding assays measure the ability of modified antihistamines to displace known standards from the H1, M1, M2, and M3 receptors, wherein H1 is a histamine receptor, and M1, M2, and M3 are cholinergic (muscarinic) receptors. Similar assays are performed with H1 and dopamine receptors (D1, D2 and D3), and with H1 and adrenergic receptors (α1 and α2).

The binding studies against the histamine receptor, H1, indicate binding affinity, and therefore, the results of the binding assays are an indication of the activity of the modified antihistamine compound. The binding studies against the muscarinic receptors indicate the extent to which the compounds bind the muscarinic receptors responsible for anti-cholinergic activity of the compound. Binding to muscarinic receptors results in several undesired side effects of many known antihistamines, e.g., dry-mouth. A decrease in the binding of the compounds to the M1-M3 receptors, relative to the binding of the compound to the H1 receptor, is an indication of the greater specificity of the compound for the histamine receptor over the muscarinic receptor. Moreover, a drug with increased specificity for the histamine receptor possesses less anti-cholinergic side effects.

The H1 binding of the modified antihistamines of the invention (also referred to herein as "test compounds" or "compounds of the invention") is determined by measuring the specific binding of a given test compound, or series of test compounds, to the H1 receptor, and comparing it with the specific binding of known standard (i.e., reference compound). Reference compounds used in this H1 binding assay include, for example, triprolidine ($K_i$ 3.3 nM), chlorpheniramine ($K_i$ 103.0 nM), pyrilamine ($K_i$ 1.9 nM), cyproheptadine ($K_i$ 8.5 nM), cimetidine ($K_i$>10,000) and dimaprit ($K_i$>10,000). (See e.g., Chang et al., J. Neurochem., 32:1653-63 (1979) (with modifications); Martinez-Mir, et al., Brain Res., 526:322-27 (1990); and Haaksme, et al., Pharmac. Ther., 47:73-104 (1990).

For example, in one embodiment of the H1 binding assay, the H1 receptor is from bovine cellular membranes, and a radioligand, [$^3$H]Pyrilamine (15-25 Ci/mmol) at a final ligand concentration of 2.0 nM is used to detect specific binding for the H1 receptor. The assay characteristics include a $K_D$ (binding affinity) of 1.3 nM and a $B_{max}$ (receptor number) of 6.2 fmol/mg tissue (wet weight). Tripolidine (10 µM) is used as the non-specific determinant, reference compound and positive control. Binding reactions are carried out in 50 mM NA-KPO$_4$ (pH 7.5) at 25° C. for 60 minutes. The reaction is terminated by rapid vacuum filtration onto glass fiber filters. The level of radioactivity trapped on the filters is measured and compared to control values to ascertain any interaction between a given test compound and the H1 binding site.

The M1 binding assay determines the M1 binding of a test compound by measuring the specific binding of a given test compound to M1 and comparing it with the specific binding of a reference compound. (See e.g., Buckley, et al., Mol. Pharmacol. 35:469-76 (1989) (with modifications)). Reference compounds used in the M1 binding assay include, for example, scopolamine, MethylBr ($K_i$ 0.09 nM); 4-DAMP methiodide ($K_i$ 0.27 nM); pirenzepine ($K_i$ 2.60 nM); HHSID ($K_i$ 5.00 nM); and methoctramine ($K_i$ 29.70 nM).

For example, in one embodiment of the M1 binding assay, the M1 muscarinic receptor is a human recombinant M1 expressed in CHO cells, and a radioligand, [$^3$H]-scopolamine, N-methyl chloride (80-100 Ci/mmol) at a final ligand concentration of 0.5 nM is used to detect specific binding for M1. (−)-scopolamine, methyl-, bromide (methylscopolamine bromide). The assay characteristics include a $K_D$ (binding affinity) of 0.05 nM and a $B_{max}$ (receptor number) of 4.2 pmol/mg protein (1.0 µM) is used as the non-specific determinant, reference compound and positive control. Binding reactions are carried out in PBS for 60 minutes at 25° C. The reaction is terminated by rapid vacuum filtration onto glass fiber filters. The level of radioactivity trapped on the filters is measured and compared to control values to ascertain any interaction between a given test compound and the cloned muscarinic M1 binding site.

The M2 binding assay determines the M2 binding of a test compound by measuring the specific binding of a given test compound to M2 and comparing it with the specific binding of a reference compound. (See e.g., Buckley, et al., Mol. Pharmacol. 35:469-76 (1989) (with modifications)). Reference compounds used in the M2 binding assay include, for example, scopolamine, MethylBr ($K_i$ 0.3 nM); 4-DAMP methiodide ($K_i$ 20.7 nM); methoctramine ($K_i$ 20.460 nM); HHSID ($K_i$ 212.7 nM); and pirenzepine ($K_i$ 832.9 nM).

For example, in one embodiment of the M2 binding assay, the M2 muscarinic receptor is a human recombinant M2 expressed in CHO cells, and a radioligand, [3H]-scopolamine, N-methyl chloride (80-100 Ci/mmol) at a final ligand concentration of 0.5 nM is used to detect specific binding for M1. The assay characteristics include a $K_D$ (binding affinity) of 0.29 nM and a $B_{max}$ (receptor number) of 2.1 pmol/mg protein. (−)-scopolamine, methyl-, bromide (methylscopolamine bromide) (1.0 µM) is used as the non-specific determinant, reference compound and positive control. Binding reactions are carried out in PBS for 60 minutes at 25° C. The reaction is terminated by rapid vacuum filtration onto glass fiber filters. The level of radioactivity trapped on the filters is measured and compared to control values to ascertain any interaction between a given test compound and the cloned muscarinic M2 binding site.

The M3 binding assay determines the M3 binding of a test compound by measuring the specific binding of a given test compound to M3 and comparing it with the specific binding of a reference compound. (See e.g., Buckley, et al., Mol. Pharmacol. 35:469-76 (1989) (with modifications)). Reference compounds used in the M3 binding assay include, for example, scopolamine, MethylBr ($K_i$ 0.3 nM); 4-DAMP methiodide ($K_i$ 0.8 nM); HHSID ($K_i$ 14.5 nM); pirenzepine ($K_i$ 153.3 nM); and methoctramine ($K_i$ 700.0 nM).

For example, in one embodiment of the M3 binding assay, the M3 muscarinic receptor is a human recombinant M3 expressed in CHO cells, and a radioligand, [$^3$H]-scopolamine, N-methyl chloride (80-100 Ci/mmol) at a final ligand concentration of 0.2 nM is used to detect specific binding for M1. The assay characteristics include a $K_D$ (binding affinity) of 0.14 nM and a $B_{max}$ (receptor number) of 4.0 pmol/mg protein. (−)-scopolamine, methyl-, bromide (methylscopolamine bromide) (1.0 µM) is used as the non-specific determinant, reference compound and positive control. Binding reactions are carried out in 50 mM TRIS-HCl (pH 7.4) containing 10 mM MgCl$_2$, 1 mM EDTA for 60 minutes at 25° C. The reaction is terminated by rapid vacuum filtration onto glass fiber filters. The level of radioactivity trapped on the filters is measured and compared to control values to ascertain any interaction between a given test compound and the cloned muscarinic M3 binding site.

Preferred in vitro selection criteria for modified antihistamines of the invention are shown in Table 3.

TABLE 3

| In Vitro Binding Criteria | |
| --- | --- |
| H1 Binding (Primary Target) | Ki < 150 nMolar |
| Off Target Binding | |
| Cholinergic M1 | Ki > 10 uM |
| Cholinergic M2 | Ki > 10 uM |
| Cholinergic M3 | Ki > 10 uM |

H1 binding (primary target binding) and M1, M2 and M3 binding (off target binding) are determined using the H1, M1, M2 and M3 binding assays described above.

Other in vitro selection criteria for modified antihistamines of the invention include hERG binding.

Primary target binding and off target binding are determined as described above. If the test compound exhibits the desired primary target (H1) binding and primary target/off target binding ration, hERG binding (off target binding) is determined using a hERG block comparative study to evaluate the effect of a given test compound on cloned hERG channels expressed in mammalian cells. (See e.g., Brown and Rampe, Pharmaceutical News 7:15-20 (2000); Rampe et al., FEBS Lett., 417:28-32 (1997); Weirich and Antoni, Basic Res. Cardiol. 93 Suppl. 1:125-32 (1998); and Yap and Camm, Clin. Exp. Allergy, 29 Suppl 3, 174-81 (1999)).

Off target binding of hERG, the cardiac potassium channel responsible for the rapid delayed rectifier current ($I_{Kr}$) in human ventricles, is evaluated because inhibition of $I_{Kr}$ is the most common cause of cardiac action potential prolongation by non-cardiac drugs. (See Brown and Rampe (2000), Weirich and Antoni (1998); and Yap and Camm (1999)). Increased action potential duration causes prolongation of the QT interval that has been associated with a dangerous ventricular arrhythmia, torsade de pointes. (Brown and Rampe (2000)).

In the hERG assay, hERG channels are expressed in a human embryonic kidney cell line (HEK293) that lacks endogenous $I_{Kr}$. Expression in a mammalian cell line is preferable to transient expression in Xenopus oocytes, as the latter demonstrates a consistent 10-100 fold lower sensitivity to hERG channel blockers. (See, Rampe 1997).

In one embodiment of the hERG assay, the positive control (i.e., reference compound) is terfenadine (Sigma, St. Louis Mo.), which has been shown, at a concentration of 60 nM, to block hERG current by approximately 75%. Test compounds are delivered in HEPES-buffered physiological saline (HB-PS)+0.1% dimethyl sulfoxide (DMSO). Each test compound is applied at a concentration of 10 µM to the HEK293 cells expressing hERG (n>3, where n=the number of cells). Cells are exposed to the test compound for the time necessary to reach steady-state block, but not longer than 10 minutes. The positive control (60 mM terfenadine) is applied to two cells (n>2).

The hERG-exposed cells are then transferred to the recording chamber and superfused with HB-PS solution. The pipette solution for whole cell recordings includes potassium aspartate (130 mM), $MgCl_2$ (5 mM), EGTA (5 mM), ATP (4 mM), and HEPES (10 mM) at a pH adjusted to 7.2 with KOH. Onset and steady state block of hERG current due to the test compound are measured using a pulse pattern with fixed amplitudes (depolarization: +20 mV for 2 seconds; repolarization: –50 mV for 2 seconds), repeated at 10 second intervals, from a holding potential of –80 mV. Peak tail current is measured during the 2 second step to –50 mV. A steady state is maintained for at least 30 seconds before applying the test compound or positive control compound. Peak tail currents are measured until a new steady state is achieved.

Figure 3:
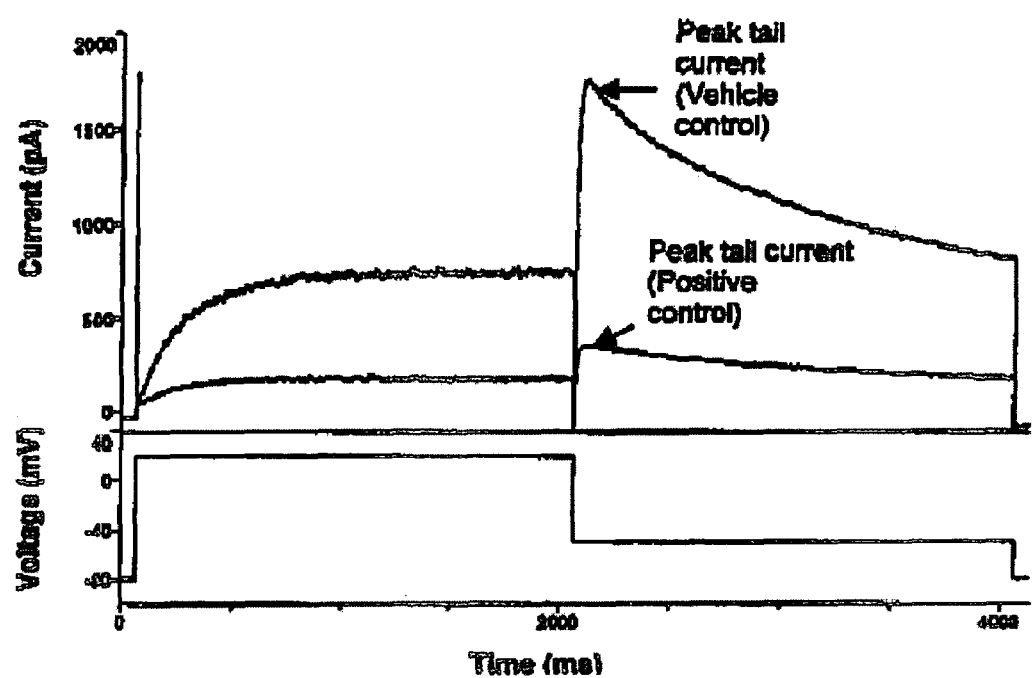
FIG. 3 is a graph depicting typical hERG current tracings recorded at 22° C. for a vehicle control and a positive control.

Typical hERG current tracings recorded at 22° C. for a vehicle control and a positive control are shown in FIG. 3. Superimposed records in control and after application of a test compound. The lower panel shows voltage stimulus (prepulse +20 mV; test pulse, –50 mV; holding potential, –80 mV).

In addition to the preferred, most preferred and the other in vitro selection criteria described above, modified antihistamines of the invention are selected using the following preferred in vivo sleep-wake and physiological assessments:

NonREM Sleep: Modified antihistamines are selected if, in adult, male Wistar rats, (i) peak nonREM amount exceeds 55% nonREM per hour by no later than the third hour post-treatment; and (ii) the nature of this increase in non-REM sleep is such that the net cumulative total increase in nonREM sleep in the initial 6 hours post-treatment (adjusted for baseline at the corresponding circadian time 24 hours earlier, and relative to Vehicle control treatment) is not less than 20 minutes in total for compound doses that produces maximum sleep consolidation as measured by sleep bout length, when drug is delivered orally.

The term "nonREM peak sleep time" is defined as an absolute peak amount of nonREM sleep per hour post treatment, with drug administration occurring at Circadian Time (CT) 18, which is 6 hours after lights off in a nocturnal laboratory rat when housed in a LD 12:12 (12-hours light and 12 hours dark) light-dark cycle. The nominal criteria of 55% nonREM sleep per hour is equivalent to 33 minutes of nonREM sleep per hour.

As used herein, the term "cumulative nonREM sleep" is defined as the net total aggregate increase in the number of minutes of nonREM sleep, measured through out the entire duration of a drug's soporific effect, which typically, but not always occurs in the first 6 hours post-treatment, adjusted for the net total aggregate number of minutes of nonREM sleep that occurred during the corresponding non-treatment baseline times of day recorded 24 hours earlier, relative to like vehicle control treatment.

As defined herein, the term "sleep bout" refers to a discrete episode of continuous or near continuous sleep, comprised of nonREM sleep, REM sleep, or both nonREM and REM sleep stages, delimited prior and after the episode by greater than two contiguous 10 second epochs of wakefulness. The following non-limiting description illustrates this concept: WWWWSSSSWSSSSSSSWWSSSSSSSW-WWW, wherein each letter represents the predominant state of arousal (S=sleep, W=wake) observed each 10 seconds. The measured sleep "bout" is 21 ten-second epochs or 3.5 minutes in duration.

Sleep Consolidation: Modified antihistamines are selected if, in adult male Wistar rats, (i) the absolute duration of longest continuous sleep episodes (i.e., "sleep bout") post-treatment is greater than 13 minutes in duration; (ii) the net longest sleep bout post treatment is greater than or equal to 3 minutes when adjusted for baseline 24 hours earlier and calculated relative to vehicle treatment; and (iii) the mean absolute duration of every sleep bout when averaged per hour, on an hour by hour basis, is greater than or equal to 5 minutes. The aforementioned selection criteria assume that stages of sleep and wakefulness are determined continuously every 10 seconds (e.g., 10 second sleep scoring "epochs"), that sleep and wakefulness are measured polygraphically using EEG and EMG criteria, and sleep episodes (comprised of nonREM and/or REM sleep) are defined as continuous "bouts" until the episode is interrupted by greater than two contiguous 10 second epochs of wakefulness.

As used herein, the term "longest sleep bout length" is defined as the total number of minutes an animal remains asleep (nonREM and/or REM sleep stages) during the single longest sleep bout that occurred beginning in a given hour post-treatment. The "sleep bout length" measurement criteria assumes sleep is measured continuously in 10 second epochs, and is scored based upon the predominant state, computed or otherwise determined as a discrete sleep stage (where sleep stages are defined as nonREM sleep, REM sleep, or wakefulness) during the 10 second interval that defines the epoch.

The term "average sleep bout length" is defined as the average duration (in minutes) of every and all sleep episodes or bouts that began in a given hour, independent of the individual duration of each episode or bout.

Concurrently Measured Side Effects: Modified antihistamines are selected if, in adult, male Wistar rats, these compounds (i) do not produce appreciable amounts of rebound insomnia; (ii) do not appreciably inhibit REM sleep; and (iii) do not disproportionately inhibit locomotor motor activity and/or motor tone relative to the normal effects of sleep itself. The threshold definitions for these three side-effect variables are as follows:

"Rebound insomnia" is defined as period of rebound, paradoxical, or compensatory wakefulness that occurs after the sleep promoting effects of a hypnotic or soporific agent. Rebound insomnia is typically observed during the usual circadian rest phase 6-18 hours post-treatment at CT-18 (6 hours after lights-off, given LD 12:12), but can occur at any time during the initial 30 hours post-treatment. Rebound is considered unacceptable when, in the adult, male Wistar rat, excess cumulative wakefulness associated with rebound insomnia is greater than 20% of the net cumulative increase in sleep produced by the hypnotic or soporific effects of a compound.

In adult, male Wistar rats, rebound insomnia manifests as an increase in wakefulness relative to corresponding times at baseline (24 hours earlier) subsequent to a drug-induced sleep effect, and rebound insomnia is measured cumulatively. The following non-limiting description illustrates this measurement: Compound A, administered to laboratory rats at CT-18 (6 hours after lights-off, given LD 12:12), produced a 50 minute cumulative increase in sleep time (relative to baseline sleep measures 24 hours earlier) during the initial 6 hours post-treatment. After the sleep promoting effects of the compound subsided, the animals demonstrated a cumulative increase in wakefulness relative to baseline 24 hours earlier. Because the soporific effect of the compound produced 50 minutes of additional sleep, a subsequent cumulative increase in wakefulness (rebound insomnia) of greater than 10 minutes total would be unacceptable.

"REM sleep inhibition" is defined as the reduction of REM sleep time post-treatment at CT-18 (6 hours after lights-off; LD 12:12) or at CT-5 (5 hours after lights-on; LD 12:12). Compounds that reduce REM sleep time by greater than 15 minutes (relative to baseline and adjusted for vehicle treatment) when administered at either CT-18 or CT-5 are considered unacceptable.

As defined herein, "disproportionate locomotor activity inhibition" is a reduction of locomotor activity that exceeds the normal and expected reduction in behavioral activity attributable to sleep. Logic dictates that if an animal is asleep, there will normally be a corresponding reduction in locomotor activity. If a hypnotic or soporific compound reduces locomotor activity levels in excess of 20% greater than that explained by sleep alone, the compound is deemed unacceptable. Locomotor activity (LMA) or motor tone may be quantified objectively using any form of behavioral locomotor activity monitor (non-specific movements, telemetry-based activity monitoring, 3-dimensional movement detection devices, wheel running activity, exploratory measures, electromyographic recording, etc.) so long as it is measured concurrently with objective sleep-wakefulness measures in the same animal.

In one embodiment, locomotor activity within the animal's cage is measured using a biotelemetry device surgically implanted in the animal's peritoneal cavity; the implantable device and associated telemetry receiver detects if and how much animal moves within the cage. Sleep and wakefulness is measured in 10 second epochs simultaneously. Counts of locomotor activity per unit time are divided by the concurrent amount of wakefulness per the same unit, yielding a "locomotor activity intensity" (LMAI) measure for that unit time. Hypnotic or soporific compounds administered at CT-18 (6 hours after lights-off; LD 12:12) that decrease locomotor activity per unit time awake by greater than 20% relative to vehicle would be judged unacceptable.

In a more preferred embodiment, the modified antihistamines of the invention are selected using the in vivo sleep-wake and physiological assessment criteria shown in Table 4:

TABLE 4

| SCORE-2000 | Absolute Value | Change from baseline value relative to vehicle only |
|---|---|---|
| NonREM Peak Time | >55% sleep/hour peak | Not applicable |
| Cumulative NonREM | Not applicable | >20 minutes at ED100 for MSBL at $T_{1-6}$ |
| Longest Sleep Bout | >17 minutes absolute peak | >5 minutes |
| Average Sleep Bout | >6 minutes absolute peak | Not used in SAR cuts |
| Rebound insomnia | <20% of net NonREM sleep gain | Not applicable |
| REM Sleep inhibition | not applicable | not to exceed 15 minutes, Rx at CT5 |
| LMAI | not applicable | not to exceed 20% LMAI reduction |

Methods for evaluating these sleep-wake and physiological assessment criteria are described above. The "absolute value" shown in second column of Table 4 refers to the value as determined for each test compound, while the "change" value shown in the third column of Table 6 reflects an adjusted value in which the absolute value is the difference from vehicle, when the vehicle values are adjusted for baseline.

In some embodiments, the longest sleep bout is greater than 13 minutes in duration. In others, it is greater than 17 minutes in duration. In some embodiments, the net longest sleep bout post treatment is greater than or equal to 3 minutes in duration. In others, it is greater than or equal to 6 minutes in duration.

Other in vivo sleep-wake and physiological assessment criteria used to select modified antihistamines of the invention include measurement of acute body temperature and latent body temperature as a change in baseline relative to vehicle. The acute body temperature change should not exceed −0.50° C., and the latent body temperature change should not exceed +0.50° C. at Time 1-6 hours. The acute body temperature ($T_{1-6}$) is adjusted for the corresponding baseline measured 24 hours earlier, relative to vehicle (the decrease from vehicle). The latent body temperature, measured 7-18 hours post drug treatment ($T_{7-18}$), is adjusted for the corresponding baseline measured 24 hours earlier, relative to vehicle (the decrease from vehicle).

The invention provides a method of modulating sleep by administering to a subject a therapeutically effective amount of a compound of Formula A-AAA or (I)-(VI) or a pharmaceutically effective salt thereof. The method modulates sleep several ways including decreasing the time to sleep onset, increasing the average sleep bout length, and increasing the maximum sleep bout length.

The language "pheniramine-like compounds" is intended to include antihistamines that include two aryl groups linked to the same atom, not linked through a tricyclic ring system. In addition, pheniramine-like compounds are distinguished from diphenhydramine-like compounds by the lack of an oxygen atom linking the carbon atom, which is attached to the aryl groups, to a piperidine ring. In certain embodiments, the pheniramine-like compounds are represented by Formula (I) and Formula (II):

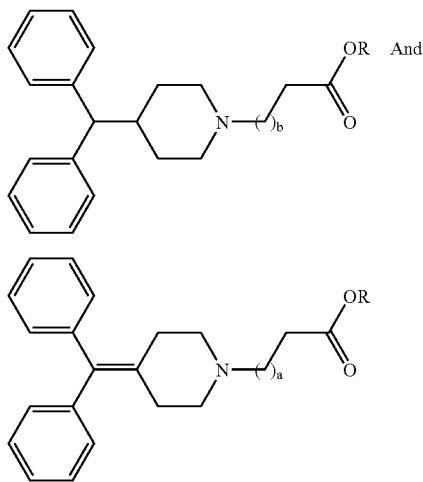

wherein a=0 through 5, b=0 through 5, and R is H or any group which imparts properties to the therapeutic compound to promote penetration into the CNS and to modify the half-life of the compound.

The language "diphenhydramine-like compounds" is intended to include antihistamines that include two aryl groups linked to the same atom, not linked through a tricyclic ring system, and are distinguished by the presence of an oxygen atom linking the carbon atom, which is attached to the aryl groups, to a piperidine ring. In certain embodiments, the diphenhydramine-like compounds are represented by Formula (III):

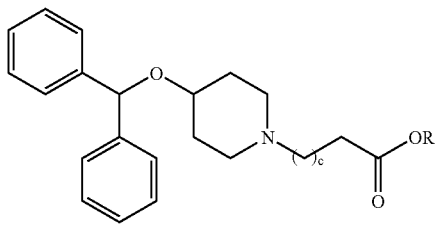

wherein c=0 through 5, and R is H or any group which imparts properties to the therapeutic compound to promote penetration into the CNS and to modify the half-life of the compound.

The language "doxepin-like compounds" is intended to include analogs of doxepin or antihistamines that include two aryl groups linked to the same atom that are linked through a tricyclic ring system, e.g. a seven membered ring (i.e., similar to that of doxepine). In addition, doxepin-like compounds may posses a piperidine ring or the ring can be replaced by a linear structure, e.g., an alkylene group (i.e., similar to that of doxepine). In certain embodiments, the doxepin-like compounds are represented by Formulae (VIa) and (VIb):

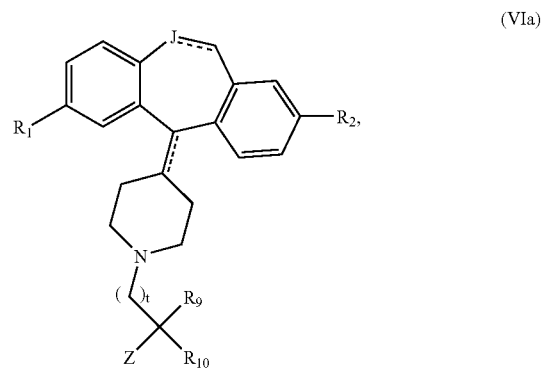

where the dashed bond is present or absent, t is between 0 and 6; J is O, S, CH (when a double bond is present), $CH_2$, or C(O), $R_1$ and $R_2$ are, independently, H, F, Cl, Br, $CF_3$, $CH_3$, OH, $OCH_3$, $CH_2OCH_3$, $CH_2OCH_2CH_3$; $R_9$–$R_{10}$ are H, $CH_3$ or $CH_2CH_3$, or are lower alkyl or lower heteroalkyl as necessary to form a spiro ring of size 3 to 7; and Z is $CO_2H$, $CONHS(O)_2$-Aryl, $CONHS(O)_2$-Alkyl or

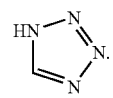

When Z is COOH, at least one of $R_1$ and $R_2$ and at least one of $R_9$ and $R_{10}$ is not H.

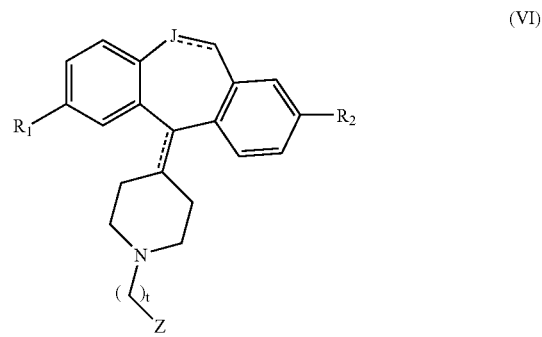

wherein the dashed line represents the presence or absence of a bond; $R_1$ and $R_2$ are substituents that are selected such that the compound can perform its intended function, e.g., substituents that are described for antihistamines; J is O, S, CH (when a double bond is present, or $CH_2$ and t 1 to 6. Any member of the alkylene linker is substituted with one or more substituents, and substituents on two different atoms can be connected to form a ring of size 3 to 7, or substituents on the same atom can be connected to form a spiro ring of size 3 to 7. In one embodiment, t is 1 to 4. In a specific embodiment, t is 1, 2, or 3. Z is COOH or COOR, where R is straight chain or branched lower alkyl. When Z is COOH, the linker is not unsubstituted, and at least one of $R_1$ and $R_2$ is not H.

The language "triprolidine-like compounds" is intended to include antihistamines that include two aryl groups linked to the same atom, not linked through a tricyclic ring system, and are distinguished by the presence of a pyrrolidine ring. In certain embodiments, the triprolidine-like compounds are represented by Formula (IV):

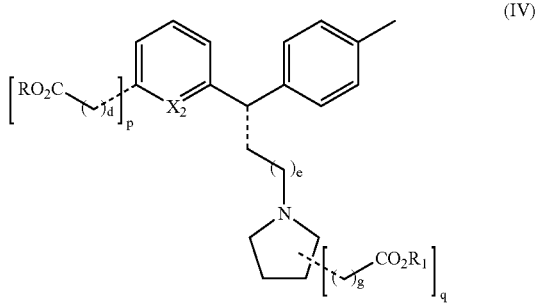

wherein d=0 through 5, e=0 through 4, g=0 through 5, the dashed line represents a single or double bond, R and $R_1$ are independently H or any group which imparts properties to the therapeutic compound to promote penetration into the CNS and to modify the half-life of the compound, and p and q are 0 or 1. In certain embodiments, p and q are not both 1. The $(CH_2)_m$ linker to the ester or carboxylic acid group, can be substituted with one or more substituents. In some embodiments, the COOH is replaced by a bioisostere, Z, as defined above.

The language "acrivastine analogs" is intended to include the particular embodiment of Formula (IV), wherein the side chain that contains the $CO_2R$ is an acrylate, e.g., acrylic acid (as depicted in Scheme 1).

The language "pheniramine analogs" is intended to include antihistamines that include two aryl groups linked to the same atom, not linked through a tricyclic ring system. In addition, pheniramine analogs are distinguished by the presence of a dimethylamine moiety. In certain embodiments, the pheniramine analogs are represented by Formula (V):

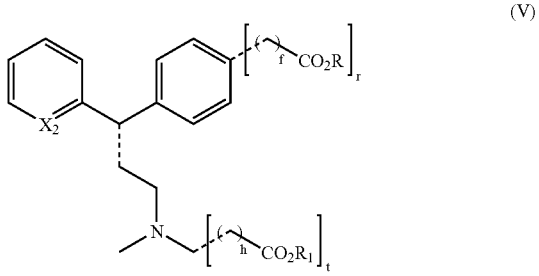

wherein f=0 through 5, h=0 through 5, the dashed line represents a single or double bond, R and $R_1$ are independently H or any group which imparts properties to the therapeutic compound to promote penetration into the CNS and to modify the half-life of the compound, $X_2$ is CH or N, and r and t are 0 or 1. In certain embodiments, r and t are not both 1. The $(CH_2)_m$ linker to the ester or carboxylic acid group, can be substituted with one or more substituents.

An antihistamine of the instant invention may be substituted by one or more substituents, which are selected and positioned within the molecule such that the compound is able to perform its intended function. For example, the substituent(s) can be located on any available position, such as, the aryl rings, the spacer molecule, the drug activity modulating moiety, any branching moieties, or on other substituents. Exemplary substituents include substituted or unsubstituted alkyl, alkenyl, alkynyl, and aromatic or aryl moieties as defined herein. In particular, the antihistamines of the invention may be substituted by substituents including, but not limited to, hydrogen; halogen, e.g. bromide, chloride, or fluoride; dimethylaminocarbonyl; fluoroalkyl, e.g., trifluoromethyl; hydroxy; alkyl, e.g., $C_{1-6}$ alkyl, e.g., methyl or ethyl; alkoxy, e.g., $C_{1-6}$ alkoxy, e.g., methoxy or propoxy; carboxylic acid; methylhydroxy; methylcarbonyl; cyano; aminomethyl; (aminoalkyl); ethoxycarbonylmethoxy; cyanomethyloxy; (acetoxyethyl)oxy; (hydroxyoxyethyl)oxy; morphilinoethyloxy; (tetrazol-5-yl)methyloxy; carboxymethyloxy; dimethylaminocarbonylmethyloxy; morphilinocarbonylmethyloxy; (1-ethoxycarbonyl-1-methylethyl)oxy; (1-carboxy-1methylethyl)oxy; (2-methoxyethyl)oxy; (1-dimethylaminocarbonyl-1-methylethyl)oxy; (1-ethoxycarbonyl) cyclobutoxy; (1-carboxy)cyclobutoxy; (1;1-dimethyl-2-hydroxyethyl)oxy; (2;2-dimethyl-2-hydroxyethyl)oxy; acyloxy; cycloalkyl; arylalkyl; alkoxycarbonyl; and substituted or unsubstituted amines.

In certain embodiments, the aryl rings may be substituted with one or more substituents, each of which may be different or the same, and include, for example, hydrogen, halogens, alkyl, fluoroalkyl, e.g., trifluoromethyl, hydroxy, alkoxy, and other substituents, such as, —(O)$_u$—(CH$_2$)$_t$—C(O)OR$_4$, —(O)$_u$—(CH$_2$)$_t$—OC(O)R$_4$, —(O)$_u$—(CH$_2$)$_t$—C(O)—NR$_5$R$_6$ or —(O)$_u$—(CH$_2$)$_t$—NHC(O)O—R$_4$ wherein: t is an integer, such as an integer from zero to about three, and the methylene group —(CH$_2$)$_t$— can be substituted or unsubstituted; and R$_4$, R$_5$ or R$_6$ are independently hydrogen, an aliphatic group, a substituted aliphatic group, an aromatic group, a substituted aromatic group or a non-aromatic heterocyclic group. Alternatively, R$_5$ and R$_6$, taken together with the nitrogen atom to which they are bonded, can form a non-aromatic heterocyclic ring.

Suitable substituents on an aliphatic group, aromatic group (carbocyclic and heteroaryl), non-aromatic heterocyclic ring or benzyl group include, for example, an electron withdrawing group, a halogen, azido, cyano, fluoroalkyl, e.g., trifluoromethyl, carboxylic acid, hydroxy, —CONR$_8$, R$_9$, —NR$_8$R$_9$, —OS(O)$_2$ NR$_8$R$_9$, —S(O)$_2$ NR$_8$R$_9$, sulfonic acid, sulfonamide, guanidino, —(O)$_u$—(CH$_2$)$_t$—C(O)OR$_4$, —(O)$_u$—(CH$_2$)$_t$—OC(O)R$_4$, —(O)$_u$—(CH$_2$)$_t$—C(O)—NR$_5$R$_6$, —(O)$_u$—(CH$_2$)$_t$—NHC(O)O—R$_4$, -Q-H, -Q-(aliphatic group), -Q-(substituted aliphatic group), -Q-(aryl), -Q-(aromatic group), -Q-(substituted aromatic group), -Q-(CH$_2$)$_p$-(substituted or unsubstituted aromatic group), -Q-(non-aromatic heterocyclic group) or-Q-(CH$_2$)$_p$-(non-aromatic heterocyclic group) wherein: p is an integer from 1-5; R$_4$, R$_5$ or R$_6$ are independently —H, an aliphatic group, a substituted aliphatic group, an aromatic group, a substituted aromatic group, a non-aromatic heterocyclic group, —NHC(O)—O-(aliphatic group), —NHC(O)—O-(aromatic group) or —NHC(O)—O-(non-aromatic heterocyclic group); R$_5$ and R$_6$, taken together with the nitrogen atom to which they are bonded, can form a non-aromatic heterocyclic ring; t is an integer from zero to about three; the methylene group, —(CH$_2$)$_t$—, can be substituted or unsubstituted; and Q is —O—, —S—, —S(O)—, —S(O)$_2$—, —OS(O)$_2$—, —C(O)—, —OC(O)—, —C(O)O—, —C(O)C(O)—O—, —O—C(O)C(O)—, —C(O)NH—, —NHC(O)—, —OC(O)NH—, —NHC(O)O—, —NH—C(O)—NH—, —S(O)$_2$NH—, —NHS(O)$_2$—, —N(R$_7$)—, —C(NR$_7$)NHNH—, —NHNHC(NR$_7$)—, —NR$_8$C(O)— or —NR$_8$S(O)$_2$— wherein: R$_7$ is hydrogen, an aliphatic group, a benzyl group, an aryl group or non-aromatic heterocyclic group; R$_8$ and R$_9$ are independently hydrogen, hydroxy, an aliphatic group, a substituted aliphatic group, a benzyl group, an aryl group or non-aromatic heterocyclic group; and u is zero or one.

A substituted non-aromatic heterocyclic ring, benzyl group or aromatic group can also have an aliphatic or substituted aliphatic group, as a substituent. In addition, a substituted aliphatic group can also have an oxo group, epoxy group, non-aromatic heterocyclic ring, benzyl group, substituted benzyl group, aromatic group or substituted aromatic group as a substituent. A substituted non-aromatic heterocyclic ring can also have =O, =S, =NH or =N(aliphatic, aromatic or substituted aromatic group) as a substituent. A substituted aliphatic, substituted aromatic, substituted non-aromatic heterocyclic ring or substituted benzyl group can have more than one substituent. Acyl groups include substituted and unsubstituted aliphatic carbonyl, aromatic carbonyl, aliphatic sulfonyl and aromatic sulfonyl. Suitable electron withdrawing groups include, for example, alkylimines, alkylsulfonyl, carboxamido, carboxylic alkyl esters, —CH=NH, —CN, —NO$_2$ and halogens.

In certain embodiments of the invention, the therapeutic compound has a favorable biological property. In one embodiment of the invention, the invention is a method of treating a sleep disorder. The method comprises administering an effective amount of an antihistamine compound, such that the sleep disorder is treated, wherein the antihistamine compound has a favorable biological property (FBP).

The language "favorable biological property (FBP)" includes one or more biological properties that allow the compound to perform its intended function in an enhanced manner. Examples of favorable biological properties include but are not limited to induction of a discrete sleep or hypnotic state, activity of the therapeutic compound for a discrete period of time, penetration through the blood brain barrier into the CNS, e.g., resulting from lipophilicity of substituents or conformational lipophilicity (i.e., lipophilicity as a result of a particular conformation, such as internal salt formation between a carboxylate anion and a protonated amine), modulation of the half-life of the therapeutic compound, in vivo hydrolysis of an ester by esterases that allows sequestration of the therapeutic compound in the CNS, an alteration of charge, an alteration of pharmacology-kinetics, an alteration of log P by a value of 1 or more, increased receptor selectivity, reduced peripheral half-life, the ability to increase dosage, increased peripheral elimination, decreased anti-muscarinic activity, decreased anti-cholinergic, and any combination thereof. It should be understood that the language "FPB" is intended to include a single property or a combination of two or more properties. In particular embodiments of the invention, the therapeutic compound induces a discrete sleep or hypnotic state by penetration into the CNS. In certain embodiments of the invention, the FBP includes increased concentration within the CNS for a discrete period of time as a result of a slower rate of conversion to the corresponding carboxylic acid by in vivo esterase activity within the CNS as compared with the periphery. In another embodiment of the invention, the FBP includes increased concentration within the CNS for a discrete period of time as a result of the existence of an ionic bond that includes the carboxylate ion of the corresponding carboxylic acid, e.g., zwitterion species formation with a nitrogen atom within the compound or salt bridge formation.

In certain embodiments, wherein the therapeutic compound is active for a discrete period of time, the FBP is a reduced ability of the subject to form a tolerance to the therapeutic compound. The language "tolerance" includes the natural tendency of a subject to become less affected by continued administration of a particular therapeutic compound due to repeated exposure to the compound. It should be noted that tolerance is typically increased coincident with the increased time that a compound is present in its active state within the subject. Reduced tolerance would coincide with increased therapeutic effectiveness.

The language "discrete sleep or hypnotic state" include a state of consciousness that is induced by the presence of active therapeutic compound of the invention, for a defined period of time. This is in contrast to the lingering hangover effect resulting from the existing treatments, e.g., antihistamines, used for their sedative effect that maintain active drug concentrations for extended periods of time in the periphery.

The language "discrete period of time" includes a defined period of time in which the therapeutic compound is active, and depends upon the physical and reactive properties of the ester group. In one embodiment of the invention, the half-life of the therapeutic compound is 1 to 8 hours. In a preferred embodiment, the half-life of the therapeutic compound is 6 hours.

The language "sequestration" includes having enhanced concentration in the CNS and more rapid elimination from the periphery. The product of hydrolysis can exit the brain by various carboxylate excretion mechanisms, possibly at a slower rate than from the periphery producing a CNS sequestration of the carboxylate for a defined, or discrete, period of time. In one embodiment of the invention, elimination of the hydrolyzed carboxylate-containing metabolite occurs predominately by excretion though the kidneys, due to enhanced polarity of the metabolite, either as the free carboxylate or after Phase II further metabolism. In another embodiment, elimination occurs predominately by metabolism in the liver, e.g. hydrolysis of the ester followed by glucuronidation, and excretion into the bile. In certain embodiments, the brain assists in the elimination.

Another embodiment of the current invention is a method of modulating a sleep disorder target comprising administering to a subject an effective amount of a therapeutic compound, such that the therapeutic compound penetrates into the CNS and modulates the sleep disorder target, wherein the therapeutic compound is as described above and comprises any one of the following formulae:

[CA]-(SP)$_n$-[DA],

[CA]-(SP)$_n$-[EG],

[AD]-(SP)$_n$-[EG],

[AH]-(SP)$_n$-[DA], or

[AH]-(SP)$_n$-[EG]

wherein CA is a moiety that modulates an active CNS target receptor or a collection of active CNS target receptors, AD is a moiety that agonizes an adenosine receptor or a collection of adenosine receptors, AH is a moiety that antagonizes a histamine receptor or a collection of histamine receptors, DA is a drug activity modulating moiety that provides the ability to modulate the activity of the therapeutic compound, EG is an ester group that modifies the half-life of the therapeutic compound, SP is a spacer molecule, and n is 0 or 1.

In an additional embodiment, the invention is a CNS disorder target modulator comprising the formula:

[CA]-(SP)$_n$-[DA], or

[CA]-(SP)$_n$-[EG]

wherein CA is a moiety that modulates an active CNS target receptor or a collection of active CNS target receptors, DA is a drug activity modulating moiety that provides the ability to modulate the activity of the therapeutic compound, EG is an ester group that modifies the half-life of the therapeutic compound, SP is a spacer molecule, and n is 0 or 1.

Another embodiment of the invention is a sleep disorder target modulator comprising the formula:

[CA]-(SP)$_n$-[EG]

wherein CA is a moiety that modulates an active CNS target receptor or a collection of active CNS target receptors, EG is an ester group that modifies the half-life of the therapeutic compound, SP is a spacer molecule, and n is 0 or 1.

In a particular embodiment of the invention, a sleep disorder target modulator comprises the formula:

[AH]-(SP)$_n$-[DA] or

[AH]-(SP)$_n$-[EG]

wherein AH is a moiety that antagonizes a histamine receptor or a collection of histamine receptors, DA is a drug activity modulating moiety that provides the ability to modulate the activity of the therapeutic compound, EG is an ester group that modifies the half-life of the therapeutic compound, SP is a spacer molecule, and n is 0 or 1.

In accord with the invention, particular embodiments of the pheniramine-like therapeutic compound used for treating CNS disorders, e.g., sleep disorders, are:

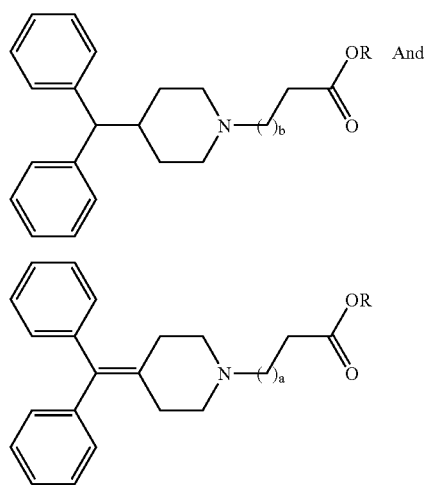

wherein a=0 through 5, b=0 through 5, and R is H or any group which imparts properties to the therapeutic compound to promote penetration into the CNS and to modify the half-life of the compound. In another embodiment of the therapeutic compound used for the treatment of a disorder, the diphenhydramine-like therapeutic compound is:

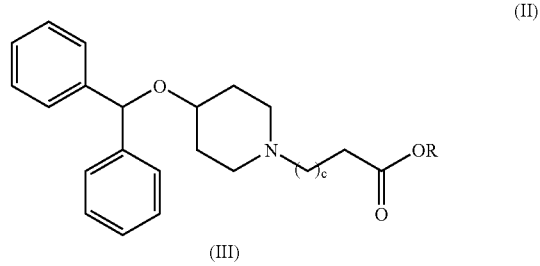

c=0 through 5, and R is H or any group which imparts properties to the therapeutic compound to promote penetration into the CNS and to modify the half-life of the compound.

In another embodiment of the therapeutic compound used for the treatment of a disorder, the triprolidine-like therapeutic compound is:

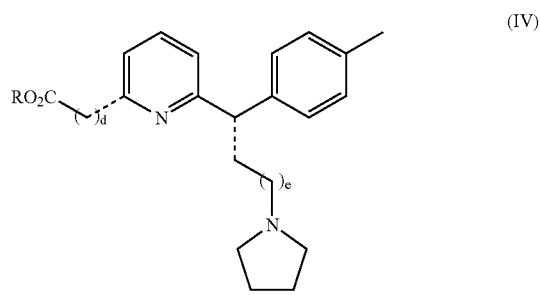

wherein d=0 through 5, e=0 through 4, the dashed line represents a single or double bond, and R is H or any group which imparts properties to the therapeutic compound to promote penetration into the CNS and to modify the half-life of the compound.

In another embodiment of the therapeutic compound used for the treatment of a disorder, the pheniramine analog therapeutic compound is:

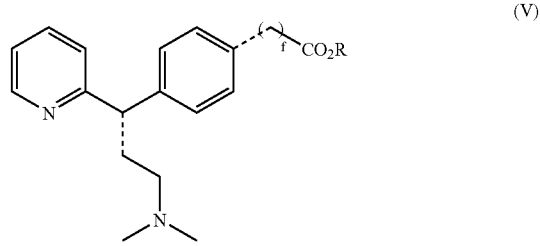

wherein f=0 through 5, the dashed line represents a single or double bond, and R is H or any group which imparts properties to the therapeutic compound to promote penetration into the CNS and to modify the half-life of the compound.

In preferred embodiments of the invention, a=0 or 1; b=0 or 1; c=0 or 1; d=1 or 2; e=1 or 2; and f=1 or 2. In particular embodiments of Formulae (I), (II), (III), (IV), and (VI), R is a bulky ester.

In one embodiment, the compound of the invention is doxepin, pheniramine, diphenhydramine, triprolidine, or acrivastine.

An additional embodiment of the invention is the composition of several analogs of doxepin and acrivastine. The structures of several compounds, as well as their activity, are shown in Scheme 1. These compounds have demonstrated anti-H1 activity related to other antihistamine compounds of the invention.

In certain embodiments, the $R_1$ substituents will alter the in vivo half-life of the drug. In certain embodiments, the $R_2$ substituents enhance the H1 receptor binding affinity. In addition, the spacer molecule, e.g., the $(CH_2)_m$ linker to the carboxylic acid group, can be substituted with one or more substituents. In one embodiment, the spacer molecule is

SCHEME 1

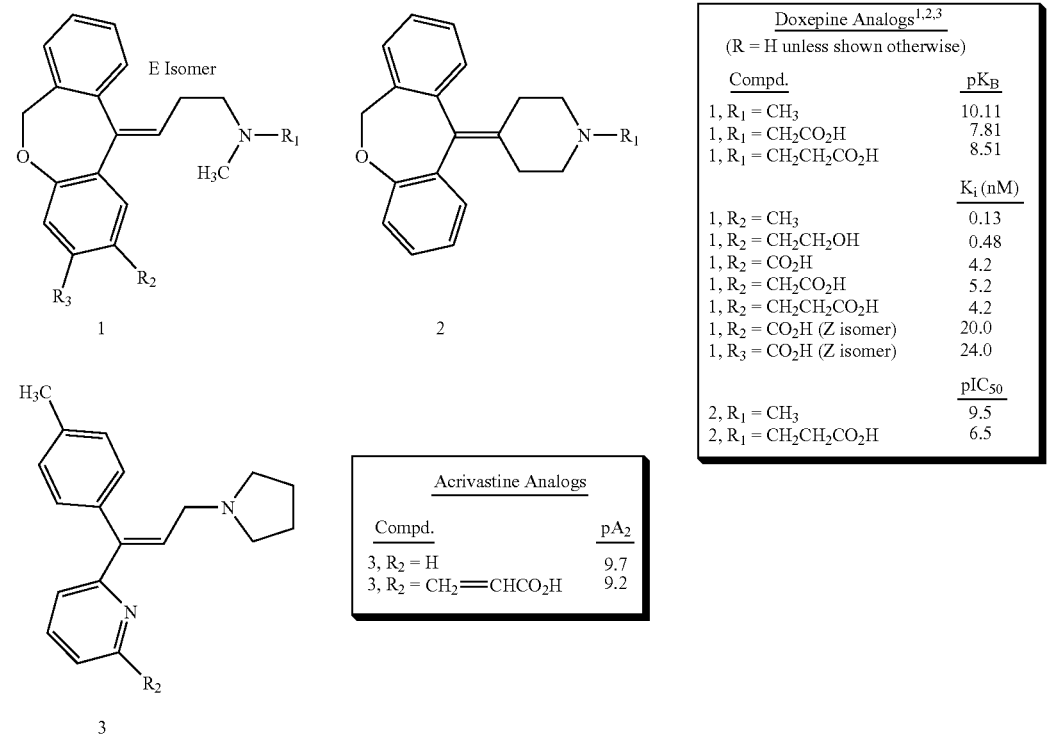

References:
[1] H. Muramatsu et al, Chem. Pharm. Bull. 41(11), 1987 (1993),
[2] N. Iwasaki et al, Chem. Pharm. Bull. 42(11), 2285 (1994),
[3] E. Ohshima, et al., J. Med. Chem. 35, 2074 (1992).

In particular embodiments of the invention, the doxepin-like therapeutic compound is represented by the following formula:

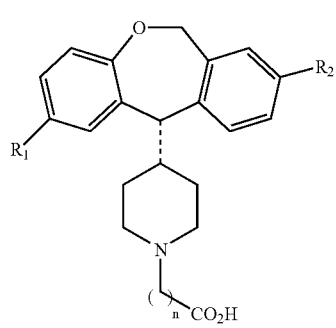

(VI)

wherein
the dashed line represents a single or double bond;
$R_1$=H, OH, $CH_2OH$, $CH_2CH_2OH$;
$R_2$=H, $CH_3$, $CF_3$, Cl, Br; and
n is 1, 2, or 3.

mono-substituted. In another embodiment of the invention, the spacer molecule is disubstituted. In particular embodiments, the linkers of the invention may be geminally-dialkylated, e.g., gem-dimethylated, singly substituted with a substituent other than a noncyclic alkyl group, e.g., a heteroatom, or a cyclic substituent wherein one or more of the carbons of the spacer molecule is contained in the ring, e.g., heterocycle (e.g., tetrahydrofuran or tetrahydropyran), or cyclic alkyl, e.g., cyclopropyl. However, the substitution of the spacer molecule is independent of the substitution at the $R_1$ and $R_2$ positions.

In specific embodiments of the invention which are directed to doxepin-like compounds, such that when $R_1$ and $R_2$ are both H, the alkyl spacer molecule to the carboxylic acid is singly or doubly substituted with alkyl, including gem-dialkyl substitution, e.g., gem-dimethyl substitution. In certain embodiments, the compound of the invention is not a doxepin-like compound of Formula (V), wherein the alkylene spacer molecule is unsubstituted, and $R_1$ and $R_2$ are selected from the group consisting of H, halogen $CF_3$, OH, $C_{1-6}$ alkyl, $C_{1-6}$ alkoxy. In another embodiment, $R_1$ and $R_2$ are not both H when the alkylene spacer molecule is unsubstituted. In one embodiment, n is not 2 or 3 when the spacer molecule is unsubstituted.

Another embodiment of the invention is a pharmaceutical composition comprising a therapeutic compound as prepared according to the methodology of this invention, and a pharmaceutically acceptable carrier.

In another embodiment, the invention is intended to include any novel compounds, including compounds prepared as intermediates, described herein. The scope of the present invention is also intended to include the existence of stereocenters within the compounds of the invention, including compounds in both their racemic and stereoisomer enriched forms. Additionally, the compounds described above are intended to include analogs containing art-recognized substituents that do not significantly effect the analog's ability to perform its intended function. Furthermore, any novel synthesis of the compounds of the invention described herein, is also intended to be included within the scope of the present invention.

Assays can be used to design and/or select compounds useful within the present invention. The SCORE method, described in Example 10, would be an example of such an assay. Multiple assay components, such as total sleep time, cumulative nonREM sleep profile, maximum nonREM sleep bout length, average nonREM sleep bout length, nonREM sleep time, nonREM onset of action profile, sleep latency, REM sleep time, REM sleep bout length, cumulative REM sleep profile, maximum wake bout length, average wake bout length, locomotor activity, locomotor activity intensity, body temperature, and drinking are used to define compounds that would be useful in the present invention. For example, in determining therapeutic compounds that would be useful as sedatives or wake-promoting compounds, all of the components listed above would be used in determining a preferred therapeutic compound. Antidepressant therapeutic compounds would use the components of total sleep time, cumulative nonREM sleep profile, maximum nonREM sleep bout length, REM sleep time, REM sleep bout length, locomotor activity, locomotor activity intensity, and body temperature for determination of preferred therapeutic compounds.

EXEMPLIFICATION OF THE INVENTION

The invention is further illustrated by the following examples that should not be construed as limiting.

Synthetic Preparation

Several synthetic protocols for compounds of the invention and intermediates thereto are shown below and are further depicted in the appropriate schemes. The compounds shall be herein referred to as Series in direct reference to the associated compound labeling number.

EXAMPLE 1

Synthesis of Antihistamine Intermediates

Several synthetic protocols for compounds of the invention are shown below and are further depicted in Scheme 2.

4-[diphenyl(hydroxy)methyl]-1-methylpiperidine (9). A solution of benzophenone (60 g, 0.33 mol) in anhydrous THF (200 mL) was added dropwise over a period of 20 min to a Grignard reagent that was prepared from 59 g (0.44 mol) of freshly distilled 4-chloro-1-methylpiperidine, Mg (1.3 mol) in THF (1L). After stirring overnight, the reaction mixture was quenched ($H_2O$, then dilute HCl) and extracted (2×500 mL) with ethyl acetate. The combined organics were dried with $Na_2SO4$, filtered, and evaporated to dryness to give 89.5 g of alcohol 9. This alcohol was used without further purification. The structure was confirmed by $^1H$ NMR.

4-(Diphenylmethylidene)-1-methylpiperidine (10). Alcohol 9 (27.3 g, 97 mmol) was suspended in concentrated HCl (360 mL) and heated at reflux (oil bath temperature above 96° C.) for 2 h. The mixture was cooled in an ice bath followed by the addition of ethyl acetate (300 mL). A solution of sodium hydroxide (200 g) in water (400 mL), cooled to 10° C., was added dropwise to the acidic mixture until the pH was 14. Ethyl acetate (200 mL) was then added and the organic layer was separated and washed with brine (200 mL). The combined aqueous layers were extracted with ethyl acetate (2×300 mL). The combined organic layers were dried, filtered, and concentrated to give 23 g of the product as a brown oil. $^1H$ NMR confirmed the structure of the product.

4-(Diphenylmethyl)-1-methylpiperidine (12). Solid sodium borohydride (6 g, 160 mmol) and solid alcohol 9 (4.5 g, 16 mmol) were mixed to a fairly homogeneous solid mixture using a spatula. With rapid $N_2$ flow through the system, the solid mixture was added intermittently (cautiously and in small portions over a period of 45 min) to stirred trifluoroacetic acid (200 mL) cooled to 0° C. Extra caution was taken during the addition of the $NaBH_4$ mixture to prevent localized heating and rapid build-up of pressure from the evolving and highly flammable $H_2$. After the addition was complete, the reaction mixture was evaporated to dryness. The above procedure was repeated using 5.2 g of 9 and proportional amounts of the other reagents. The combined residues from the two experiments were diluted with $EtOAc/CH_2Cl_2$ followed by the addition of aqueous NaOH and then solid NaOH until the aqueous layer maintained a pH of 11. The organic layer was dried with $Na_2SO_4$, filtered, and evaporated to an oil that solidified. Chromatography over silica gel using 10% MeOH/10% $Et_3N$ in EtOAc gave 6.75 g of 12 as a white crystalline solid.

1-ethoxycarbonyl 4-(diphenylmethylidene)piperidine (19). Alkene-amine 10 (23 g) was suspended in toluene (150 mL), whereupon dry potassium carbonate (13 g) was added. The mixture was then stirred for 15 minutes, filtered, and the filtrate concentrated to yield 18.5 g of purified 1-methyl 4-(diphenylmethylidene)-piperidine. This purified material was dissolved in dry toluene (100 mL), whereupon dry potassium carbonate (38 g, 275 mmol) was added. Ethyl chloroformate (26.7 g, 245 mmol, 3.5 equiv.) was added slowly with stirring and the mixture was heated at reflux overnight. The reaction mixture was cooled to room temperature and the mixture was then filtered. The reaction vessel and filter cake were subsequently washed with toluene (50 mL) and the filtered solid was then partitioned between water (125 mL) and ethyl acetate (100 mL). Stirring was required to dissolve the potassium carbonate within the solid and the layers were subsequently separated. The organic layer was dried with $Na_2SO_4$, filtered, and concentrated to yield 2.9 g of starting amine. The toluene layer obtained from washing the reaction vessel and the filter cake was dried with $Na_2SO_4$, filtered, concentrated, and the residue purified by flash chromatography (5/1 heptane/EtOAc) to yield 11.47 g (51%) of 19. $^1H$ NMR confirmed the structure of the product and the starting amine. (Carbamate 21 was similarly prepared.)

4-(diphenylmethylidene)piperidine (20). Sodium hydroxide (15.85 g, 396 mmol) in water (30 mL) was added to the carbamate 1-ethoxycarbonyl 4-(diphenylmethylidene)piperidine 19 (11.47 g, 35.7 mmol) dissolved in ethanol (150 mL). The mixture was heated at reflux overnight. The reaction mixture was cooled to room temperature was then partitioned between water (100 mL) and ethyl acetate (150 mL). The mixture was stirred to dissolve the solid and the layers were separated. The organic layer was washed with brine (100 mL) and the separate aqueous layers were extracted with ethyl acetate (100 mL). The combined organic layers were dried with $Na_2SO_4$, filtered, and concentrated. The yellow oil was dried by high vacuum to give 6.7 g (75%) of 20 as a yellow-white waxy solid. $^1$H NMR was used to confirm the structure of the product. (Amine 22 was similarly prepared.)

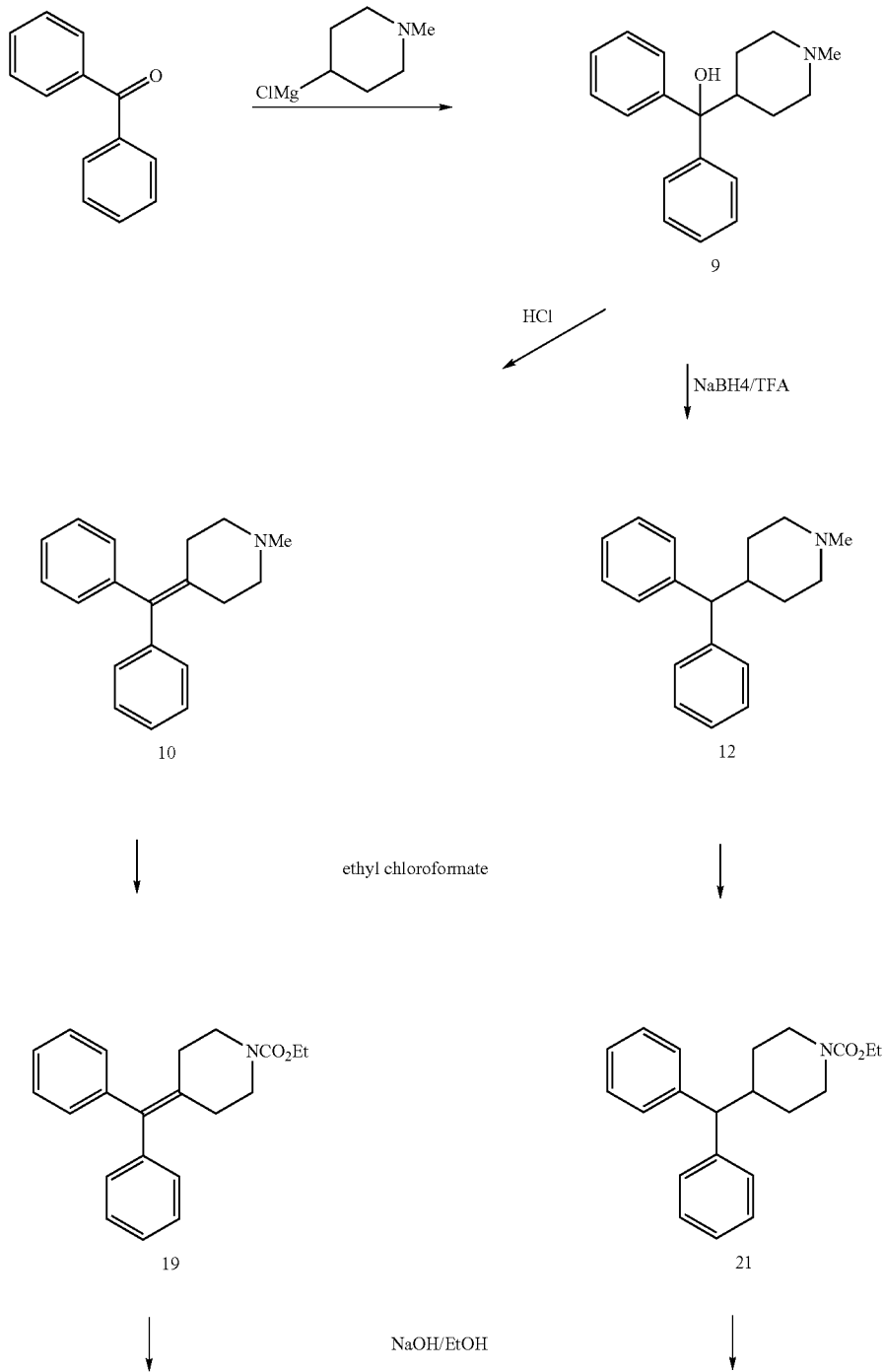

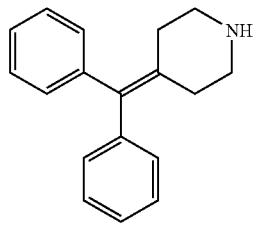

20

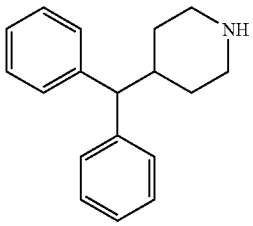

22

Synthesis of Antihistamines from Intermediates

Several synthetic protocols for the preparation of antihistamines from the synthetic intermediates described in Example 1 are shown below in Examples 2-5 and are further depicted in Scheme 3.

EXAMPLE 2

Pheniramine-Like Series 11 Experimental

Isobutyl 3-[4-(diphenylmethylidene)piperidin-1-yl]propanoate (11e). A solution of 20 (0.782 g, 3.14 mmol), isobutyl acrylate (0.56 mL, 3.89 mmol) and ethanol (5 mL) was shaken at 75° C. for 2 h, then evaporated to dryness to give 1.04 g of 11e as a viscous yellow oil that was used without further purification. The structure was confirmed by $^1$H NMR. (Propanoate esters 11b, 11c, and 11f were similarly prepared (see synthesis of cyclopentyl acrylate in the Scheme 6).

Isopropyl 3-[4-(diphenylmethylidene)piperidin-1-yl]propanoate (11d). Sodium hydride (60% dispersion in mineral oil, about 15 mg) was added to a stirred solution of 11b (1.20 g, 3.5 mmol) in 2-propanol (15 mL). Although after 1 h there was no insoluble solid, TLC showed evidence of degradation to the acid 1a, and the mixture was then stirred for an additional 48 h. The mixture was concentrated, suspended in a small amount of 1:1 heptane:ethyl acetate, filtered to remove insoluble solid (323 mg, a) and purified by flash chromatography to yield 560 mg (43%) of 11d. The structures were confirmed by $^1$H NMR and LC/MS. (Propanoate ester 11f was similarly prepared (this represents a second method for preparing 11f.)

Cyclopentyl 3-[4-(diphenylmethylidene)piperidin-1-yl]propanoate, oxalic acid salt (11f-Ox). A solution of oxalic acid (190 mg, 2.11 mmol) in ethanol (3 mL) was added in one aliquot to a stirred solution of 11f (885 mg, 2.26 mmol) in warm ethanol (5.5 mL). The mixture became solid after 10 seconds of stirring. The solid mass was broken up and after 1.5 h of stirring, the solid was collected by suction filtration and washed with ethanol. After drying, the oxalate salt 11f-Ox was obtained as white powder (961 mg, 96%). $^1$H NMR, MS, and elemental analyses were consistent with the structure of the product. (The oxalate salt of 11d was similarly prepared.)

Ethyl 3-[4-(diphenylmethylidene)piperidin-1-yl]propanoate, HCl salt (11c-HCl). 2 M HCl/ether (1.45 mL) was added to a stirred solution of 11c (812 mg, 2.32 mmol) in isopropyl ether (40 mL). After stirring for 30 min, the resulting precipitate was filtered, washed with isopropyl ether, and recrystallized from boiling H$_2$O (2 mL) to give 608 mg of the hydrochloride salt of 11c-HCl as a creamy white powder. The structure was confirmed by $^1$H NMR, MS, and elemental analysis. (The HCl salt of 11e was similarly prepared.)

The HCl salt of carboxylic acid 11a was prepared in a manner equivalent to that used to prepare 16a-HCl (see experimental for the 16 series).

EXAMPLE 3

Pheniramine-Like Series 13 Experimental

Methyl 3-[4-(Diphenylmethyl)piperidin-1-yl]propanoate (13b). A solution of methyl acrylate (699 mg, 8.12 mmol) in MeOH (3 mL) was added to a solution of 22 (1.99 g, 7.92 mmol) in MeOH (8 mL). After shaking at 75° C. for 3 h, the reaction mixture was evaporated to dryness. Chromatography over silica gel (4:1 heptane/EtOAc) gave 2.54 g of 13b as a colorless viscous oil, which crystallized on standing. The structure was confirmed by $^1$H NMR. (Propanoate esters 13c and 13e were similarly prepared.)

Isopropyl 3-[4-(Diphenylmethyl)piperidin-1-yl]propanoate (13d). A dispersion of NaH (~20 mg of a 60% oil dispersion) was added to a solution of 13b (799 mg, 2.37 mmol) in isopropyl alcohol (10 mL). The resulting mixture was immediately stoppered tightly and stirred at RT for 2 h. The reaction mixture was evaporated to dryness and chromatographed over silica gel using 3:1 heptane/EtOAc to give 0.75 g of 13d as a colorless viscous oil. The structure was confirmed by $^1$H NMR. (Propanoate esters 13e and 13f were similarly prepared using isobutanol and cyclopentanol, respectively (as mentioned above, 13e was also prepared by the previous method using isobutyl acrylate).)

Isobutyl 3-[4-(Diphenylmethyl)piperidin-1-yl]propanoate, oxalic acid salt (13e-oxalate). A solution of oxalic acid (138 mg, 1.53 mmol) in H$_2$O (3 mL) was added to a stirred solution of 13e (583 mg, 1.54 mmol) in ethyl alcohol (3 mL), whereupon no precipitate was formed. Evaporation to dryness gave a solid which was recrystallized from boiling isopropyl alcohol to give 622 mg of the oxalate salt of 13e (13e-oxalate) as a white crystalline solid. The structure was confirmed by $^1$H NMR, MS, and elemental analysis. (Oxalate salts of 13c, 13d, and 13f were similarly prepared.)

Carboxylic acid 13a was prepared in a manner equivalent to that followed to prepare 16a (see experimental for the 16 series).

EXAMPLE 4

Pheniramine-Like Series 15 Experimental

Isopropyl [4-(diphenylmethylidene)piperidin-1-yl]ethanoate (15d). A mixture of amine 20 (779 mg, 3.12 mmol), isopropyl bromoacetate (575 mg, 3.18 mmol), $K_2CO_3$ (1.34 g, 3 eq), and acetonitrile (28 mL) was stirred at reflux overnight. The reaction mixture was filtered, evaporated to dryness, and then chromatographed over silica gel using 5:1 heptane/EtOAc to give 0.78 g of 15d as an oil that crystallized on standing. The structure was confirmed by $^1$H NMR. (Acetate esters 15b and 15c were similarly prepared.)

Cyclopentyl [4-(diphenylmethylidene)piperidin-1-yl]ethanoate (15e. A solution of 15b (1.02 g, 3.17 mmol) in anhydrous THF (10 mL) was added (under $N_2$) to a mixture of isobutyl alcohol (10 mL) and sodium hyride (258 mg of a 60% oil dispersion). After stirring for 1 h, the reaction mixture was partitioned between water and EtOAc, wherein a small amount of brine was added to prevent emulsion formation. The organic layer was then removed, the aqueous layer was extracted further with EtOAc, and the combined organics were dried with $Na_2SO4$, filtered, and evaporated to dryness. Chromatography over silica gel using 5:1 heptane/EtOAc gave 0.8 g of 15e as an oil. (Acetate ester 15f was similarly prepared.)

Isopropyl [4-(diphenylmethylidene)piperidin-1-yl]ethanoate, oxalic acid salt (15d-oxalate). A solution of oxalic acid (234 mg, 2.6 mmol) in ethanol (4 mL) was added dropwise to a stirred solution of 15d (910 mg, 2.6 mmol) in ethanol (12 mL). After cooling the reaction mixture to −15° C. for 15 min, the solid was filtered, washed with cold ethanol, and vacuum dried to give 891 mg of 15d-oxalate as a white crystalline solid. The structure of the product was confirmed by $^1$H NMR, MS, and elemental analysis. (The oxalate salts of 15c, 15e, and 15f were similarly prepared.)

EXAMPLE 5

Pheniramine-Like Series 16 Experimental

Methyl [4-(Diphenylmethyl)piperidin-1-yl]ethanoate (16b). A mixture of 22 (2.18 g, 8.68 mmol), methyl bromoacetate (1.44 g, 9.39 mmol), acetonitrile (40 mL), and $K_2CO_3$ (5.54 g, 4.6 eq) was stirred at reflux overnight, evaporated to dryness and chromatographed over silica gel using 4:1 heptane/EtOAc to give 1.3 g of 16b as a white solid. The structure was confirmed by $^1$H NMR. (Acetate esters 16c and 16d were similarly prepared.)

Isobutyl [4-(Diphenylmethyl)piperidin-1-yl]ethanoate (16e). A mixture of 16b (700 mg), isobutyl alcohol (10 mL), anhydrous THF (5 mL), and sodium hydride (15 mg of a 60% oil dispersion) was prepared in a sealed vial and was shaken at 75° C. for 3 h, and subsequently poured over a $H_2O$/EtOAc two-phase mixture. The aqueous layer was removed and extracted once with EtOAc. The combined organics were dried with $Na_2SO_4$, filtered, and evaporated to dryness. Chromatography over silica gel using 5:1 heptane/EtOAc gave 665 mg of 16e as a colorless oil. The structure of the product was confirmed by $^1$H NMR. (Acetate ester 16f was similarly prepared.)

Isobutyl [4-(Diphenylmethyl)piperidin-1-yl]ethanoate, oxalic acid salt (16e-oxalate). A mixture of oxalic acid (160 mg), 16e (650 mg), and isopropyl alcohol was evaporated to dryness. The resulting solid was recrystallized from boiling isopropyl alcohol to give 672 mg of the oxalate salt of 16e (16e-oxalate) as a white crystalline solid. The structure of the product was confirmed by $^1$H NMR, MS, and elemental analysis. (The oxalate salts of 16c, 16d, and 16e were similarly prepared.)

[4-(Diphenylmethyl)piperidin-1-yl]ethanoic acid, HCl salt (16a-HCl). A mixture of sodium hydroxide (6.1 g), water (25 mL), and THF (125 mL) was shaken. One fourth of both the bottom and upper layers of the resulting biphasic mixture was added to 747 mg of 16b (2.21 mmol). After stirring overnight, the reaction mixture was diluted with water and EtOAc and then acidified with concentrated HCl. After removing the organic layer, the aqueous layer was extracted twice with EtOAc. The combined organics were dried $Na_2SO_4$, filtered, evaporated to dryness, and moisture removed with ethanol to give 801 mg of 16a-HCl as a glassy solid which was scraped to a powder. $^1$H NMR spectroscopy indicated that the solid consisted of a 9:1 mixture of HCl and acetic acid salts of 16a.

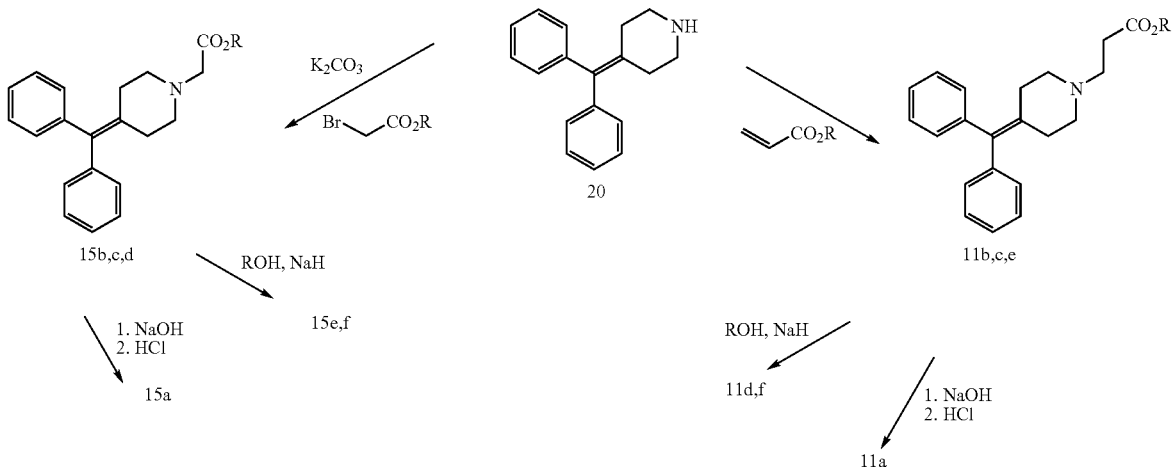

SCHEME 3

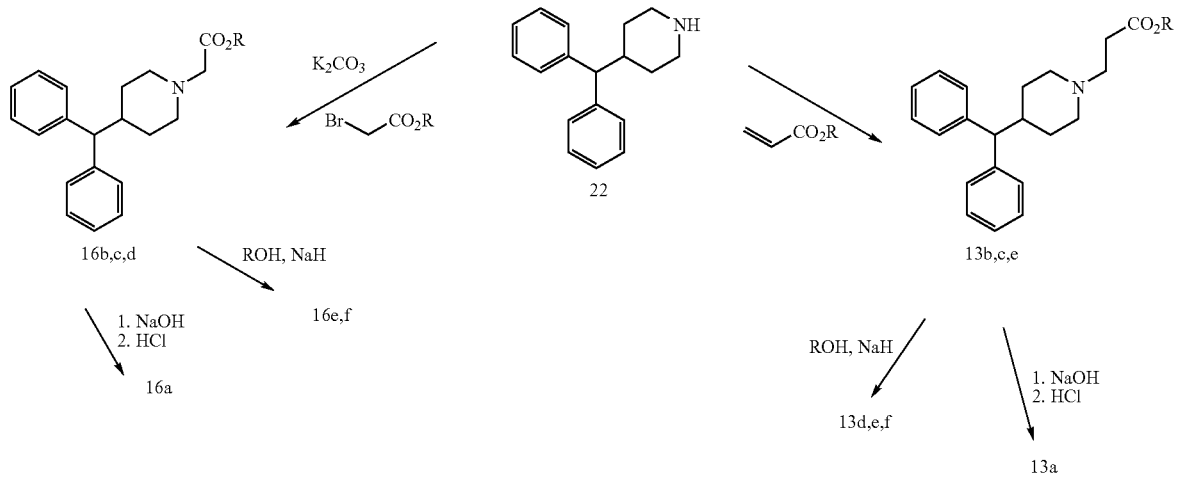

Synthesis of Antihistamines

Synthetic protocols for the preparation of antihistamines of Series 6 and 18 are shown below in Examples 6 and 7, respectively, and are further depicted in Schemes 4 and 5, respectively.

EXAMPLE 6

Diphenhydramine-Like Series 6 Experimental 4-(diphenylmethoxy)-1-(ethoxycarbonyl)piperidine (4a). 4-(Diphenylmethoxy)-1-(methyl)piperidine (prepared by neutralization of the commercial HCl salt; 4 g, 14.2 mmol, 1 equiv.) in anhydrous toluene (20 mL) was stirred at room temperature under nitrogen. Ethyl chloroformate (4.66 g, 43 mmol, 4.1 mL, 3 equiv.) was added dropwise over 5 minutes, whereupon significant effervescence was noted. The mixture was heated over the course of 1 h to reflux with an oil bath (bath temperature 104° C.). The mixture was then cooled to room temperature, whereupon more ethyl chloroformate (4 mL) was added. The mixture was heated at reflux (bath T=104° C.) for 7 h and again cooled to room temperature. The cooled mixture was concentrated and the residue purified by dry column chromatography (4×8.5 cm silica bed; 2:1 heptane:ethyl acetate) to yield 3.49 g (72%) of 4a as a slightly yellow oil. $^1$H NMR was consistent with the structure.

4-(diphenylmethoxy)piperidine (5). 4-(Diphenylmethoxy)-1-(ethoxycarbonyl)piperidine (4a) (11.45 g, 33.7 mmol) was dissolved in ethanol (72 mL). A cold solution of sodium hydroxide (8.2 g, 205 mmol) in water (12 mL) was added slowly and a small amount of heat was detected. The mixture was heated at reflux for 17 h and then cooled to room temperature. The mixture was subsequently diluted with water (100 mL) and ethyl acetate (100 mL) and stirred for 0.5 h to dissolve the resultant solid. The organic and aqueous layers were separated and the organic layer was washed with water (100 mL). The separate aqueous layers were extracted with ethyl acetate (100 mL) and the organic layers were combined, dried with $Na_2SO_4$, filtered and concentrated to yield 7.88 g (87.5%) of 5 as a viscous yellow oil. The structure was confirmed by $^1$H NMR.

Methyl 3-[4-(diphenylmethoxy)piperidin-1-yl]propanoate (6b). A solution of 4-(diphenylmethoxy)piperidine (5) (1.4 g, 5.2 mmol), methyl acrylate (560 mg, 6.5 mmol) and methanol (9.5 mL) was placed on a preheated orbital shaker at 75° C. for 3 h. The yellow solution was concentrated to yield 1.8 g (98%) of 6b as a yellow oil. The structure was confirmed by $^1$H NMR. (The propanoate esters 6c and 6e were similarly prepared.)

Isopropyl 3-[4-(diphenylmethoxy)piperidin-1-yl]propanoate (6d). Oxalyl chloride (7.27 g, 57.3 mmol, 5 mL) was added in one aliquot, with stirring, to a pre-cooled (ice bath) solution of 6a-HCl (1.14 g, 3.0 mmol) in dry THF. Once the initial effervescence ceased, the flask was sealed under nitrogen and the mixture was stirred for 1.75 h. The magnetic stirring bar was washed with dry THF upon its removal from the solution mixture and the mixture was then concentrated on a rotary evaporator to give a yellow-white solid. The solid was dried under high vacuum for 1 h. The solid was then suspended in 2-propanol (15 mL) and 4-ethylmorpholine (440 mg, 400 μL, 3.8 mmol, 1.28 equiv.) was added. Vapors formed above the suspension and the slurry became an orange-yellow solution after about 2 minutes. After having been stirred for 2.5 days, the reaction mixture was concentrated. The residue was dissolved in dichloromethane (25 mL) and washed with 1 N KOH (15 mL). The layers were separated and the aqueous layer was extracted with dichloromethane (25 mL). Both organic layers were washed with water (25 mL), combined, dried with $Na_2SO_4$, filtered and concentrated to yield 976 mg (84%) of a dark orange-yellow oil. This oil was purified by flash chromatography (2:1 heptane:ethyl acetate) to yield 774 mg (67%) of 6d as a yellow oil. $^1$H NMR and LC/MS confirmed the structure. (The propanoate ester 6f was similarly prepared.)

Isopropyl 3-[4-(diphenylmethoxy)piperidin-1-yl]propanoate (6d), Alternate procedure. Sodium hydride (60% dispersion in mineral oil, about 15 mg) was added to a stirred solution of 6b (384 mg, 1.09 mmol) in 2-propanol (8 mL). Although after only 1 h there was no insoluble solid, TLC showed evidence of degradation to the acid 6a. After confirmation by TLC that the reaction was complete, the mixture was concentrated and dissolved in a small amount of 2:1 heptane:ethyl acetate for flash chromatography. The insoluble solid was isolated by filtration (58 mg) and was shown to be 6a. The solution was purified by flash chromatography to yield 300 mg (72%) of 6d as a colorless oil. Purity (LC/MS): 99.6% (m/z=381). (The propanoate ester 6f was also prepared by this alternate procedure.)

3-[4-(diphenylmethoxy)piperidin-1-yl]propanoic acid hydrochloride (6a-HCl). A solution of sodium hydroxide (1.3 g, 32.5 mmol, 1.98 equiv.) in water (16 mL) was slowly added to a stirring solution of 6b (5.8 g, 16.4 mmol) in methanol (58 mL) at room temperature, resulting in a slight increase in temperature. The solution was heated at reflux for 1.25 h, cooled to room temperature, and concentrated. The resulting residue was dissolved in water (75 mL) and the pH was adjusted to 2 with concentrated HCl (about 2.5 mL). The thick mixture was then extracted with chloroform (3×80 mL; 6a-HCl is soluble in chloroform) and the combined organic layers were washed with brine (100 mL). The organic layers were dried with $Na_2SO_4$, filtered, and concentrated to give 6a-HCl as white needles (5.3 g, 86%). The structure was confirmed by $^1H$ NMR and LC/MS.

Ethyl 3-[4-(diphenylmethoxy)piperidin-1-yl]propanoate, oxalic acid salt (6c-Ox). A solution of oxalic acid (130 mg, 1.44 mmol) in ethanol (3 mL) was added in one aliquot to a stirred solution of ethyl 3-[4-(diphenylmethoxy)piperidin-1-yl]propanoate 6c (530 mg, 1.44 mmol) in ethanol (3 mL). The mixture became solid at the end of the addition, whereupon more ethanol (2 mL) was added to facilitate stirring. After 1 h of stirring, the solid was collected by suction filtration and washed with ethanol (2 mL). After drying, the oxalate salt 6c-Ox was obtained as white powder (595 mg, 90%). $^1H$ NMR, LC/MS, and elemental analysis were consistent with the structure. (The oxalate salts of 6d, 6e, and 6f were similarly prepared.)

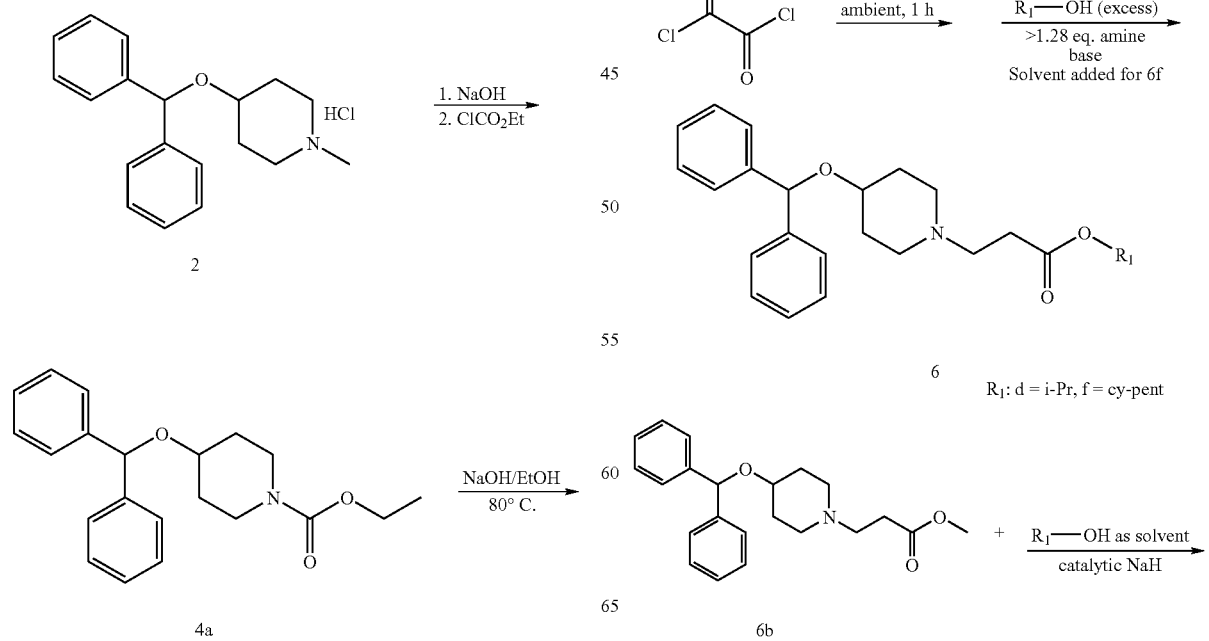

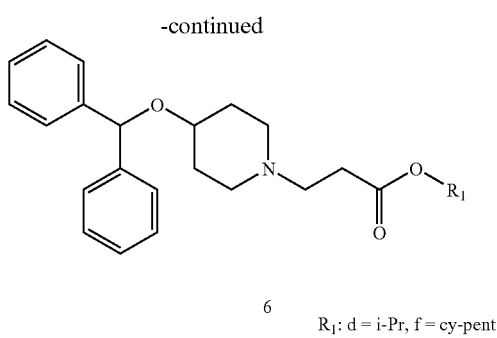

6

R₁: d = i-Pr, f = cy-pent

EXAMPLE 7

Pheniramine Analog Series 18 Experimental 4-(3-dimethylamino-1-(2-pyridyl)propyl)benzoic acid (18a). (+/−)-Brompheniramine 17 (obtained by neutralization of the maleate salt; 38 g, 120 mmol) was dissolved in dry THF under nitrogen and the solution was cooled in a dry ice/acetone bath. n-butyllithium (1.6 M, hexanes, 90 mL, 144 mmol) was added dropwise to the reaction mixture to give a red solution. After 2 h of stirring, carbon dioxide was bubbled into the solution as the bath slowly warmed to room temperature. The resulting mixture was stirred overnight and the reaction was quenched with water (500 mL). The aqueous layer was extracted with ethyl acetate (2×500 mL). The organic layer was discarded and the aqueous layer was concentrated to a yellow paste. The paste was digested in sodium hydroxide (1 N, 150 mL) and chloroform (200 mL) and the layers were separated. The aqueous layer was extracted with chloroform (200 mL) and ethyl acetate (2×150 mL). The chloroform layers were concentrated to yield unreacted 17 (17 g, 44%). The ethyl acetate layers were concentrated to 1.4 g of a complex mixture which was discarded. The aqueous layer was concentrated to a thick oil, filtered to remove insoluble solid, and dissolved in ethanol (100 mL) and water (40 mL). The pH was adjusted to 2 by the careful addition of concentrated HCl (about 17 mL). The resulting solution was concentrated, dissolved in 1:1 methanol:ethanol, filtered to remove insoluble NaCl and concentrated to a brown oil (13 g). The oil was purified by column chromatography (8.5/1/0.5 $CH_2Cl_2$/MeOH/triethylamine) to yield 18a as a white solid (3 g, 8%). The structure was confirmed by $^1$H NMR, LC/MS, and elemental analysis.

Ethyl 4-[3-dimethylamino-1-(2-pyridyl)propyl]benzoate (18c). Acid 18a (927 mg, 3.26 mmol) was stirred in oxalyl chloride (5 mL) at room temperature for 2 minutes and dry toluene (4 mL) was added to facilitate stirring. After 1 h, the mixture was concentrated. Ethanol (10 mL) and triethylamine (1.35 mL) were added and the dark yellow mixture was stirred overnight. The mixture was then concentrated and partitioned between ethyl acetate (25 mL) and water (25 mL). The layers were separated and the aqueous layer was extracted with ethyl acetate (10 mL). The combined organic layers were washed with water (20 mL) and the combined aqueous layers were extracted with ethyl acetate (20 mL). The combined organic layers were dried with $Na_2SO_4$, filtered, and concentrated to yield 18c as an oil. Purification by flash chromatography (4/1 $CH_2Cl_2$/MeOH) yielded 18c (136 mg) as a yellow oil. The structure was confirmed by $^1$H NMR and LC/MS. (Esters 18d, 18e, and 18f were similarly prepared.)

Ethyl 4-(3-dimethylamino-1-(2-pyridyl)propyl)benzoate, oxalic acid salt (18c-Ox). A solution of oxalic acid (52 mg, 0.58 mmol) in ethanol (0.5 mL) was added in one aliquot to a stirred solution of 18c (185 mg, 0.59 mmol) in ethanol (0.5 mL). The mixture became solid after 30 seconds of stirring. The solid mass was broken up, ethanol (0.75 mL) was added, and the solid was collected by suction filtration after 1.5 h of stirring and subsequently washed with ethanol. After drying, the oxalate salt 18c-Ox was obtained as white powder (167 mg, 72%). $^1$H NMR, LC/MS, and elemental analyses were consistent with the structure of the product. (The oxalate salt of 18e was prepared similarly.)

SCHEME 5

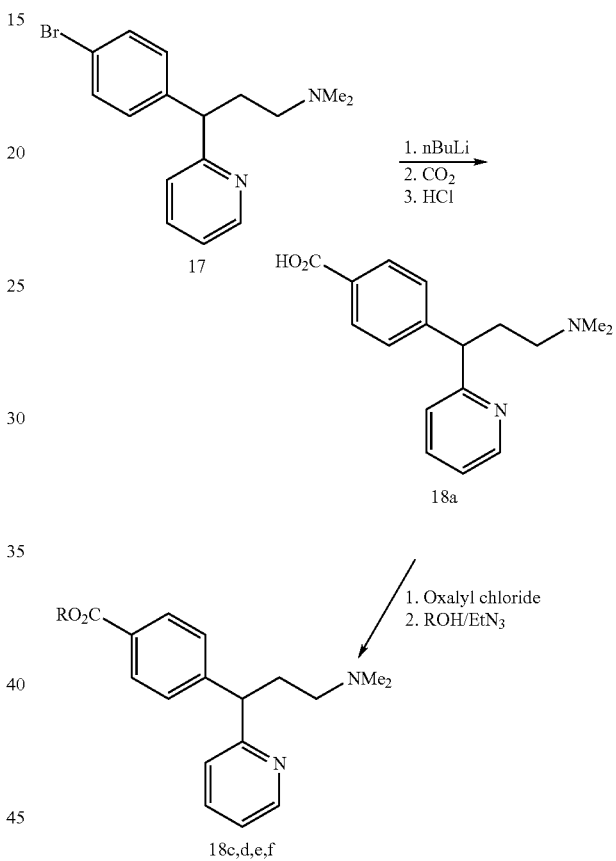

Synthesis of Triprolidine Series

Synthetic protocols for the preparation of the triprolidine series are shown below in Examples 8 and are further depicted in Scheme 6.

EXAMPLE 8

Triprolidine-Like Series 7 Experimental

6-Bromo-2-pyridyl 4-tolyl ketone (3). A solution of 1 (50.02 g, 0.211 mol) was added to a stirred and cooled (−78° C.) solution of 1.6 M n-BuLi/hexanes (132 mL) over a period of 1 h and 20 min. After an additional 15 min at −78° C., a solution of p-tolunitrile (25.64 g, 0.219 mol) in anhydrous THF (100 mL) was added rapidly (4 min) and the reaction mixture was stirred for another 4.75 h. During this time the temperature was controlled to rise slowly from −78° C. to −20° C. The reaction was stirred at room temperature overnight and then quenched by the addition of 2 N HCl (500 mL). The organic layer was dried with Na₂SO₄, filtered, and evaporated to a solid. Recrystallization from boiling ethanol gave 36.74 g of ketone 3 as an off-white crystalline solid. The structure of the product was confirmed by $^1$H NMR.

Cyclopentyl acrylate. Acryloyl chloride (75 mL) was added to a stirred solution of cyclopentanol (88 g, 1 mol) and triethylamine (175 mL) in dry THF (500 mL) at a rate slow enough to prevent overheating of the reaction. The reaction mixture was allowed to stand overnight, filtered through a pad of Celite, evaporated to an oil, and distilled to give cyclopentyl acrylate as a colorless liquid (bp 74-79/~60 mm Hg). The structure of the product was confirmed by $^1$H NMR.

Ethyl(E)-3-[6-(4-toluoyl)-2-pyridyl]acrylate (5c). A mixture of ketone 3 (16.90 g, 61.2 mmol), triphenylphosphine (1.64 g, 6.25 mmol), tributylamine (15 mL), and ethyl acrylate (16 mL) was stirred and heated (hot bath at 125-135° C.) for 7 h. Two additional aliquots of ethyl acrylate (7 mL each) were added at 4 h and 6 h. After the reaction was cooled to room temperature, the reaction mixture was poured over water (300 mL) and EtOAc (300 mL). The aqueous layer was extracted further with EtOAc. The combined organics were dried with Na₂SO₄, filtered, and evaporated to dryness. Chromatography over silica gel using heptane/EtOAc (starting at 8:1) gave 15.49 g of 5c as a yellow crystalline solid. The structure was confirmed by $^1$H NMR. (Keto-acrylates 5e and 5f were similarly prepared using isobutyl acrylate and cyclopentyl acrylate, respectively.)

(2-pyrrolidinoethyl)triphenylphosphonium bromide. A mixture of 2-phenoxyethyl bromide (90.6 g, 0.45 mol), triphenylphosphine (119.2 g, 0.45 mol), and phenol (854 g) was heated to a melt and then stirred over a hot oil bath (107-114° C.) for ~24 h. The reaction mixture was extracted with 6:1 heptane/EtOAc (3×2 L), 9:1 heptane/EtOAc (3×0.5 L), and heptane (300 mL) to give an oil that solidified. After dissolving the reaction mixture in DMSO, the mixture was warmed, treated with pyrrolidine (150 mL), and stirred over a hot oil bath (50-55° C.) for 1.5 h. The reaction mixture was cooled to room temperature, seeded for crystallization, and treated slowly and intermittently with increasing amounts of t-butyl methyl ether (TBME) until it was evident that crystallization was complete. The solid was filtered, washed with TBME and then with heptane, and vacuum dried to give 90.27 g of the desired product. The structure was confirmed by $^1$H NMR.

Triprolidine E,E-7c. A solution of 25 mL of 1.6 M n-BuLi/hexanes was added to a stirred and cooled (0° C.) suspension of (2-pyrrolidinoethyl)triphenylphosphonium bromide (17.24 g, 39.18 mmol) in dry THF (250 mL) over a period of ~4 min. The ylide-forming reaction mixture was stirred an additional 10 min at 0° C., followed by the addition of one aliquot of a solution of 5c (4.52 g, 15.3 mmol) in dry THF (75 mL). After stirring at 0° C. for only 2 min, the reaction mixture was quenched by the addition of water (100 mL). The reaction mixture was then extracted twice with EtOAc and the combined organics were dried with Na₂SO₄, filtered, and evaporated to dryness. Chromatography over silica gel using MeOH/EtOAc (starting at 5% MeOH) gave 1.42 g (25%) of E,E-7c as a yellow crystalline solid and 2.42 g (42%) of E,Z-7c. The structure of the products were confirmed by $^1$H NMR and MS. (Triprolidine ester E,E-7e was similarly prepared.)

Triprolidine E,E-7f. Sodium hydride (25 mg of a 60% oil dispersion) was added to a solution of E,E-7c (1.116 g, 2.96 mmol) in cyclopentanol (10 mL) and dry THF (8 mL). After stoppering the reaction flask, the reaction mixture was stirred at room temperature for 1.5 h and quenched by the addition of saturated brine (30 mL). The mixture was extracted twice with EtOAc and the combined organics were dried with Na₂SO₄, filtered, and evaporated to dryness. Chromatography over silica gel using MeOH/EtOAc (starting at 2% MeOH) gave 1.04 g of the desired product as a viscous oil. The structure of the product was confirmed by $^1$H NMR. (Triprolidine esters E,E-7d was similarly prepared.)

Triprolidine E,E-7e-oxalate. A solution of oxalic acid (362 mg, 4 mmol) in ethanol (4 mL) was added to a stirred solution of E,E-7e (1.63 g) in EtOH. After evaporating to dryness, the resulting oil was dissolved in EtOAc and again evaporated to dryness, whereupon a solid was generated. Recrystallization from boiling EtOAc gave 1.59 g of the oxalate salt of as an off-white powder. The structure was confirmed by $^1$H NMR, MS, and elemental analysis. (The oxalate salts of the E,E-isomers of 7c, 7d, and 7f were similarly prepared.)

SCHEME 6

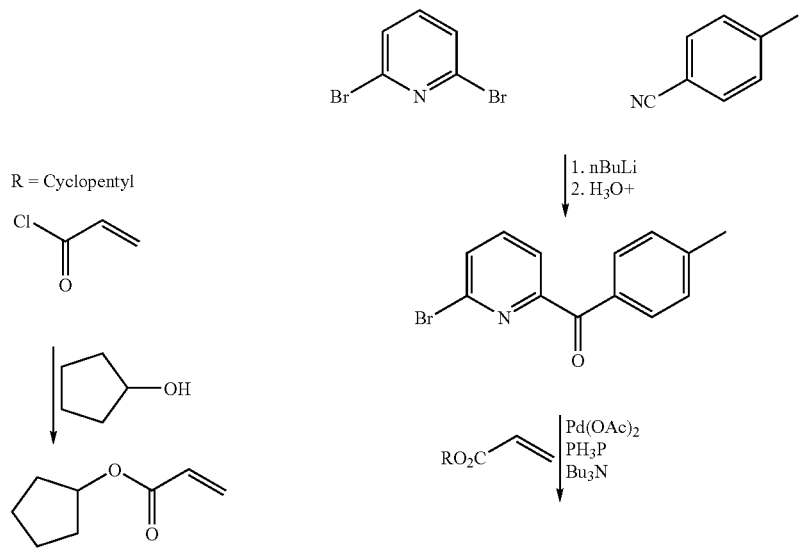

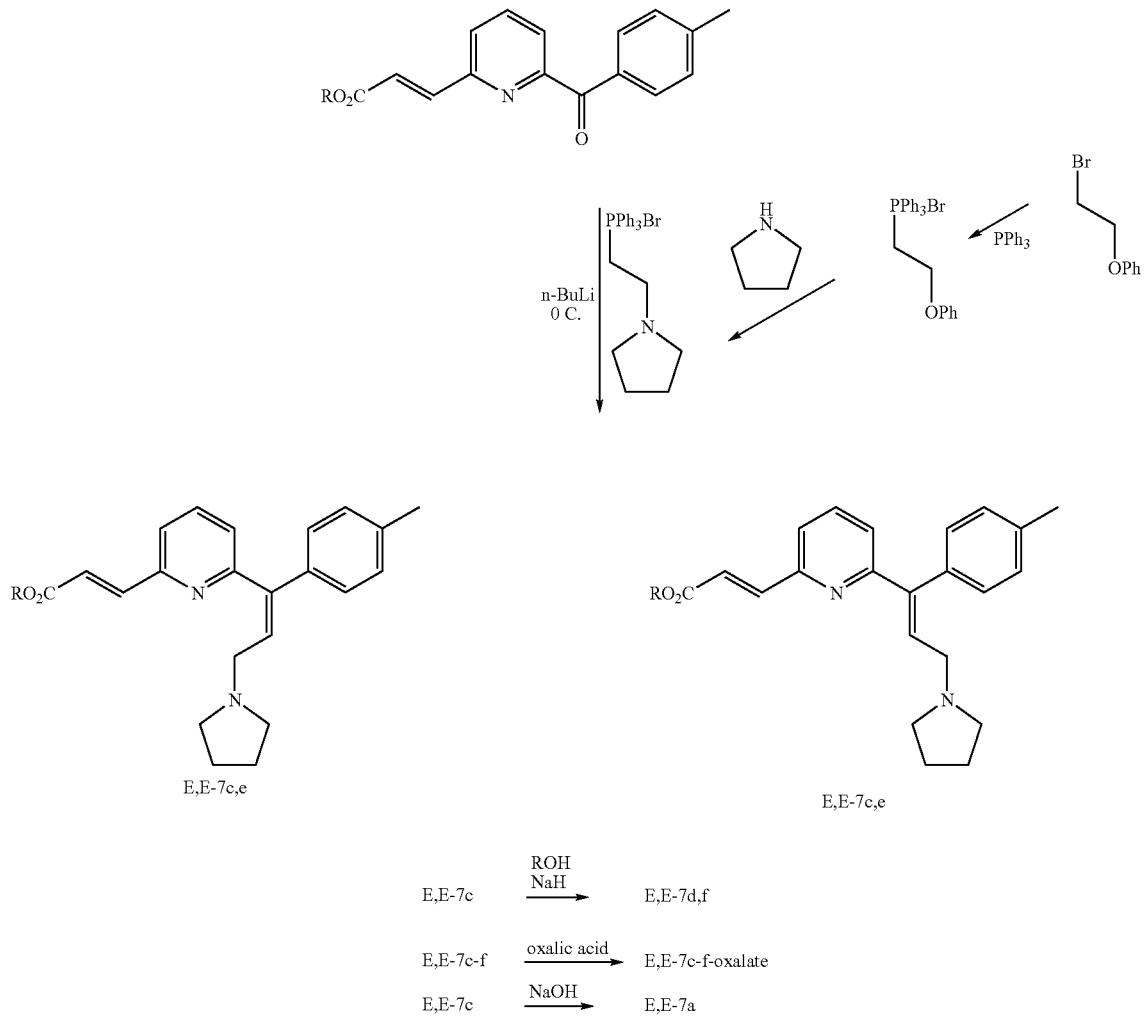

Triprolidine acid E E-7a was prepared in a manner similar to that used to prepare acids 11a 13a, 15a, and 16a described above.

EXAMPLE 9

Doxepin-Like Series Experimental

Step 1:

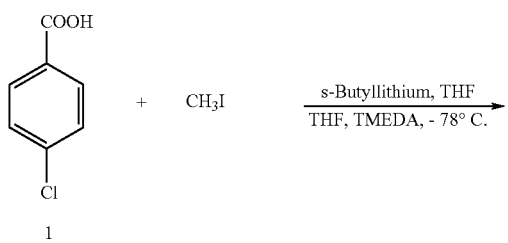

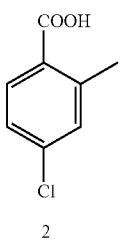

A mixture of THF (150 mL) and N,N,N',N'-tetramethyl-ethylenediamine (27.8 mL, 0.1853 mol, 2.5 eq.) was cooled to −78° C. s-Butyllithium (0.2 mol) was added slowly (40 min) maintaining the temperature between −65 to −78° C. After an additional 20 min stirring, 4-chlorobenzoic acid (11.60 g, 0.0741 mol, 1.0 eq.) dissolved in THF (150 mL) was added over a period of 60 minutes while maintaining the temperature between −65 to −78° C. After 2 h, iodomethane added, and stirring continued for 1 hour, at which time the cooling bath was removed. Water (164 mL) was added slowly and the reaction mixture was allowed to warm to room temperature. The layers were then separated, and the aqueous layer was washed with tert-butyl methyl ether (3×100 mL), and acidified with HCl to pH 1-2. The product was subsequently collected by filtration, washed with water, and dried under vacuum at 60° C. to give compound 2 (10.63 g, 84.0%). ¹H NMR was consistent with the structure.

Step 2:

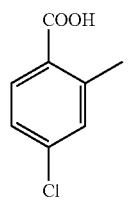

2

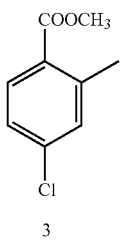

3

Compound 2 (10.62 g, 62.3 mmol, 1.0 eq.) was dissolved in methanol (200 mL) and thionyl chloride (11.3 mL, 155.25 mmol, 2.5 eq.) was added slowly. The reaction solution was refluxed for 5 h, the solvent was removed, and the oil was taken up in methylene chloride (200 mL). The organic layer was washed with H₂O (3×100 mL), dried over MgSO₄, filtered, concentrated, and dried to give compound 3 (10.86 g, 94.4%). The structure was confirmed by ¹H-NMR.

Step 3:

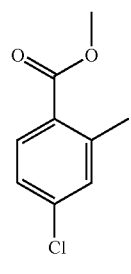

3

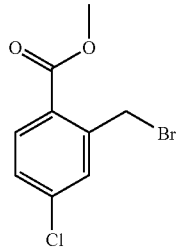

4

Compound 4 (10.86 g, 58.8 mmol, 1.0 eq.) was dissolved in carbon tetrachloride (100 mL), and N-bromosuccinimide (15.7 g, 88.2 mmol., 1.5 eq.) was added followed by benzoylperoxide (0.05 g). The mixture was refluxed overnight. The reaction mixture was then filtered, and the solids were washed with dichloromethane. The combined organic filtrate was concentrated and dried to give compound 4 (7.1 g, 45.8%). The structure was confirmed by ¹H NMR.

Step 4:

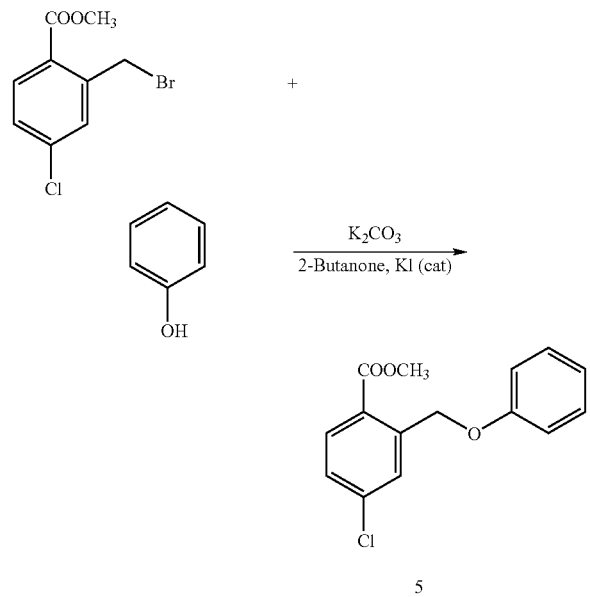

5

Phenol (2.79 g, 29.63 mmol, 1.1 eq.) was dissolved in 2-butanone (75.0 mL) and potassium carbonate (11.17 g, 80.82 mmol., 3.0 eq.) was added, followed by compound 4 (7.1 g, 26.94 mmol., 1.0 eq.) dissolved in 2-butanone (75.0 mL). A catalytic amount of potassium iodide (0.05 g) was added and the mixture was refluxed overnight. The cooled reaction mixture was filtered and the solids were washed with 2-butanone. The combined filtrate was taken up in ethyl acetate (75 mL) and was washed with 5% aqueous NaOH (2×50 mL), brine (40 mL), and water (50 mL). The organic phase was concentrated and purified on silica gel to give compound 5 (9.32 g). The structure confirmed product by ¹H NMR.

Step 5:

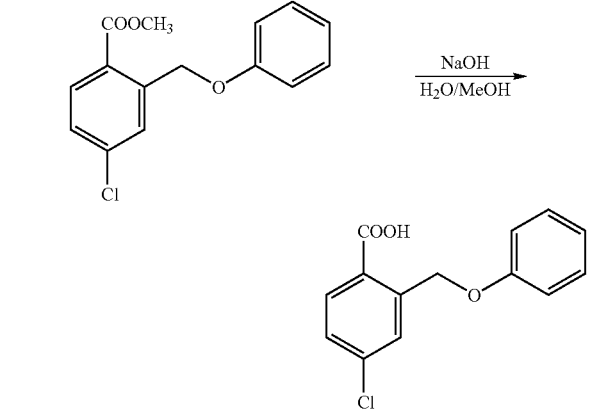

6

A solution of NaOH (4.0 g, 3.0 eq.) in H₂O (20 mL) was added to compound 5 (9.32 g, 1.0 eq.) dissolved in MeOH (50 mL), and refluxed for 45 min. After cooling, the solvent was removed, H₂O added (100 mL), and aqueous layer (aq. Extract-1) washed with ethyl acetate. The product was extracted into the ethyl acetate layer. The organic phase was then washed with water/5% NaOH (3×75 mL) (aq. Extract-2). Each of the aqueous extracts 1 and 2 (which were not combined) was acidified to pH 1-2 with HCl. The white precipitate obtained was taken up in dichloromethane (3×75 mL). After removal of the solvent and drying, aq. Extract-1 gave 1.61 g solid containing some product but mostly compound 1, and aq. Extract-2 gave 5.68 g product (compound 6). The structures were confirmed by ¹H NMR.

Step 6:

Compound 6 (6.0 g, 22.84 mmol., 1.0 eq.) was dissolved in dichloromethane (75.0 mL) and trifluoroacetic anhydride (7.2 g, 34.26 mmol., 1.5 eq.) was added, followed by a catalytic amount of borontrifluoride etherate (0.4 mL). Reaction mixture was heated to 40° C. for 4 h. The reaction mixture was washed with water (50 mL), saturated NaHCO₃ (2×50 mL), and water (50 mL). The organic phase was dried over MgSO₄, filtered and concentrated. The crude product was purified on 120 g RediSep column using gradient elution, heptane/ethylacetate to give compound 7 (3.69 g, 66.0%). The structure was confirmed by ¹H NMR and LC/MS.

Step 7:

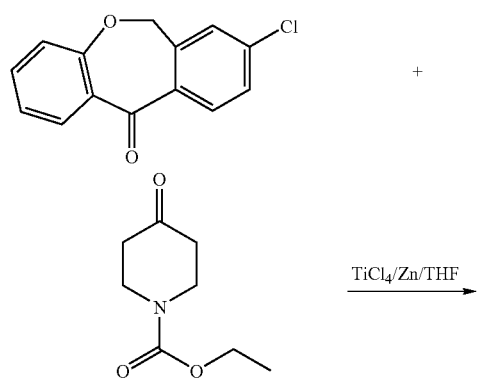

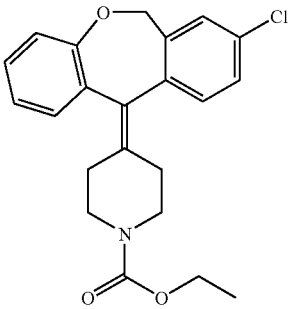

8

The ketone 7, was subjected to McMurray reaction. Accordingly, titanium chloride (4.05 mL, 36.85 mmol.) was slowly added to a mixture of zinc dust (5.31 g, 81.2 mmol., 5.4 eq.) in anhydrous THF (60 mL) at 0° C. The mixture was then refluxed for 2.5 hours. N-carbethoxy-4-piperidone, (5.5 mL, 36.3 mmol., 2.4 eq.) and ketone 7 (3.69 g, 15.12 mmol., 1.0 eq.) were dissolved in anhydrous THF (40.0 mL) and added to the titanium (0) mixture, and the reaction mixture was refluxed for 6 h. An aq. solution of K₂CO₃ (150 mL of 10% aqueous solution) was then added and stirred for 30 min. The mixture was subsequently filtered over pad of celite, and the solids were washed with ethylacetate. The layers were separated and the organic phase was collected, dried over MgSO₄, and concentrated to give the compound 8 (8.15 g, 80.0% pure by HPLC). The structure was confirmed by ¹H NMR and LC/MS.

Step 8:

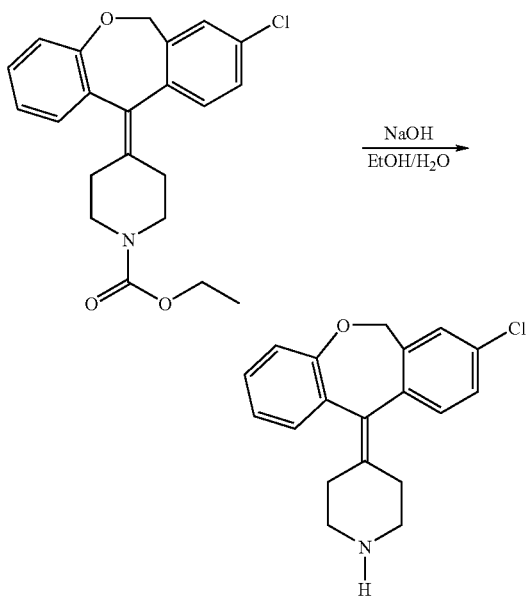

Compound 8 was dissolved in ethanol (60.0 mL), and an aq. solution of sodium hydroxide (10.2 g, 254.76 mmol., 12.0 eq.) in H₂O (15.0 mL) was added and refluxed overnight. The solids were filtered off, and then washed with ethanol. The filtrate was concentrated and the oily residue was taken up in dichloromethane (155 mL) and H₂O (40 mL). The aqueous layer was extracted with CH₂Cl₂ (3×50 mL) and combined with the organic layer. The combined organic phase was washed with brine, dried over NaSO₄, filtered and concentrated to give 3.95 g of crude compound 9. The structure of compound 9 was confirmed by H NMR and LC/MS and the crude material was taken to the next step without purification.

Step 9:

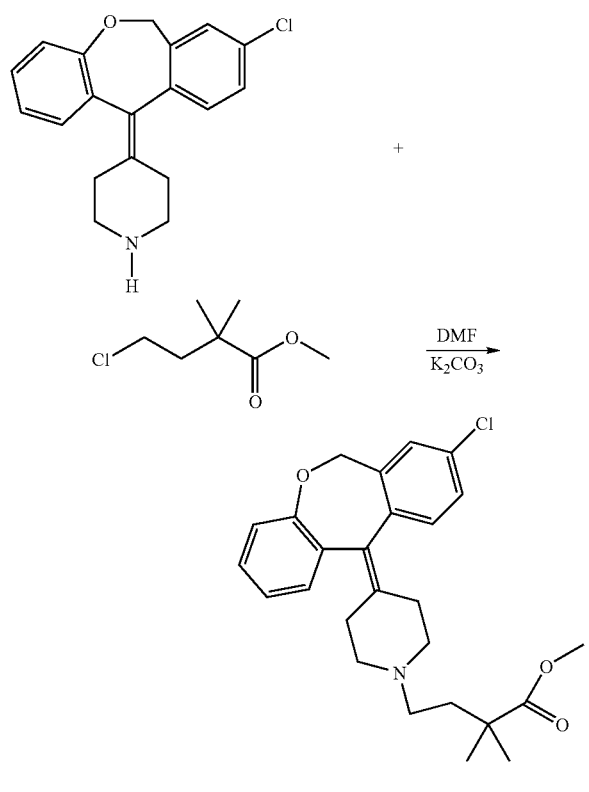

Compound 9 (2.0 g, 6.41 mmol., 1.0 eq.), K₂CO₃ (1.77 g, 12.82 mmol., 2.0 eq.), halide (5.28 g, 32.05 mmol., 5.0 eq.) and DMF (25.0 mL) were combined and heated to 100° C. overnight. The crude reaction mixture was mixed with H₂O (30 mL) and CH₂Cl₂ (35 mL). The organic phase was separated and the aqueous phase was washed with CH₂Cl₂ (2×25 mL). The combined organic phase was washed with brine and concentrated. The crude material was purified on a silica column to give compound 10 (1.2 g). The structure was confirmed by ¹H NMR and LC/MS.

Step 10:

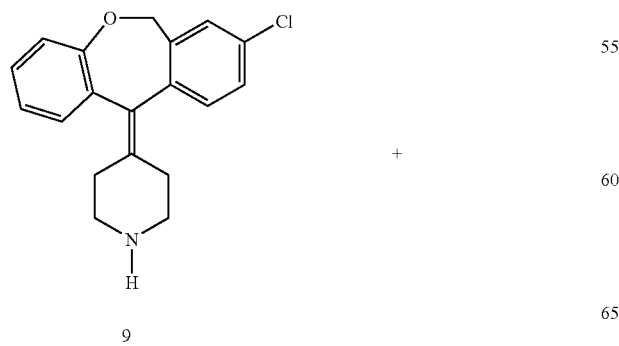

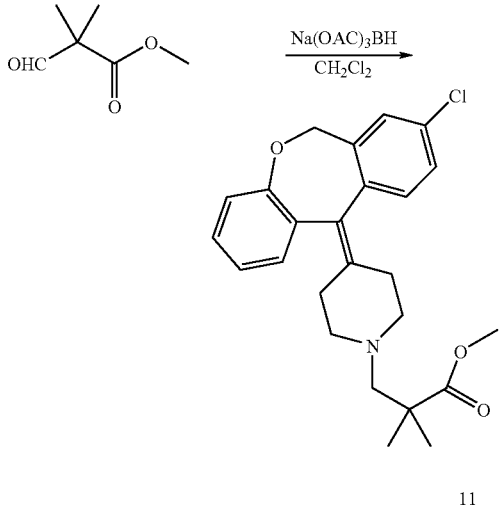

Compound 9 (2.0 g, 6.41 mmol, 1.0 eq.), aldehyde (1.7 g, 13 mmol, 2.0 eq.) and CH₂Cl₂ (20 mL) were taken in a flask under nitrogen and cooled to 0° C. Na(OAc)₃BH (2.6 g, 12.32 mmol, 1.9 eq.) was added in controlled aliquots and stirred at 0° C. for 30 min. the reaction mixture was allowed to reach room temperature and stirred overnight. The mixture was then diluted with CH₂Cl₂ (40 mL), an aq. solution of satd. NaHCO₃ (30 mL) was subsequently added, and the reaction mixture was stirred for 10 min. The organic phase was separated and the aq. phase was extracted with CH₂Cl₂ (2×25 mL). The combined organic layer was dried (NaSO₄), concentrated, and the crude material was purified on a silica column to give compound 11 (1.72 g). The structure was confirmed by ¹H NMR and LC/MS.

Step 11:

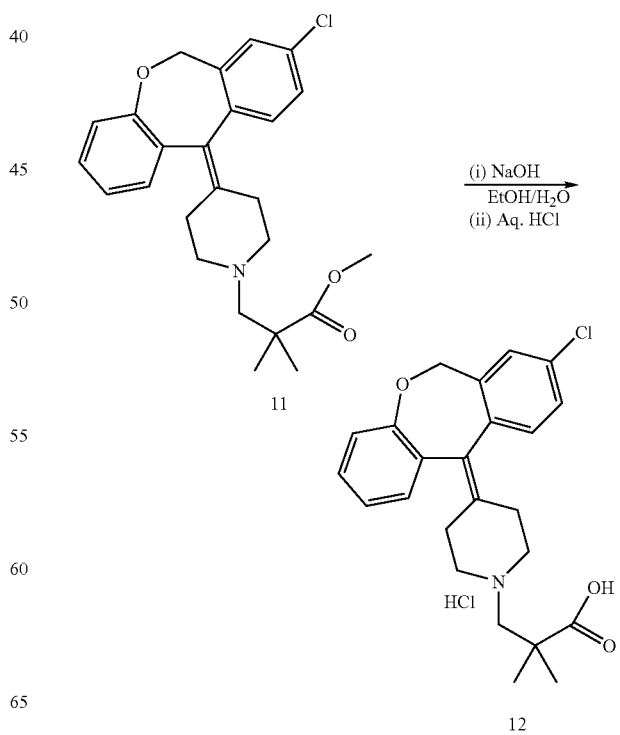

Compound 11 (1.6 g, 3.76 mmol, 1 eq.) was dissolved in ethanol (40.0 mL). An aq. solution of sodium hydroxide (2.0 g, 50 mmol., 13.0 eq.) in $H_2O$ (9.0 mL) was added and refluxed overnight. The solids were filtered off, and the solvents were then distilled off. The residue was taken up in $H_2O$ (40 mL) and acidified with HCl to pH 1 and stirred for 20 min. The resulting solids were filtered, washed with heptane, and dried under high vacuum to give the compound 12 (1.59 g). The structure of the compound 12 was confirmed by $^1H$ NMR, LC/MS and elemental analysis.

Schemes 7 through 15, shown below, depict the synthesis of several doxepin-like compounds of the invention, with various degrees of substitution (i.e., various substituents at the $R_1$ and $R_2$ positions, on the spacer molecule, and combinations thereof)

SCHEME 7

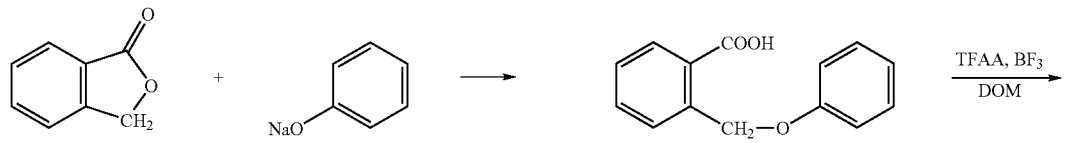

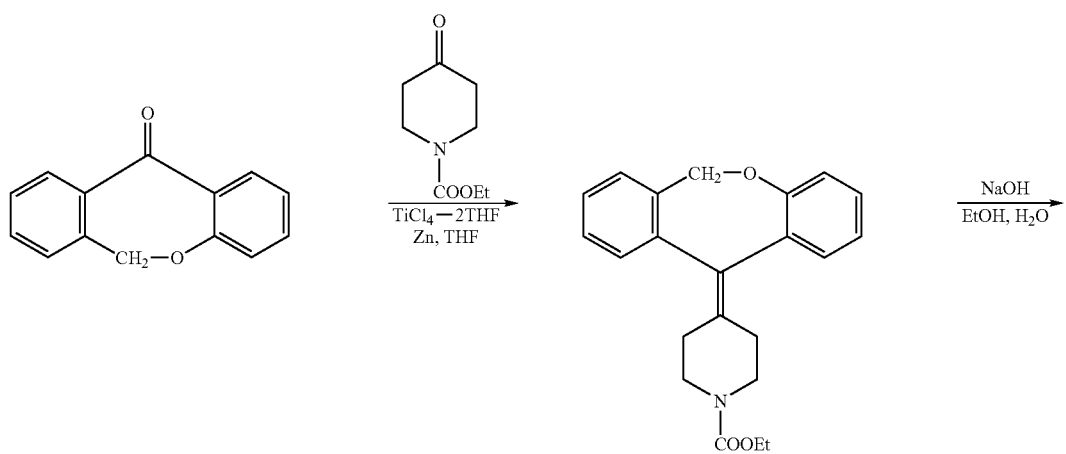

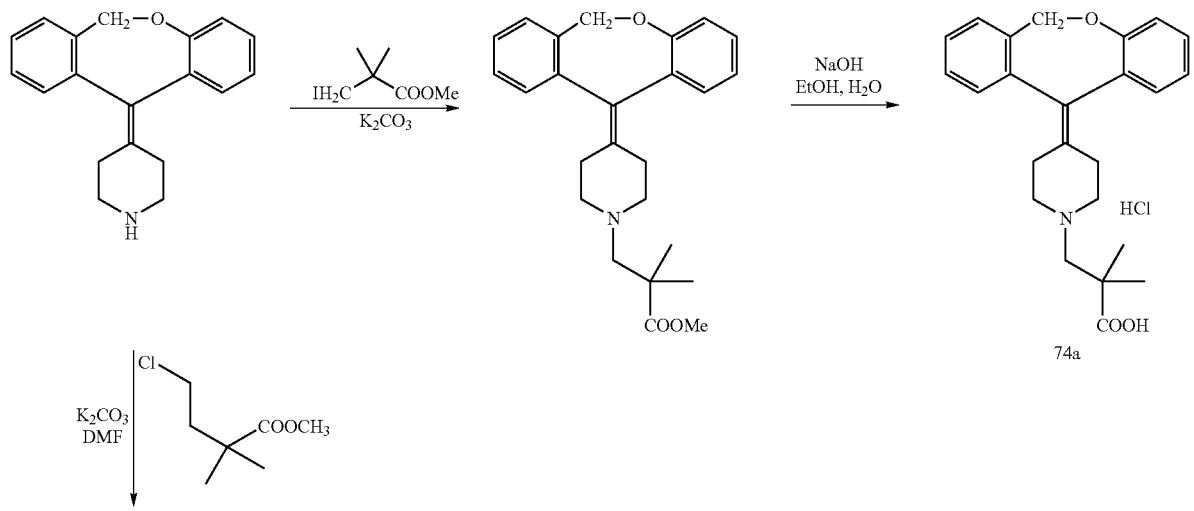

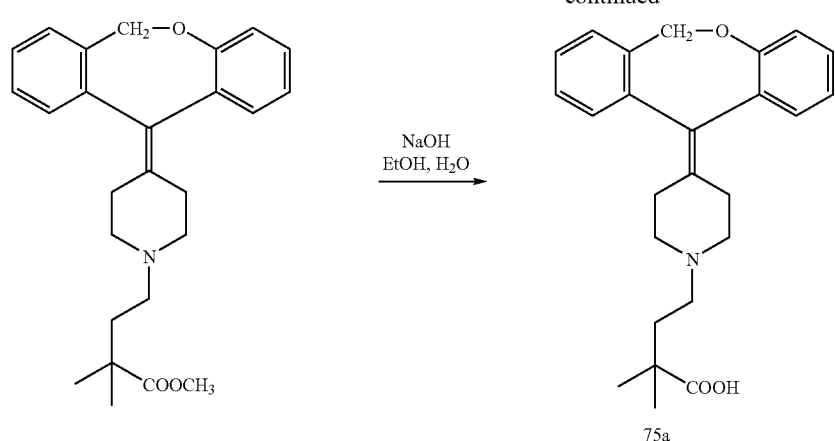
SCHEME 8
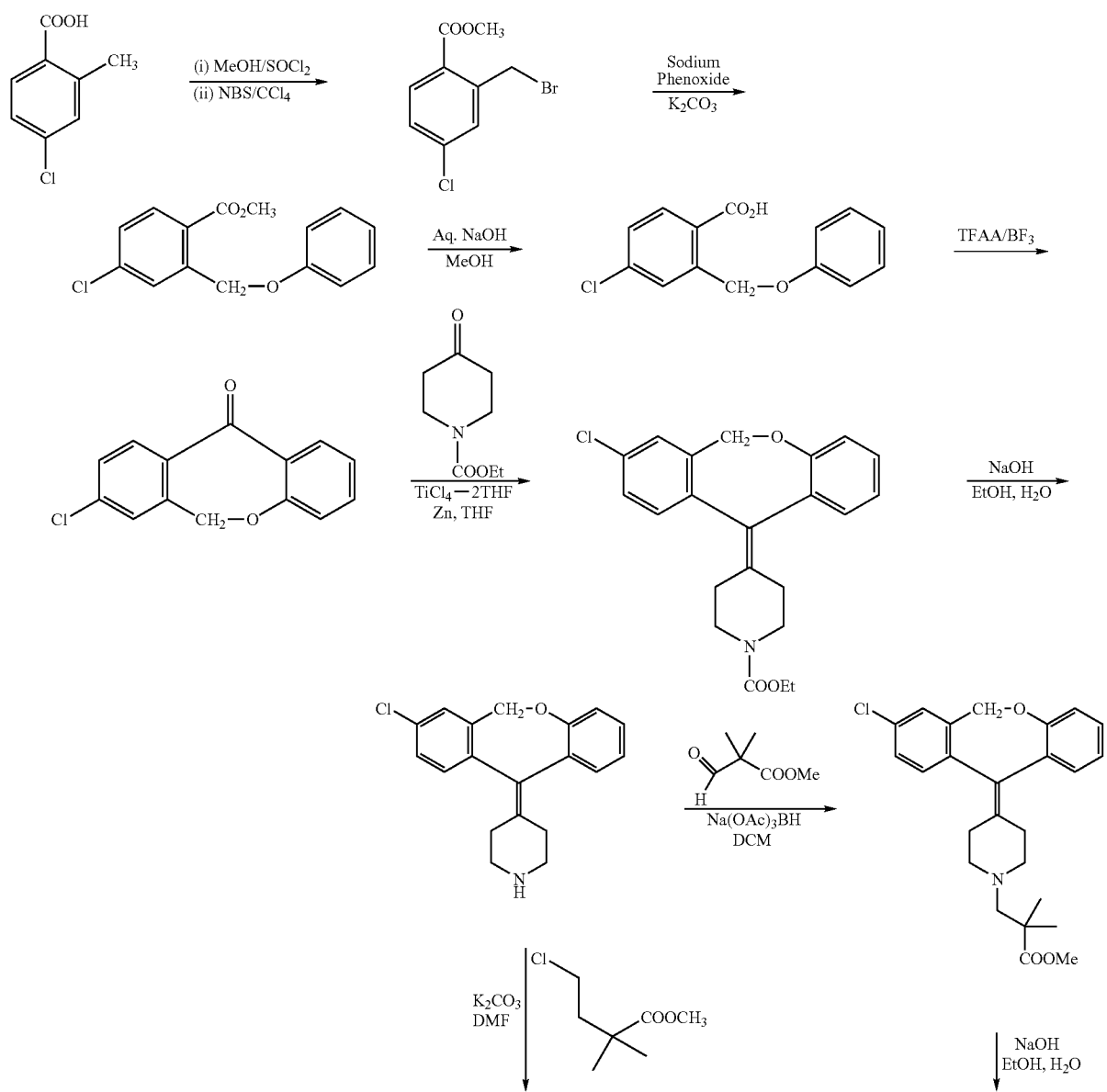

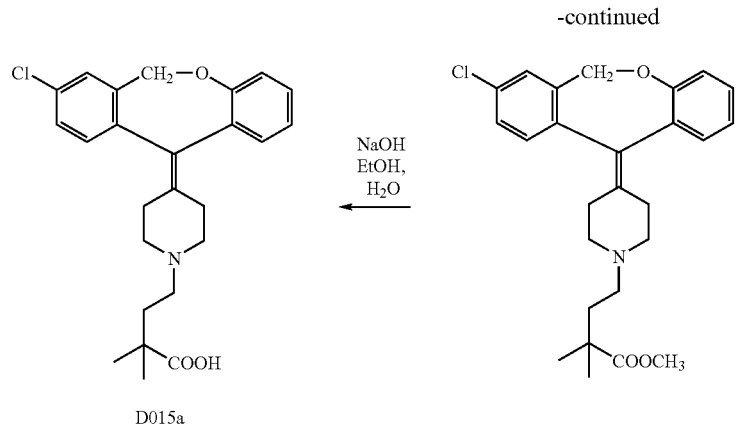
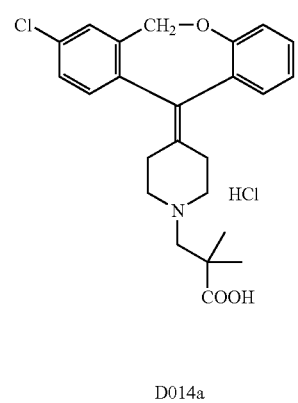
SCHEME 9
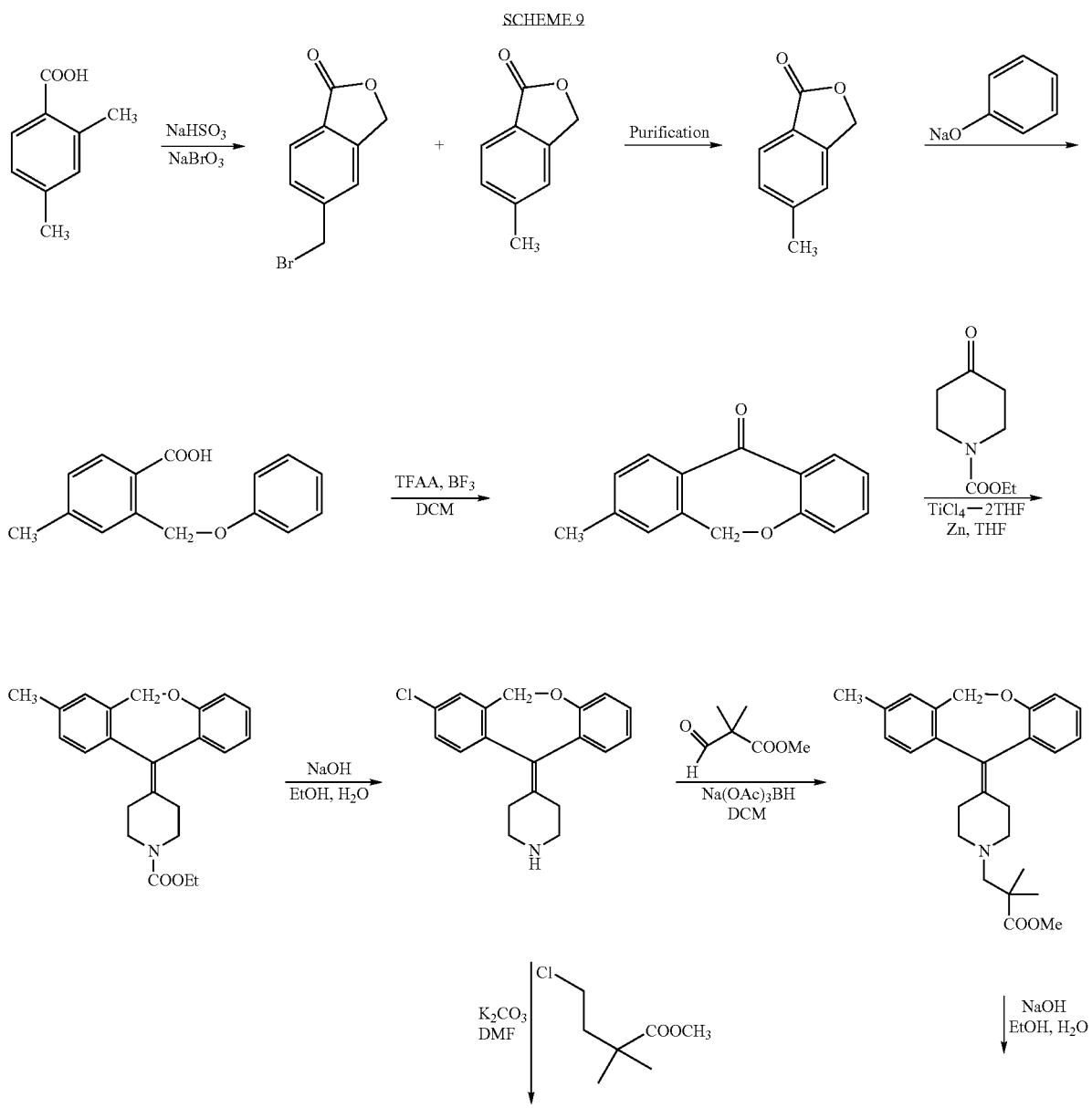

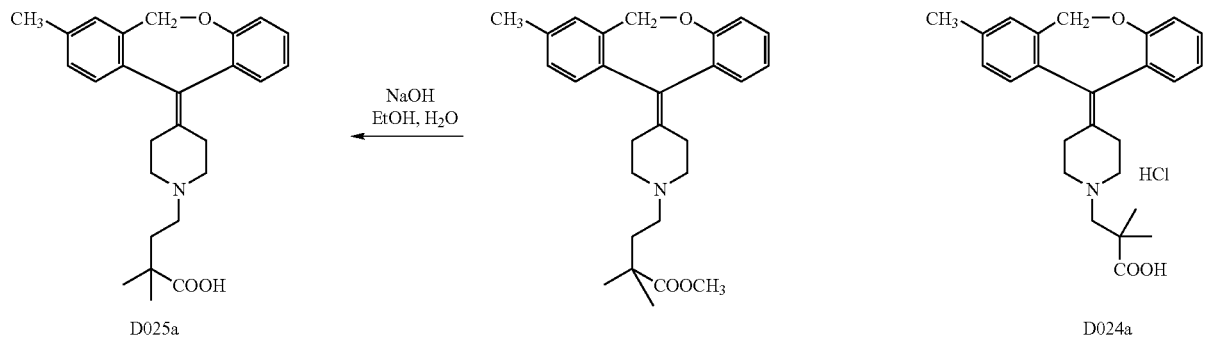
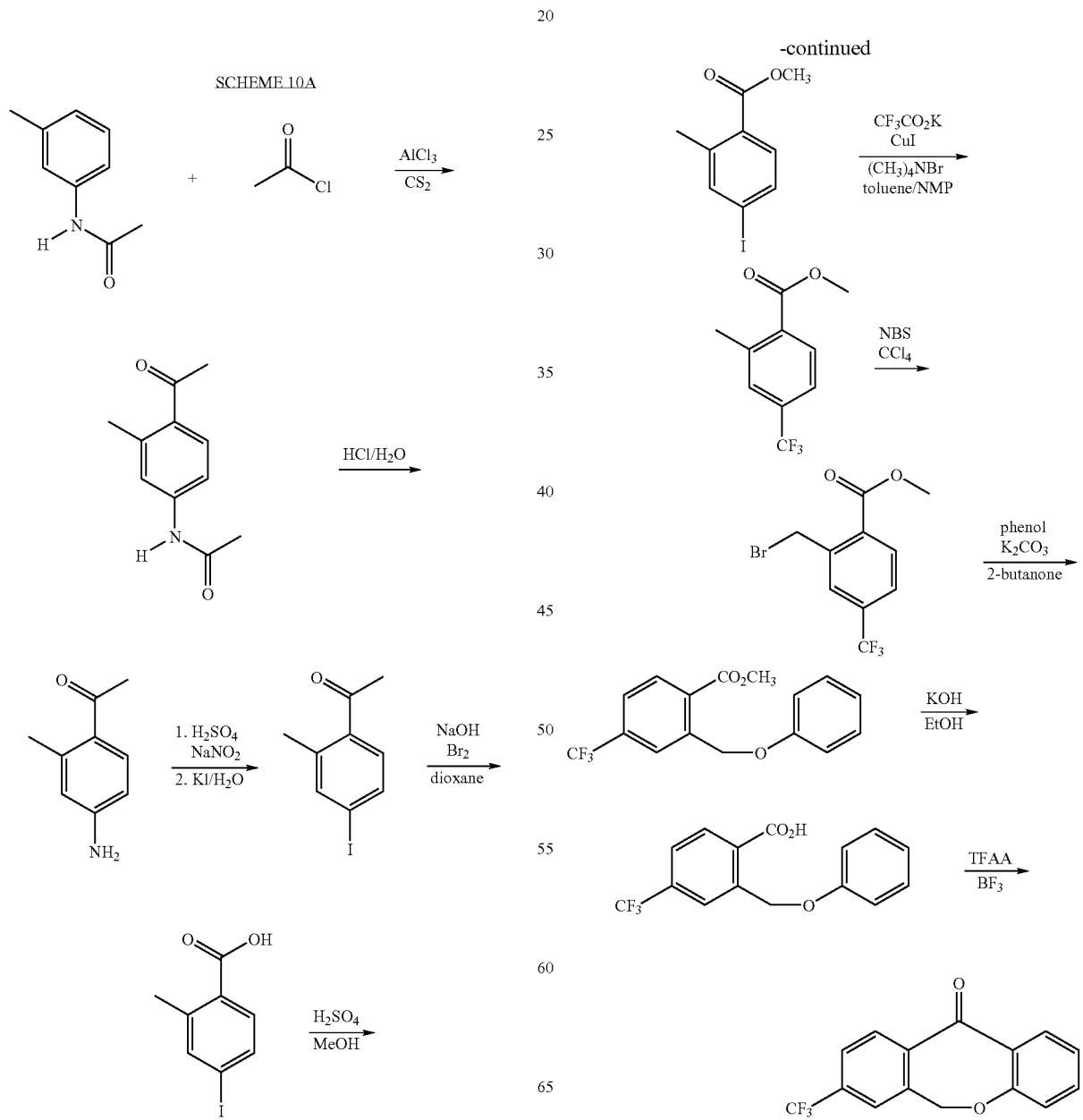
SCHEME 10A

SCHEME 10B
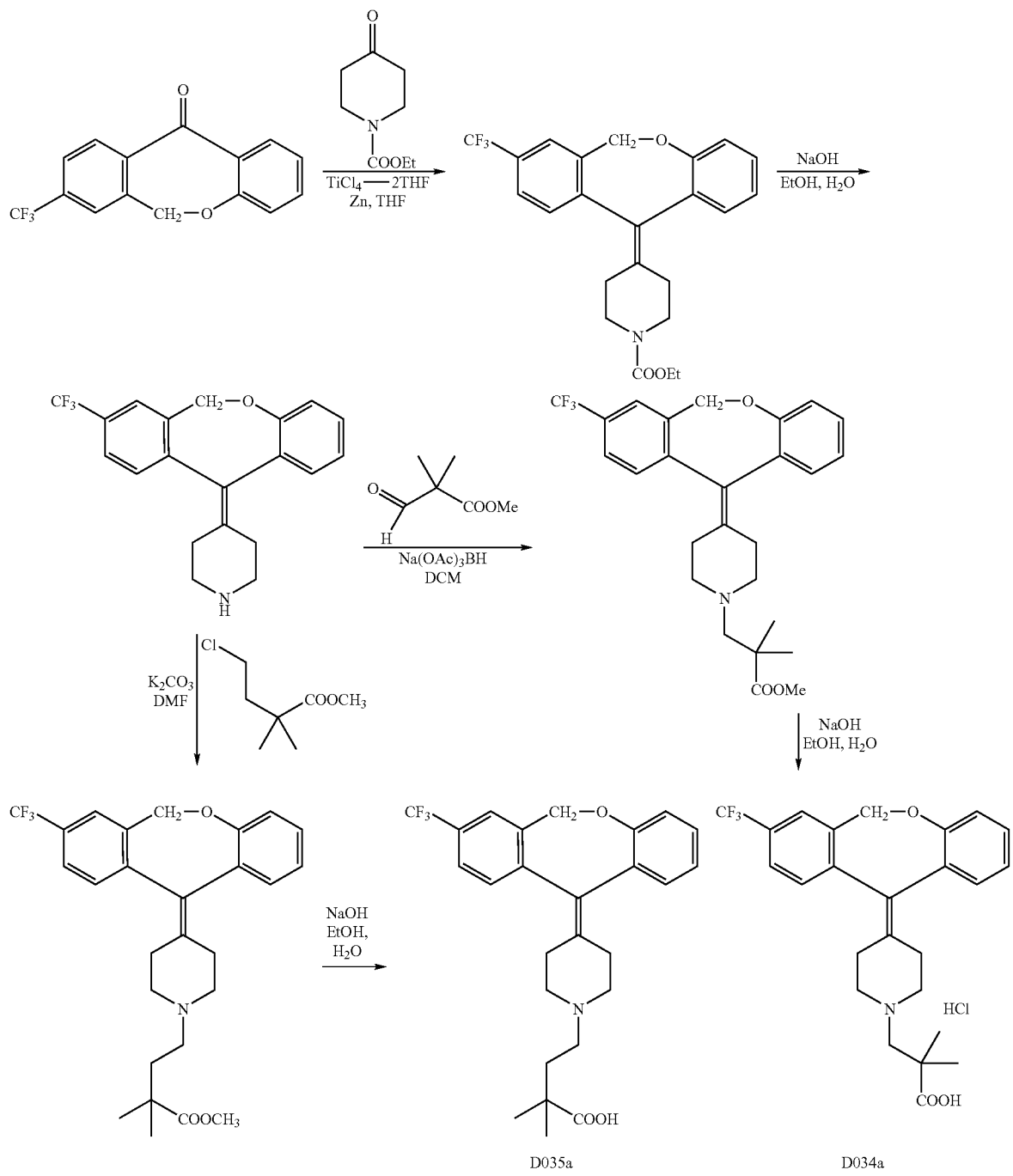
SCHEME 11
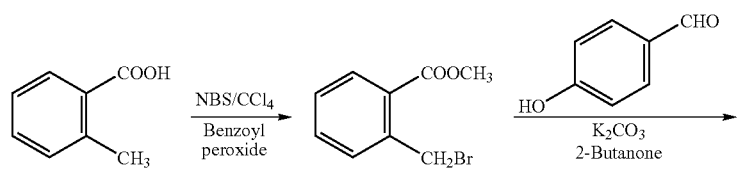

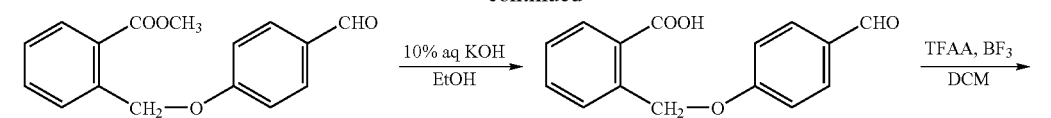
-continued
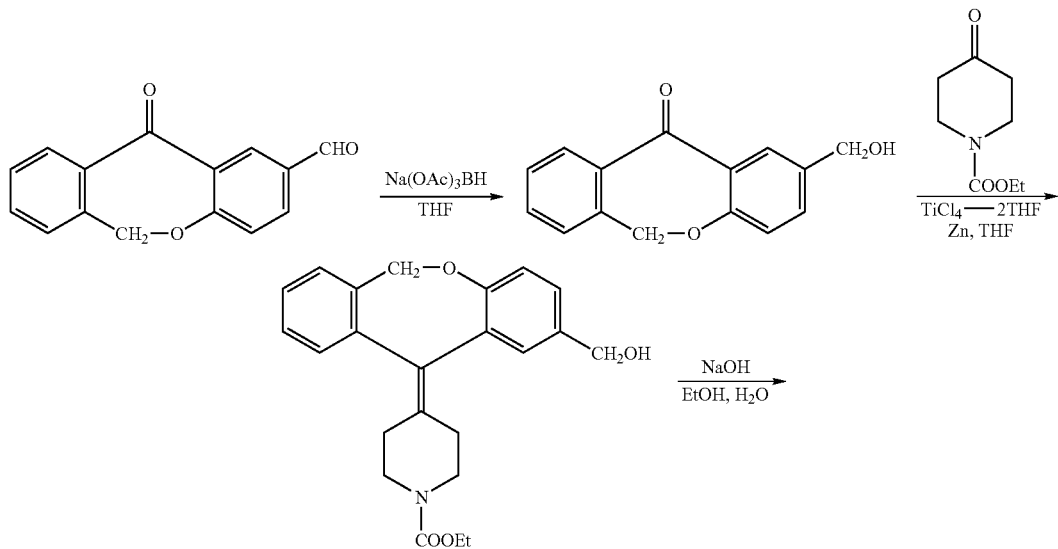
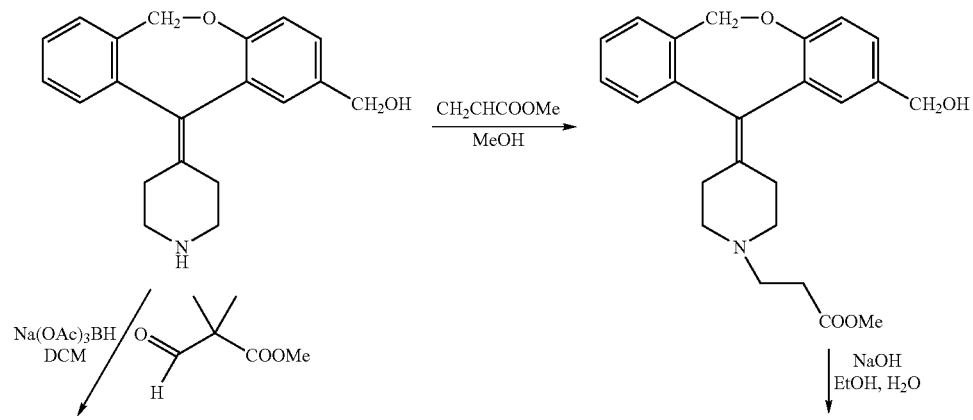
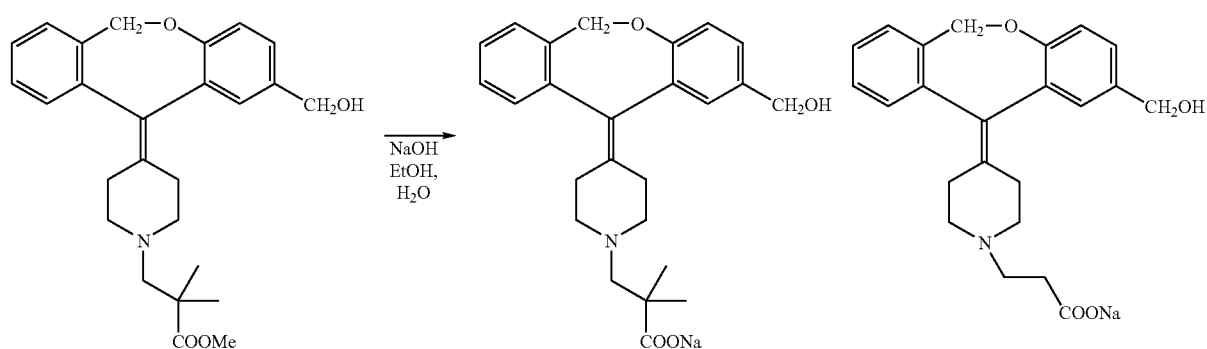

SCHEME 12
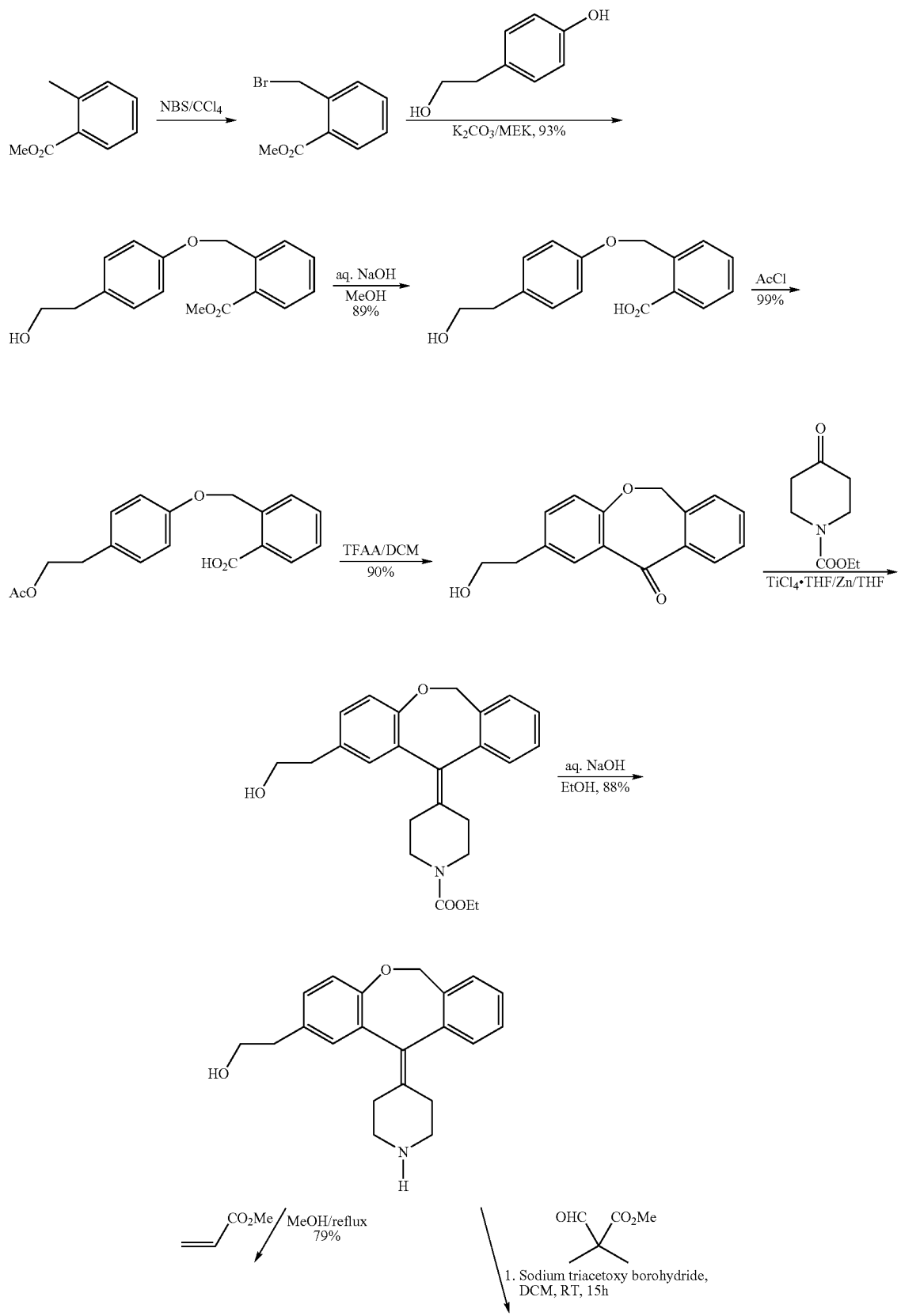

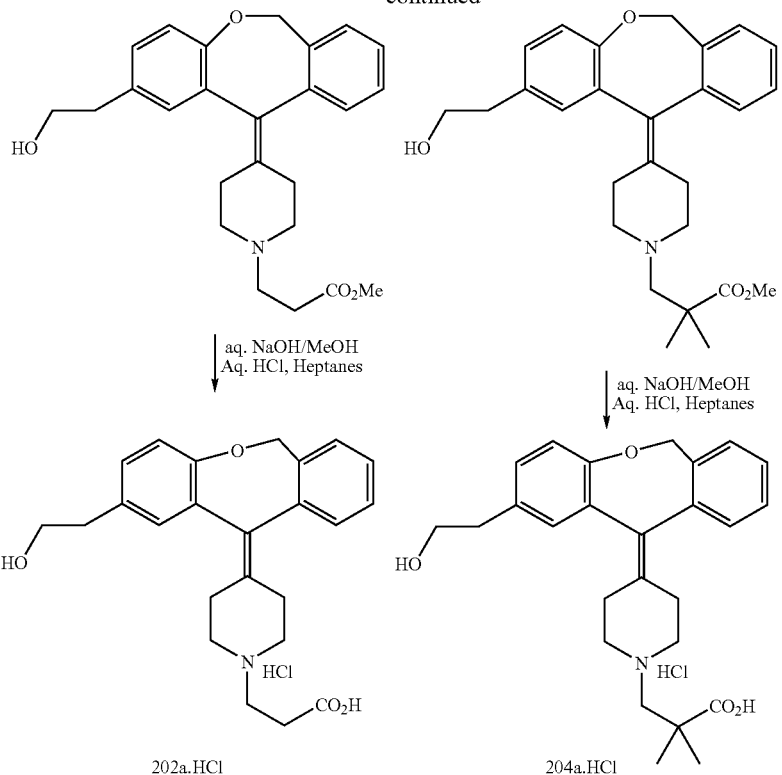
-continued
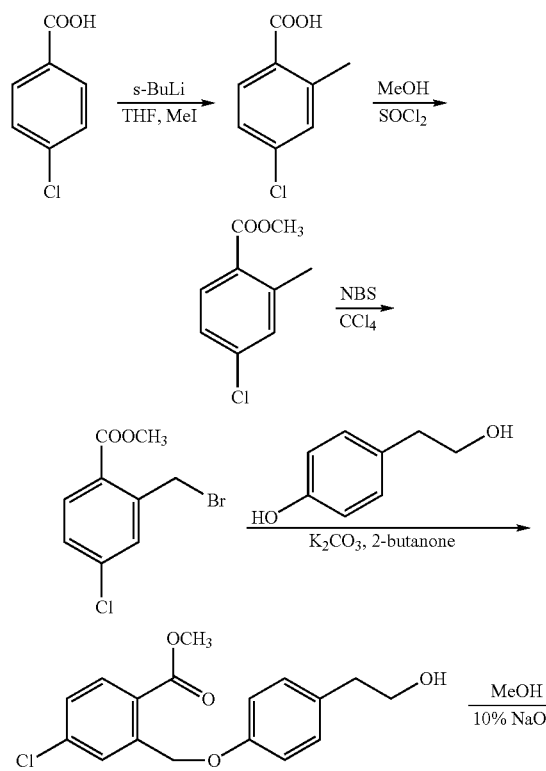
SCHEME 13
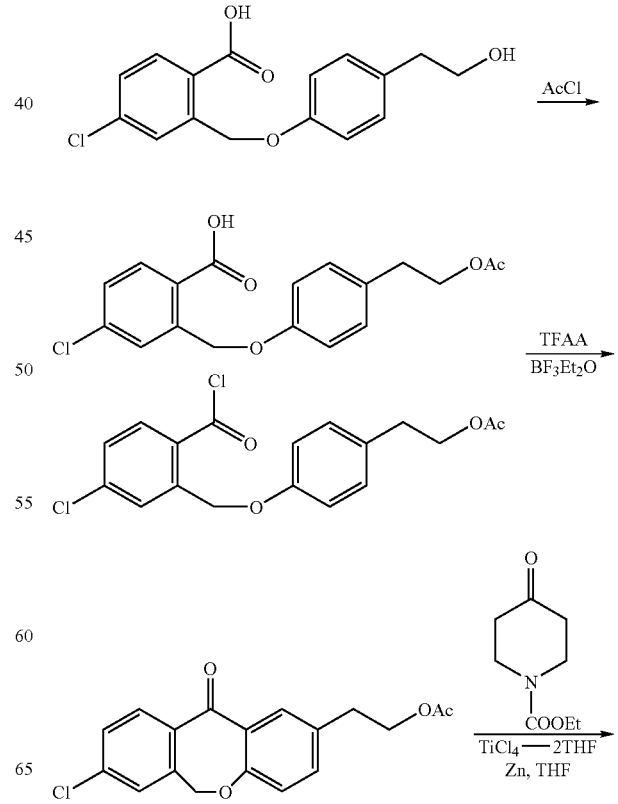
-continued

187
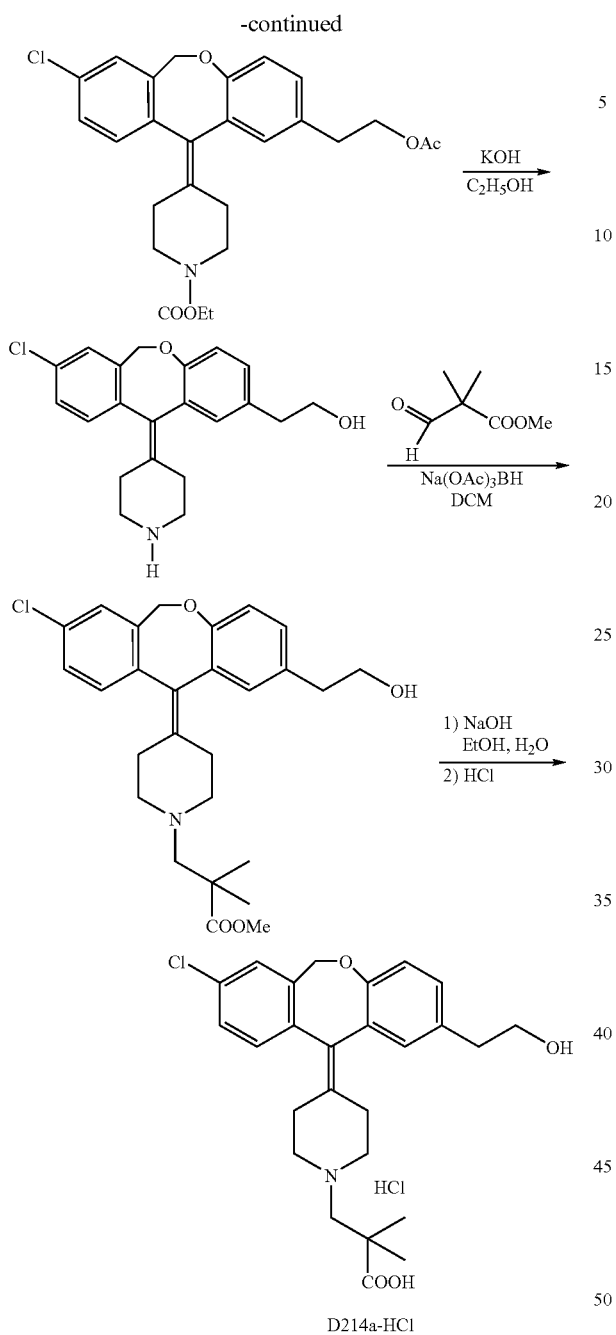
188
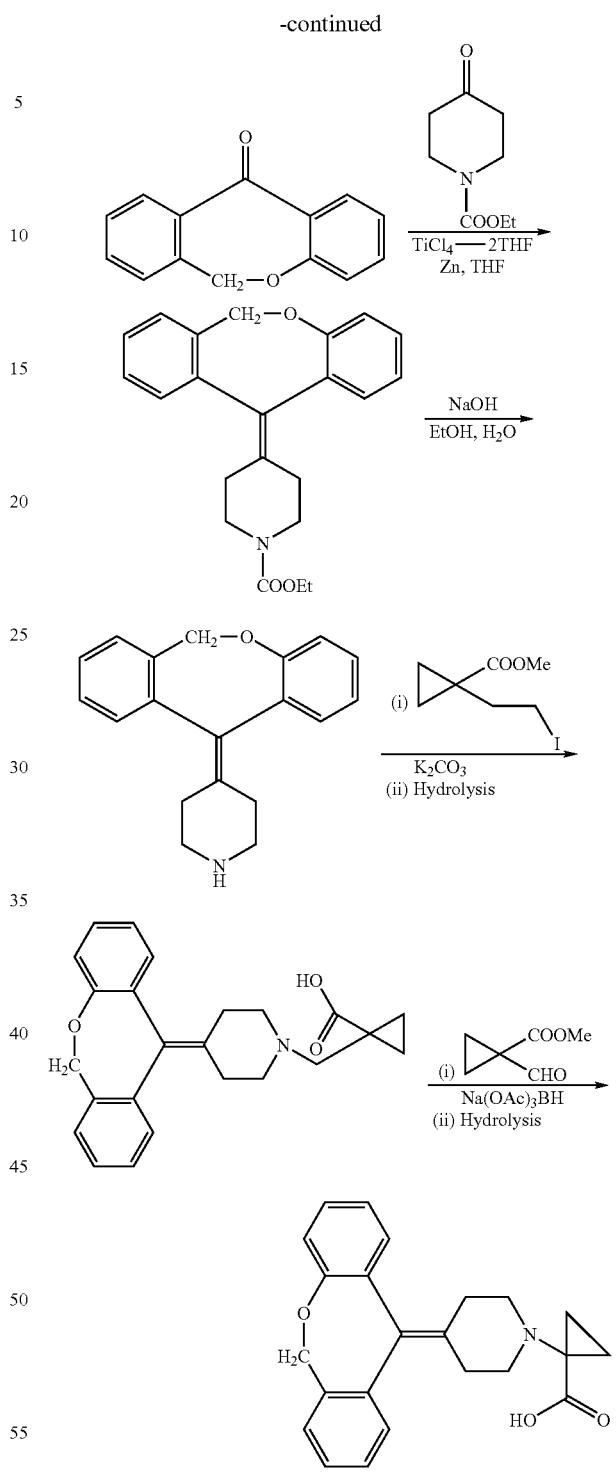
SCHEME 14
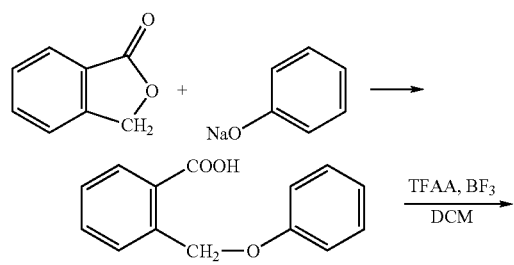
SCHEME 15

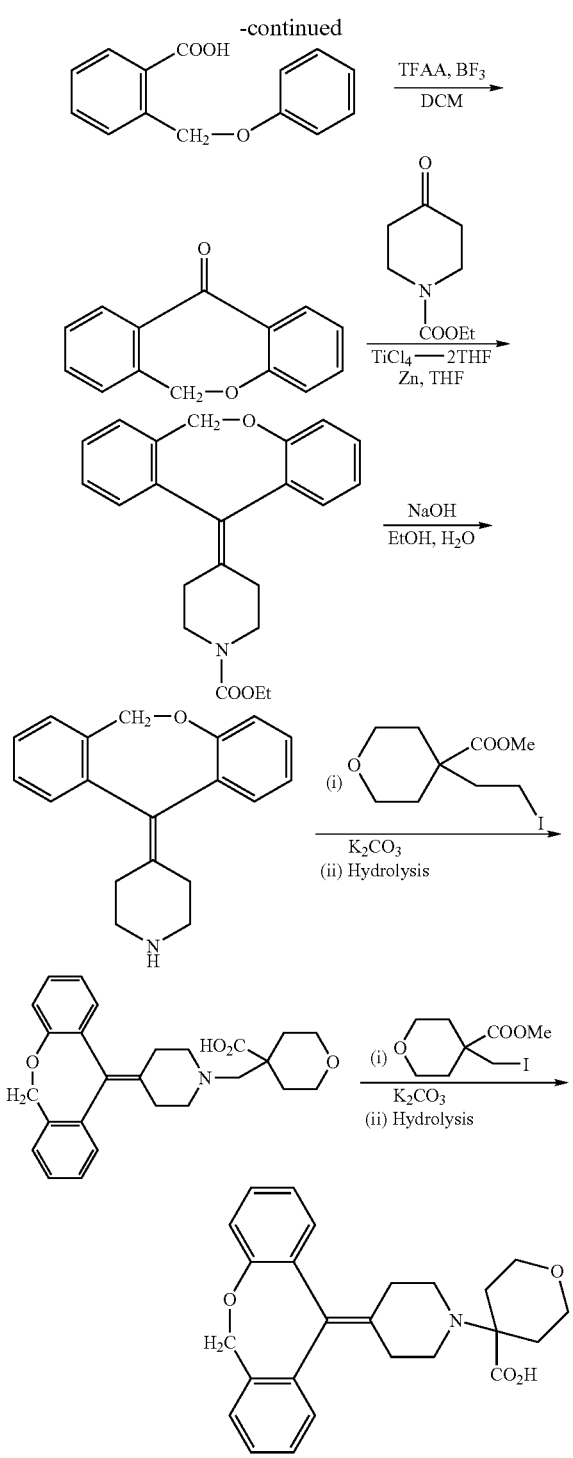

EXAMPLE 10

Sleep in mammals can be divided into sleep occurring during periods of rapid eye movement (REM), accompanied by substantial brain activity, and periods of non-REM (NREM) sleep, accompanied by decreased brain activity. Typically, a normal nighttime sleep period is occupied primarily by NREM sleep, and thus NREM cumulation can serve as a measure of total sleep cumulation, e.g., significantly decreased NREM can be associated with insomnia and an accumulation of "sleep debt", e.g., an accumulated physiological need for sleep that tends to persist until a sufficient amount of additional sleep is accumulated. Thus, an increase in NREM associated with a treatment can indicated the treatment's effectiveness in treating insomnia.

Sleep quality can be associated with sleep continuity or sleep maintenance. For example, a subject with sleep apnea wakes up numerous times during a sleep period, e.g., the subject has difficulty maintaining continuous sleep. Although such a subject can accumulate a typical nights length of sleep, e.g., 8 hours, the sleep is unrefreshing due to the waking caused by the sleep apnea. Thus, an increase in the longest uninterrupted sleep bout (LUSB) associated with a treatment can indicate the treatment's effectiveness in enhancing sleep continuity, and therefore in treating sleep maintenance insomnia.

Sleep-wakefulness, locomotor activity and body temperature were monitored in Male Wistar rats treated with three chemical formulations, individually including three antihistamine-class compounds of the invention, 11f, 15f, and 6f. Treatments were administered at CT-18 (Circadian Time, 6 hours after lights-off) and produced robust soporific effects characterized by increased nonREM sleep time, increased sleep continuity, but without evidence of REM sleep inhibition or rebound insomnia. The general experimental conditions utilized in testing the above listed compounds of the invention are described below.

I. Animals & Surgery. Adult, male Wistar rats (250 g at time of surgery, Charles River Laboratories) were anesthetized (Nembutal, 62 mg/kg) and surgically prepared with a cranial implant to permit chronic electro-encephalogram (EEG) and electromyogram (EMG) recording. Body temperature and locomotor activity were monitored via a miniature transmitter (Minimitter) surgically placed in the abdomen. The cranial implant consisted of stainless steel screws (two frontal [+3.2 AP from bregma, ±2.0 ML] and two occipital [−6.9 AP, ±5.5 ML]) for EEG recording. Two Teflon-coated stainless steel wires were positioned under the nuchal trapezoid muscles for EMG recording. All leads were soldered to a miniature connector prior to surgery, and gas sterilized in ethylene oxide. The implant assembly was affixed to the skull with dental acrylic. A minimum of three weeks was allowed for surgical recovery.

II. Recording environment. Each rat was permanently housed in its own individual recording cage located within separate, ventilated compartments of custom-designed stainless steel cabinets. Each Nalgene microisolator cage was enhanced with a filter-top riser and low-torque swivel-commutator. Food and water were available ad libitum. A 24-hr light-dark cycle (12 hours light, 12 hours dark) was maintained throughout the study using 4-watt fluorescent bulbs 5 cm from the cage. Animals were undisturbed for at least 48 hours before and after treatments.

III. Automated physiological monitoring. Sleep and wakefulness were determined using "SCORE-2000™" an internet-based sleep-wake and physiological monitoring system. The system monitored amplified EEG (bandpass 1-30 Hz), integrated EMG (bandpass 10-100 Hz), body temperature and non-specific locomotor activity (LMA) via telemetry, and drinking activity, continuously and simultaneously. Arousal states were classified on-line as NREM sleep, REM sleep, wake, or theta-dominated wake every 10 seconds using EEG feature extraction and pattern-matching algorithms. The classification algorithm used individually-taught EEG-arousal-state templates, plus EMG criteria to differentiate REM sleep from theta-dominated wakefulness, plus behavior-dependent contextual rules (e.g., if the animal was drinking, it is awake). Drinking and locomotor activity (LMA) were recorded as discrete events every 10 seconds, while body temperature was recorded each minute. Locomotor activity was detected by a telemetry receiver (Minimitter, Sunriver, Oreg.) beneath the cage. Telemetry measures (LMA and body temperature) were not part of the scoring algorithm; thus, sleep-scoring and telemetry data were independent measures.

IV. Treatments and study design.
  A. Timing of treatment. Compounds were administered at CT-18, the peak of the activity-dominated period, in order to ensure sufficient time was allowed to view the time course of the treatment effect before lights-on (6 hours post-treatment).
  B. Vehicle and route of administration. Compounds were suspended in sterile 0.25% or 0.5% methylcellulose (1-2 ml/kg). Treatments were administered as an intraperitoneal bolus.
  C. Study design and controls. A parallel group study design was employed. Vehicle controls were drawn from a large pool (N>200): a subset of the pooled vehicle controls was selected, based on computerized matching with the 24-hour pre-treatment baseline of the active treatment group.
  D. Drugs tested. Three (3) antihistaminergic novel chemical compounds of the current invention were tested for this proof of principle study, 11f (30 and 10 mg/kg), and 6f (30 mg/kg) and 15f (30 mg/kg).

Results of Compounds Tested 11f significantly increased total sleep time for 3 hours post-treatment after both 30 mg/kg and 10 mg/kg treatments (N=11 and 9, respectively, where N is the number of animals per dose group), and increased sleep continuity, as assessed by sleep bout length. The effect on maximum sleep bout length (a measure of sleep continuity) during the initial 5 hours post-treatment sleep bout versus dose is shown in FIG. 1(c). 11f increased sleep continuity at both 10 and 30 mg/kg doses relative to vehicle control. The treatment effects of Zolpidem are also shown for comparison.

A concomitant reduction in locomotor activity paralleled the sleep inducing effects of 11f. These effects were prototypical for sedative-hypnotic/soporific agents and compared equal or better to therapeutic doses of the sedative hypnotic market leader—Ambien® (Zolpidem). 11f did not, however, produce REM sleep inhibition or rebound insomnia at 10 mg/kg or 30 mg/kg in male Wistar rats. REM sleep inhibition and rebound insomnia are undesirable side effects commonly observed in currently marketed prescription sedative hypnotics. A comparison of the total sleep time resulting from 11f (30 mg/kg), the sedative hypnotic positive control standard (Zolpidem, 10 mg/kg), and the vehicle control as a function of time from the administration of the dose is depicted as a time series plot in FIG. 1(a). The time series plot shows the sleep patterns before and after treatment, wherein the arrow indicates the primary soporific effect of 11f.

The cumulative effect on total sleep time (TST) during the initial 5 hours post-treatment, relative to baseline (BL), for 11f (HY2325), Zolpidem, and the vehicle control is shown in FIG. 11(b). It is apparent that 11f (30 mg/kg) induced more TST than Zolpidem (10 mg/kg).

6f (N=5) and 15f (N=5), compounds of the invention related to HY2325-01, also produced an increase in non-REM sleep time for 2-3 hours post-treatment relative to the vehicle control animals. In addition, 6f and 15f did not produce REM sleep inhibition or rebound insomnia under the conditions studied.

11f, 6f and 15f, are representative novel antihistaminergic soporific chemical compounds of the invention. 11f increased sleep, e.g., sleep time and sleep continuity (sleep bout lengths), in laboratory rats in a dose-dependent fashion. Single doses of 6f and 15f also increased sleep in laboratory rats.

Additional compounds of the invention were tested using the above methodology, and the results are shown below in Table 5.

TABLE 5

| Compound at CT-18) | Dose (mg/kg) | Onset (minutes) | Duration (hrs) | Average Bout-Length (minutes) | Maximum Bout Length (minutes) | NREM Peak (%/hr) | NREM Accum. (minutes) | Rebound Insomnia | Motor Inhibition | REM Inhibition |
|---|---|---|---|---|---|---|---|---|---|---|
| Ambien (Zolpidem) | 30 IP | 5 | 3-4 | 5.8 | 13.1 | 58.2 | 58.7 | YES | YES | YES |
| Doxepin-like | | | | | | | | | | |
| (8a) | 30 PO | 90 | 4-5 | 11 | 25.1 | 72.0 | 44.8 | NO | NO | YES |
| (73a) | 30 PO | 65 | 5-6 | 12.2 | 28.9 | 75.5 | 65.8 | NO | NO | NO |
| (74a) | 30 PO | 45 | 5-6+ | 14.5 | 27.6 | 62.2 | 47.3 | NO | NO | NO |
| (75a) | 30 PO | 70-80 | 5-6 | 9.9 | 22.3 | 64.4 | 43.4 | NO | NO | NO |
| (75a) | 30 PO | 70-85 | 4 | 6.8 | 13.6 | 58.8 | 33.9 | NO | NO | NO |
| (75a) | 45 PO | 70-85 | 5 | 10.8 | 19.4 | 58.2 | 33.9 | NO | NO | NO |
| (7a) | 30 PO | 130 | 5-6 | 7.3 | 16.9 | 56.9 | 29.5 | NO | NO | NO |
| (7d) | 30 PO | 85 | 5 | 12.9 | 25.0 | 76.9 | 54.1 | NO | NO | NO |
| Pheniramine-like | | | | | | | | | | |
| (11a) | 30 PO | 85 | 6 | 11.2 | 18.7 | 67.3 | 41.2 | Minor | NO | NO |
| (11d) | 30 PO | 135 | 6 | 11.0 | 20.1 | 58.5 | 55.5 | NO | NO | NO |
| (11e) | 30 PO | 80 | 6 | 8.3 | 19.1 | 59.6 | 49.6 | NO | NO | NO |
| Diphenhydramine-like | | | | | | | | | | |
| (53a) | 30 PO | 30 | 4 | 4.3 | 9.1 | 49.2 | 17.4 | NO | NO | NO |
| (6a) | 30 PO | 65 | 5 | 7.0 | 12.8 | 56.4 | 26.5 | NO | NO | NO |

TABLE 5-continued

| Compound at CT-18 | Dose (mg/kg) | Onset (minutes) | Duration (hrs) | Average Bout-Length (minutes) | Maximum Bout Length (minutes) | NREM Peak (%/hr) | NREM Accum. (minutes) | Rebound Insomnia | Motor Inhibition | REM Inhibition |
|---|---|---|---|---|---|---|---|---|---|---|
| Triprolidine-like | | | | | | | | | | |
| (16a) | 30 PO | 180 | 5 | 5.4 | 11.8 | 57.9 | 20.7 | NO | NO | NO |

Note:
PO is oral administration and
IP is intraperitoneal administration.

EXAMPLE 11

H1, M1, M2 and M3 Binding Assays For Series 11 Compounds

I. Introduction

The following binding assays were performed on the Series 11 compounds described above by displacement of known standards from the H1, M1, M2, and M3 receptors, wherein H1 is a histamine receptor, and M1, M2, and M3 are muscarinic receptors.

The binding studies against the histamine receptor, H1, indicate binding affinity, and therefore the results of the binding assays are an indication of the activity of the compound.

In addition, the binding studies against the muscarinic receptors indicate the extent to which the compounds bind the muscarinic receptors, responsible for anti-cholinergic activity of the compound. Binding to muscarinic receptors results in several undesired side effects of many known antihistamines, e.g., dry-mouth. A decrease in the binding of the compounds to the M1-M3 receptors, relative the binding of the compound to the H1 receptor, is an indication of the greater specificity of the compound for the histamine receptor over the muscarinic receptor. Moreover, a drug with increased specificity for the histamine receptor would possess less anti-cholinergic side effects.

II. Binding Assays

The H1 binding of antihistamines of the invention (also referred to herein as "test compounds" or "compounds of the invention") is determined by measuring the specific binding of a given test compound, or series of test compounds, to the H1 receptor, and comparing it with the specific binding of a known standard (i.e., reference compound). Reference compounds used in this H1 binding assay include, for example, triprolidine ($K_i$ 3.3 nM), chlorpheniramine ($K_i$ 103.0 nM), pyrilamine ($K_i$ 1.9 nM), cyproheptadine ($K_i$ 8.5 nM), cimetidine ($K_i$>10,000) and dimaprit ($K_i$>10,000). (See e.g., Chang et al., J. Neurochem., 32:1653-63 (1979) (with modifications); Martinez-Mir, et al., Brain Res., 526:322-27 (1990); and Haaksme, et al., Pharmac. Ther., 47:73-104 (1990).

In this H1 binding assay, the H1 receptor was from bovine cellular membranes, and a radioligand, [$^3$H]Pyrilamine (15-25 Ci/mmol) at a final ligand concentration of 2.0 nM was used to detect specific binding for the H1 receptor. The assay characteristics include a $K_D$ (binding affinity) of 1.3 nM and a $B_{max}$ (receptor number) of 6.2 fmol/mg tissue (wet weight). Tripolidine (10 μM) was used as the non-specific determinant, reference compound and positive control. Binding reactions were carried out in 50 mM NA-KPO$_4$ (pH 7.5) at 25° C. for 60 minutes. The reaction was terminated by rapid vacuum filtration onto glass fiber filters. The level of radioactivity trapped on the filters was measured and compared to control values to ascertain any interaction between a given test compound and the H1 binding site.

The M1 binding assay determines the M1 binding of a test compound by measuring the specific binding of a given test compound to M1 and comparing it with the specific binding of a reference compound.

In one embodiment of the M1 binding assay, the M1 muscarinic receptor was a human recombinant M1 expressed in CHO cells, and the reference compounds used in the M1 binding assay include, for example, scopolamine, MethylBr ($K_i$ 0.09 nM); 4-DAMP methiodide ($K_i$ 0.27 nM); pirenzepine ($K_i$ 2.60 nM); HHSID ($K_i$ 5.00 nM); and methoctramine ($K_i$ 29.70 nM). (See e.g., Buckley, et al., Mol. Pharmacol. 35:469-76 (1989) (with modifications)).

In this M1 (human recombinant) binding assay, a radioligand, [$^3$H]-scopolamine, N-methyl chloride (80-100 Ci/mmol) at a final ligand concentration of 0.5 nM was used to detect specific binding for M1. The assay characteristics include a $K_D$ (binding affinity) of 0.05 nM and a $B_{max}$ (receptor number) of 4.2 pmol/mg protein. (−)-scopolamine, methyl-, bromide (methylscopolamine bromide) (1.0 μM was used as the non-specific determinant, reference compound and positive control. Binding reactions were carried out in 50 mM TRS-HCl (pH 74) containing 10 mM MgCl$_2$, 1 mM EDTA for 60 minutes at 25° C. The reaction was terminated by rapid vacuum filtration onto glass fiber filters. The level of radioactivity trapped on the filters was measured and compared to control values to ascertain any interaction between a given test compound and the cloned muscarinic M1 binding site.

In another embodiment of the M1 binding assay, the M1 receptor was from bovine striatal membranes. Reference compounds for use in this embodiment of the M1 binding assay include, for example, atropine ($K_i$ 0.4 nM); pirenzipine ($K_i$ 4.5 nM); and telenzepine ($K_i$ 64.5 nM). (See Watson et al., Life Sciences, 32:3001-11 (1983), with modifications; and Luthin and Wolfe, Molec. Pharmac., 26:164-69 (1984)).

In this M1 assay, a radioligand, [$^3$H]-pirenzepine (70-80 Ci/mmol) at a final ligand concentration of 1.0 nM was used to detect specific binding for M1. The assay characteristics include a $K_D$ (binding affinity) of 2.2 nM and a $B_{max}$ (receptor number) of 1.4 pmol/mg protein. Atropine sulfate (0.1 μM was used as the non-specific determinant, reference compound and positive control. Binding reactions were carried out in 25 mM HEPES (pH 7.4) for 60 minutes at 25° C. The reaction was terminated by rapid vacuum filtration onto glass fiber filters. The level of radioactivity trapped on the filters was measured and compared to control values to ascertain any interaction between a given test compound and the muscarinic M1 binding site.

The M2 binding assay determines the M2 binding of a test compound by measuring the specific binding of a given test compound to M2 and comparing it with the specific binding of a reference compound.

In one embodiment, the M2 receptor was a human recombinant M2 expressed in CHO cells. Reference compounds used in this M2 binding assay include, for example, scopolamine, MethylBr ($K_i$ 0.3 nM); 4-DAMP methiodide ($K_i$ 20.7 nM); methoctramine (K 20.4 nM); HHSID ($K_i$ 212.7 nM); and pirenzepine ($K_i$ 832.9 nM). (See e.g., Buckley, et al., Mol. Pharmacol. 35:469-76 (1989) (with modifications)).

In this M2 (human recombinant) binding assay, a radioligand, [$^3$H]-scopolamine, N-methyl chloride (80-100 Ci/mmol) at a final ligand concentration of 0.5 nM was used to detect specific binding for M2. The assay characteristics include a $K_D$ (binding affinity) of 0.29 nM and a $B_{max}$ (receptor number) of 2.1 pmol/mg protein. (−)-scopolamine, methyl-, bromide (methylscopolamine bromide) (1.0 μM) was used as the non-specific determinant, reference compound and positive control. Binding reactions were carried out in 50 mM TRS-HCl (pH 74) containing 10 mM MgCl$_2$, 1 mM EDTA for 60 minutes at 25° C. The reaction was terminated by rapid vacuum filtration onto glass fiber filters. The level of radioactivity trapped on the filters was measured and compared to control values to ascertain any interaction between a given test compound and the cloned muscarinic M2 binding site.

In another embodiment of the M2 binding assay, the M2 receptor was from rat cardiac membranes. Reference compounds for use in this embodiment of the M2 binding assay include, for example, atropine ($K_i$ 0.7 nM); 4-DAMP methiodide ($K_i$ 3.0 nM); methoctramine ($K_i$ 11.8); AF-DX 116 ($K_i$ 63.0 nM); HHSID ($K_i$ 151.7 nM); and pirenzipine ($K_i$ 273.5 nM). (See Hammer et al., Life Sciences, 38:1653-62 (1986), with modifications; Wang et al., Life Sciences, 41:1751-60 (1987); and Elberlein, et al., TIPS, 50 (1989)).

In this M2 assay, a radioligand, [$^3$H]-AF-DX 384 (70-120 Ci/mmol) at a final ligand concentration of 3.0 nM was used to detect specific binding for M2. The assay characteristics include a $K_D$ (binding affinity) of 6.4 nM and a $B_{max}$ (receptor number) of 2.1 pmol/mg protein. Methoctramine (10 μM) was used as the non-specific determinant, reference compound and positive control. Binding reactions were carried out in 10 mM Na—KPO$_4$ (pH 7.4) for 60 minutes at 25° C. The reaction was terminated by rapid vacuum filtration onto glass fiber filters. The level of radioactivity trapped on the filters was measured and compared to control values to ascertain any interaction between a given test compound and the muscarinic M2 binding site.

The M3 binding assay determines the M3 binding of a test compound by measuring the specific binding of a given test compound to M3 and comparing it with the specific binding of a reference compound.

In one embodiment, the M3 was a human recombinant M3 expressed in CHO cells. Reference compounds used in the M3 binding assay include, for example, scopolamine, MethylBr ($K_i$ 0.3 nM); 4-DAMP methiodide ($K_i$ 0.8 nM); HHSID ($K_i$ 14.5 nM); pirenzepine ($K_i$ 153.3 nM); and methoctramine ($K_i$ 700.0 nM). (See e.g., Buckley, et al., Mol. Pharmacol. 35:469-76 (1989) (with modifications)).

In this M3 (human recombinant) binding assay, a radioligand, [$^3$H]-scopolamine, N-methyl chloride (80-100 Ci/mmol) at a final ligand concentration of 0.2 nM was used to detect specific binding for M1. The assay characteristics include a $K_D$ (binding affinity) of 0.14 nM and a $B_{max}$ (receptor number) of 4.0 pmol/mg protein. (−)-scopolamine, methyl-, bromide (methylscopolamine bromide) (1.0 μM) was used as the non-specific determinant, reference compound and positive control. Binding reactions were carried out in 50 mM TRIS-HCl (pH 7.4) containing 10 mM MgCl$_2$, 1 mM EDTA for 60 minutes at 25° C. The reaction was terminated by rapid vacuum filtration onto glass fiber filters. The level of radioactivity trapped on the filters was measured and compared to control values to ascertain any interaction between a given test compound and the cloned muscarinic M3 binding site.

In another embodiment of the M3 binding assay, the M3 receptor was from guinea pig ileum membranes. Reference compounds for use in this embodiment of the M3 binding assay include, for example, 4-DAMP methiodide ($K_i$ 37.5 nM); and HHSID ($K_i$ 281.0 nM); (See Hanack and Pfeiffer, Digestion, 45:196-201 (1990), with modifications; Vanderheyden et al., J. Neurolog. Sci., 97:67-80 (1990)); and Smith, et al., J. Pharmacol. Exp. Ther., 256(3):1173-81 (1990)).

In this M3 assay, a radioligand, [3H]-scopolamine, N-methyl chloride (70-87 Ci/mmol) at a final ligand concentration of 1.0 nM was used to detect specific binding for M2. The assay characteristics include a $K_D$ (binding affinity) of 1.4 nM and a $B_{max}$ (receptor number) of 7.7 fmol/mg protein. 4-DAMP methiodide (10 μM) was used as the non-specific determinant, reference compound and positive control. Binding reactions were carried out in 30 mM HEPES (pH 7.4) containing 142 mM NaCl, 5.6 nM KCl, 2.2 mM CaCl$_2$, 3.6 mM Na$_2$CO$_3$, 1 mM MgCl$_2$ and 5.6 glucose for 2 hours at 37° C. The reaction was terminated by rapid vacuum filtration onto glass fiber filters. The level of radioactivity trapped on the filters was measured and compared to control values to ascertain any interaction between a given test compound and the muscarinic M3 binding site.

III. Results

The data in Table 6 show the results of the assays, described above, performed on the Series 11 compounds, as indicated.

TABLE 6

| Compound number | | H1 | | M1 | | M2 | | M3 | |
| --- | --- | --- | --- | --- | --- | --- | --- | --- | --- |
| | | IC50 | Ki | IC50 | Ki | IC50 | Ki | IC50 | Ki |
| Acid | 11a | 3.08E−7 | 1.19E−7 | >1.0E−5 | >1.0E−5 | >1.0E−5 | >1.0E−5 | >1.0E−5 | >1.0E−5 |
| Isopropyl | 11d | 3.78E−7 | 1.47E−7 | 8.00E−6 | 6.96E−7 | 8.29E−7 | 2.70E−7 | 6.08E−6 | 2.70E−6 |
| Isobutyl | 11e | 7.18E−7 | 2.79E−7 | 3.76E−6 | 2.89E−7 | 3.55E−6 | 1.15E−6 | 2.59E−6 | 7.10E−7 |
| Cyclopentyl | 11f | 1.07E−6 | 4.16E−7 | 2.21E−6 | 1.70E−7 | — | | | |
| S-THF | 11g | 1.96E−7 | 8.61E−8 | 4.68E−6 | 3.60E−7 | 5.70E−6 | 2.08E−6 | 5.71E−6 | 1.56E−6 |
| R-THF | 11h | 2.01E−7 | 8.83E−8 | 2.24E−6 | 1.72E−7 | 2.14E−6 | 6.97E−7 | 2.20E−6 | 6.03E−7 |
| THP | 11i | 2.00E−7 | 8.78E−8 | 2.21E−6 | 1.70E−8 | | 7.20E−8 | 2.33E−6 | 1.03E−6 |

IV. Conclusions

A. An interesting trend that is exhibited by the data in Table 6, shows that the tetrahydrofuran and tetrahydropyran esters appear to show a greater affinity for the H1 receptor than the non-oxygen substituted esters.

This increased affinity may be an indication of increased water solubility or that the altered ring conformation may have any affect on the steric properties at the carbonyl of the ester, e.g., a beneficial change in the ring conformation due to the presence of the oxygen. Alternatively, the presence of the oxygen may lend itself to alteration of the physical properties of the molecule in other ways, e.g., the electronic properties help to control ester cleavage, or the presence of the oxygen adds to receptor affinity through increased binding interactions with the receptor.

B. In addition the data indicates that the compounds have greater affinity for the H1 receptors as compared with the M1, M2, and M3 receptors, which as described above, indicates that these drugs should result in the reduction of anti-cholinergic side effects.

C. Table 6 also indicates that the binding data for the enantiomeric compounds, 11h and 11g, do not result in a substantial difference in binding affinity towards the H1 receptor, but do show a substantial difference in binding affinity towards the muscarinic receptors. This indicates that the muscarinic receptors may have a stereochemical preference, and therefore the selectivity of the receptor may be used to assist in the selection of a therapeutic compound that would provide reduced side effects.

D. In addition, it can be seen in from the data in Table 6 that the corresponding acid of the therapeutic ester compound loses detectable affinity for the muscarinic receptors. This property, as describe above, can be used to reduce anti-cholinergic side-effects of the therapeutic compound.

EXAMPLE 12

H1, M1, M2 and M3 Binding Assays for Additional Compound Series

I. Introduction

The following binding assays were performed on additional compounds described above by displacement of known standards from the H1, M1, M2, and M3 receptors, wherein H1 is a histamine receptor, and M1, M2, and M3 are muscarinic receptors.

The binding studies against the histamine receptor, H1, indicate binding affinity, and therefore the results of the binding assays are an indication of the activity of the compound.

In addition, the binding studies against the muscarinic receptors indicate the extent to which the compounds bind the muscarinic receptors, responsible for anti-cholinergic activity of the compound. Binding to muscarinic receptors results in several undesired side effects of many known antihistamines, e.g., dry-mouth. A decrease in the binding of the compounds to the M1-M3 receptors, relative the binding of the compound to the H1 receptor, is an indication of the greater specificity of the compound for the histamine receptor over the muscarinic receptor. Moreover, a drug with increased specificity for the histamine receptor would possess less anti-cholinergic side effects.

II. Binding Assays

The binding assays for H1 was the same as described in Example 11 and the M1, M2, and M3 binding assays are the same as those described in Example 11 for human recombinant expressed cells.

III. Results

The data in Table 7 show the results of the assays, described above, performed on various compounds of the invention, as indicated.

TABLE 7

| $H_1$ Antagonist Series Receptor Binding Data ($K_i$ nM) | | | | |
|---|---|---|---|---|
| | $H_1$ | $M_1$ | $M_2$ | $M_3$ |
| Doxepin-like | | | | |
| (8a) | 62.5 | >10,000 | >10,000 | >10,000 |
| (73a) | 42.8 | >10,000 | >10,000 | >10,000 |
| (74a) | 109 | >10,000 | >10,000 | >10,000 |
| (75a) | 47.9 | >10,000 | 3,331 | >10,000 |
| (7a) | 55.1 | >10,000 | >10,000 | >10,000 |
| (dox7d-oxalate) | 198 | >10,000 | >10,000 | >10,000 |
| Diphenhydramine-like | | | | |
| (53a) | 16.1 | >10,000 | >10,000 | >10,000 |
| (6a) | 56.1 | >10,000 | >10,000 | 8,900 |
| Triprolidine-like | | | | |
| (16a) | 43.9 | >10,000 | >10,000 | >10,000 |

IV. Conclusions

The data indicates that the compounds have greater affinity for the H1 receptors as compared with the M1, M2, and M3 receptors, which as described above, indicates that these drugs should result in the reduction of anti-cholinergic side effects.

EXAMPLE 13 hERG Binding Assay for Additional Compound Series

I. Introduction

The following hERG block comparative study was used to evaluate the effect of a given test compound on cloned hERG channels expressed in mammalian cells. (See e.g., Brown and Rampe, Pharmaceutical News 7:15-20 (2000); Rampe et al., FEBS Lett., 417:28-32 (1997); Weirich and Antoni, Basic Res. Cardiol. 93 Suppl. 1:125-32 (1998); and Yap and Camm, Clin. Exp. Allergy, 29 Suppl 3, 174-81 (1999)).

Off target binding of hERG, the cardiac potassium channel responsible for the rapid delayed rectifier current ($I_{Kr}$) in human ventricles, is evaluated because inhibition of $I_{Kr}$ is the most common cause of cardiac action potential prolongation by non-cardiac drugs. (See Brown and Rampe (2000), Weirich and Antoni (1998); and Yap and Camm (1999)). Increased action potential duration causes prolongation of the QT interval that has been associated with a dangerous ventricular arrhythmia, torsade de pointes. (Brown and Rampe (2000)).

II. Binding Assays

In the hERG assay, hERG channels were expressed in a human embryonic kidney cell line (HEK293) that lacks endogenous $I_{Kr}$. Expression in a mammalian cell line is preferable to transient expression in Xenopus oocytes, as the latter demonstrates a consistent 10-100 fold lower sensitivity to hERG channel blockers. (See, Rampe 1997).

In this hERG assay, the positive control (i.e., reference compound) was terfenadine (Sigma, St. Louis Mo.), which has been shown, at a concentration of 60 nM, to block hERG current by approximately 75%. Test compounds were delivered in HEPES-buffered physiological saline (HB-PS)+ 0.1% dimethyl sulfoxide (DMSO). Each test compound was applied at a concentration of 10 μM to the HEK293 cells expressing hERG (n≧3, where n=the number of cells). Cells were exposed to the test compound for the time necessary to reach steady-state block, but not longer than 10 minutes. The positive control (60 mM terfenadine) was applied to two cells (n≧2).

The hERG-exposed cells were then transferred to the recording chamber and superfused with HB-PS solution. The pipette solution for whole cell recordings included potassium aspartate (130 mM), $MgCl_2$ (5 mM), EGTA (5 mM), ATP (4 mM), and HEPES (10 mM) at a pH adjusted to 7.2 with KOH. Onset and steady state block of hERG current due to the test compound were measured using a pulse pattern with fixed amplitudes (depolarization: +20 mV for 2 seconds; repolarization: –50 mV for 2 seconds), repeated at 10 second intervals, from a holding potential of –80 mV. Peak tail current was measured during the 2 second step to –50 mV. A steady state was maintained for at least 30 seconds before applying the test compound or positive control compound. Peak tail currents were measured until a new steady state was achieved.

Typical hERG current tracings recorded at 22° C. for a vehicle control and a positive control are shown in FIG. 3. Superimposed records in control and after application of a test compound. The lower panel shows voltage stimulus (prepulse +20 mV; test pulse, –50 mV; holding potential, –80 mV).

EXAMPLE 14

Determination of Receptor Selectivity

In one embodiment of the present invention, the selectivity for H1 is increased relative other receptors (i.e., resulting highly soporific compounds with fewer unwanted side effects from binding at adrenergic, muscarinic, serotonergic, and other receptors).

In this regard, a binding assay comparison of (8a), a doxepine-like compound, was performed using a variety of receptor types, shown below in Table 9, to determine receptor selectivity. As is evident from the results shown below the selectivity of (8a) for H1 is dramatically improved over the precursor molecule doxepin.

TABLE 8

| | Percent Inhibition (1.0E–6) | |
|---|---|---|
| Receptor | Doxepin | (8a) |
| Adrenergic, Alpha 1, Non-selective | 92.1 | 1.7 |
| Adrenergic, Alpha 2, Non-selective | 53.5 | –1.8 |
| Histamine, H1 | 100.5 | 89.1 |
| Histamine, H2 | 74.7 | 33.4 |
| Muscarinic, M1 (Human Recombinant) | 88.9 | 3.3 |

TABLE 8-continued

| | Percent Inhibition (1.0E–6) | |
|---|---|---|
| Receptor | Doxepin | (8a) |
| Muscarinic, M2 (Human Recombinant) | 74.0 | 8.2 |
| Muscarinic, Non-selective, Central | 95.2 | 4.4 |
| Muscarinic, Non-selective, Peripheral | 88.4 | 15.0 |
| Norepinephrine Transporter | 97.8 | –3.9 |
| Serotonin Transporter | 75.3 | 9.3 |
| Serotonin, Non-selective | 68.4 | 17.0 |
| Sigma, Non-selective | 52.5 | –2.9 |
| HERG | 23%** | 4% |

**Seldane, etc. = 100%

EXAMPLE 15

Fluphenazine, Perphenazine and Thioradizine Analogs

Sleep-wakefulness, locomotor activity and body temperature of Male Wistar rats treated with the several classes of sleep-inducing compounds described below are monitored as described in Example 10. H1 binding of these classes of sleep-inducing compounds is assayed as described in Examples 11 and 12, and receptor selectivity is assayed as described in Example 13.

One class of sleep-inducing compounds relates to the antihistamines fluphenazine, perphenazine and thioradizine:

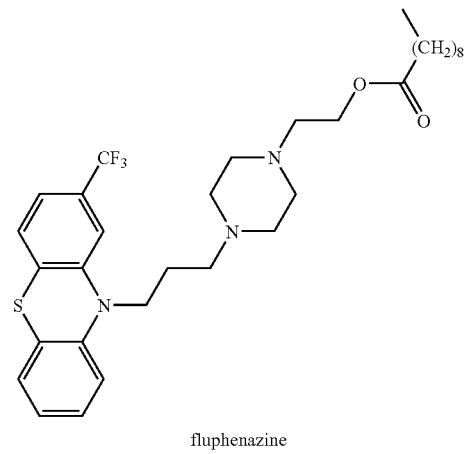

fluphenazine

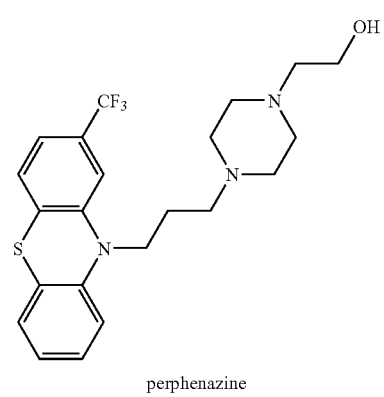

perphenazine

-continued

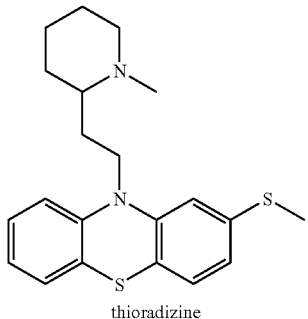

thioradizine

Sleep-inducing derivatives of fluphenazine, perphenazine and thioradizine are represented by the formula UU:

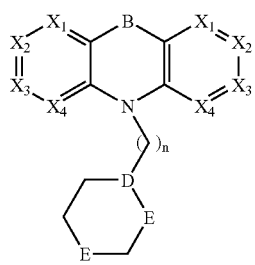

where:

In one embodiment, the modified antihistamines have a linker A with the following structure

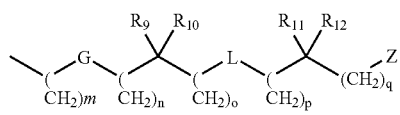

where m n, o, p, q are, individually, 0-6, the $CH_2$ groups are optionally branched, and any member of the alkylene linker (e.g., the portion of the molecule connecting the piperidine ring with the Z group) is substituted with one or more substituents; G and L are, individually, absent, O, S, SO, $SO_2$ or C(O); $R_9$-$R_{12}$ are H, $C_1$-$C_5$ straight chain or branched alkyl (optionally containing a heteroatom). Optionally, substituents on adjacent atoms are connected to form a ring of size 3-7 or substituents on the same atom (i.e., geminal substituents) are connected to form a ring of size 3-7; and Z is $CO_2H$, $CONHS(O)_2$-Aryl (optionally substituted), $CONHS(O)_2$-Alkyl (optionally substituted), $CONHS(O)_2$-Heteroaryl (optionally substituted), $SO_3H$, $SO_2H$, $S(O)_2NHCO$-alkyl, $S(O)_2NHCO$-aryl, $S(O)NHCO$-alkyl, $S(O)NHCO$-aryl, $P(O)(OH)_2$, $P(O)OH$, N,

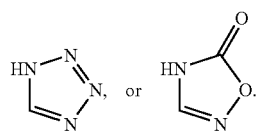

In another embodiment, the modified antihistamines have a linker with the following structure

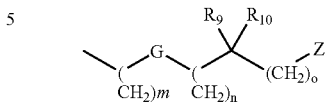

where m n, and o, are, individually, 0-6, and the $CH_2$ groups in the linker are optionally branched; X is absent or O, S, SO, $SO_2$, or C(O); $R_9$-$R_{10}$ are H, $C_1$-$C_5$ straight chain or branched alkyl (optionally containing a heteroatom), and/or are connected to form a ring of size 3-7; Z is $CO_2H$, $CONHS(O)_2$-Aryl, $CONHS(O)_2$-Alkyl, or

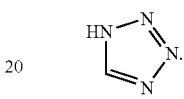

In yet another embodiment, the modified antihistamines have a linker with the following structure

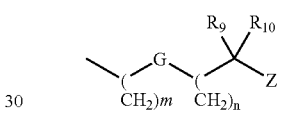

where m and n are, individually, 0-4, and the $CH_2$ moieties are optionally branched; X is absent or O or S; $R_9$-$R_{10}$ are H, $C_1$-$C_3$ alkyl, optionally with heteroatom substitution, branching and/or connected to form a ring of size 3-5; Z is $CO_2H$, $CONHS(O)_2$-Aryl, $CONHS(O)_2$-Alkyl, or

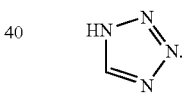

In still another embodiment, the modified antihistamines have a linker with the following structure

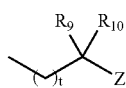

where t is between 0 and 6; $R_9$-$R_{10}$ are H, $CH_3$ or $CH_2CH_3$, and are optionally connected to form a spiro ring of size 3 to 6; and Z is $CO_2H$, $CONHS(O)_2$-Aryl, $CONHS(O)_2$-Alkyl or

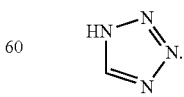

Sleep-inducing derivatives of promethazine are further characterized as possessing the following functional criteria: (i) an inhibition constant ($K_i$) with regard to H1 receptor binding of less than 500 nM; (ii) a $K_i$ with regard to off target binding to an off target selected from the group consisting of M1, M2, M3, D1, D2, D3, α1 and α2 that is more than 10 times greater than the $K_i$ with regard to the H1 receptor; (iii) a nonREM peak time value that is greater than 55% non-REM sleep per hour by the third hour after said compound is administered to a subject; (iv) a cumulative total increase in nonREM sleep not less than 20 minutes for compound doses that produce maximum sleep consolidation; (v) a longest sleep bout that is greater than 13 minutes in duration; (vi) net longest sleep bout post treatment is greater than or equal to 3 minutes when adjusted using a baseline value obtained at least 24 hours prior to administration of said compound to a subject; (vii) an average sleep bout that is greater than 5 minutes at absolute peak; (viii) administration of said compound to a subject does not produce appreciable amounts of rebound insomnia; (ix) administration of said compound to a subject does not appreciably inhibit REM sleep; and (x) and administration of said compound to a subject does not disproportionately inhibit locomotor activity relative to the normal effects of sleep.

One example of a fluphenazine, perphenazine and thioradizine analog fulfilling the selection criteria for an effective sleep modulating compound is Compound UU1, which has the following chemical structure:

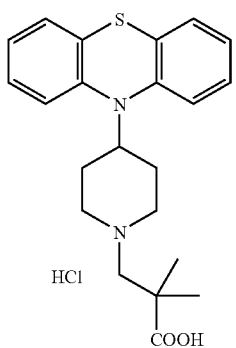

Compound UU1 is a specific compound derived from the generic structure of Compound UU, wherein the linker A has the following structure:

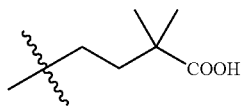

Compound UU1 has the following functional criteria: (i) an inhibition constant ($K_i$) with regard to H1 receptor binding of less than 500 nM; (ii) a $K_i$ with regard to off target binding to an off target selected from the group consisting of M1, M2, M3, D1, D2, D3, α1 and α2 that is more than 10 times greater than the $K_i$ with regard to the H1 receptor; (iii) a nonREM peak time value that is greater than 55% non-REM sleep per hour by the third hour after said compound is administered to a subject; (iv) a cumulative total increase in nonREM sleep not less than 20 minutes for compound doses that produce maximum sleep consolidation; (v) a longest sleep bout that is greater than 13 minutes in duration; (vi) net longest sleep bout post treatment is greater than or equal to 3 minutes when adjusted using a baseline value obtained at least 24 hours prior to administration of said compound to a subject; (vii) an average sleep bout that is greater than 5 minutes at absolute peak; (viii) administration of said compound to a subject does not produce appreciable amounts of rebound insomnia; (ix) administration of said compound to a subject does not appreciably inhibit REM sleep; and (x) and administration of said compound to a subject does not disproportionately inhibit locomotor activity relative to the normal effects of sleep.

More specifically, Compound UU1 has a strong binding affinity for the H1 receptor as measured in the H1 binding assay ($K_i$=13.6 nM). Additionally, it has shown a much weaker binding affinity for the cholinergic (muscarinic) receptors M1, M2 and M3 (>10,000).

Figure 4:
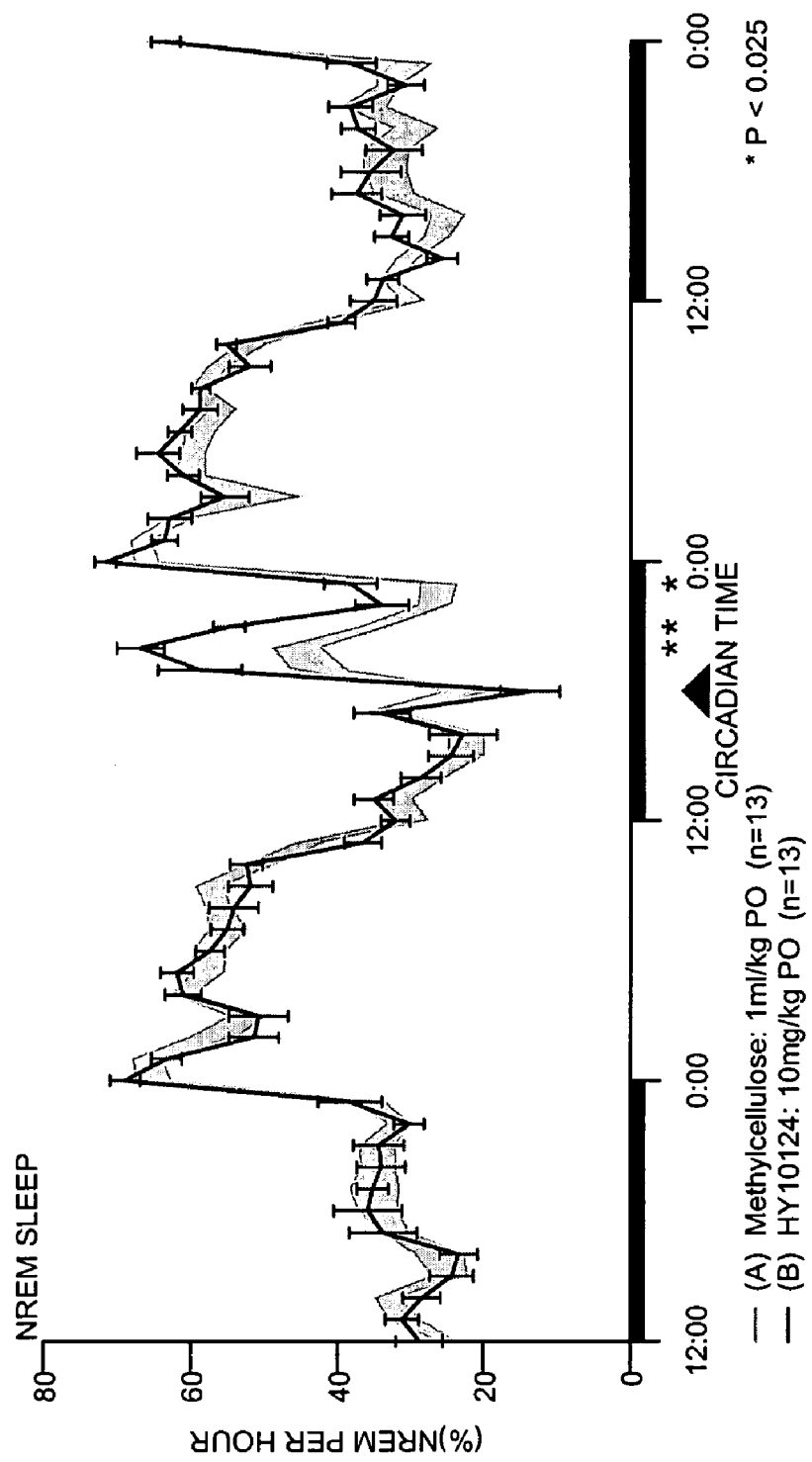
FIG. 4 is a graph depicting the sleep consolidating effects of compound UU1 (HY10124) administered at a concentration of 10 mg/kg at CT-18 (triangle).

As shown in FIG. 4, treatment of rats with Compound UU1 significantly increased total sleep time post-treatment. In this figure, Compound UU1, 10 mg/kg PO (HY10124), treatment is indicated by the thin line; mean±SEM, and the methylcellulose vehicle control (1 ml/kg PO) treatment is indicated by the wide grey line; ±SEM. The time of treatment is indicated by a triangle. Thirteen rats were treated with Compound UU1, and thirteen rats were treated with vehicle.

Figure 5:
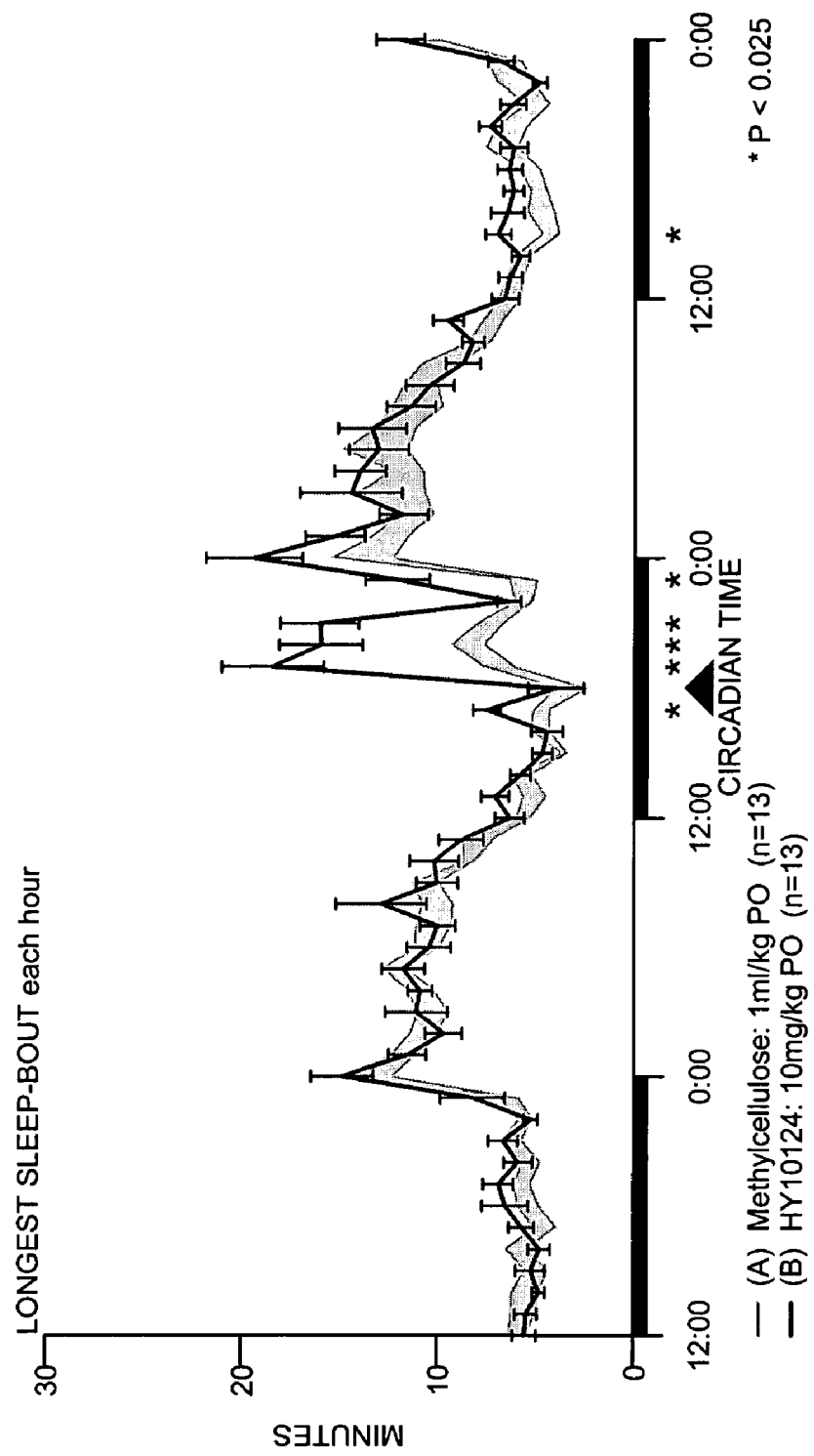
FIG. 5 is a graph depicting the sleep continuity promoting effects of compound UU1 (HY10124) administered at a concentration of 10 mg/kg at CT-18 (triangle).

As shown in FIG. 5, Compound UU1 increased sleep continuity, as assessed by sleep bout length at 10 mg/kg in male Wistar rats. In this figure, Compound UU1, 10 mg/kg PO (HY10124), treatment is indicated by the thin line; mean±SEM, and the methylcellulose vehicle control (1 mg/kg PO) treatment is indicated by the wide grey line; +SEM. The time of treatment is indicated by a triangle. Thirteen rats were treated with Compound UU1, and thirteen rats were treated with vehicle.

Compound UU1 has sedative hypnotic qualities that include increased sleep time and increased sleep consolidation. Compound UU1 showed no evidence of causing disproportional locomotor inhibition or body temperature adverse effects in rats.

EXAMPLE 16

Schering Plough (Dual H1/H3 Antagonist)

Sleep-wakefulness, locomotor activity and body temperature of Male Wistar rats treated with the several classes of sleep-inducing compounds described below are monitored as described in Example 10. H1 binding of these classes of sleep-inducing compounds is assayed as described in Examples 11 and 12, and receptor selectivity is assayed as described in Example 13.

One class of sleep-inducing compounds relates to the antihistamine Schering Plough (Dual H1/H3 Antagonist):

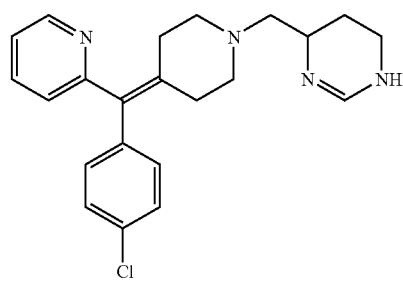

Schering-Plough (Dual H1/H3 Antagonist)

Sleep-inducing derivatives of Schering Plough (Dual H1/H3 Antagonist) are represented by the formula of Compound U:

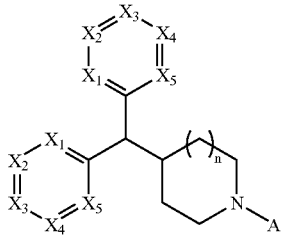

where:

In one embodiment, the sleep modulating compound has a linker A with the following

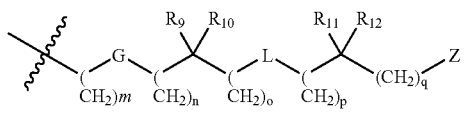

where m n, o, p, q are, individually, 0-6, the $CH_2$ groups are optionally branched, and any member of the alkylene linker (e.g., the portion of the molecule connecting the piperidine ring with the Z group) is substituted with one or more substituents; G and L are, individually, absent or O, S, SO, $SO_2$, or C(O); $R_9$-$R_{12}$ are H, $C_1$-$C_5$ straight chain or branched alkyl (optionally containing a heteroatom). Optionally, substituents on adjacent atoms are connected to form a ring of size 3-7 or substituents on the same atom (i.e., geminal substituents) are connected to form a ring of size 3-7; and Z is $CO_2H$, $CONHS(O)_2$-Aryl (optionally substituted), $CONHS(O)_2$-Alkyl (optionally substituted), $CONHS(O)_2$-Heteroaryl (optionally substituted), $SO_3H$, $SO_2H$, $S(O)_2NHCO$-alkyl, $S(O)_2NHCO$-aryl, $S(O)NHCO$-alkyl, $S(O)NHCO$-aryl, $P(O)(OH)_2$, $P(O)OH$,

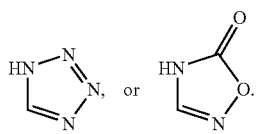

In another embodiment, the sleep modulating compound has the following structure

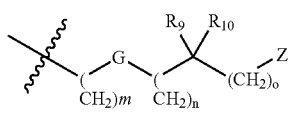

where m n, and o, are, individually, 0-6, and the $CH_2$ groups in the linker are optionally branched; G is absent or O, S, SO, $SO_2$, or C(O); $R_9$-$R_{10}$ are H, $C_1$-$C_5$ straight chain or branched alkyl (optionally containing a heteroatom), and/or are connected to form a ring of size 3-7; Z is $CO_2H$, $CONHS(O)_2$-Aryl, $CONHS(O)_2$-Alkyl, or

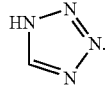

In yet another embodiment, the sleep modulating compound has the following structure

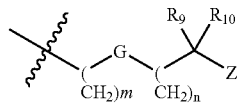

where m and n are, individually, 0-4, and the $CH_2$ moieties are optionally branched; G is absent or O, S, SO, $SO_2$, or C(O); $R_9$-$R_{10}$ are H, $C_1$-$C_3$ alkyl, optionally with heteroatom substitution, branching and/or connected to form a ring of size 3-5; Z is $CO_2H$, $CONHS(O)_2$-Aryl, $CONHS(O)_2$-Alkyl, or

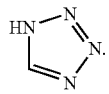

In still another embodiment, the sleep modulating compound has the following structure

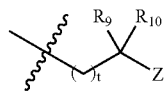

where t is between 0 and 6; $R_9$-$R_{10}$ are H, $CH_3$ or $CH_2CH_3$, and are optionally connected to form a spiro ring of size 3 to 6; and Z is $CO_2H$, $CONHS(O)_2$-Aryl, $CONHS(O)_2$-Alkyl or

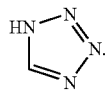

One example of a Schering-Plough Dual H1/H3 Antagonist Analog fulfilling the selection criteria for an effective sleep modulating compound is Compound U1, which has the following chemical structure:

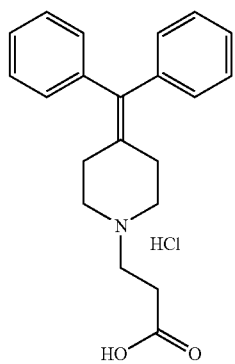

Compound U1 is a specific compound derived from the generic structure of Compound U, wherein the linker A has the following structure:

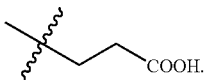

Compound U1 has the following functional criteria: (i) an inhibition constant ($K_i$) with regard to H1 receptor binding of less than 500 nM; (ii) a $K_i$ with regard to off target binding to an off target selected from the group consisting of M1, M2, M3, D1, D2, D3, α1 and α2 that is more than 10 times greater than the $K_i$ with regard to the H1 receptor; (iii) a nonREM peak time value that is greater than 55% nonREM sleep per hour by the third hour after said compound is administered to a subject; (iv) a cumulative total increase in nonREM sleep not less than 20 minutes for compound doses that produce maximum sleep consolidation; (v) a longest sleep bout that is greater than 13 minutes in duration; (vi) net longest sleep bout post treatment is greater than or equal to 3 minutes when adjusted using a baseline value obtained at least 24 hours prior to administration of said compound to a subject; (vii) an average sleep bout that is greater than 5 minutes at absolute peak; (viii) administration of said compound to a subject does not produce appreciable amounts of rebound insomnia; (ix) administration of said compound to a subject does not appreciably inhibit REM sleep; and (x) and administration of said compound to a subject does not disproportionately inhibit locomotor activity relative to the normal effects of sleep.

More specifically, Compound U1 has a strong binding affinity for the H1 receptor as measured in the H1 binding assay ($K_i=119$ nM). Additionally, it has shown a much weaker binding affinity for the cholinergic (muscarinic) receptors M1, M2 and M3 (>10,000).

Figure 6:
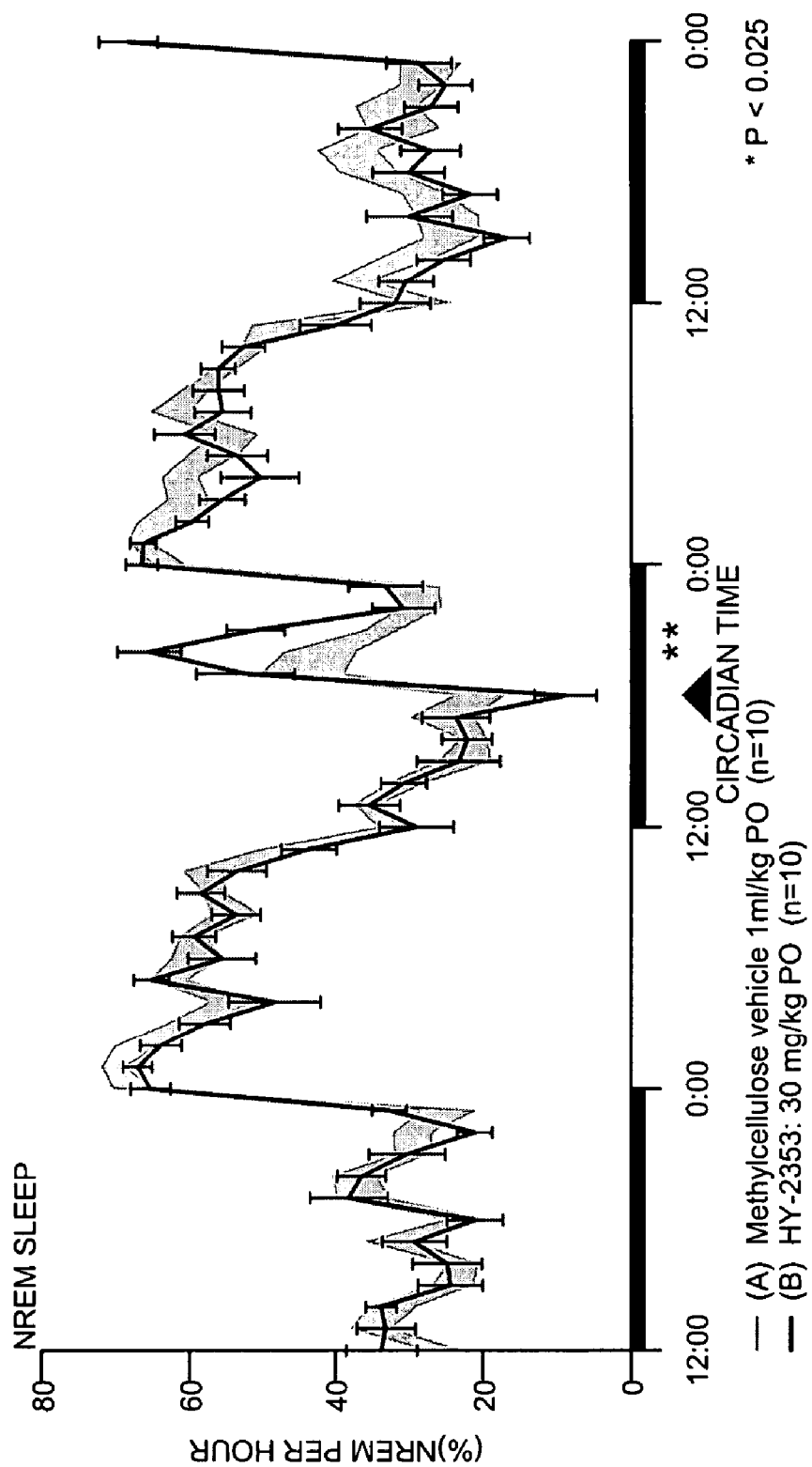
FIG. 6 is a graph depicting the sleep consolidating effects of compound U1 (HY2353) administered at a concentration of 30 mg/kg at CT-18 (triangle).

As shown in FIG. 6, treatment of rats with Compound U1 significantly increased total sleep time post-treatment. In this figure, Compound U1, 10 mg/kg PO (HY2353), treatment is indicated by the thin line; mean±SEM, and the methylcellulose vehicle control (1 mg/kg PO) treatment is indicated by the wide grey line; ±SEM. The time of treatment is indicated by a triangle. Ten rats were treated with Compound U1, and ten rats were treated with vehicle.

Figure 7:
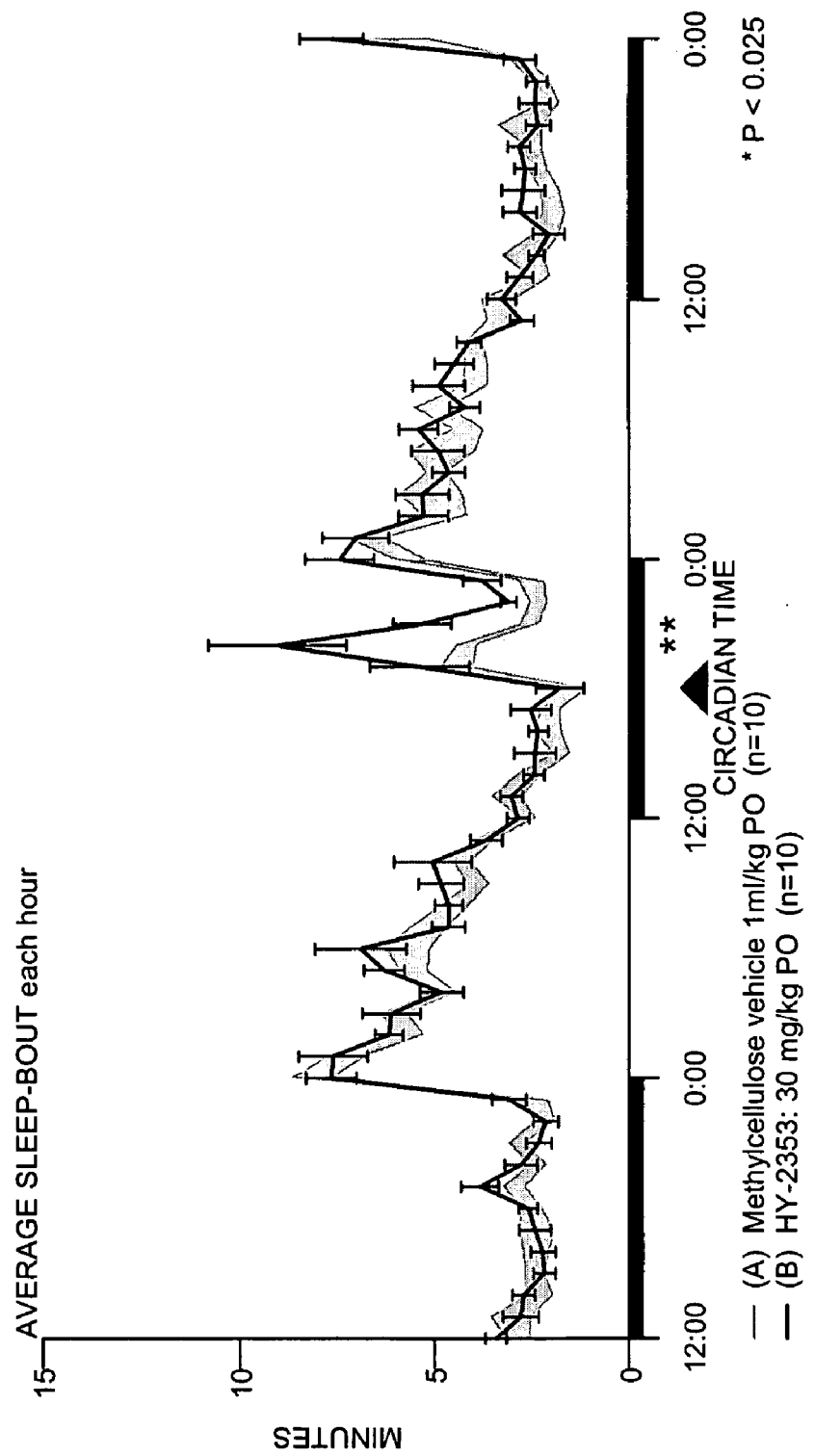
FIG. 7 is a graph depicting the sleep continuity promoting effects of compound U1 (HY2353) administered at a concentration of 30 mg/kg at CT-18 (triangle).

As shown in FIG. 7, Compound U1 increased sleep continuity, as assessed by sleep bout length at 10 mg/kg in male Wistar rats. In this figure, Compound U1, 10 mg/kg PO (HY2353), treatment is indicated by the thin line; mean±SEM, and the methylcellulose vehicle control (1 mg/kg PO) treatment is indicated by the wide grey line; ±SEM. The time of treatment is indicated by a triangle. Ten rats were treated with Compound U1, and ten rats were treated with vehicle.

Compound U1 has sedative hypnotic qualities that include increased sleep time and increased sleep consolidation (sleep continuity). Compound U1 showed no evidence of causing disproportional locomotor inhibition or body temperature adverse effects in rats.

EXAMPLE 17

Clozapine, Loxapine, and Quetiapine Compounds

Sleep-wakefulness, locomotor activity and body temperature of male Wistar rats treated with the several classes of sleep-inducing compounds described below are monitored as described in Example 10. H1 binding of these classes of sleep-inducing compounds is assayed as described in Examples 11 and 12, and receptor selectivity is assayed as described in Example 13.

One class of sleep-inducing compounds relates to the antihistamines clozapine, loxapine, and quetiapine:

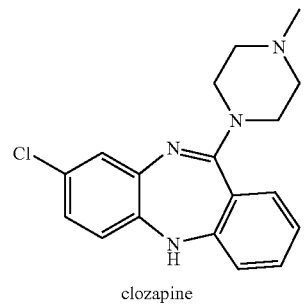
clozapine

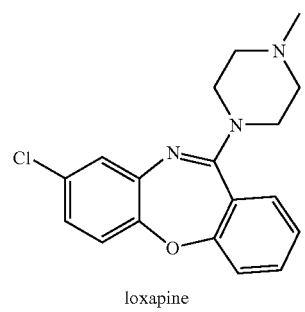
loxapine

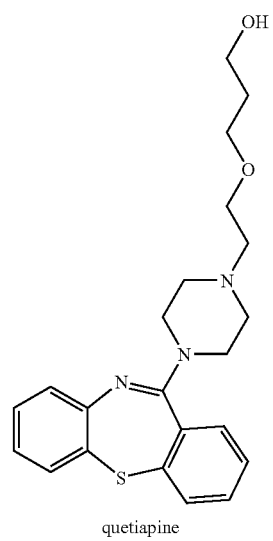
quetiapine

Sleep-inducing derivatives of loxapine, and ciuetiapine are represented by the formula of Compound SS:

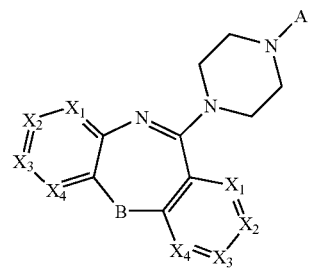

where

In one embodiment, the sleep modulating compound has a linker A with the following structure:

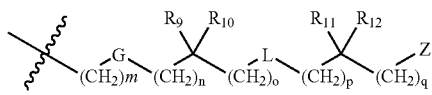

where m n, o, p, q are, individually, 0-6, the $CH_2$ groups are optionally branched, and any member of the alkylene linker (e.g., the portion of the molecule connecting the piperidine ring with the Z group) is substituted with one or more substituents; G and L are, individually, absent or O, S, SO, $SO_2$, or C(O); $R_9$-$R_{12}$ are H, $C_1$-$C_5$ straight chain or branched alkyl (optionally containing a heteroatom). Optionally, substituents on adjacent atoms are connected to form a ring of size 3-7 or substituents on the same atom (i.e., geminal substituents) are connected to form a ring of size 3-7; and Z is $CO_2H$, $CONHS(O)_2$-Aryl (optionally substituted), $CONHS(O)_2$-Alkyl (optionally substituted), $CONHS(O)_2$-Heteroaryl (optionally substituted), $SO_3H$, $SO_2H$, $S(O)_2NHCO$-alkyl, $S(O)_2NHCO$-aryl, $S(O)NHCO$-alkyl, $S(O)NHCO$-aryl, $P(O)(OH)_2$, $P(O)OH$, N, or

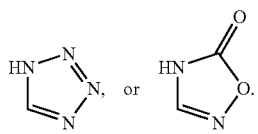

In another embodiment, the sleep modulating compound has the following structure

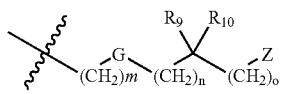

where m n, and o, are, individually, 0-6, and the $CH_2$ groups in the linker are optionally branched; G is absent or O, S, SO, $SO_2$, or C(O); $R_9$-$R_{10}$ are H, $C_1$-$C_5$ straight chain or branched alkyl (optionally containing a heteroatom), and/or are connected to form a ring of size 3-7; Z is $CO_2H$, $CONHS(O)_2$-Aryl, $CONHS(O)_2$-Alkyl, or

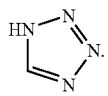

In yet another embodiment, the sleep modulating compound has the following structure

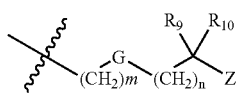

where m and n are, individually, 0-4, and the $CH_2$ moieties are optionally branched; G is absent or O, S, SO, $SO_2$, or C(O); $R_9$-$R_{10}$ are H, $C_1$-$C_3$ alkyl, optionally with heteroatom substitution, branching and/or connected to form a ring of size 3-5; Z is $CO_2H$, $CONHS(O)_2$-Aryl, $CONHS(O)_2$-Alkyl, or

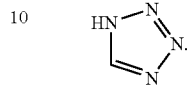

In still another embodiment, the sleep modulating compound has the following structure

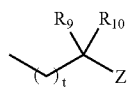

where t is between 0 and 6; $R_9$-$R_{10}$ are H, $CH_3$ or $CH_2CH_3$, and are optionally connected to form a spiro ring of size 3 to 6; and Z is $CO_2H$, $CONHS(O)_2$-Aryl, $CONHS(O)_2$-Alkyl or

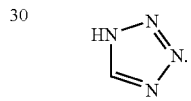

Sleep-inducing derivatives of fluphenazine, perphenazine and thioradizine are further characterized as possessing the following functional criteria: (i) an inhibition constant ($K_i$) with regard to H1 receptor binding of less than 500 nM; (ii) a $K_i$ with regard to off target binding to an off target selected from the group consisting of M1, M2, M3, D1, D2, D3, α1 and α2 that is more than 10 times greater than the $K_i$ with regard to the H1 receptor; (iii) a nonREM peak time value that is greater than 55% nonREM sleep per hour by the third hour after said compound is administered to a subject; (iv) a cumulative total increase in nonREM sleep not less than 20 minutes for compound doses that produce maximum sleep consolidation; (v) a longest sleep bout that is greater than 13 minutes in duration; (vi) net longest sleep bout post treatment is greater than or equal to 3 minutes when adjusted using a baseline value obtained at least 24 hours prior to administration of said compound to a subject; (vii) an average sleep bout that is greater than 5 minutes at absolute peak; (viii) administration of said compound to a subject does not produce appreciable amounts of rebound insomnia; (ix) administration of said compound to a subject does not appreciably inhibit REM sleep; and (x) and administration of said compound to a subject does not disproportionately inhibit locomotor activity relative to the normal effects of sleep.

One example of a Clozapine, Loxapine and Quetiapine Analog fulfilling the selection criteria for an effective sleep modulating compound is Compound SS1, which has the following chemical structure:

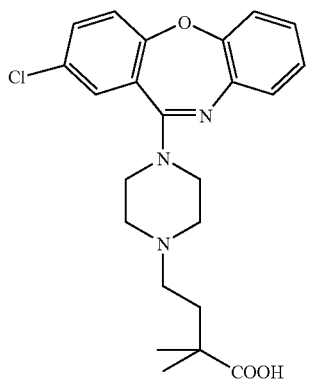

Compound SS1 is a specific compound derived from the generic structure of Compound SS, wherein the linker A has the following structure:

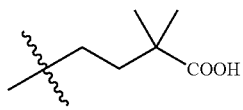

By fulfilling several in vitro and in vivo criteria, Compound SS1 is a promising sleep modulating compound. More specifically, Compound SS1 has a strong binding affinity for the H1 receptor as measured in the H1 binding assay ($K_i$=23.9 nM). Additionally, it has shown a much weaker binding affinity for the cholinergic (muscarinic) receptors M1, M2 and M3 (>10,000).

Figure 8:
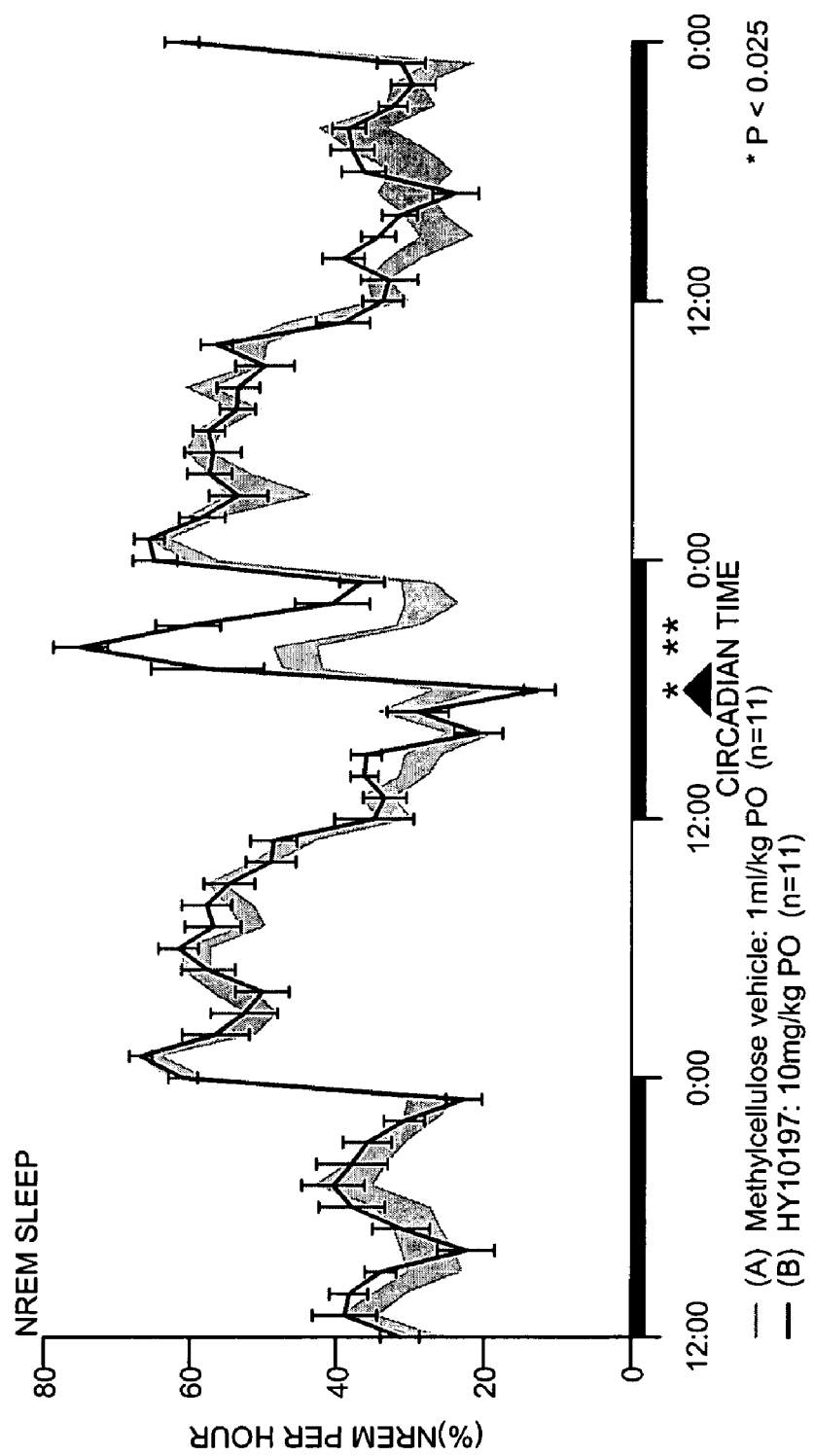
FIG. 8 is a graph depicting the sleep consolidating effects of compound SS1 (HY10197) administered at a concentration of 10 mg/kg at CT-18 (triangle).

As shown in FIG. 8, treatment of rats with Compound SS1 significantly increased total sleep time post-treatment. In this figure, Compound SS1, 10 mg/kg PO (HY10197), treatment is indicated by the thin line; mean±SEM, and the methylcellulose vehicle control (1 mg/kg PO) treatment is indicated by the wide grey line; ±SEM. The time of treatment is indicated by a triangle. Eleven rats were treated with Compound SS1, and eleven rats were treated with vehicle.

Figure 9:
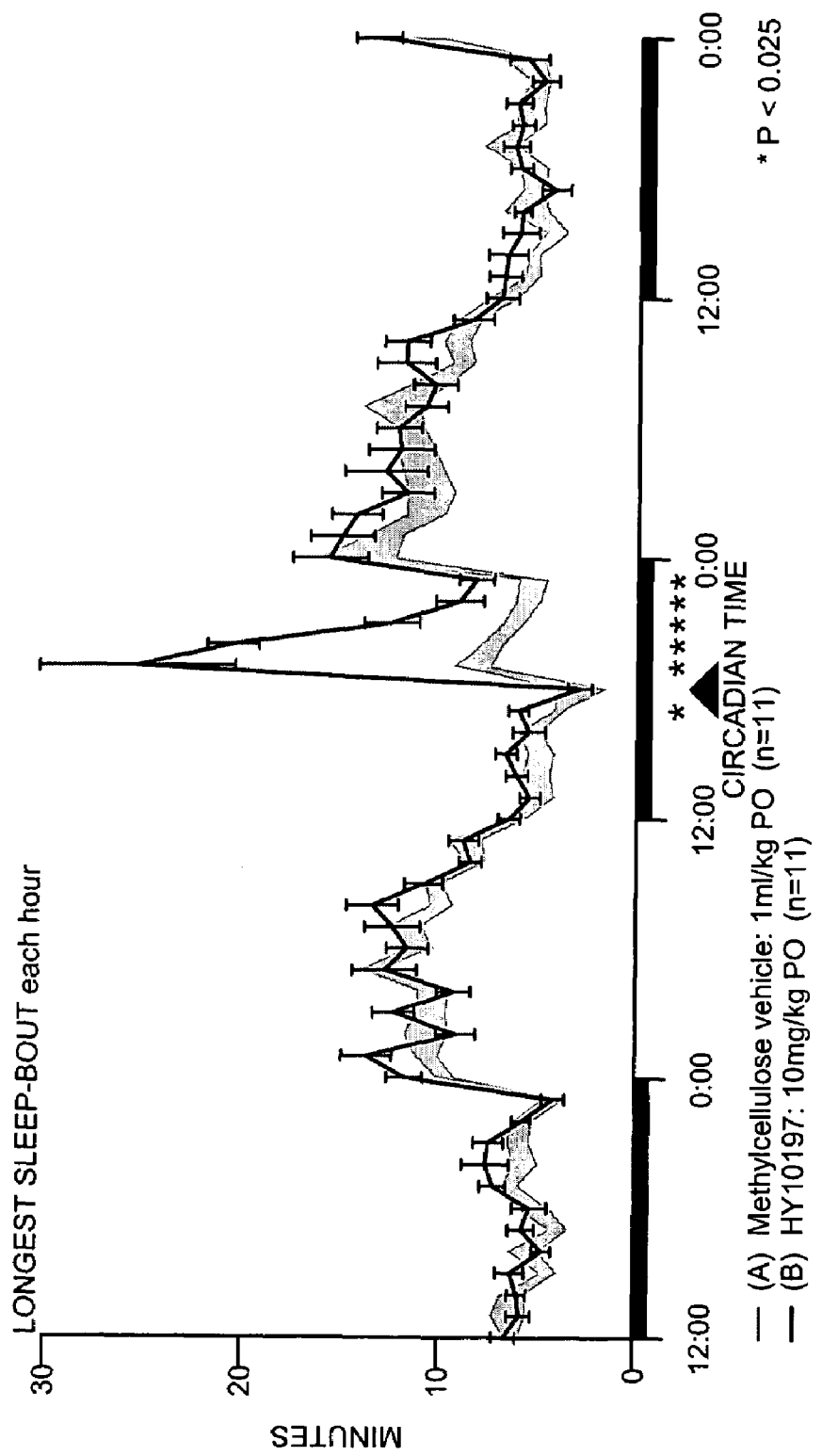
FIG. 9 is a graph depicting the sleep continuity promoting effects of compound SS1 (HY10197) administered at a concentration of 10 mg/kg at CT-18 (triangle).

As shown in FIG. 9, Compound SS1 increased sleep continuity, as assessed by sleep bout length at 10 mg/kg in male Wistar rats. In this figure, Compound SS1, 10 mg/kg PO (HY10197), treatment is indicated by the thin line; mean±SEM, and the methylcellulose vehicle control (1 mg/kg PO) treatment is indicated by the wide grey line; SEM. The time of treatment is indicated by a triangle. Eleven rats were treated with Compound SS1, and eleven rats were treated with vehicle.

Compound SS1 has sedative hypnotic qualities that include increased sleep time and increased sleep consolidation (sleep continuity). Compound SS1 showed no evidence of causing disproportional locomotor inhibition or body temperature adverse effects in rats.

Another example of a Clozapine, Loxapine and Quetiapine Analog fulfilling the selection criteria for an effective sleep modulating compound is Compound SS2, which has the following chemical structure:

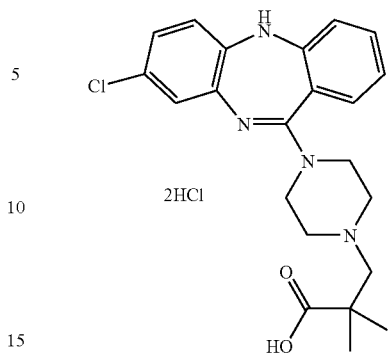

Compound SS2 is a specific compound derived from the generic structure of Compound SS, wherein the linker A has the following structure:

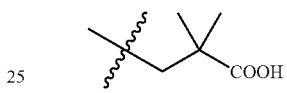

By fulfilling several in vitro and in vivo criteria, Compound SS2 is a promising sleep modulating compound. More specifically, Compound SS2 has a strong binding affinity for the H1 receptor as measured in the H1 binding assay ($K_i$=23.4 nM). Additionally, it has shown a much weaker binding affinity for the cholinergic (muscarinic) receptors M1, M2 and M3 (>10,000).

Figure 10:
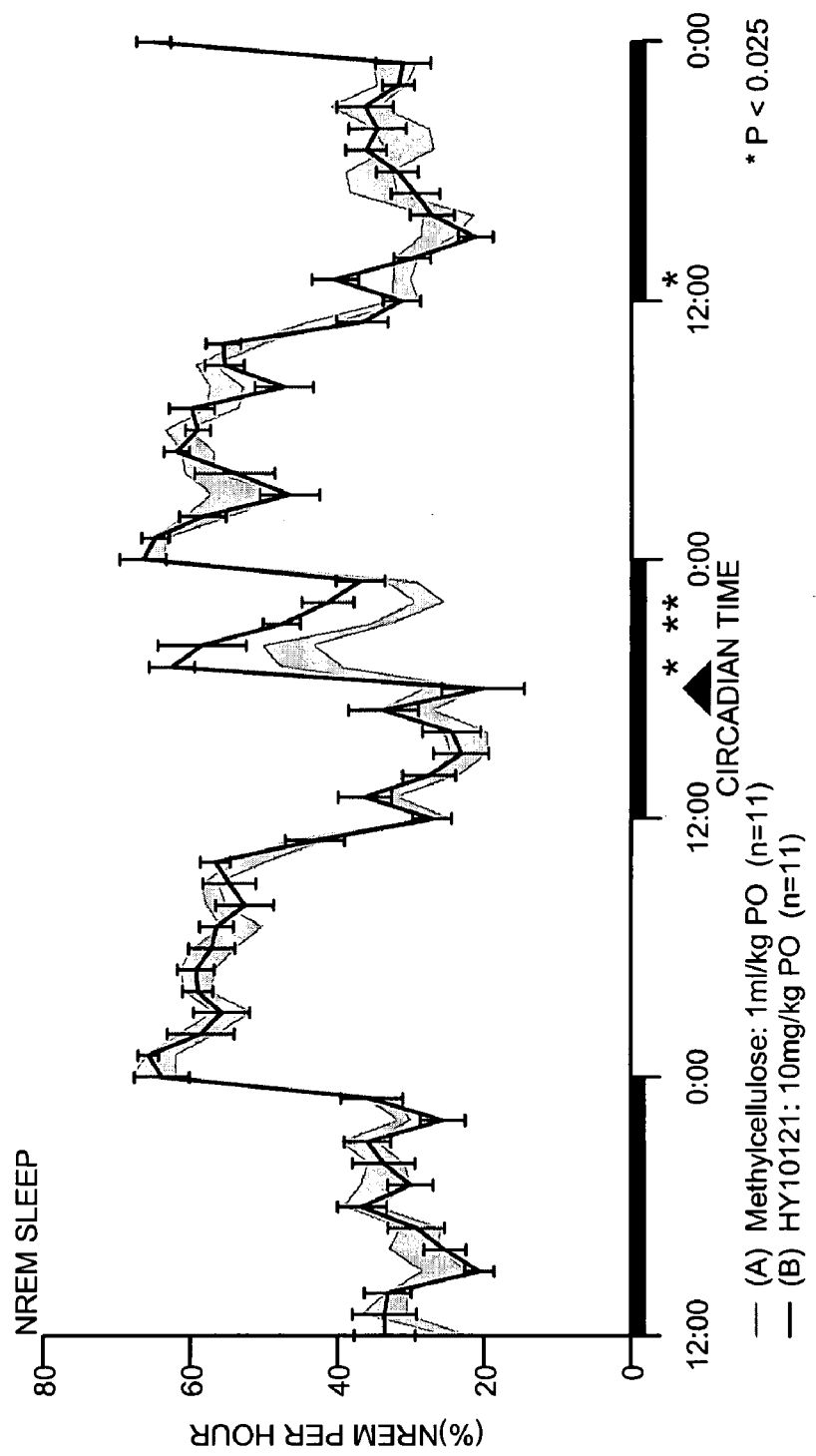
FIG. 10 is a graph depicting the sleep consolidating effects of compound SS2 (HY10121) administered at a concentration of 10 mg/kg at CT-18 (triangle).

As shown in FIG. 10, treatment of rats with Compound SS2 significantly increased total sleep time post-treatment. In this figure, Compound SS2, 10 mg/kg PO (HY1021), treatment is indicated by the thin line; mean±SEM, and the methylcellulose vehicle control (1 mg/kg PO) treatment is indicated by the wide grey line; ±SEM. The time of treatment is indicated by a triangle. Eleven rats were treated with Compound SS1, and eleven rats were treated with vehicle.

Figure 11:
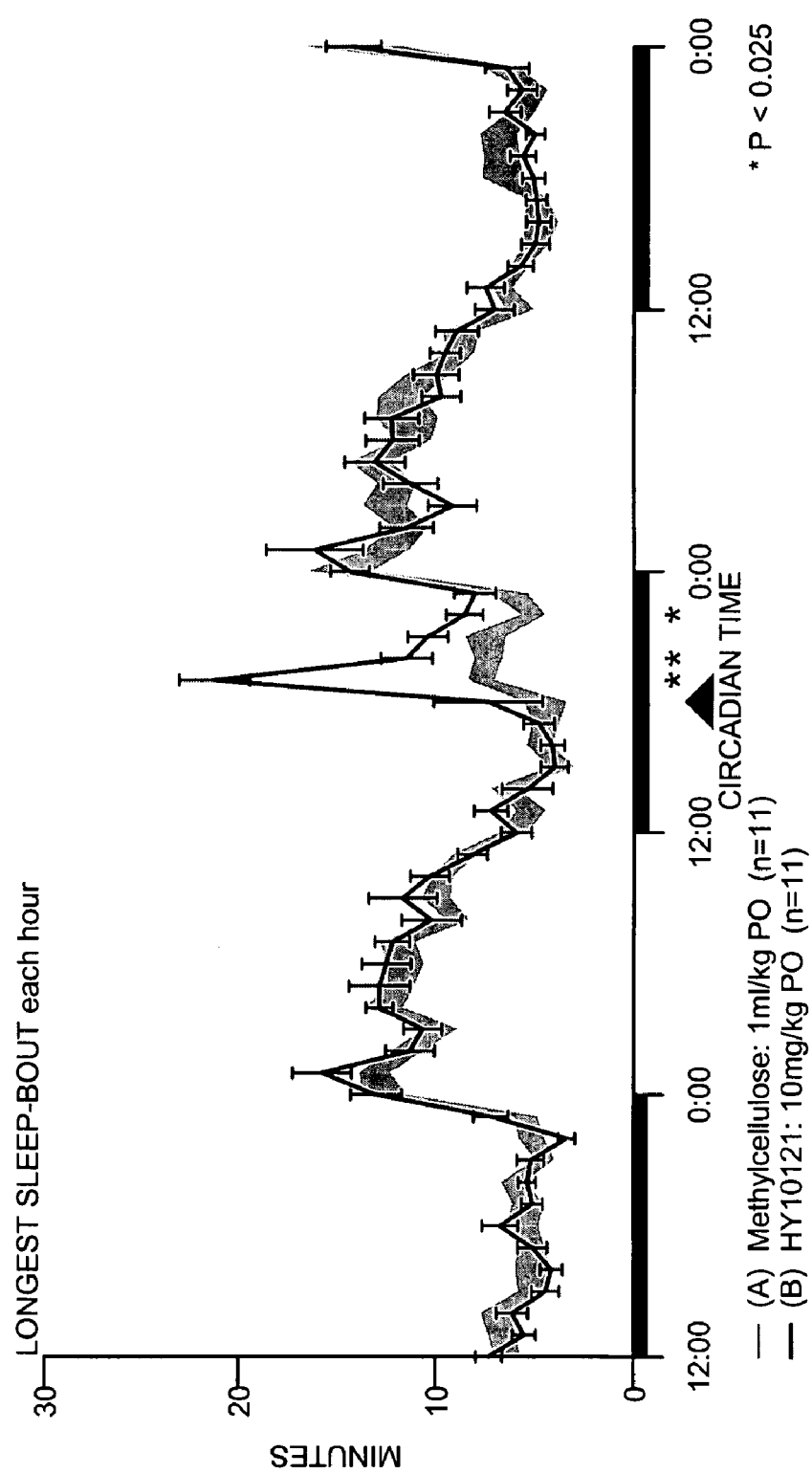
FIG. 11 is a graph depicting the sleep continuity promoting effects of compound SS2 (HY10121) administered at a concentration of 10 mg/kg at CT-18 (triangle).

As shown in FIG. 11, Compound SS2 increased sleep continuity, as assessed by sleep bout length at 10 mg/kg in male Wistar rats. In this figure, Compound SS2, 10 mg/kg PO (HY10121), treatment is indicated by the thin line; mean±SEM, and the methylcellulose vehicle control (1 mg/kg PO) treatment is indicated by the wide grey line; SEM. The time of treatment is indicated by a triangle. Eleven rats were treated with Compound SS2, and eleven rats were treated with vehicle.

Compound SS2 has sedative hypnotic qualities that include increased sleep time and increased sleep consolidation (sleep continuity). Compound SS2 showed no evidence of causing disproportional locomotor inhibition or body temperature adverse effects in rats.

EXAMPLE 18

Clinical Evaluation of Antihistamine Compounds

The goal of a human clinical trial is to collect data on the effects of modified antihistamines. Such data includes, for example, clinical signs and symptoms from physical exam, adverse events, laboratory safety (e.g., hematology, serum clinical chemistry, urinalysis), vital signs (e.g., blood pressure, heart rate, temperature, respiratory rate), and electrocardiogram (ECG) data.

The clinical trials are conducted as follows:

I. Subject Selection

A minimum of 18 subjects are used (2 enrollment groups of 9 subjects each). Subject candidates fulfilling the following inclusion criteria are eligible for participation in the study:

Healthy adult male subjects, 18-45 years of age.

Weighing at least 60 kg and within 15% of their ideal weights (see Table of Desirable Weights of Adults, Metropolitan Life Insurance Company, 1983).

Medically healthy subjects with clinically insignificant screening results (e.g., laboratory profiles, medical histories, ECGS, physical exam).

Subject candidates fulfilling one of the following exclusion criteria are ineligible for participation in the study:

History or presence of significant cardiovascular, pulmonary, hepatic, renal, hematologic, gastrointestinal, endocrine, immunologic, dermatologic, neurologic, or psychiatric disease.

History or presence of sleep disorders.

History of chronic or seasonal allergies requiring treatment with H1 receptor antagonists (i.e., terfenadine, astemizole) within the 90 days prior to the study.

History or presence of alcoholism or drug abuse within the past 2 years.

Tobacco or nicotine use within the 90 days prior to the study.

Known hypersensitivity or idiosyncratic reaction to the study drug, possible excipients of the study formulation (Captisol®; sodium saccharin, F.C.C.; glycerin, U.S.P.; orange flavor; methylcellulose 400 centipoise, U.S.P.; opurified water), or related compounds.

Donation (standard donation amount or more) of blood or blood products within 90 days prior to the study.

Participation in another clinical trial within 90 days prior to the first dose.

History or presence of any disease, medical condition, or surgery, which may have an effect on drug absorption, metabolism, distribution, or excretion.

Weight loss or gain (±10%) within 30 days prior to the study.

Regular consumption of (e.g., more days than not) excessive quantities of caffeine-containing beverages (e.g., more than 5 cups of coffee or equivalent per day) within 30 days prior to the study.

Any condition that, in the opinion of the Investigator or Sponsor makes the subject unsuitable for the study.

Use of any prohibited prior or concomitant medications.

Each subject who completes the study screening assessments, meets all eligibility criteria, and is accepted for the study is assigned a unique identification number and receives designated doses of the modified antihistamine and placebo according to a randomization scheme. The randomization scheme is available only to the clinic pharmacy staff preparing the drug (who are not involved in the administration of the drug) and is not made available to the subjects, analysts, or members of the staff responsible for the monitoring and evaluation of the adverse experiences.

Subjects may be withdrawn from the study by the Principal Investigator for the following reasons:

Secondary occurrence of a major exclusion criteria.

To protect their health.

Adverse events.

Difficulties in blood collection.

To protect the integrity of the study.

Protocol violation.

Failure to comply with study directions.

The clinical report includes reasons for subject withdrawals as well as details relevant to withdrawal. Subjects withdrawn from the trial prior to study completion undergo all procedures scheduled for study completion. Subjects withdrawn due to any adverse event (whether serious or non-serious) or clinically significant abnormal laboratory test values are evaluated by the Investigator, or a monitoring physician, and are treated and/or followed up until the symptoms or values return to normal or acceptable levels, as judged by the Investigator.

II. Study Restrictions

Subjects do not take prescription or over-the-counter medication (including herbal products) during the 7 days preceding the study until the final sample of the final pharmacokinetic sampling period has been collected. Additionally, consumption of foods and beverages containing the following substances is prohibited as indicated:

Methylxanthine: 72 hours before each dosing and throughout the period of sample collection, i.e., caffeine beverages and equivalents (e.g., chocolate bars) are prohibited.

Alcohol: 72 hours before each dosing and throughout the period of sample collection.

All medications taken during the 30 days prior to study start are recorded. Any medications taken for chronic or seasonal allergies in the 90 days prior to the study is recorded.

Pre-Study Subject Screening: The Informed Consent Form is administered at screening. Within 14 days prior to dosing, medical history and demographic data, including name, sex, age, race, body weight (kg), height (cm), alcohol use, and tobacco use are recorded. Each subject receives a physical examination including complete vital signs, 12-lead ECG, and laboratory tests as specified. The laboratory tests include the following:

a) Hematology including hemoglobin, MCV, red blood cell count, hematocrit, MCHC, white blood cell count with differential platelet count and MCH;

b) Serum Chemistry including bun, albumin, ALT (SGOT), creatinine, alkaline phosphatase, glucose, total bilirubin, creatine phosphokinase (CPK), sodium, uric acid, AST (SGOT) and triglycerides;

c) Urinalysis including appearance and color, glucose, nitrite, pH, ketones, urobilinogen, specific gravity, bilirubin, leukocytes, protein and blood;

d) Additional Tests including HIV, urine drug screen, HbsAg, cannabinoids, HCV, benzodiasepines, HCV, amphetamines, hepatitis A (IgM), opiates, alcohol, cocaine, and continine.

Subject Management: Subjects are housed from at least 36 hours before dosing until completion of the 24-hour postdose events. They will return for a follow-up visit one week following the final dose or upon early withdrawal.

Subjects remain semi-recumbent in bed for the first 4 hours following drug administration. However, should adverse events occur at any time, subjects are placed in an appropriate position or are permitted to lie down on their right side. Subjects do not engage in strenuous activity at any time during the confinement period.

Standard meals are provided on Day 1 and Day 2. On Day 1, subjects are required to fast for a minimum of 10 hours overnight before dosing and for at least 4 hours thereafter.

However, if the option for a previous dose in the fed state is used in Period 3 of Group 2, a standard high-fat meal is given 30 minutes prior to dose. In this case, the high-fat breakfast (i.e., approximately 50% of calories from fat) consists of two eggs fried in butter, two strips of bacon, two slices of buttered toast, four ounces of hash brown potatoes, and eight ounces of whole milk. Foods and beverages containing caffeine or equivalent (e.g., chocolate bars) are prohibited during confinement.

Water is not permitted from 2 hours before until 2 hours after dosing. Water is allowed at all other times. Standard meals are provided at approximately 4 and 9 hours after dosing, and at appropriate times thereafter.

III. Drug Administration

Subjects receive the dose for each period as assigned according to the randomization schedule for dosing sequence for each dose (enrollment) group. Subjects receive the assigned dose in a glass dosing cup, and within each dose group, all doses, active and placebo, are administered at the same volume to maintain the double-blind. Subjects are instructed to swallow the dose.

A total of 240 mL of water is given with dosing. A designated portion of the water (assigned by pharmacist based on dosing volume) is added to the emptied dosing cup, swirled to rinse, and swallowed by the subject. This process is repeated twice and then the remainder of the water is consumed by the subject.

The starting dose for the first human dose level is based on the toxicity and safety profiles in the preclinical studies. The equivalent body surface area conversion from human to rat is 1/6 (Toxicological Handbook, Michael J. Dereleko, CRC press, Boca Raton, Fla.). Based on NOAEL of 30 mg/kg/day for rat and body surface equivalent criteria, the equivalent dose in an individual of 60 kg is 300 mg/day (1/6×30 mg/kg/day [rat NOAEL]×60 kg). Based on NOAEL dose in rat (30 mg/kg/day), the dose of 3 mg is approximately 1/10 of the NOAEL dose in rats. The highest dose proposed of 160 mg is also below the NOAEL in rats.

If a dose limiting toxicity (Grade 3 or 4 according to the grade scale modified from the WHO Common Toxicity Criteria—Appendix 1) deemed to be related to the study medication is observed in any 2 of the 6 subjects at any dose level, dose escalations are stopped, and the prior dose is considered the maximum tolerated dose (MTD).

If one subject at any dose level experiences a dose limiting toxicity, the Principal Investigator (in consultation with the Sponsor) decides, using good clinical judgment, whether to proceed to the next dose level as planned, or to adjust the next dose level downward from the dose planned. This consultation is done for all groups following the previous dose group to decide whether to proceed with planned doses or to adjust doses downward. Additionally, the planned doses may be substituted with intermediate doses if emerging safety or tolerability issues become apparent (i.e., there does not have to be a Grade 3 or 4 event) from the preceding dose that suggests the need to escalate more slowly.

Dose increments is only permitted if, in the opinion of the Principal Investigator, adequate safety and tolerability have been demonstrated at the previous lower dose. In all cases, the Principal Investigator uses good clinical judgment to decide whether to adjust the dose or to stop the study based on an assessment of all factors relevant to the safety of the subjects.

The Principal Investigator reviews check-in data (e.g., physical examination results, vital signs, questionnaire, and clinical laboratory results (e.g., serum chemistry, hematology, urinalysis, and urine drug screen) for clinically significant changes since screening or the previous period. The Principal Investigator determines if the subject will be dosed or withdrawn for the study based on this review.

IV. Clinical Observation

A hematology panel, a serum chemistry panel and a urinalysis is performed at screening, at each check-in, 24 hours following each dose, and one week following the final dose, or upon early withdrawal. Blood samples (approximately 7 mL) are collected from an indwelling intravenous catheter into evacuated glass tubes containing sodium heparin predose and at 0.25, 0.5, 0.75, 1.0, 1.5, 2, 3, 4, 6, 8, 10, 12, 18, and 24 hours postdose. Urine samples are collected predose and during the 0-8 hour interval each period. Samples collected during the interval are not pooled. Each void is considered a sample. The voiding times are at will, not scheduled (with the exception of the predose void and the void at the end of the 8 hour interval).

Vital signs are measured during the screenings. When the time of vital signs coincides with an ECG only, the vital signs are taken 10 minutes prior to the ECG. When the time of vital signs coincides with a blood draw or a blood draw and ECG, the vital signs are taken 10 minutes prior to the blood draw. Respirations and temperature is monitored at check-in, 24 hours following each dose, and one week following the final dose, or upon early withdrawal. Single measurements of blood pressure and heart rate are taken after a minimum of 5 minutes in a semi-recumbent position. Measurements taken during study confinement will be monitored with an AVS machine at check-in; 0 (predose); 0.25, 0.5, 0.75, 1, 1.5, 2, 3, 4, 6, 8, 10, 12, 18, and 24 hours postdose; and one week following the final dose, or upon early withdrawal. For any heart rate measurement greater than 100 beats per minute, the heart rate will be rechecked two minutes later. On Day 1, at approximately 24 hours prior to dosing, 3 measurements of blood pressure and heart rate, taken 2 minutes apart, are taken as described as described above.

A standard 12-lead ECG is performed for each subject at screening, on Day 1 at times coinciding with Day 1 times of 1 hours prior to dose and 1, 1.5, 2, 3, 4, and 6 hours postdose; on Day 1 at 1 hour predose and 1, 1.5, 2, 3, 4, 6, and 24 hours postdose; and one week following the final dose or upon early withdrawal. Additional ECGs may be performed at other times if deemed necessary. All standard 12-lead ECGs are recorded for 10 seconds. Timing and registration technique for ECGs is standardized for all subjects. Subjects should be lying down for at least 1 minute prior to each 12-lead ECG evaluation. The Principal Investigator evaluates PR, QRS, QT, and QTc intervals. When the time of ECGs coincides with a blood draw, the ECG will be taken following the draw.

A physician examines each subject at screening, each check-in, 24 hours following each dose, and one week following the final dose, or upon early withdrawal. Additional examinations are performed at other times if deemed necessary.

Immediately before vital signs measurements 1 hour predose and at 1, 2, 6, and 24 hours postdose (the vital signs are taken 10 minutes prior to the blood draw designated at these times), subjects are presented a visual analogue scale and asked to draw a vertical mark across a 100 mm line at the point ranging between Very Sleepy and Alert/Wide Awake, which best describes their level of alertness at that time.

The subjects are instructed to inform the study physician or staff of any adverse events or intercurrent illnesses experienced during the trial. Additionally, a specific inquiry regarding adverse events is conducted prior to dosing, at 2, 4, 8, and 24 hours postdose, and one week following the final dose, or upon early withdrawal. Questions are posed in a non-specific manner so as not to bias the response.

Any subject who has any adverse event (whether serious or non-serious) or clinically significant abnormal laboratory test values is evaluated by the Investigator, or a monitoring physician, and is treated and/or followed up until the symptoms or values return to normal or acceptable levels, as judged by the Investigator. A physician, either on-site or at a nearby hospital emergency room, administers treatment of any serious adverse events. Where appropriate, medical tests and examinations are performed to document resolution of event(s). Outcome is classified as, e.g., resolved, improved, unchanged, worse, fatal, or unknown (lost to follow-up).

V. Reporting

All adverse events occurring during the clinical trial are recorded. Adverse events are coded using MedDRA (version 4.1). An adverse event/experience (AE) is any unwarranted medical occurrence in a patient or clinical investigation subject administered a pharmaceutical product that does not necessarily have a causal relationship with this treatment (ICH/WHO). An adverse event (AE) is, therefore, any unfavorable and unintended sign, (including, for example, an abnormal laboratory finding), symptom, or disease temporally associated with the use of a medical product, whether or not considered related to the medical product (ICH/WHO).

The Investigator reviews each event and assesses its relationship to drug treatment (i.e., unrelated, unlikely, possibly, probably, almost certainly). Each sign or symptom reported is graded on a 3-point severity scale (mild, moderate, or severe) and the date and time of onset, time relationship to drug dosing, duration, and outcome of each event is noted. The following definitions for rating severity are used: (1) Mild: The adverse event is easily tolerated and does not interfere with daily activity; (2) Moderate: The adverse event interferes with daily activity, but the subject is still able to function; (3) Severe: The adverse event is incapacitating and requires medical intervention.

If any of the above adverse events are serious, special procedures are followed. All serious adverse events are reported to the Sponsor within 24 hours and followed by written reports within 48 hours, whether or not the serious events are deemed drug-related.

A Serious Adverse Event (SAE) is any untoward medical occurrence that, at any dose, results in death, is life-threatening, results in permanently disability or incapacitation, requires inpatient hospitalization, prolongs inpatient hospitalization, is a congenital anomaly, may jeopardize the subject or may require intervention to prevent one or more of the other outcomes listed above.

VI. Pharmacokinetics

The following pharmacokinetic parameters are computed from the individual plasma concentrations of the modified antihistamine compound using a noncompartmental approach and appropriate validated pharmacokinetic software (e.g., WinNonlin Professional). Concentration values reported as BLQ are set to zero. If concentration data are available, interim calculations are done (non-QC.d data) between periods if possible. Dose escalation does not depend on pharmacokinetic calculations.

Descriptive statistics, including mean, standard deviation, coefficient of variation, geometric mean, median, minimum and maximum are computed for each pharmacokinetic parameter by dose group. Descriptive statistics for natural-log transformed AUC(0-t), AUC(0-inf), and Cmax for each compound being evaluated are provided for each dose level. In addition, mean and median concentration versus time graphs are provided.

Dose proportionality following study medication is explored by analyzing natural log-transformed pharmacokinetic variables AUC(0-t), AUC(0-inf), and Cmax with a linear model including the natural log-transformed dose as covariates. Dose proportionality is concluded if the 95% confidence interval for the slope of the covariate includes the value of 1. Dose linearity for AUC(0-t), AUC(0-inf), and Cmax is also explored by a linear model.

VII. Assessment of Safety

A by-subject treatment-emergent adverse event data listing including verbatim term, preferred term, treatment, severity, and relationship to treatment is provided.

The number of subjects experiencing adverse events and number of adverse events is summarized by dose level using frequency counts.

Safety data including laboratory evaluations and vital signs assessments is summarized by dose level and time point of collection. Descriptive statistics are calculated for quantitative safety data and frequency counts are compiled for classification of qualitative safety data. In addition, a mean change from baseline table is provided for vital signs and a shift table describing out of normal range shifts is provided for clinical laboratory results.

ECG results are classified as normal and abnormal and summarized using frequency counts by dose group and time point of collection; Descriptive statistics are calculated for PR, QRS, QT, and QTc intervals.

Changes in physical exams are described in the text of the final report.

Heart rate data are summarized by treatment group and time point using descriptive statistics, as will individual change from baseline values. Mean change from baseline results are used to compare active dose groups to placebo at each time point. Data from six completed subjects per dose level should provide 80% certainty to detect a difference of 20 beats per minute. An interim analysis is completed following each period.

VIII. Assessment of Efficacy

VAS sedation scores are summarized by time point of collection for each dose level using descriptive statistics.

EXAMPLE 19

Pre-Clinical Evaluation of Antihistamine Compounds

Prior to human clinical testing of an antihistamine of the invention (also referred to herein as a test compound), pre-clinical testing is performed. Pre-clinical evaluation includes the following tests:

i. Preclinical Absorption, Distribution, Metabolism and Excretion

A test compound is administered to rats, dogs, and cynomolgus monkeys at a dose of 3 mg/kg orally and intravenously. Plasma samples are collected from all species for pharmacokinetic analysis. The Tmax (in hours) and half-life (in hours) for a test compound in each animal model is determined.

The brains are collected from rats after oral administration to determine brain levels of the parent drug. The brain and free drug levels in plasma are compared in the rat to determine if the free drug in plasma is in equilibrium with the brain (free drug to plasma ratio of 1).

The urine of each animal species administered the test compound is tests for unchanged test compound, as well as metabolites.

Cytochrome P450 inhibition is studied for a given test compound in vitro to determine if the test compound inhibits the activity of CYP 1A2, 2C9, 2C19, 2D6, or 3A in a commercially available human microsomal preparation. In addition, the in vitro rate of metabolism in rat, dog, monkey, and human hepatocyte cultures is determined for each test compound.

ii. Cardiac Effects Focus

The primary toxicological issue that is evaluated during the clinical candidate selection phase of the project is QT interval prolongation. Historically, H1 antagonists have been associated with this effect. QT prolongation in rare instances can evolve into life-threatening cardiac arrhythmias. The best in vitro test to predict the likelihood of a compound causing QT prolongation, the hERG binding assay, is the test system chosen to study the potential of a given test compound to produce this effect. The human hERG channel, transfected to a stable cell line, was studied electrophysiologically and the percent inhibition of the channel current was reported. In a screening assay mode, the % inhibition of channel current at the test concentration of a given compound is determined. To put this in perspective, Seldane is used as a positive control produces 100% block of the channel at 60 nM. The IC50 and peak plasma levels are determined for each test compound.

To determine if a test compound produces produce any changes in QT interval, the compound is studied in telemetered Beagle dogs. Dogs are implanted with devices to continuously monitor ECG and arterial blood pressure. Dogs (groups of 4) are studied in a Latin square cross-over design, with each dog receiving 3 different doses and a placebo. Two studies are conducted with doses of 0.3, 1, 3, 10, and 30 mg/kg. Changes in QT or corrected QT interval are recorded for each dose of test compound administered. The effect on heart rate and blood pressure are also monitored.

iii. Acute Rat Study

The purpose of this study is to evaluate the toxicity and maximum tolerated dose (MTD) of the test compounds when given via oral gavage to rats. Male Crl: CD®(SD)IGS BR rats (3/group) were assigned to 5 groups. At initiation of dosing, animals are approximately 7 weeks old with body weights ranging from 150 to 250 g. Each group receives either 50, 100, 150, 200, or 250 mg/kg of HY2901 once daily for 5 days. All surviving animals are sacrificed on Day 6. Assessment of toxicity is based on mortality, clinical observations, and body weight data.

iv. Acute Dog Study

The purpose of this study is to evaluate the toxicity and the maximum-tolerated dose (MTD) of a test compound when given as escalating doses via oral gavage to dogs. Two male purebred Beagles are assigned to the study. At initiation of dosing, animals are at least 6 months old with body weights ranging from 8.0 to 10.9 kg. Dogs received dose preparations containing the test compound once daily for 3 days in escalating doses of 25, 50, or 75 mg/kg, no dose on Day 4, and one dose of 40 mg/kg on Day 5. Dogs are not dosed on Day 4 due to the incidence and severity of clinical signs of toxicity observed at 75 mg/kg.

The dogs are observed at 0.25, 0.5, 0.75, 1.0, 1.5, and 2.0 hours±5 minutes and 4, 6, 8, and 24 hours±15 minutes postdose. They are weighed on Days 1 and 6.

Electrocardiograms are performed and blood pressures are taken prior to dosing and at 1, 4, and 24 hours after the 40 mg/kg dose on Day 5.

v. 14-Day Rat Study with Recovery Study

The purpose of this study is to evaluate the toxicity of a given test compound when administered via oral gavage to rats for at least 14 days and to assess the reversibility, persistence, or delayed occurrence of any effects after a recovery period of up to 14 days.

Male and female Crl:CD®(SD)IGS BR rats are assigned to seven groups, four main study groups and three groups for toxicokinetics. Each group receives dose preparations containing 0.25% methylcellulose, 400 cps in 200 mM acetate buffer, or 10, 30, or 150 mg of test article/kg of body weight (mg/kg/day) at a dose volume of 5 mL/kg.

Assessment of toxicity is based on mortality, clinical and ophthalmic observations, body weights, food consumption, clinical pathology, organ weights, and macroscopic and microscopic findings. Blood samples are collected for toxicokinetic evaluation.

vi. 14-Day Dog Study with Recovery Phase

The toxicity and the toxicokinetics of a test compound when administered daily via oral gavage (Phase 1) or capsules (Phase 2) to dogs for at least 14 days is determined. The reversibility, persistence, or delayed occurrence of observable effects following a 7-day (Phase 1) or 14-day (Phase 2) recovery period is also assessed. Doses of 3, 10, 30, and 70 mg/kg/day are studied.

The above methods and protocols are useful in the preclinical evaluation of other antihistamines of the invention.

Incorporation By Reference

The entire contents of all patents, published patent applications and other references cited herein are hereby expressly incorporated herein in their entireties by reference.

Equivalents

Those skilled in the art will recognize, or be able to ascertain, using no more than routine experimentation, many equivalents to specific embodiments of the invention described specifically herein. Such equivalents are intended to be encompassed in the scope of the following claims.

What is claimed is:

1. A compound having the formula

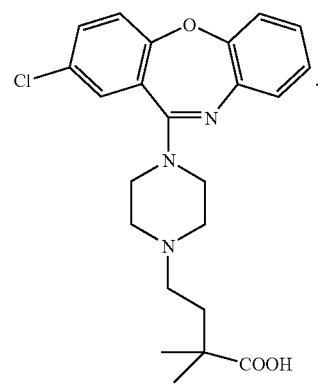

* * * * *